United States Patent
Young et al.

(10) Patent No.: US 10,557,776 B2
(45) Date of Patent: Feb. 11, 2020

(54) FLUID ANALYSIS AND MONITORING USING OPTICAL SPECTROMETRY

(71) Applicant: Virtual Fluid Monitoring Services LLC, Houma, LA (US)

(72) Inventors: Dustin Young, Blanchard, LA (US); Mark Chmielewski, Duluth, MN (US); Chris Morton, Duluth, MN (US); Michael Siers, Duluth, MN (US); Scott Rudder, Hoperwell, NJ (US)

(73) Assignee: Virtual Fluid Monitoring Services, LLC, Houma, LA (US)

( * ) Notice: Subject to any disclaimer, the term of this patent is extended or adjusted under 35 U.S.C. 154(b) by 0 days.

(21) Appl. No.: 16/173,182

(22) Filed: Oct. 29, 2018

(65) Prior Publication Data

US 2019/0101473 A1   Apr. 4, 2019

Related U.S. Application Data

(63) Continuation of application No. 15/997,612, filed on Jun. 4, 2018, which is a continuation-in-part of
(Continued)

(51) Int. Cl.
*G01N 1/10* (2006.01)
*G01N 33/28* (2006.01)
(Continued)

(52) U.S. Cl.
CPC ............... *G01N 1/10* (2013.01); *F01M 11/10* (2013.01); *G01J 3/4406* (2013.01); *G01N 15/06* (2013.01);
(Continued)

(58) Field of Classification Search
None
See application file for complete search history.

(56) References Cited

U.S. PATENT DOCUMENTS 3,751,661 A   8/1973   Packer et al.
3,859,851 A   1/1975   Urbanosky
(Continued)

FOREIGN PATENT DOCUMENTS

GB   2368391   5/2002
JP   H04-50639 A   2/1992
(Continued)

OTHER PUBLICATIONS

Knauer et al., "Soot Structure and Reactivity Analysis by Raman Microspectroscopy, Temperature-Programmed Oxidation, and High-Resolution Transmission Electron Microscopy", J. Phys. Chem. v. 113, pp. 13871 to 13880, 2009.
(Continued)

*Primary Examiner* — Charles D Garber
*Assistant Examiner* — Steven M Christopher
(74) *Attorney, Agent, or Firm* — Jason P. Mueller; Adams and Reese, LLP

(57) ABSTRACT

Systems, methods, and computer-program products for fluid analysis and monitoring are disclosed. Embodiments include a removable and replaceable sampling system and an analytical system connected to the sampling system. A fluid may be routed through the sampling system and data may be collected from the fluid via the sampling system. The sampling system may process and transmit the data to the analytical system. The analytical system may include a command and control system to receive and store the data in a database and compare the data to existing data for the fluid in the database to identify conditions in the fluid. Fluid conditions may be determined using machine learning models that are generated from well-characterized known training data. Predicted fluid conditions may then be used to automatically implement control processes for an operating machine containing the fluid.

12 Claims, 59 Drawing Sheets

Related U.S. Application Data application No. 15/139,771, filed on Apr. 27, 2016, now Pat. No. 10,151,687.

(60) Provisional application No. 62/237,694, filed on Oct. 6, 2015, provisional application No. 62/205,315, filed on Aug. 14, 2015, provisional application No. 62/153,263, filed on Apr. 27, 2015, provisional application No. 62/598,912, filed on Dec. 14, 2017, provisional application No. 62/596,708, filed on Dec. 8, 2017, provisional application No. 62/569,384, filed on Oct. 6, 2017, provisional application No. 62/514,572, filed on Jun. 2, 2017.

(51) Int. Cl.

| | | |
|---|---|---|
| *G06F 17/14* | (2006.01) | |
| *F01M 11/10* | (2006.01) | |
| *G01N 35/00* | (2006.01) | |
| *G01N 21/31* | (2006.01) | |
| *G01N 21/64* | (2006.01) | |
| *G01N 15/06* | (2006.01) | |
| *G01J 3/44* | (2006.01) | |
| *G01N 15/14* | (2006.01) | |
| *G01N 21/65* | (2006.01) | |
| *G01N 21/85* | (2006.01) | |
| *G06N 3/08* | (2006.01) | |
| *G01N 21/94* | (2006.01) | |
| *G01N 15/00* | (2006.01) | |
| *G01N 21/3577* | (2014.01) | |
| *G01N 21/35* | (2014.01) | |

(52) U.S. Cl.
CPC ..... *G01N 15/0656* (2013.01); *G01N 15/1404* (2013.01); *G01N 21/31* (2013.01); *G01N 21/64* (2013.01); *G01N 21/65* (2013.01); *G01N 21/85* (2013.01); *G01N 21/94* (2013.01); *G01N 33/2858* (2013.01); *G01N 33/2876* (2013.01); *G01N 33/2888* (2013.01); *G01N 35/00871* (2013.01); *G06F 17/141* (2013.01); *G06N 3/08* (2013.01); *F01M 2011/144* (2013.01); *F01M 2011/148* (2013.01); *F01M 2011/1446* (2013.01); *F01M 2011/1466* (2013.01); *F01M 2011/1473* (2013.01); *F01M 2011/1493* (2013.01); *G01N 21/3577* (2013.01); *G01N 21/643* (2013.01); *G01N 2015/003* (2013.01); *G01N 2015/0053* (2013.01); *G01N 2015/0662* (2013.01); *G01N 2015/0687* (2013.01); *G01N 2015/0693* (2013.01); *G01N 2021/3595* (2013.01); *G01N 2021/6417* (2013.01); *G01N 2035/00881* (2013.01)

(56) References Cited

U.S. PATENT DOCUMENTS

| | | | |
|---|---|---|---|
| 4,396,259 A | 8/1983 | Miller | |
| 4,963,745 A | 10/1990 | Maggard | |
| 4,994,671 A | 2/1991 | Safinya et al. | |
| 5,139,334 A | 8/1992 | Clarke | |
| 5,161,409 A | 11/1992 | Hughes et al. | |
| 5,167,149 A | 12/1992 | Mullins et al. | |
| 5,194,910 A | 3/1993 | Kirkpatrick, Jr. et al. | |
| 5,201,220 A | 4/1993 | Mullins et al. | |
| 5,266,800 A | 11/1993 | Mullins | |
| 5,331,156 A | 7/1994 | Hines et al. | |
| 5,349,188 A | 9/1994 | Maggard | |
| 5,360,738 A | 11/1994 | Jones et al. | |
| 5,497,008 A | 3/1996 | Kumakhov | |
| 5,557,103 A | 9/1996 | Hughes et al. | |
| 5,598,451 A | 1/1997 | Ohno et al. | |
| 5,604,441 A | 2/1997 | Freese et al. | |
| 5,684,580 A | 11/1997 | Cooper et al. | |
| 5,701,863 A | 12/1997 | Cemenska et al. | |
| 5,717,209 A | 2/1998 | Bigman et al. | |
| 5,739,916 A | 4/1998 | Englehaupt | |
| 5,751,415 A | 5/1998 | Smith et al. | |
| 5,754,055 A | 5/1998 | McAdoo et al. | |
| 5,859,430 A | 1/1999 | Mullins et al. | |
| 5,939,717 A | 8/1999 | Mullins | |
| 5,982,847 A | 11/1999 | Nelson | |
| 5,986,755 A | 11/1999 | Ornitz et al. | |
| 5,999,255 A | 12/1999 | Dupee et al. | |
| 6,028,667 A | 2/2000 | Smith et al. | |
| 6,100,975 A | 8/2000 | Smith et al. | |
| 6,274,865 B1 | 8/2001 | Schroer et al. | |
| 6,289,149 B1 | 9/2001 | Druy et al. | |
| 6,350,986 B1 | 2/2002 | Mullins et al. | |
| 6,452,179 B1 | 9/2002 | Coates et al. | |
| 6,474,152 B1 | 11/2002 | Mullins et al. | |
| 6,507,401 B1 | 1/2003 | Turner et al. | |
| 6,707,043 B2 | 3/2004 | Coates et al. | |
| 6,734,963 B2 | 5/2004 | Gamble et al. | |
| 6,753,966 B2 | 6/2004 | Von Rosenberg | |
| 6,775,162 B2 | 8/2004 | Mihai et al. | |
| 6,779,505 B2 | 8/2004 | Reischman et al. | |
| 6,897,071 B2 | 5/2005 | Sonbul | |
| 6,956,204 B2 | 10/2005 | Dong et al. | |
| 6,989,680 B2 | 1/2006 | Sosnowski et al. | |
| 7,043,402 B2 | 5/2006 | Phillips et al. | |
| 7,095,012 B2 | 8/2006 | Fujisawa et al. | |
| 7,391,035 B2 | 6/2008 | Kong et al. | |
| 7,581,434 B1 | 9/2009 | Discenzo et al. | |
| 7,589,529 B1 | 9/2009 | White et al. | |
| 7,842,264 B2 | 11/2010 | Cooper et al. | |
| 7,855,780 B1 | 12/2010 | Djeu | |
| 8,018,596 B2 | 9/2011 | Salerno et al. | |
| 7,938,029 B2 | 10/2011 | Campbell et al. | |
| 8,155,891 B2 | 4/2012 | Kong et al. | |
| 8,781,757 B2 | 7/2014 | Farquharson et al. | |
| 9,261,403 B2 | 2/2016 | Walton et al. | |
| 9,341,612 B2 | 5/2016 | Gorritxategi et al. | |
| 9,606,063 B2 | 3/2017 | Lee et al. | |
| 2002/0030868 A1 | 3/2002 | Salomaa | |
| 2004/0046121 A1 | 3/2004 | Golden et al. | |
| 2004/0241045 A1 | 12/2004 | Sohl et al. | |
| 2006/0053005 A1 | 3/2006 | Gulati | |
| 2006/0169033 A1 | 8/2006 | Discenzo | |
| 2006/0283931 A1 | 12/2006 | Polli et al. | |
| 2007/0078610 A1 | 4/2007 | Adams et al. | |
| 2007/0143037 A1 | 6/2007 | Lundstedt et al. | |
| 2009/0211379 A1* | 8/2009 | Reintjes | G01N 1/14 73/863.23 |
| 2010/0255518 A1* | 10/2010 | Goix | G01N 21/6428 435/16 |
| 2011/0155923 A1 | 6/2011 | Ukon et al. | |
| 2011/0198500 A1 | 8/2011 | Hotier et al. | |
| 2011/0261354 A1 | 10/2011 | Sinfield et al. | |
| 2013/0050696 A1* | 2/2013 | Antunovich | G01N 21/65 356/301 |
| 2014/0188404 A1 | 7/2014 | Von Herzen et al. | |
| 2014/0188407 A1 | 7/2014 | Von Herzen et al. | |
| 2014/0212986 A1 | 7/2014 | Angelescu et al. | |
| 2014/0229010 A1* | 8/2014 | Farquharson | G01N 33/22 700/272 |
| 2015/0211971 A1 | 7/2015 | Little, III et al. | |
| 2015/0300945 A1 | 10/2015 | Gao et al. | |
| 2016/0069743 A1 | 3/2016 | McQuilkin et al. | |
| 2016/0187277 A1 | 6/2016 | Potyrailo et al. | |
| 2016/0195509 A1 | 7/2016 | Jamieson et al. | |
| 2016/0313237 A1* | 10/2016 | Young | G01N 21/31 |
| 2016/0363728 A1 | 12/2016 | Wang et al. | |

(56) References Cited

U.S. PATENT DOCUMENTS

| | | |
|---|---|---|
| 2017/0016843 A1 | 1/2017 | Gryska et al. |
| 2017/0234819 A1 | 8/2017 | Lilik et al. |

FOREIGN PATENT DOCUMENTS

| | | |
|---|---|---|
| JP | H04-77648 A | 3/1992 |
| JP | H09-138196 A | 5/1997 |
| JP | 2000-509155 A | 7/2000 |
| JP | 2003-534528 A | 11/2003 |
| JP | 2004020412 | 1/2004 |
| JP | 2011-133370 A | 7/2011 |
| JP | 2012-112759 A | 6/2012 |
| JP | 2012-136987 A | 7/2012 |
| JP | 2014-130141 A | 7/2014 |
| RU | 2516200 C2 | 5/2014 |
| WO | 0136966 | 5/2001 |

OTHER PUBLICATIONS

Feraud et al., "Independent Component Analysis and Statistical Modelling for the Identification of Metabolomics Biomarkers in 1H-NMR Spectroscopy", Journal of Biometrics & Biostatistics, vol. 8, issue 4, pp. 1 to 8, 2017.

"Raman Applications Throughout the Petroleum Refinery Blending to Crude Unit", Apr. 26, 2018, APACT Conference, Newcastle, United Kingdom.

Gebarin S. | On-line and In-line Wear Debris Detectors: What's Out There? On-line article, https://machinerylubrication.com/Articles/Print/521.

Cheng B. et al | "Thermal Oxidation Characteristic of Ester Oils Based on Raman Spectroscopy".

Cooper D.| "SFG Spectroscopy is Key to Oil Industry Research", Phonics Spectra, Mar. 2014.

"Accurate and Dependable Choice for In-Service Oil and Fuel Analysis", https://www.azom.com/article.aspx?ArticleID=14948.

Ge , et al | "Raman Spectroscopy of Diesel and Gasoline Engine-Out Soot Using Different Laser Power" www.researchgate.net/publication/328528476.

"Breakthrough study opens door to broader biomedical applications for Raman spectroscopy", Feb. 19, 2013, by IOS Press.

* cited by examiner

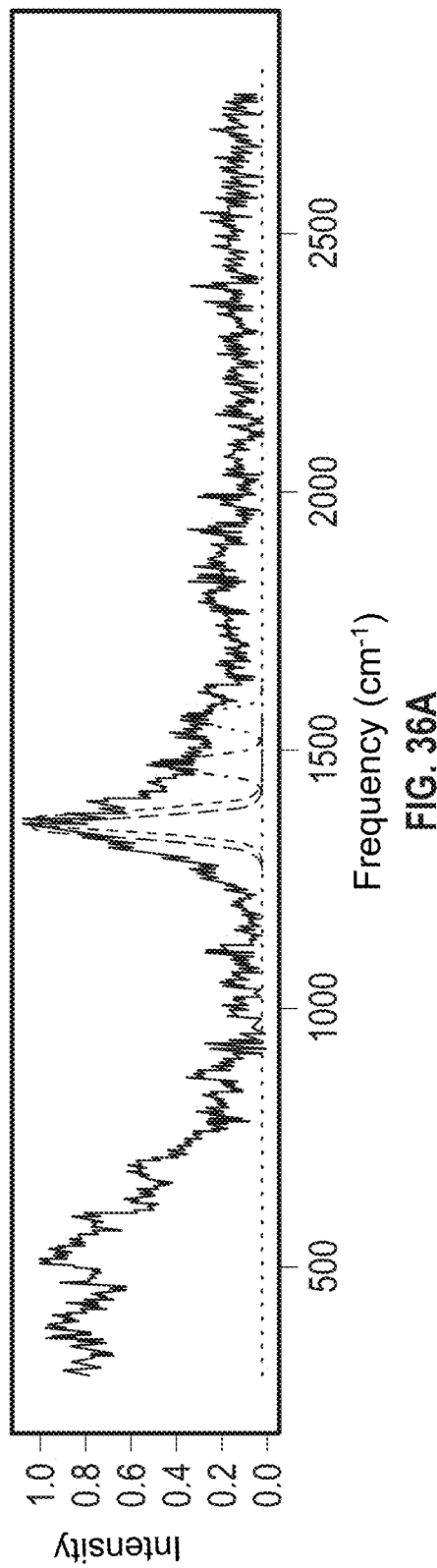
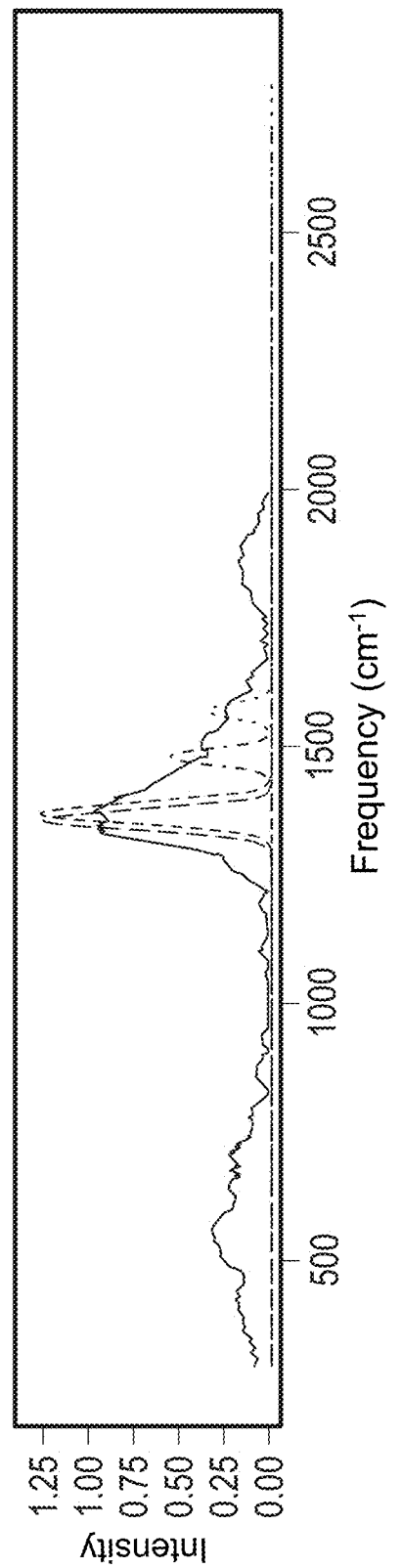
FIG. 36A
FIG. 36B

| | ...$f_0$ $f_1$ $f_2$ $f_3$ $f_4$ $f_5$ $f_6$ $f_7$ $f_8$ $f_9$ $f_{10}$ $f_{11}$ $f_{12}$ $f_{13}$ $f_{14}$... | ← 140 |
|---|---|---|
| S | $a_0$ $a_1$ $a_2$ $a_3$ $a_4$ $a_5$ $a_6$ $a_7$ $a_8$ $a_9$ $a_{10}$ $a_{11}$ $a_{12}$ $a_{13}$ $a_{14}$ | ← 150 |

FIG. 40

| | ...$f_0$ $f_1$ $f_2$ $f_3$ $f_4$ $f_5$ $f_6$ $f_7$ $f_8$ $f_9$ $f_{10}$ $f_{11}$ $f_{12}$ $f_{13}$ $f_{14}$... |
|---|---|
| s1 | $a_0$ $a_1$ $a_2$ $a_3$ $a_4$ $a_5$ $a_6$ $a_7$ $a_8$ $a_9$ $a_{10}$ $a_{11}$ $a_{12}$ $a_{13}$ $a_{14}$ |
| s2 | $b_0$ $b_1$ $b_2$ $b_3$ $b_4$ $b_5$ $b_6$ $b_7$ $b_8$ $b_9$ $b_{10}$ $b_{11}$ $b_{12}$ $b_{13}$ $b_{14}$ |
| s3 | $c_0$ $c_1$ $c_2$ $c_3$ $c_4$ $c_5$ $c_6$ $c_7$ $c_8$ $c_9$ $c_{10}$ $c_{11}$ $c_{12}$ $c_{13}$ $c_{14}$ |
| s4 | $d_0$ $d_1$ $d_2$ $d_3$ $d_4$ $d_5$ $d_6$ $d_7$ $d_8$ $d_9$ $d_{10}$ $d_{11}$ $d_{12}$ $d_{13}$ $d_{14}$ |
| s5 | $e_0$ $e_1$ $e_2$ $e_3$ $e_4$ $e_5$ $e_6$ $e_7$ $e_8$ $e_9$ $e_{10}$ $e_{11}$ $e_{12}$ $e_{13}$ $e_{14}$ |

FIG. 41

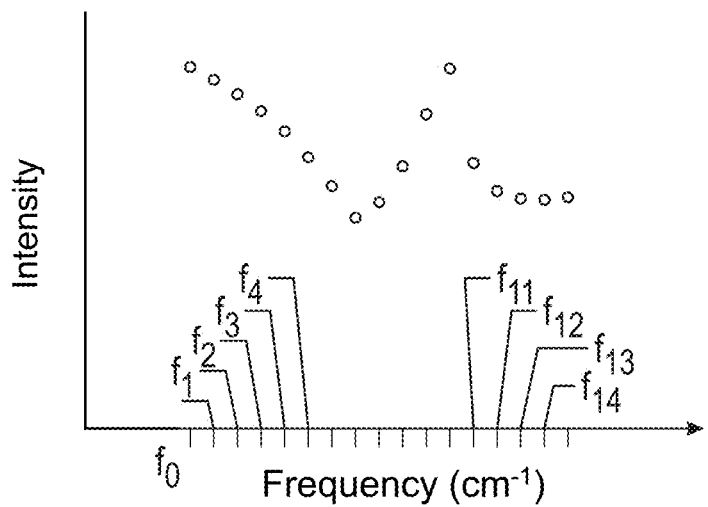

FIG. 42

FLUID ANALYSIS AND MONITORING USING OPTICAL SPECTROMETRY

CROSS-REFERENCE TO RELATED APPLICATIONS

This application is a continuation of U.S. patent application Ser. No. 15/997,612, filed Jun. 4, 2018, which is a continuation-in-part of U.S. patent application Ser. No. 15/139,771, filed Apr. 27, 2016, which claims the benefit of U.S. Provisional Patent Application No. 62/237,694, filed Oct. 6, 2015, U.S. Provisional Patent Application No. 62/205,315, filed Aug. 14, 2015, and U.S. Provisional Patent Application No. 62/153,263, filed Apr. 27, 2015. U.S. patent application Ser. No. 15/997,612 also claims the benefit of U.S. Provisional Patent Application No. 62/598,912, filed Dec. 14, 2017, U.S. Provisional Patent Application No. 62/596,708, filed Dec. 8, 2017, U.S. Provisional Patent Application No. 62/569,384, filed Oct. 6, 2017, and U.S. Provisional Patent Application No. 62/514,572, filed Jun. 2, 2017. The contents of the above-referenced patent applications are incorporated herein by reference in their entireties.

BRIEF DESCRIPTION OF THE DRAWINGS

The accompanying drawings form a part of the disclosure and are incorporated into the subject specification. The drawings illustrate example embodiments and, in conjunction with the specification and claims, serve to explain various principles, features, or aspects of the disclosure. Certain embodiments are described more fully below with reference to the accompanying drawings. However, various aspects be implemented in many different forms and should not be construed as limited to the implementations set forth herein. Like numbers refer to like, but not necessarily the same or identical, elements throughout.

FIG. 36A illustrates the data of FIG. 35B after it has been pre-processed, according to an example embodiment of the present disclosure.

FIG. 36B shows the data of FIG. 35C after it has been pre-processed, according to an example embodiment of the present disclosure.

FIG. 40 is a table of feature area values each corresponding to respective frequency values according to an example embodiment of the present disclosure.

FIG. 41 is a table of feature area values vs. frequency for a plurality of systems, according to an example embodiment of the present disclosure.

FIG. 42 is a data plot of computed areas vs. frequency illustrating minima that may be used to identify spectral features, according to an example embodiment of the present disclosure.

DETAILED DESCRIPTION

Figure 1:
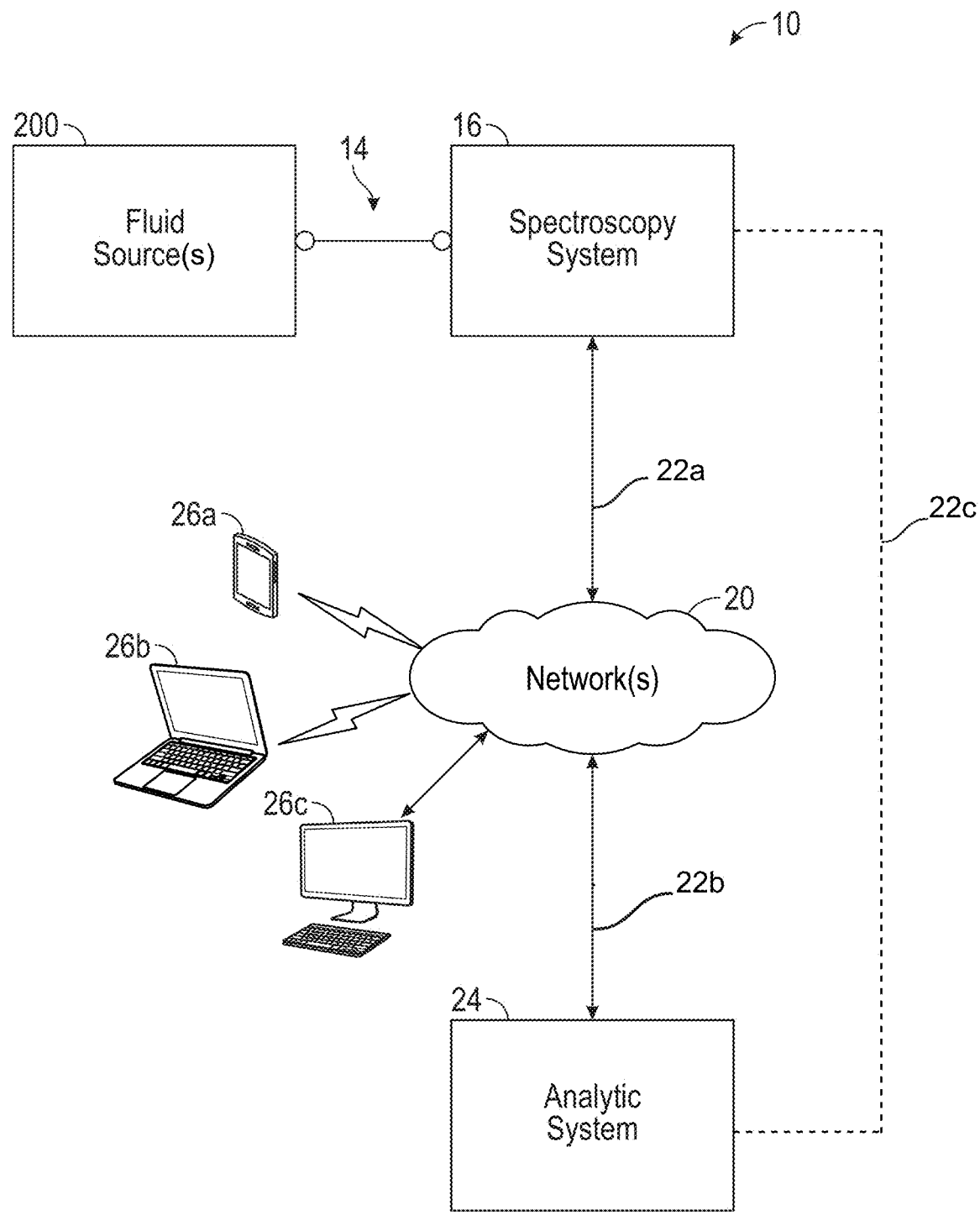
FIG. 1 is a schematic of a fluid analysis and monitoring system, according to an example embodiment of the present disclosure.

One of the keys to keeping machinery operating at optimal performance is monitoring and analyzing working fluids, including lubricant oils, for characteristics such as contamination, chemical content, and viscosity. The existence or amount of debris and particles from wearing parts, erosion, and contamination provide insights about issues affecting performance and reliability. Indeed, accurately and effectively analyzing and trending data about a fluid may be critical to the performance and reliability of a particular piece of equipment. The benefits of improved predictive monitoring and analysis of fluids include: optimized machinery performance, optimized maintenance planning and implementation, lower operational and maintenance costs, fewer outages, improved safety, and improved environmental impacts.

The present disclosure provides improved systems and methods for fluid monitoring and analysis. Disclosed systems and methods accurately and effectively gather, trend and analyze key data for improved proactive predictive maintenance. Embodiments of the present disclosure include automated systems that directly monitor multiple conditions of a fluid, for example, engine oil actively flowing through working engines. In embodiments, a single system is provided that actively monitors the condition of fluids flowing through multiple pieces of machinery, for example, oils flowing through multiple engines, on a set schedule or on-demand as directed by an operator using a web-based portal or a mobile application. Fluids may be analyzed while machinery is on-line such that normal operation is not disrupted. Fluids can be effectively monitored and analyzed real-time, that is, a report can be sent to an operator in minutes. This is a significant improvement over conventional oil analysis systems, which may involve collecting a sample from a specific piece of machinery and sending it off-site for analysis—often taking 3 to 7 days to get results back, which are additionally prone to human error.

Embodiments of the present disclosure include collecting optical spectroscopy data from fluid samples such as oil and sending that data to an analytic system that then determines fluid/oil characteristics and/or identifies potential issues with a particular piece of machinery. Monitored conditions may include determining a presence of a wear metal in the oil, the presence of an amount of an additive in the oil, the presence of water in the oil, the total acid number (TAN) of the oil, the total base number (TBN) of the oil, the presence of coolant in the oil, the presence of fuel in the oil, and/or the particle count of particulate matter (e.g., soot and other particles) within the oil. For example, specific engine problems, such as a bearing that is wearing or a gasket that is leaking, may be identified based on specific materials (e.g., particular wear metals) identified in an engine oil. Additional variables (e.g., temperature, pressure, and viscosity of the fluid/oil) may be monitored and data associated with these variables may be analyzed in conjunction with spectroscopic information to further characterize conditions of the fluid/oil.

Embodiments of the present disclosure include hardware that directly couples to a piece of machinery (e.g., an engine), and collects spectral data, and other data characterizing a fluid, in-situ, while the machinery is in operation. The collected data is then analyzed using machine learning computational techniques and compared with an evolving collection of reference data stored in one or more databases. For example, machine learning models that characterize various known materials in a fluid may be built and stored in a database. Such models may be constructed by using machine learning techniques to identify composition dependencies of spectral features for well-characterized training data.

Training data may include spectroscopic data for a plurality of samples of a fluid/oil having known concentrations of an impurity of contaminant of interest as characterized by an analytical laboratory using conventional analytical techniques. Spectral training data may be obtained for contamination targets, such as fuel or coolant contamination, by producing physical samples having known concentrations (e.g., serial dilution) of fuel or coolant. Degradation samples, which are positive for a specific degradation target (e.g., soot, wear metal, etc.) may be obtained from an analytical laboratory that evaluates used oil samples though conventional means. Samples obtained from an analytical laboratory may be completely characterized using a battery of conventional analytical techniques. Resulting machine learning models may include classifier models, decision tree models, regression models, etc.

Then, spectroscopic data that is gathered, in-situ, in real-time (i.e., while equipment is operating) may be analyzed using similar machine learning techniques to determine correlations with the stored models to determine a presence of one or more known components within the otherwise unknown mixture of materials found in the fluid or lubricating oil of the operating machine. For example, a classifier model may be used to predict whether data from newly analyzed sample has a concentration above or below a predetermined threshold for one or more contaminants of interest (e.g., soot, coolant, fuel, etc., in the oil).

Such analytical methods may allow preventive measures to be taken (e.g., by an operator or automatically by a control system) to avoid critical failures and to promote proper functioning, performance, and longevity of operating machinery through the use of informed proactive operation and maintenance practices based on the analysis of the fluid condition.

As described in greater detail below, a fluid analysis system may be provided that performs Raman spectroscopic measurements to detect molecular vibrational characteristics of opaque fluids such as motor oil. The system may use a Raman probe and a Raman sub-sampling system. The system may also include multiple excitation sources, a detection system, and an optical switch, as well as power, and control circuitry housed in a single enclosure that is provided with active cooling systems. The system may collect, process, and analyze data from multiple fluid sources. One or more analytical systems may be provided that analyze such data using machine learning computational techniques to determine fluid conditions, in-situ, in real-time (i.e., while a piece of machinery is in operation).

Embodiments of the present disclosure, which are discussed in detail herein, include a Raman spectral excitation and detection system that is directly coupled to operating machinery that gathers Raman spectral data from working fluids, in-situ, while the machine is operating (i.e., in real time). Disclosed systems further include an analytical system that performs fluid analysis using machine learning techniques to determine the composition of the working fluids.

Raman spectroscopy allows determination of spectral characteristics in the ultraviolet, near-infrared, and infrared spectrum. Accordingly, a broad array of target materials may be optically identified using a single technique. In this regard, Raman spectroscopy provides advantages over other spectroscopic techniques, including techniques that are based on the use of infrared and near infrared radiation. Traditionally, application of Raman spectroscopy has not been used to analyze complex fluids such as opaque fluids (e.g., motor oil) because Raman spectroscopy can produce auto-fluorescence signals that often dominate and essentially mask the Raman signal, particularly in opaque fluid samples.

Disclosed embodiments of the present disclosure, including systems, methods, and computer program products, provide improved fluid analysis capabilities that include Raman spectroscopy techniques that are reliably and efficiently used for analysis of opaque fluids such as motor oil. For example, disclosed methods provide a power calibration technique that overcomes conventions problems associated with using Raman spectroscopy techniques to investigate chemical compositions (i.e., specific targets including wear metals, soot, etc.) in motor oil. A disclosed power calibration technique determines an optimal intensity level of incident radiation to generate a suitable Raman signal while avoiding auto-fluorescence effects. Analytic models disclosed herein may then be used to analyze resulting Raman spectral data, as well as other fluid data (e.g., temperature, viscosity, etc.) and other optical sensor information to identify a variety of contaminants, wear metals, oil dilution fluids, etc., to allow prediction and diagnosis of fluid conditions. Analytical models may also take into account fluorescence and absorbance spectral data along with Raman spectral data to provide a complete characterization of fluids of interest.

FIG. 1 is a schematic of a fluid analysis and monitoring system 10, according to an example embodiment of the present disclosure. System 10 includes one or more fluid sources 200 and a spectroscopy system 16 that are operationally coupled (e.g., optically coupled, mechanically coupled, electrically coupled, electromechanically coupled, and/or electro-optically coupled). In this regard, a coupling assembly 14 may provide a mechanical and fluidic coupling between fluid source 200 and spectroscopy system 16. Coupling system 14 may additionally provide electrical and optical coupling between fluid source 200 and spectroscopy system 16. As such, coupling system 14 may include various coupling mechanisms and/or coupling devices, including tubing, fittings, optical fiber cables, etc.

As described in greater detail below, spectroscopy system 16 may perform spectroscopy measurements on fluids provided by fluid source 200. Spectroscopic data determined by spectroscopy system 16 may then transferred to other devices via a wired or wireless network 20 through wired or wireless links 22a and 22b. Various user devices 26a, 26b, 26c, etc., may communicate with spectroscopy system 16 via network 20 to perform data analysis operations and to provide command and control instructions to spectroscopy system 16. Spectroscopy system 16 may further communicate with one or more analytic systems 24 via network 20 through wired or wireless links 22a and 22b. Spectroscopy system 16 may further communicate directly with analytic system 24 through one or more direct wired or wireless links 22c.

Analytic system 24 may perform a statistical analysis on data received from spectroscopy system 16 to determine conditions of the fluid/oil. For example, analytic system 24 may determine a chemical composition of the fluid. Analytic system 24 may further determine a concentration of various contaminants in the fluid. Analytic system 24 may be implemented in a variety of ways. In a non-limiting example, analytic system 24 may be implemented as a circuit element in hardware, or may be implemented in firmware or software of a computing system. Analytic system 24 may be implemented on a local computing device or may be implemented in a cloud based computing platform using cloud based tools. In a further embodiment, analytic system 24 may be implemented in a data center or other server based environment using a service provider's tools or using custom designed tools.

According to an embodiment, fluid source 200 may be a mechanical device such as an engine, generator, turbine, transformer, etc., that employs a fluid (e.g., an oil) as a lubricant, as a hydraulic working fluid, etc. An example of an engine may be an internal combustion engine. Fluid source 200 may be a single engine or may include groups of different types of engines. Example engines may include one or more of: a two-stroke engine, a four-stroke engine, a reciprocating engine, a rotary engine, a compression ignition engine, a spark ignition engine, a single-cylinder engine, an in-line engine, a V-type engine, an opposed-cylinder engine, a W-type engine, an opposite-piston engine, a radial engine, a naturally aspirated engine, a supercharged engine, a turbocharged engine, a multi-cylinder engine, a diesel engine, a gas engine, or an electric engine. In other embodiments, system 10 for a fluid analysis and monitoring system may include various other fluid sources 200. In other embodiments, fluid source 200 may be associated with an oil drilling operation, an oil refinery operation, a chemical processing plant, or other industrial application for which fluid monitoring may be desired.

Figure 2:
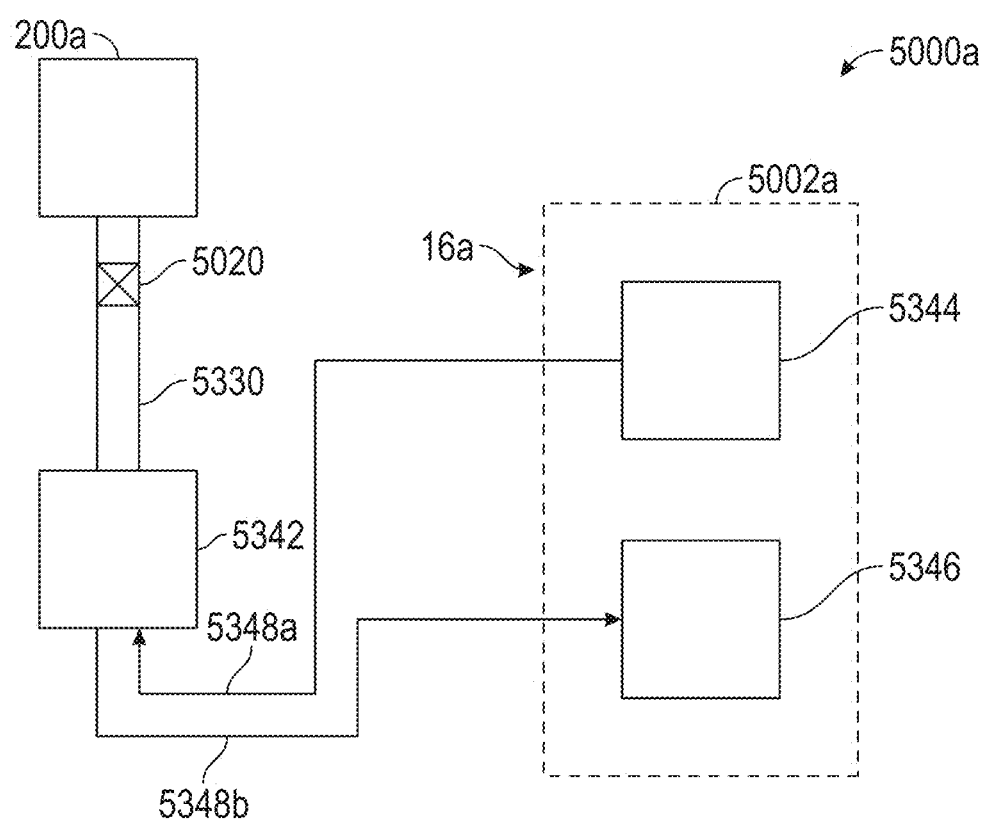
FIG. 2 is a schematic of a spectroscopy system connected to a fluid source, according to an example embodiment of the present disclosure.

FIG. 2 is a schematic of a spectroscopy system 5000a connected to a fluid source 200a, according to an example embodiment of the present disclosure. System 5000a may include a sample chamber 5330 that is fluidly connected to fluid source 200a. A valve 5020 may be provided to control flow of fluid into sample chamber 5330 from fluid source 200a. Fluid source 200a may provide fluid to sample chamber 5330 through actuation of valve 5020.

System 5000a may further include a spectroscopy system 16a that may include an excitation source 5344 that generates electromagnetic radiation and a detection system 5346 that detects electromagnetic radiation. Excitation source 5344 and detection system 5346 may be housed in an enclosure 5002a. Excitation source 5344 may be optically coupled to an optical probe 5342 via fiber optic cables 5348a. Similarly, detection system 5346 may be optically coupled to optical probe 5342 via fiber optic cables 5348b. Optical probe 5342 may be optically coupled to sample chamber 5330. Electromagnetic radiation generated by excitation source 5344 may be provided to optical probe 5342 which may couple the electromagnetic radiation into sample chamber 5330.

Electromagnetic radiation, provided to the fluid in sample chamber 5330 by optical probe 5342, may interact with fluid in sample chamber 5330. Upon interaction with the fluid sample, electromagnetic radiation may be reflected, absorbed, scattered, and emitted from the fluid. The scattered and emitted radiation may then be received by optical probe 5342 and provided to detection system 5346 via fiber optic cables 5348b. As described in greater detail below, the reflected, absorbed, and emitted radiation depends on the composition of the fluid in fluid chamber 5330. As such, properties of the fluid may be determined by analyzing intensities of reflected, absorbed, scattered, and emitted radiation at various frequencies relative to a frequency spectrum of incident radiation generated by the excitation source 5344.

As described in greater detail below, optical probe 5342 may be Raman probe (e.g., see FIG. 25B) that may be used in a Raman sub-sampling system (e.g., see FIG. 25A), a reflection probe (e.g., see FIG. 26B) that may be used in a fluorescence sub-sampling system (e.g., see FIG. 26A) or in an absorbance/fluorescence/scatter sub-sampling system (e.g., see FIG. 29), or a transmission dip probe (e.g., see FIG. 27B), that may be used in an absorbance sub-sampling system (e.g., see FIG. 27A), in an absorbance/fluorescence/ scatter sub-sampling system (e.g., see FIG. 19) or used in a Fourier Transform Infra-Red (FTIR) absorbance sub-sampling system (e.g. see FIG. 28A).

Figure 3:
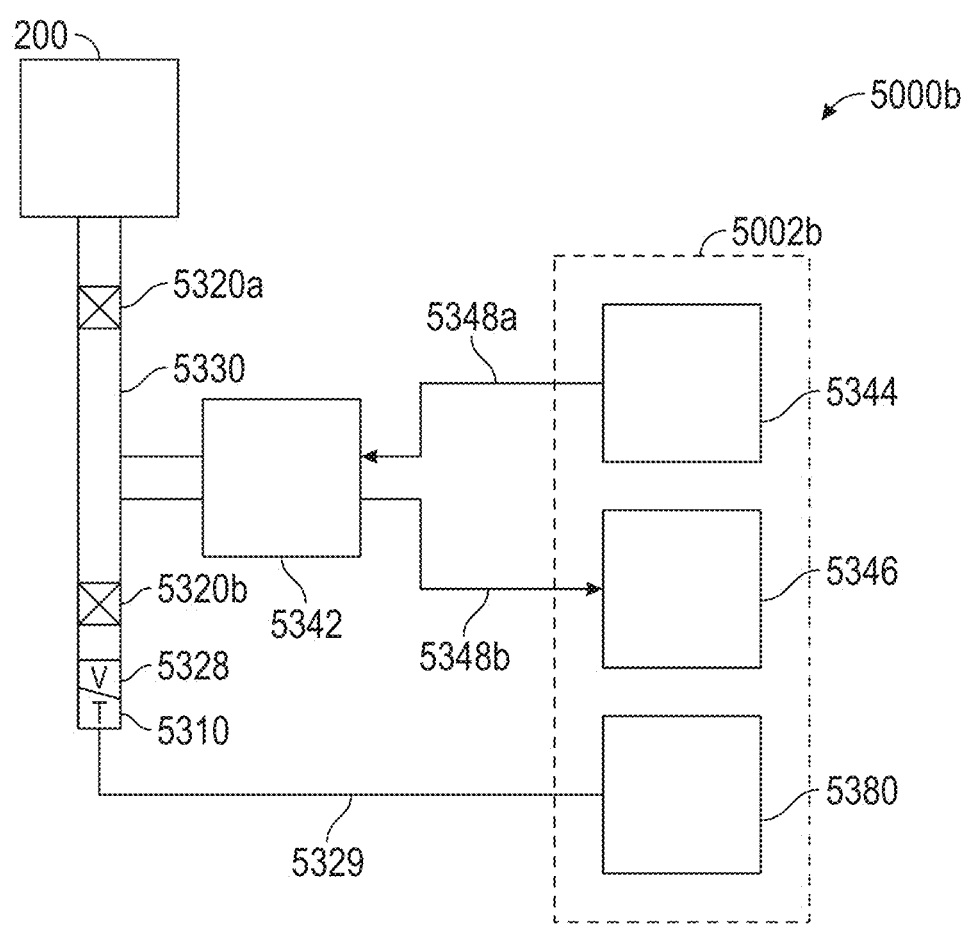
FIG. 3 is a schematic of a spectroscopy system connected to a fluid source, according to an example embodiment of the present disclosure.

FIG. 3 is a schematic of a spectroscopy system 5000b connected to a fluid source 200, according to an example embodiment of the present disclosure. System 5000b of FIG. 3 and system 5000a of FIG. 2 have a number of elements in common, while system 5000b of FIG. 3 includes additional sensors.

Like the fluid analysis system 5000a of FIG. 2, system 5000b of FIG. 3 includes sample chamber 5330 that is fluidly connected to fluid source 200. Sample chamber 5330 may include one or more valves, 5020a and 5020b, that control flow of fluid into sample chamber 5330. System 5000b similarly includes excitation source 5344 optically coupled to an optical probe 5342 via fiber optic cables 5348a, and detection system 5346 optically coupled to optical probe 5342 via fiber optic cables 5348b. According to an embodiment, excitation source 5344, detection system 5346, and control system 5380 (described below) may be housed in an enclosure 5002b. Optical probe 5342 couples electromagnetic radiation generated by excitation system 5344 into a fluid within sample chamber 5330. Optical probe 5342 similarly receives scattered and emitted radiation from sample chamber and provides it to detection system 5346.

In various embodiments, shut-off values, 5320a and 5320b, may be included on either side of optical probe 5342. Shut-off valves 5320a and 5320b may be manually or electronically controlled. In an embodiment in which the shut-off valves 5320a and 5320b are electronically controlled, a voltage may be supplied to valves 5320a and 5320b via an electrical connector (not shown). Shut-off valves 5320a and 5320b may be configured to open in response to the applied voltage. Shut-off valves 5320a and 5320b may be further configured to automatically close in response to removal of the applied voltage. As such, shut-off valves 5320a and 5320b remain closed unless the fluid analysis system is engaged.

In contrast to system 5000a of FIG. 2, system 5000b of FIG. 3 may further include additional sensors. For example, system 5000b may include a temperature sensor 5310 configured to measure a temperature of the fluid. System 5000b may further include a viscometer 5328 configured to measure a viscosity of the fluid. Temperature sensor 5310 and viscometer 5328 may be electrically connected to controller 5380 via and electrical connector 5329. Controller 5380 may be configured to process signals received from temperature sensor 5310 and viscometer 5328 to generate temperature and viscosity data. Such temperature and viscosity data may be used in further embodiments in comparison with input parameters to controller 5380 that may be configured to perform other control operations based on the input temperature and viscosity data. For example, in other embodiments described below, heating and cooling elements (not shown) may be provided that may add or subtract heat from the system to control a temperature, etc., based on temperature measurements determined by temperature sensor 5310.

According to an embodiment, controller 5380 may be a Controller Area Network (CAN) system that may be configured to communicate with temperature sensor 5310 and viscometer 5328 using digital signals. For example, temperature sensor 5310 and viscometer 5328 may communicate to with a microprocessor (not shown) via a CAN communication system. Messages associated with communications between sensors (e.g., temperature sensor 5310 and viscometer 5328) may include a CAN ID. The CAN ID may be used in determining what actions may be taken regarding specific communications. In other embodiments, temperature sensor 5310 and viscometer 5328 may communicate with a microprocessor by supplying a communication address (e.g., a MAC address, and IP address, or another type of physical address).

In further embodiments, system 5000b of FIG. 3 may contain additional sensors (not shown). For example, system 5000b may further include pressure sensors, fluid flow meters, moisture/humidity sensors, and pH sensors. System 5000b of FIG. 3 may further include sensors configured to detect particulates in the fluid. Such particulate sensors may be configured to detect large or small particles, where particles are considered to be large or small when they are larger or smaller than a predetermined size threshold.

Figure 4:
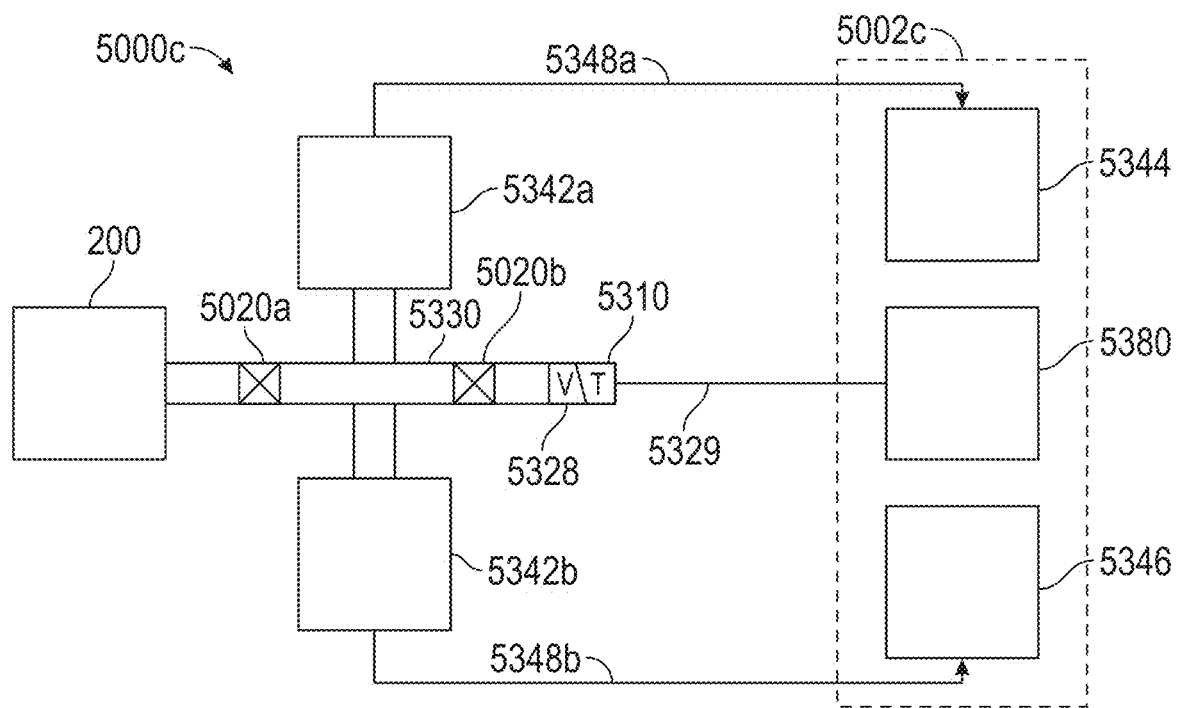
FIG. 4 is a schematic of a spectroscopy system connected to a fluid source, according to an example embodiment of the present disclosure.

FIG. 4 is a schematic of a spectroscopy system 5000c connected to a fluid source 200, according to an example embodiment of the present disclosure. Unlike system 5000a of FIG. 2 and system 5000b of FIG. 3, system 5000c of FIG. 4 is configured to measure absorption of electromagnetic radiation. In this regard, systems 5000a and 5000b, shown in FIGS. 2 and 3, respectively, used a single optical probe 5342 to couple electromagnetic radiation into and out of sample chamber 5330. As such, electromagnetic radiation received by optical probe 5342, via fiber optic cables 5348b, from sample chamber 5330 in systems 5000a and 5000b (e.g., see FIGS. 2 and 3, respectively) is of the form of reflected (i.e., scattered and/or emitted radiation) radiation.

In contrast, system 5000c shown in FIG. 4 includes two probes 5342a and 5342b. Optical probe 5342a is configured to receive electromagnetic radiation generated by excitation source 5344 via fiber optic cables 5348a and to couple the received radiation into the fluid in sample chamber 5330. Optical probe 5342b is configured to receive electromagnetic radiation that has been transmitted through sample chamber after such radiation has interacted with the fluid in sample chamber 5330. Electromagnetic radiation received by optical probe 5342b is transmitted to detection system 5346 via fiber optic cable 5348b. A spectrum of radiation transmitted through the fluid in sample chamber 5330, as measured by system 5000c, may have different spectral features from radiation reflected from the fluid as measured by systems 5000a and 5000b, of FIGS. 2 and 3, respectively. As such, spectroscopic data measured by system 5000c of FIG. 4 provides complementary information to that provided by systems 5000a and 5000b shown in FIGS. 2 and 3.

Other components of system 5000c not specifically described with reference to FIG. 4, (e.g., control system 5380, source 200, valves 5020a and 5020b, temperature sensor 5310, and viscometer 5328) are similar to corresponding components of system 5000b of FIG. 3. As with system 5000c of FIG. 3, excitation source 5344, detection system 5346, and control system 5380, of system 5000c (of FIG. 4) may be housed in an enclosure 5002c.

Figure 5:
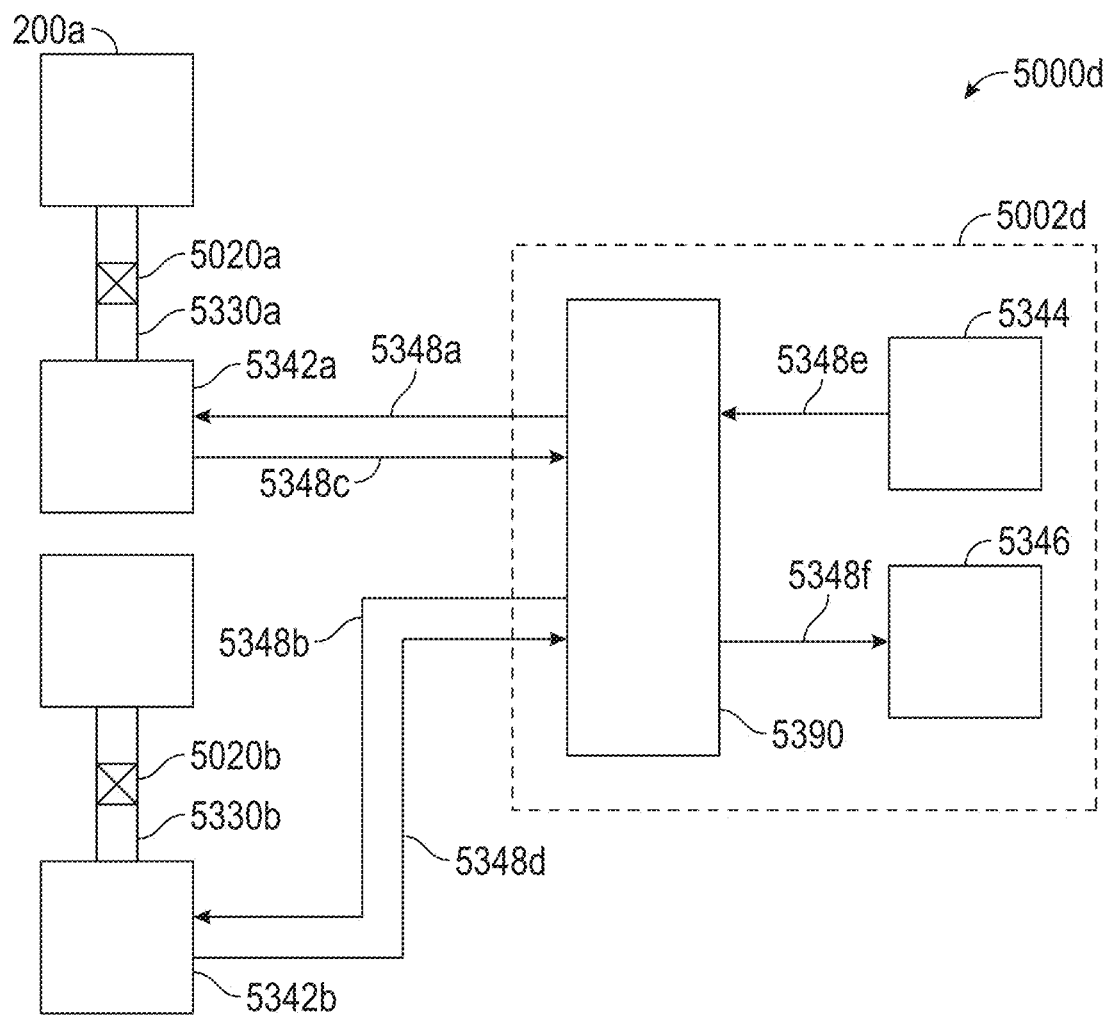
FIG. 5 is a schematic of a spectroscopy system connected to fluid sources, according to an example embodiment of the present disclosure.

FIG. 5 is a schematic of a spectroscopy system 5000d connected to fluid sources 200a and 200b, according to an example embodiment of the present disclosure. In this regard, the single engine fluid monitoring system (e.g., systems 5000a, 5000b, and 5000c, of FIGS. 2, 3, and 4, respectively) may be expanded to include a multi-engine monitoring system (e.g., system 5000d of FIG. 5) capable of monitoring a plurality of engine arranged in an array in various locations. Multi-engine monitoring systems may allow fluid monitoring on any multi-engine equipment. Specific examples of multi-engine systems that may benefit from the disclosed systems, apparatus and methods may include multi-engine ships, vessels, barges, tankers, airplanes, industrial equipment, wind farms, solar arrays, and the like.

A multi-engine configuration may require additional features or components. For example, a multi-engine configuration may include an optical switch 5390 (as described in greater detail below) to route electromagnetic radiation from a single excitation source 5344 to one of N number of outputs (i.e., multiple engines), as described in greater detail below. In certain embodiments, a degradation or reduction of signal may be associated with an optical switch. Despite the degradation or reduction of excitation signal that may occur when an optical switch is employed, use of an optical switch provides greater system control.

Fluid source 200*a* may be fluidly coupled to sample chamber 5330*a* and fluid source 200*b* may be fluidly coupled to sample chamber 5330*b*. Sample chamber 5330*a* may include a valve 5020*a*. Similarly, sample chamber 5330*b* may include a valve 5020*b*. System 5000*d* may include an excitation source 5344 and a detection system 5346 configured to generate and detect electromagnetic energy, respectively, as described above. According to an embodiment, excitation source 5344, detection system 5346, and optical switch 5390 may be housed in an enclosure 5002*d*.

As mentioned above, system 5000*d* further includes an optical switch 5390. Optical switch 5390 is optically connected to excitation source 5344 via fiber optic cable 5348*e*. Optical switch 5390 receives electromagnetic radiation from excitation source 5344 via fiber optic cable 5348*e* and may provide such radiation to optical probe 5342*a* via fiber optic cable 5348*a*. Similarly, optical switch 5390 may provide electromagnetic radiation to optical probe 5342*b* via fiber optic cable 5348*b*. Optical switch 5390 may be configured to selectively provide radiation to optical probe 5342*a* only, to optical probe 5342*b* only, or to both probes 5342*a* and 5342*b*.

Optical components may be connected to one another via optical cables having an appropriate diameter. In one embodiment an optical fiber connection may connect an electromagnetic radiation source (e.g., a laser) and an optical switch to an optical excitation fiber having a diameter of about 100 μm. In one embodiment an optical fiber connection may connect an optical switch to an optical emission fiber having a diameter of about 200 μm. In one embodiment an optical switch may be configured with one or more optical fibers having diameters of about 50 μm. In one embodiment an optical combiner may be configured with one or more optical fibers having diameters of about 200 μm. In further embodiments, various other diameter fibers may be used. For example, similar data throughput may be obtained with larger diameter fibers and decreased acquisition time. Similarly, smaller diameter fibers may be used with increased acquisition time to achieve a comparable data throughput.

Optical switch 5390 may further be configured to receive reflected, scattered, and emitted radiation from optical probe 5342*a* via fiber optic cable 5348*c* and to receive reflected, scattered, and emitted radiation from optical probe 5342*b* via fiber optic cable 5348*d*. Optical switch may then provide the received electromagnetic radiation to detection system 5346 via fiber optic cable 5348*f*.

Optical switch 5390 may be configured to selectively receive radiation from optical probe 5342*a* only, from optical probe 5342*b* only, or from both probes 5342*a* and 5342*b*. In further embodiments, fluid analysis and monitoring systems, similar to system 5000*d* of FIG. 5 may be configured to receive fluid from three fluid sources, from four fluid sources, etc. In other embodiments additional fluid sources may be monitored. While there is no specific limit to the number of fluid sources that may be monitored, in one specific embodiment, a rotary optical switch may be employed to detect up to thirty-two (32) separate fluid sources. According to an embodiment, optical switch may be configured to make electrical as well as optical communication with excitation source 4344 and a detection system 5346 and with a control system (e.g., see 5380 of FIG. 4).

Figure 6:
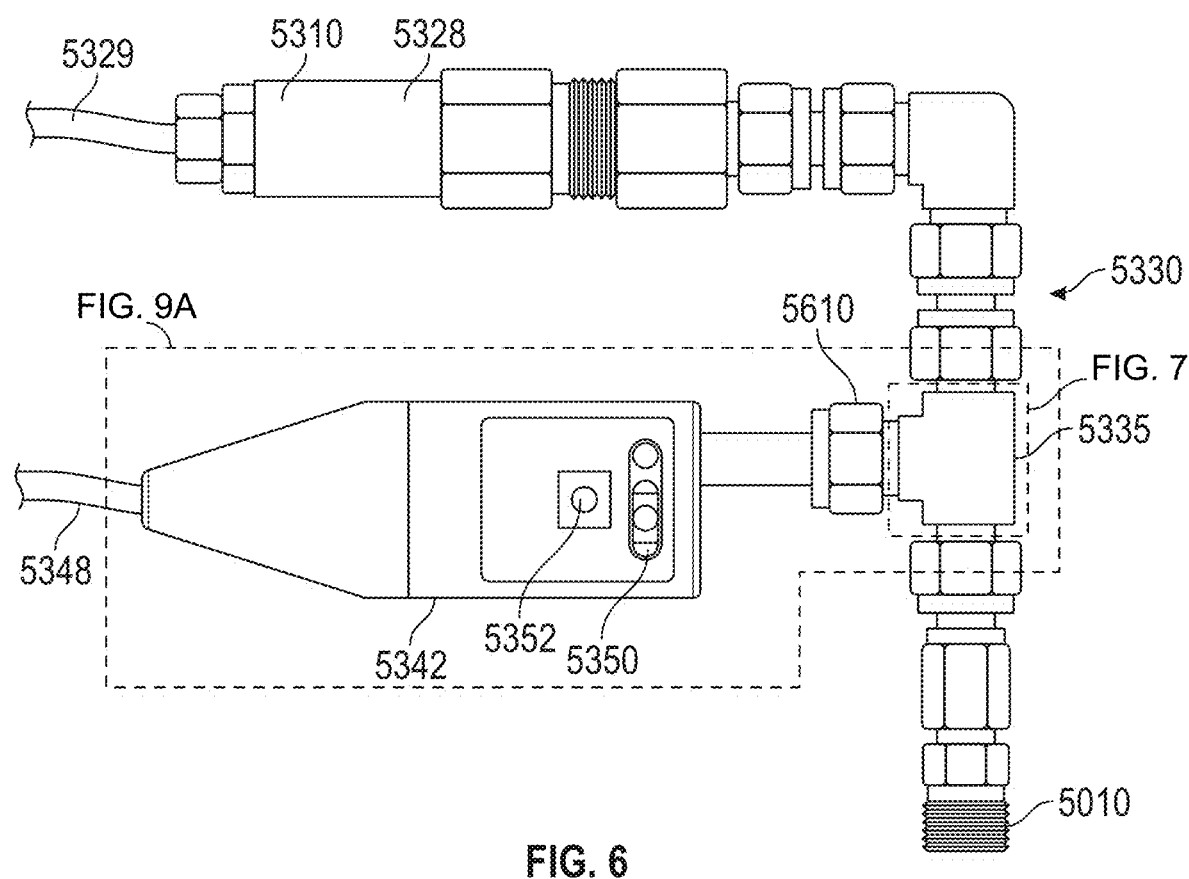
FIG. 6 shows a sample chamber with sensors, according to an example embodiment of the present disclosure.

FIG. 6 shows a sample chamber 5330 with sensors, according to an example embodiment of the present disclosure. FIG. 6 provides more realistic detail to embodiments schematically illustrated, for example, in FIG. 3. In this regard, FIG. 6 illustrates sample chamber 5330 that may be connected to a fluid source (e.g., fluid source 200 in FIG. 3) via TAP connector 5010. According to an embodiment, TAP connector 5010 may be a ¼ inch NPT, while in other embodiments, TAP connector 5010 may be any other diameter sufficient to connect to a fluid source.

FIG. 6 further illustrates a T-shaped optical sampling chamber 5335, which is described in greater detail below with reference to FIG. 7. T-shaped optical sampling chamber 5335 has a configuration in which fluid may flow thorough the sampling chamber 5335. In another embodiment, a sampling chamber may be provided that has a shape other than a T-shape but nonetheless allows fluid to flow through the chamber. In further embodiments, a sampling chamber may be provided that has a "deadhead" configuration, that is, having only a single inlet and no outlet (e.g., as shown schematically in FIGS. 2 to 5). Such a deadhead configuration may act as an optical port (that may include an optical probe) that may be connected directly into an engine galley.

T-shaped optical sampling chamber 5335 may further include a metal probe sleeve 5610 used to make a mechanical and optical connection to optical probe 5342. In this regard, optical probe 5342 may be inserted into probe sleeve and sealed into place in order to provide a closed optical sample system that is optically accessible to various sources of electromagnetic radiation (e.g., excitation source 5344 of FIG. 3). Optical probe 5342 is also shown as optically connected with a fiber optic cable 5348, which may represent one or more of fiber optic cables 5348*a* and/or 5348*b* described above with reference to FIG. 3, for example.

Optical probe 5342 is described in greater detail below with reference to FIGS. 9A to 10B. For example, as described below, optical probe 5342 may have a shutter 5350 and probe window 5352 that may be eliminated in other embodiments. FIG. 6 further illustrates details of temperature sensor 5310, viscometer 5328, and electrical connector 5329. In further embodiments, sample chamber 5330 may include valves and various other sensors (not shown), as described below with reference to FIG. 12.

Figure 7:
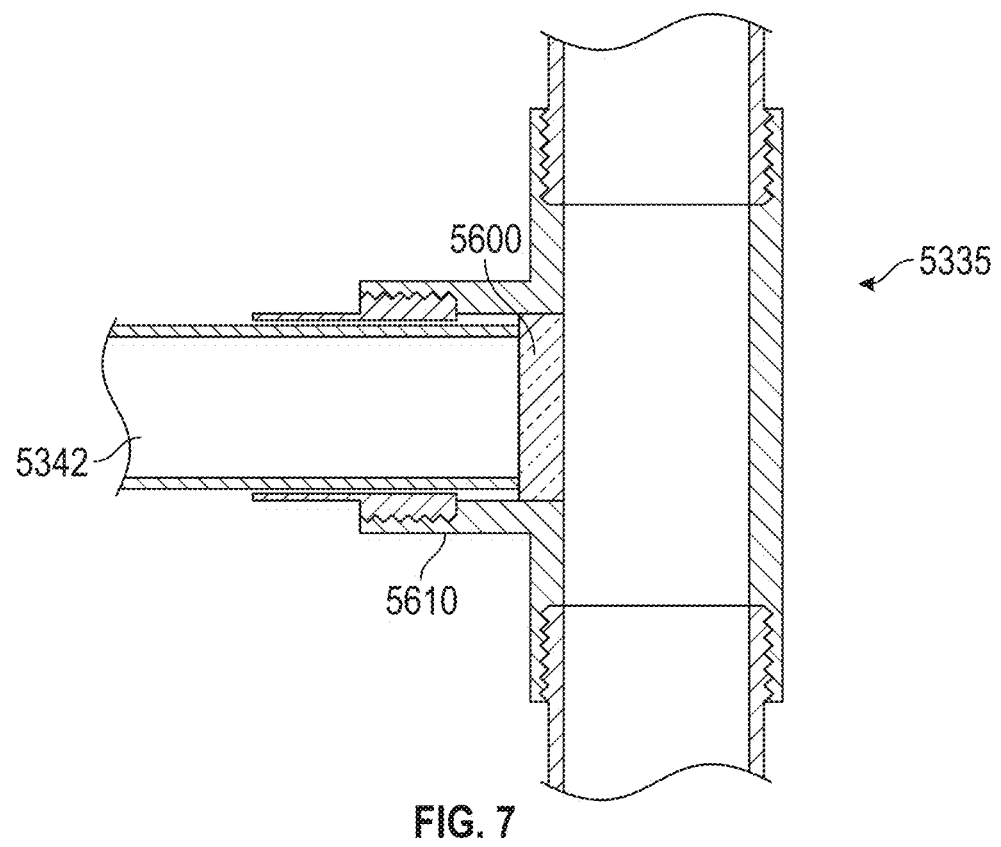
FIG. 7 shows an enlarged cross-sectional view of the T-shaped optical sampling chamber shown in FIG. 6, according to an example embodiment of the present disclosure.

FIG. 7 shows an enlarged cross-sectional view of the T-shaped optical sampling chamber 5335 shown in FIG. 6, according to an example embodiment of the present disclosure. T-shaped optical sampling chamber 5335 may include an optical window 5600 to facilitate optical measurements of fluid samples. Optical window 5600 may be translucent or transparent and may be formed using any transparent material. In a specific embodiment, the optical window may be formed using sapphire glass, for example.

Optical window 5600 may be inserted into a wall of sample chamber 5335. Further, optical window 5600 may be sealed into the wall of sample chamber 5335 using one or more gaskets and or sealing materials (e.g., epoxy, o-rings, etc.). T-shaped optical sampling chamber 5335 may include metal probe sleeve 5610 where optical probe 5342 may be inserted and sealed into place to provide a closed optical sample system. In this regard the closed optical sample system may be optically accessible to various EM excitation sources. In other embodiments, sample chamber 5335 may be configured to include a plurality of optical sample chamber windows 5600 (not shown) configured to accommodate operational attachment of a plurality of probes 5342.

Figure 8A:
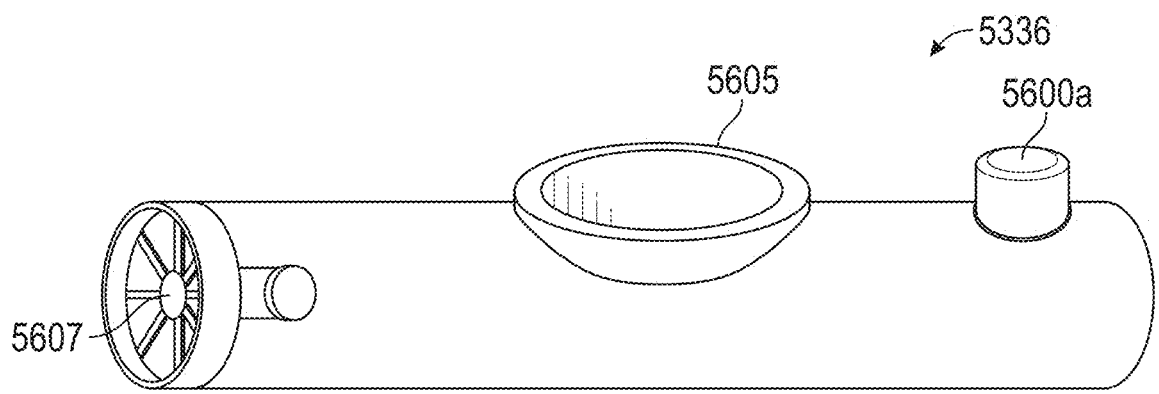
FIG. 8A is an isometric view of a sample chamber, according to an example embodiment of the present disclosure.

FIG. 8A is an isometric view of a sample chamber 5336, according to an example embodiment of the present disclosure. Sample chamber 5336 may include optical window 5600*a* that may be made of a transparent material such as sapphire glass. Optical window 5600 may have a ⅜ inch to 1 inch diameter. Other embodiments may include optical windows having other diameters and made of other materials. Chamber 5336 may further include a fluid connector 5605 that may be ½ inch NPT connector. Fluid connector 5605 may be used, for example, to remove air bubbles from the system. Chamber 5336 may further include an end cap 5607 that may be used to seal an end of chamber 5336.

Figure 8B:
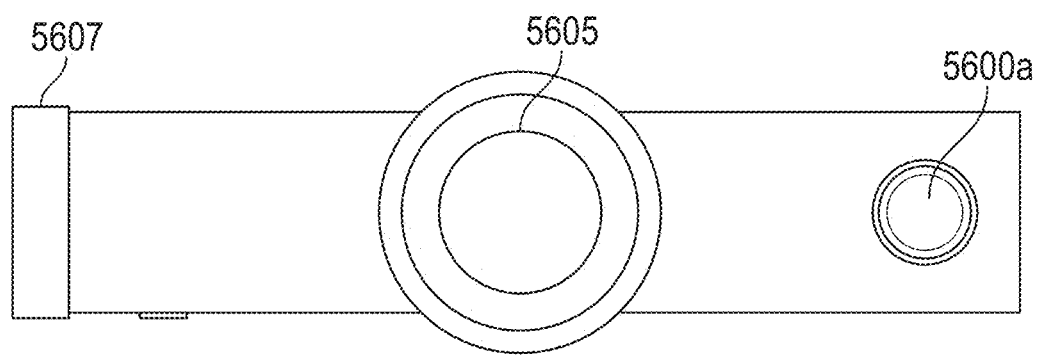
FIG. 8B is a top view of the sample chamber of FIG. 8A, according to an example embodiment of the present disclosure.

FIG. 8B is a top view of the sample chamber 5336 of FIG. 8A, according to an example embodiment of the present disclosure. FIG. 8B shows the above-described optical window 5600*a*, fluid connector 5605, and end cap 5607.

Figure 8C:
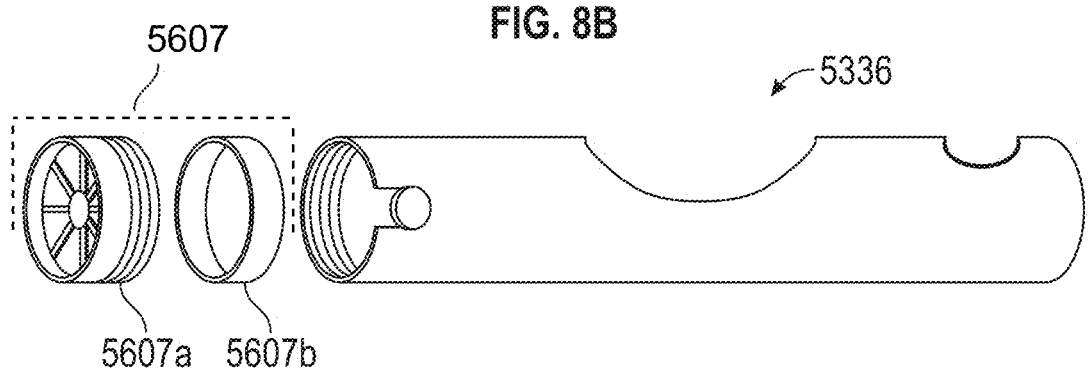
FIG. 8C is a partially exploded side view of the sample chamber of FIG. 8A, according to an example embodiment of the present disclosure.

FIG. 8C is a partially exploded side view of the sample chamber 5336 of FIG. 8A, according to an example embodiment of the present disclosure. In this view, optical window 5600*a* and fluid connector 5605 (e.g., shown in FIGS. 8A and 8B above) have been removed. Further, end cap 5607 is shown in a disassembled state. In this regard, end cap 5607 includes a threaded sealing cap 5607*a* and an interlock device 5607*b*.

Figure 8D:
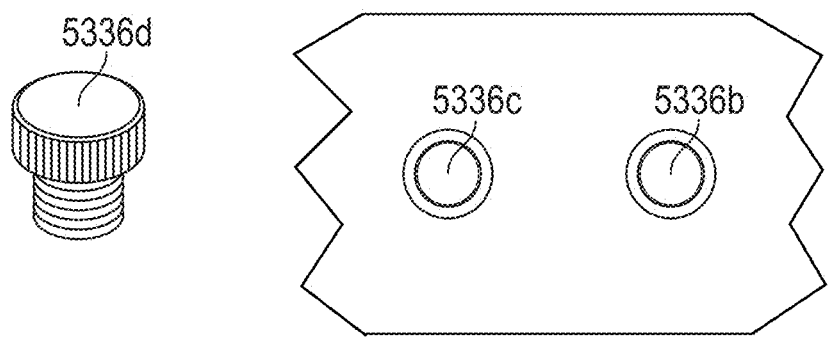
FIG. 8D shows a portion of a sampling chamber with ports for an optical probe and a viscometer, according to an example embodiment of the present disclosure.

FIG. 8D shows a portion of a sampling chamber 5336*a* with ports for an optical probe and a viscometer, according to an example embodiment of the present disclosure. FIG. 8D illustrates a side wall section 5336*a* of sample chamber 5336 (e.g., see FIG. 8A). Side wall section 5336*a* includes a first port 5336*b* and a second port 5336*c*. One or more sensor probes (e.g., temperature sensor 5310, viscometer 5328, shown in FIGS. 3, 4, and 6) may be configured as a threaded plug 5336*d*. Threaded plug 5336*d* may be configured to be installed into port 5336*b* or 5336*c* by screwing threaded plug 5336*d* into threaded portions (not shown) of port 5336*b* or 5336*c*.

Figure 9A:
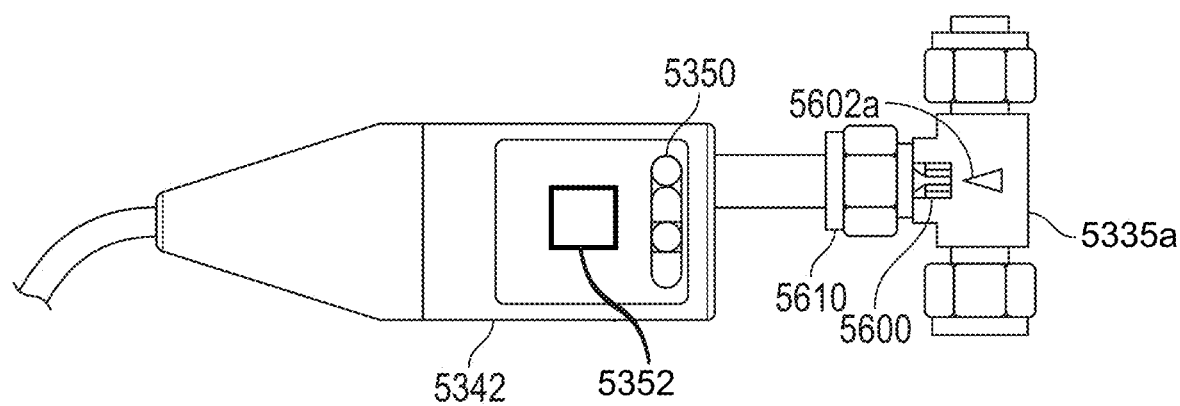
FIG. 9A shows an optical probe connected to a portion of a T-shaped optical sampling chamber shown in FIG. 6, according to an example embodiment of the present disclosure.

FIG. 9A shows an optical probe 5342 connected to a portion of a T-shaped optical sampling chamber 5335*a*, according to an example embodiment of the present disclosure.

Figure 9B:
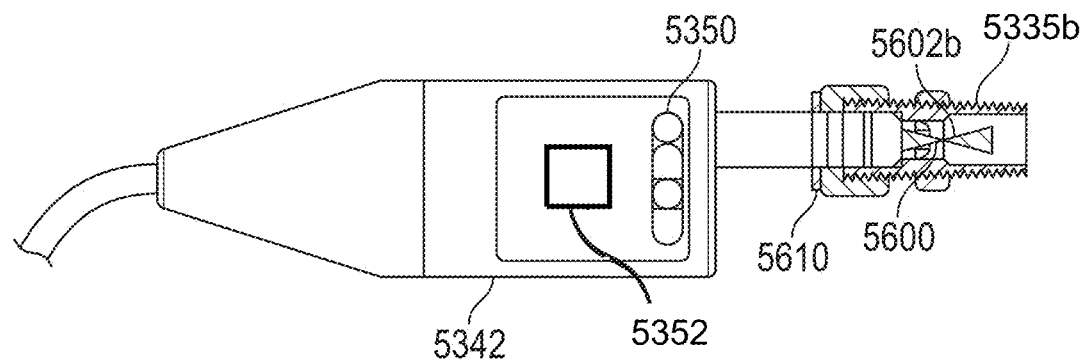
FIG. 9B shows a partial cross-sectional view of a straight-line sampling chamber connected to an optical probe, according to an example embodiment of the present disclosure.

FIG. 9B shows a partial cross-sectional view of a straight-line sampling chamber 5335*b* connected to an optical probe 5342, according to an example embodiment of the present disclosure.

In FIGS. 9A and 9B optical probe 5342 is shown having a shutter 5350. The shutter allows for observation and/or inspection of the internal area of the optical probe through an optical probe window 5352. To minimize the potential for exposure of humans to high energy laser light, the depicted shutter 5340 and probe window 5352 may be eliminated in other embodiments.

In an example embodiment, optical probe 5342 may be a Raman probe. Raman spectroscopy is a spectroscopic technique that determines information about molecular vibrations of a sample. Determined information regarding molecular vibrations may then be used for sample identification and quantitation. The technique involves providing incident electromagnetic radiation (e.g., using a laser) to a sample and detecting scattered radiation from the sample. The majority of the scattered radiation may have a frequency equal to that of the excitation source (e.g., excitation source 5344 of FIG. 3). Such scattered radiation is known as Rayleigh or elastic scattering.

A small amount of the scattered light may be shifted in frequency from the incident laser frequency due to interactions between the incident electro-magnetic waves (i.e., photons) and vibrational excitations (i.e., induced transitions between vibrational energy levels) of molecules in the sample. Plotting intensity of this frequency-shifted radiation vs. frequency, or equivalently vs. wavelength, results in a Raman spectrum of the sample containing Raman shifted peaks. Generally, Raman spectra are plotted with respect to the laser frequency so that the Rayleigh band lies at 0 $cm^{-1}$. On this scale, band positions (i.e., peaks of the spectrum) lie at frequencies that correspond to differences in vibrational energy levels of various functional groups. Typically frequencies are expressed in wavenumber units of inverse centimeters ($cm^{-1}$), as defined below.

In FIG. 9A, optical probe 5342 interfaces with optical window 5600 of a T-shaped sampling chamber 5335*a* to provide electromagnetic radiation to sampling chamber 5335*a*. Optical probe 5342 may be coupled to T-shaped sampling chamber 5335*a* via probe sleeve 5610. Electromagnetic radiation entering T-shaped sampling chamber 5335*a* through optical window 5600 forms a radiation pattern having a focal point 5602*a* within the liquid, as indicated in the cross-sectional view of T-shaped sampling chamber 5335*a* of FIG. 9A.

FIG. 9B shows optical probe 5342 interfacing with an optical chamber 5335*b* having a straight-line configuration. Optical probe 5342 may be coupled to straight-line optical chamber 5335*b* via probe sleeve 5610. Optical probe 5342 interfaces with optical window 5600 to provide electromagnetic radiation to straight-line sample chamber 5335*b*. Electromagnetic radiation entering straight-line sampling chamber 5335*b* through optical window 5600 forms a radiation pattern having a focal point 5602*b* within the liquid, as indicated in the cross-sectional view of straight-line sampling chamber 5335*b* of FIG. 9B. As described above, depicted shutter 5350 and probe window 5352 may be eliminated in other embodiments.

Figure 10:
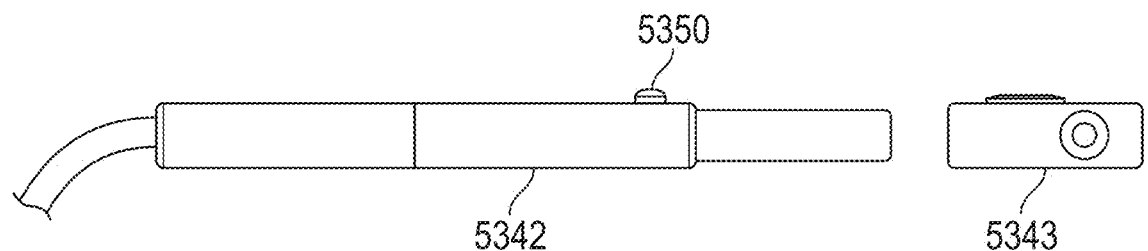
FIG. 10 shows an optical probe and cover, according to an example embodiment of the present disclosure.

FIG. 10 shows optical probe 5342 and a cover 5343, according to an example embodiment of the present disclosure. Optical probe 5342 is configured to interface with a sampling chamber, as described above. Optical probe 5342 may have an optional shutter 5350 (e.g., see FIGS. 6, 9A, 9B, and FIG. 10). As described above, optical probe 5342 may interface with T-shaped sample chamber 5335*a*, shown in FIG. 9A, or with straight-line sample chamber 5335*b*, shown in FIG. 9B. In an example embodiment, optical probe 5342 may be a Raman probe. In other embodiments, optical probe 5342 may be various other probes, as described in greater detail below. As shown in FIG. 10, optical probe 5342 may further include an optional probe cover 5343 that is configured to protect optical probe 5342 when optical probe 5342 is not installed with T-shaped sample chamber 5335*a* or with straight-line sample chamber 5335*b*.

Figure 11A:
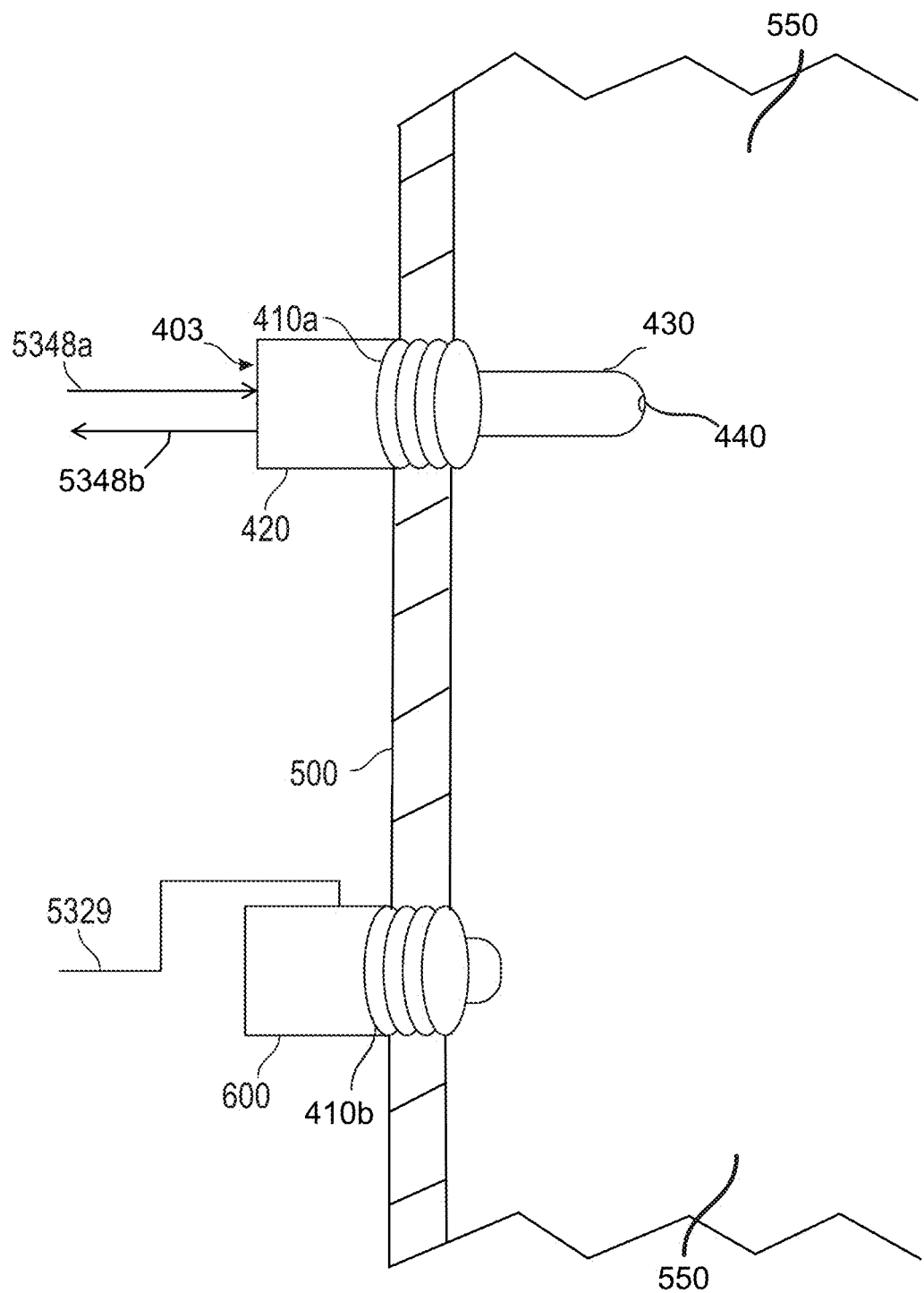
FIG. 11A is a partial cross-sectional view of a fluid source with an immersion probe and a viscometer coupled to the fluid source, according to an example embodiment of the present disclosure.

FIG. 11A is a partial cross-sectional view of a fluid source with an optical immersion probe 403 and a viscometer 600 coupled to the fluid source, according to an example embodiment of the present disclosure. In this example, immersion probes are configured to measure optical and other properties in a single fluid source. In contrast to other embodiments described above, the embodiment of FIG. 11A does not require a sample chamber. In this embodiment, optical probe 403 may be an immersion probe (e.g. ball probe) that is configured to be inserted directly into a fluid source apparatus 500. In this regard, optical probe 403 may make direct operational contact with a fluid (e.g., an oil) sample 550 within source apparatus 500. Optical probe 403 may be securely attached to source apparatus 500 via a threaded connection 410*a*. Optical probe hardening may preclude undesirable effects from various factors including dust, high temperature, low temperature, water, humidity, and/or vibrational damage. In some embodiments, an optical probe 403 may be configured to withstand temperatures of up to 250° C. As described above, optical probe 403 may receive electromagnetic radiation via fiber optic cable 5348*a* and may transmit (i.e., return) electromagnetic radiation via fiber optic cable 5348*b*.

Optical (immersion) probe 403 may also be configured to include a chassis 420. Optical probe chassis 420 may be configured to further secure optical probe 400 to source apparatus 500. Optical probe chassis 420 may be further "hardened" to withstand the stress of extreme environmental conditions. Optical probe chassis 420 may be configured to include hardening features to provide protection against vibrational stress, dust, and extreme heat and/or cold when optical probe 400 is connected to source apparatus 500.

An optical probe chassis 420 may be formed from any suitable material. Examples of suitable materials to form the chassis 420 of an immersion probe for direct immersion within the flow of an oil within an source apparatus include carbon steel, alloy-20, stainless steel, marine-grade 316 stainless steel, Hastelloy C276™ alloy, which provides corrosion resistance, etc. In one embodiment, a chassis 420 of optical probe including an immersion probe as described herein may be formed from stainless steel and may include compression fittings, couplings, and/or manifolds that permit or otherwise facilitate quick connection of the chassis 420 to conventional ports present on a source apparatus, such as an engine.

For instance, optical probe chassis 420 may include a fitting, a coupling, and/or a manifold to permit or otherwise facilitate connection to a source apparatus having port diameters ranging from about $\frac{1}{16}$th inch to about 2 inches. In certain embodiments, optical probe chassis 420 may include a tubular member having a uniform diameter having a magnitude in a range from about $\frac{1}{4}$ inch to about $\frac{1}{2}$ inch. In addition or in some embodiments, the optical probe chassis 420 may include adaptors that permit or otherwise facilitate insertion of optical (immersion) probe 403 into multiple source apparatus ports with differing diameter openings. Further or in yet other embodiments, optical probe chassis 420 may include quick-connection fittings, couplings, and/or manifolds that permit or otherwise facilitate simple and rapid removal of optical (immersion) probe 403 from a source apparatus (e.g., an engine). Removal of optical probe 403 from the source apparatus allows easy access for inspection and cleaning as needed.

In certain embodiments, an optical probe 403 that includes a chassis 420 may be configured for low pressure applications (e.g., pressure less than about 200 psi). In other embodiments, an optical probe 403 that includes the chassis 420 may be configured to withstand up to about 3,000 psi. Disclosed embodiments employing optical probe 403 configured for use under high pressure may require additional modifications to secure the chassis 420. For high-pressure applications, optical (immersion) probe 403 may be secured or otherwise affixed to chassis 420 via a weld. Specifically, as an illustration, a welded ANSI flange seal may be used to secure optical (immersion) probe 403 to chassis 420. Other probes, such as temperature sensor 5310 and viscometer 5328 (e.g., see FIG. 3) may similarly be hardened.

In other embodiments, optical probe 400 may be further configured to include a spherical lens 430. Spherical lens 430 may be configured to focus first electromagnetic radiation, transmitted into the fluid/oil sample, to a single focal point 440. Similarly special lens 430 may be configured to receive second electromagnetic radiation from the fluid/oil sample at the focal point 440. In this embodiment, there is no requirement to optimize or calibrate a focal path. The use of optical (immersion) probe 403, configured with a spherical lens 430, may allow faster, simpler installation. Removal of probe 403 for cleaning, or replacement of one or more parts, may also be simplified at least because there is no focal path calibration required.

Additional forms of data or other types of information may be obtained from the system of FIG. 11A, through use of one or more additional sensors, according to an embodiment. Data or information that may be collected includes temperature data and/or viscosity data. In this regard, sensor 600 may allow collection of viscosity data and/or temperature data. Sensor 600 may be operationally connected to source apparatus 500, which may include an engine source, through a port. Sensor may communicate electrically or optically with a controller (not shown) via connection 5329 (e.g., see FIG. 3). As illustrated in FIG. 11A, sensor 600 may be securely attached to source apparatus 500 via a threaded connection 410*b*. A variety of fasteners may be coupled to threaded connection 410*b* to secure sensor 600 to source apparatus 500.

Figure 11B:
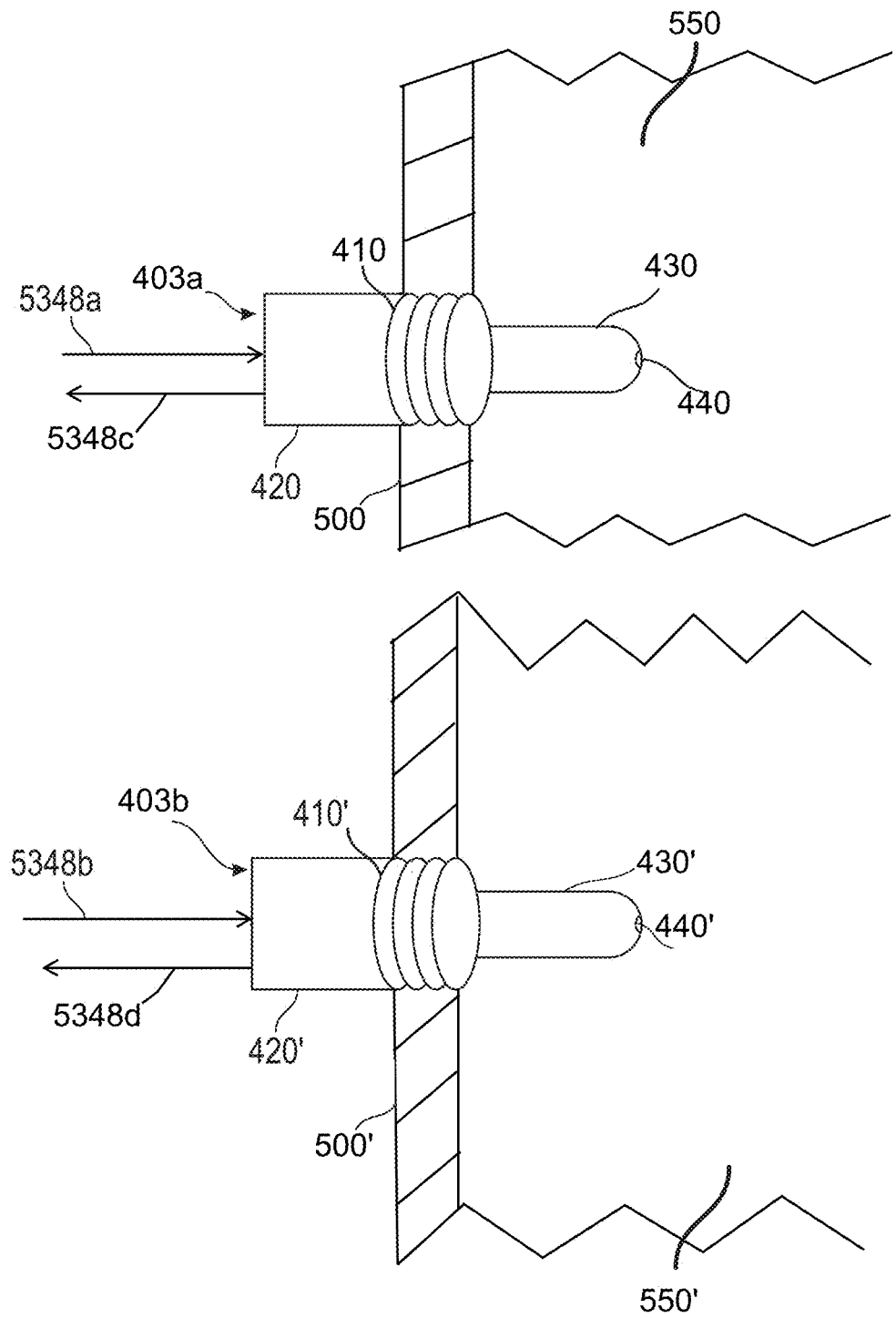
FIG. 11B shows partial cross-sectional views of two fluid sources with immersion probes connected to each fluid source, according to an example embodiment of the present disclosure.

FIG. 11B shows partial cross-sectional views of two fluid sources 500 and 500' with immersion probes 403*a* and 403*b* connected to each fluid source, according to an example embodiment of the present disclosure. As illustrated in FIG. 11B, immersion probes 403*a* and 403*b* may be provided to allow testing and monitoring of fluid samples from a plurality of sources, including source apparatus 500 and source apparatus 500'. Such probes, 403*a* and 403*b*, may be suitable for an embodiment such as system 5000*d*, described above with reference to FIG. 5. As described above with reference to FIG. 5, first electromagnetic radiation from an excitation source may directed to probes 403*a* and 403*b* via fiber optic cables 5348*a* and 5348*b*, respectively. Similarly, second electromagnetic radiation emitted from the fluid/oil may be returned to a detection system from immersion probes 403*a* and 403*b* via fiber optic cables 5348*c* and 5348*d*, respectively. Similar systems are described in U.S. patent application Ser. No. 15/139,771, the disclosure of which is hereby incorporated by reference in its entirety.

For example, U.S. patent application Ser. No. 15/139,771 discloses a multi-channel fluid monitoring system including an optical switch system (similar to switch 5390 described above with reference to FIG. 5) which gates or directs first electromagnetic radiation from an excitation source to a fluid/oil in a source apparatus, and transmits second electromagnetic radiation emitted from the oil in the source apparatus to a detection system.

As described above immersion probes 403*a* and 403*b* may be configured to be inserted into source apparatus 500 and source apparatus 500', respectively. In this way, probes 403*a* and 403*b* may be in direct, operational contact with a fluid/oil sample 550 and fluid/oil sample 550' within source apparatus 550 and 550', respectively. Optical probe 403*a* and optical probe 403*b* may be securely attached to source apparatus 550 and source apparatus 550' via threaded connections 410 and 410', respectively. Optical probe chassis 420 and optical probe chassis 420' may be configured to further secure optical probe 403*a* and optical probe 403*b* to source apparatus 500 and source apparatus 500', respectively. Optical probe chassis 420 and optical probe chassis 420' may be configured to include vibrational, dust, and heat protection when optical probe 403*a* and optical probe 403*b* are connected to source apparatus 500 and source apparatus 500', respectively.

Optical probe 403a and 403b may be further configured to include respective spherical lenses 430 and 430'. Spherical lens 430 and spherical lens 430' (e.g., lenses associated with a ball probe) focus the first electromagnetic radiation transmitted into the fluid/oil sample to respective single focal points 440 and 440'. Similarly, second electromagnetic radiation may be received from the oil sample at respective single focal points 440 and 440'. Disclosed embodiments, therefore, include a focal path that does not require optimization or calibration. The use of an optical probe 403a or 403b, configured with spherical lenses 430 and 430', respectively, may allow faster, simpler installation. Removal of probes 403a and 403b for cleaning, or replacement of one or more parts is also simplified since there is no focal path calibration required.

Figure 12:
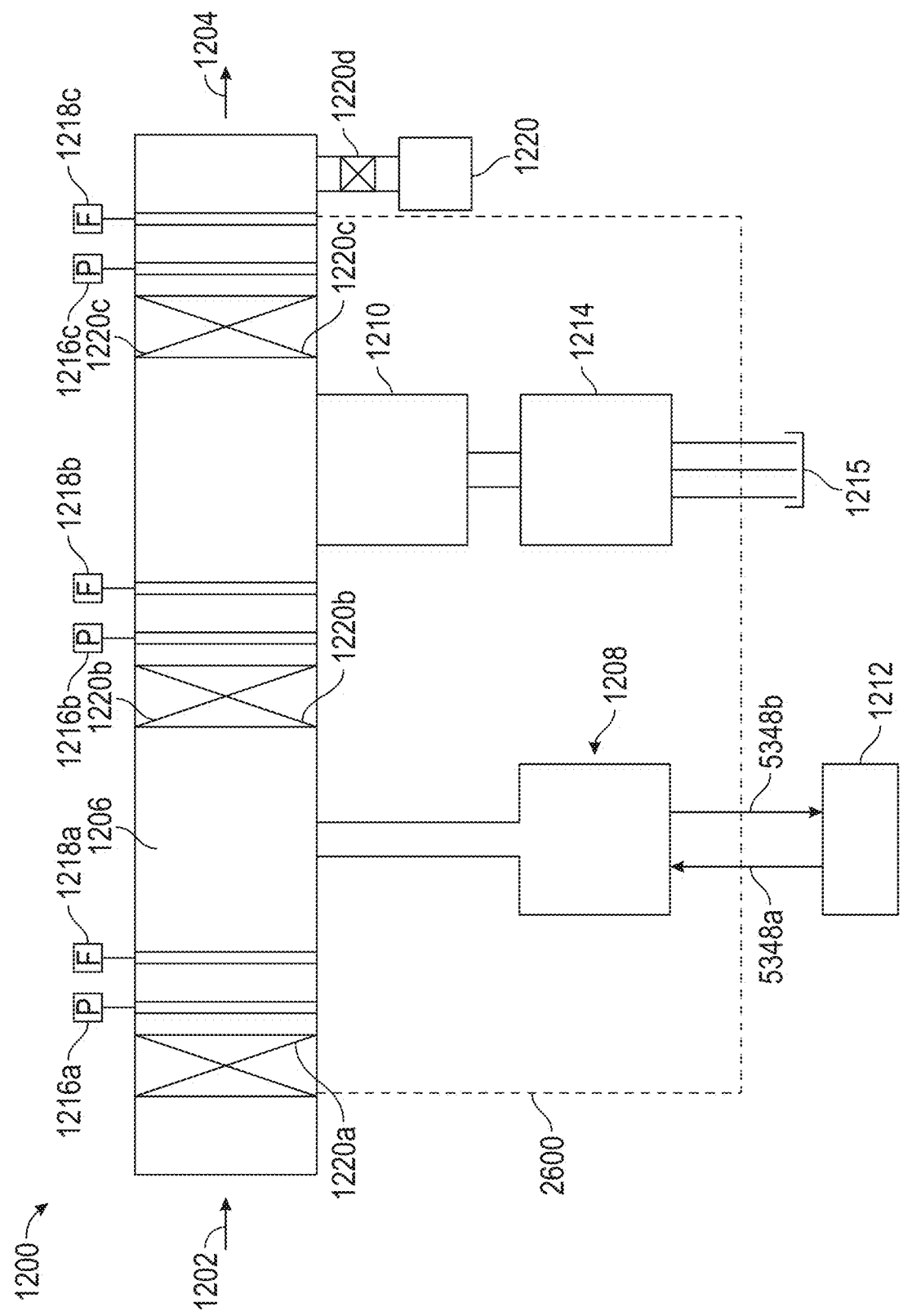
FIG. 12 is a schematic of a fluid analysis system, according to an example embodiment of the present disclosure.

FIG. 12 is a schematic of a fluid analysis system, according to an example embodiment of the present disclosure. In contrast to systems described above having only a fluid inlet (e.g., systems 5000a, 5000b, 5000c, 5000d, illustrate in FIGS. 2 to 5), system 1200 includes a fluid inlet 1202 and a fluid outlet 1204. Fluid may enter system 1200 through fluid inlet 1202, may flow through a fluid passage 1206, and may exit through fluid outlet 1204.

System 1200 may include one or more optical probes 1208 connected to an external excitation source via fiber optic cable 5348a and to an external detection system via fiber optic cable 5348b. System 1200 may include additional sensors 1210 such as a temperature sensor or viscometer. As described above, optical probe 1208 may be connected to an external excitation/detection system 1212. Additional sensors 1210 may further be connected to a control system 1214. Control system 1214 may include a CAN bus. CAN bus may be connected to various external devices via CAN connectors 1215 Further sensors may include one or more pressure sensors 1216a, 1216b, and 1216c, as well as one or more flow meters 1218a, 1218b, and 1218c. System 1200 may further include additional valves 1220a, 1220b, 1220c, and 1220d. One of valves 1220d may further include a port to allow a sample of fluid flowing through system 1200 to be manually drawn.

Figure 13A:
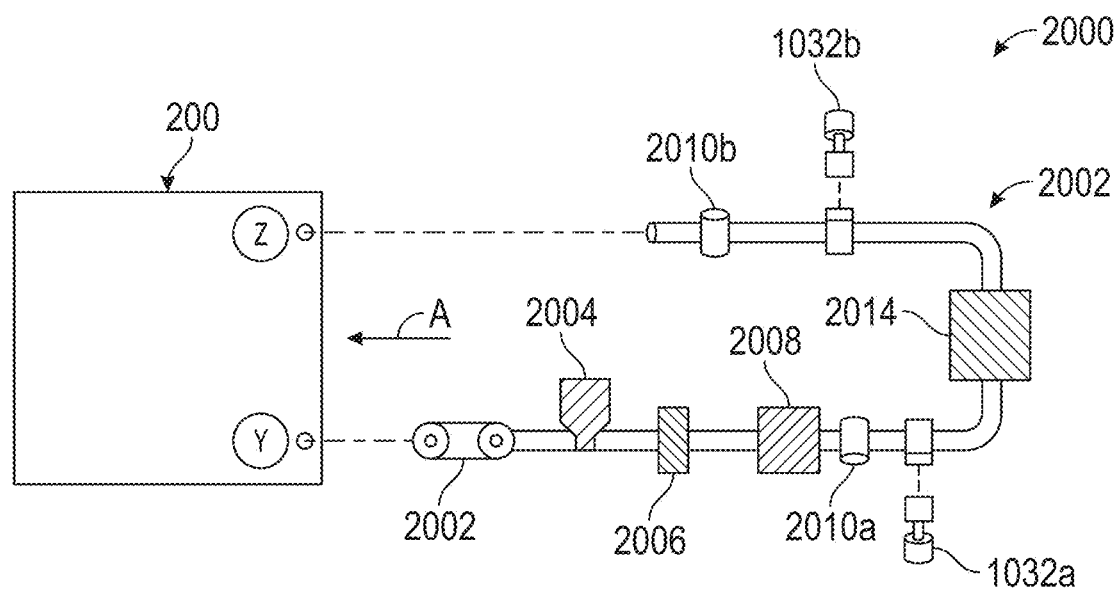
FIG. 13A shows a fluid analysis system, according to an example embodiment of the present disclosure.

FIG. 13A shows a fluid analysis system 2000, according to an example embodiment of the present disclosure. System 2000 may have a fluid flow-through configuration and may have a plurality of sensors, according to an example embodiment of the present disclosure. In this example, system 2000 may have one or more a nano chip plugs 1032a and 1032b along with other sensors. As shown, fluid analysis system 2000 with the nano chip plugs 1032a and 1032b may be constructed and configured to be installed at an engine oil pressure galley and to thereby bypass the engine back to an oil filler neck. In a bypass loop, thus created, oil may flow (i.e., may be routed) from equipment fluid access point, Y, through a programmable flow control valve 2002.

Flow control valve 2002 may be programmed to open and close to allow oil to flow through system 2000. Oil may be stationary in the system 2000 once valve 2002 is closed. This option may be added to allow a more detailed oil sample to be scanned (i.e., spectroscopic data to be measured) while the oil is stable and not flowing at pressures of, for example, 50 psi. Once the scan is complete, valve 2002 may open and allow oil to flow through the system 2000 until valve 2002 is once again closed for a future sampling time. In exemplary embodiments, this next sampling time may occur as soon as every 30 seconds. However, this system 2000 may be configured to take samples in any other time frame as needed.

Fluids, such as oil, may be routed through a pump 2004 to provide pressure when there is little or no fluid/oil pressure available. In other embodiments, pump 2004 may not be needed. In various embodiments, oil may then be routed through a pressure reducing valve 2006, oil cooler 2008, and push button oil sample valve 2010a installed for sampling of the oil before it reaches nano chip plug 1032a. Other embodiments (e.g., see FIG. 13B) may include fewer components. Oil cooler 2008 may be used inline if the oil being routed through the system 2000 is too hot (i.e., if measured temperature exceeds a predetermined temperature value). From nano chip plug 1032a, oil may be routed to a 1-μm bypass oil filter 2014 to allow more detailed analysis and to further prolong engine oil life via extra filtration of the oil sample.

In exemplary embodiments, another nano chip plug 1032b may be added after the 1-μm bypass oil filter 2014. The 1-μm oil filter 2014 may be inline of a bypass loop and may take a scan before and after fluid/oil passes through the filter 2014 in order to compare and determine how well the filtration is performing and how exactly the filter 2014 is impacting the fluid/oil sample. This particular configuration is unique because once this additional nano chip plug 1032b is added, the before and after readings (i.e., readings taken before and after the 1-μm oil filter 2014) may be compared and analyzed. The resulting data may then be used to prolong the life of the oil and provide a measureable impact that the 1-μm oil filter 2014 may be having on the oil. In contrast, it is virtually impossible to show the measureable impact of an oil filter 2014 in real-time (i.e., while the engine is running) in existing conventional systems. On the way back to the engine's oil filler neck into equipment's fluid return point, Z, oil may be passed through another push button oil sample valve 2010b.

Fluid analysis system 2000 may be used to gather samples and/or add relevant data from the samples to a database. Fluid analysis system 2000 may be connected to and to transfer data to a computational node 1004 (e.g., see FIG. 15A and related discussion below). Node 1004 may then transmit the data to a database as described above. The database may be located on a cloud based computing platform or in any known external device. In some embodiments, the node 1004 itself may house the database.

Figure 13B:
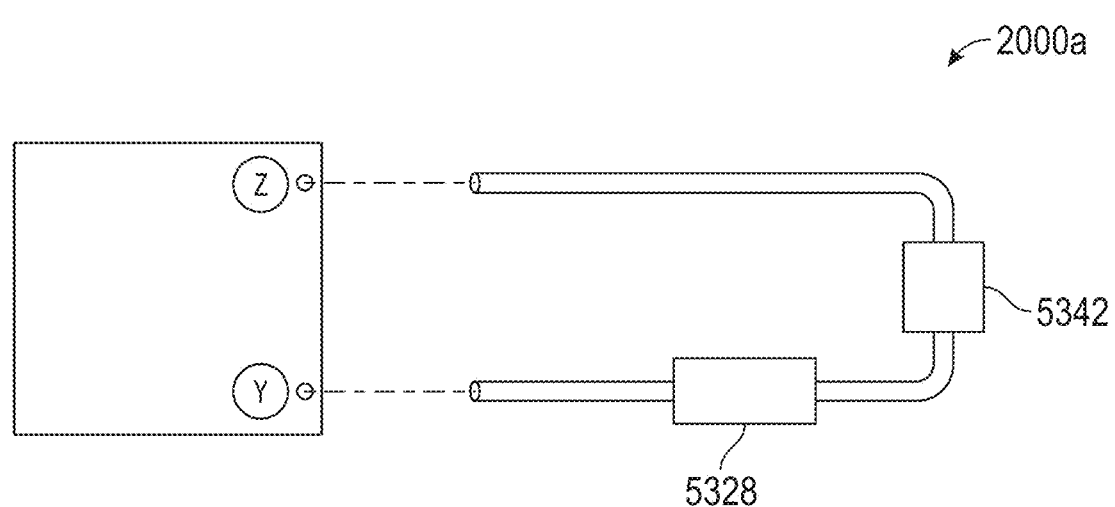
FIG. 13B shows a fluid analysis system, according to an example embodiment of the present disclosure.

FIG. 13B shows a fluid analysis system 2000a, according to an example embodiment of the present disclosure. In this example, system 2000a may be provided with only a viscometer 5328 and an optical probe 5342.

Figure 14:
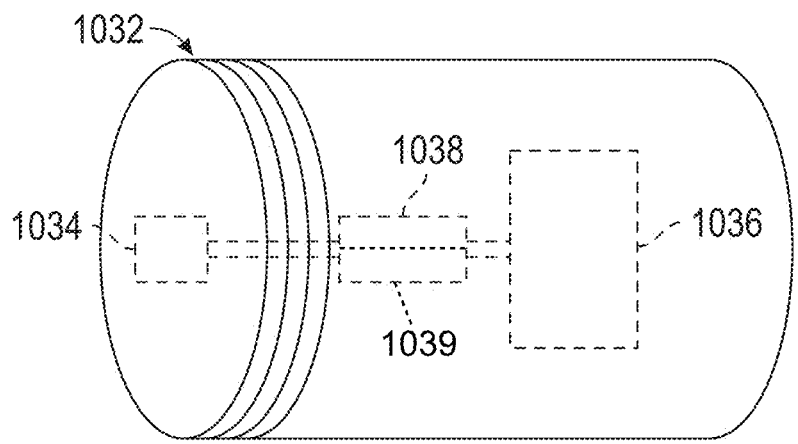
FIG. 14 shows a nano chip plug of the fluid analysis system of FIG. 13A, according to an example embodiment of the present disclosure.

FIG. 14 shows a nano chip plug of the fluid analysis system of FIG. 13B, according to an example embodiment of the present disclosure. FIG. 14 shows interior components of the nano chip plug 1032. Nano chip plug 1032 may utilize a spectral scanner/spectrometer 1034 to continuously scan and inform a user of the molecular makeup and condition of any industrial fluid/oil. Nano chip plug 1032 may further include an excitation source 1038 and a detection system 1039. Nano chip plug 1032 may further include control and communication circuitry 1036.

In exemplary embodiments, nano chip plug 1032 may have a size less than approximately 1 inch×1 inch. In other embodiments, the nano chip plug 1032 may have other sizes and configurations to perform real-time oil analysis (i.e., while an engine is operating). In exemplary embodiments, nano chip oil plug 1032 may be used for real-time oil analysis (i.e., while the engine is running) by integrating a nano chip and spectrometer 1034 into an oil plug, as illustrated, for example in FIG. 14. The oil plug may be any plug that may access the fluid being analyzed. In an exemplary embodiment, an existing oil plug in an engine/equipment may be removed, and a nano chip oil plug 1032 may be installed onto the engine/equipment in place of the existing oil plug.

Figure 15A:
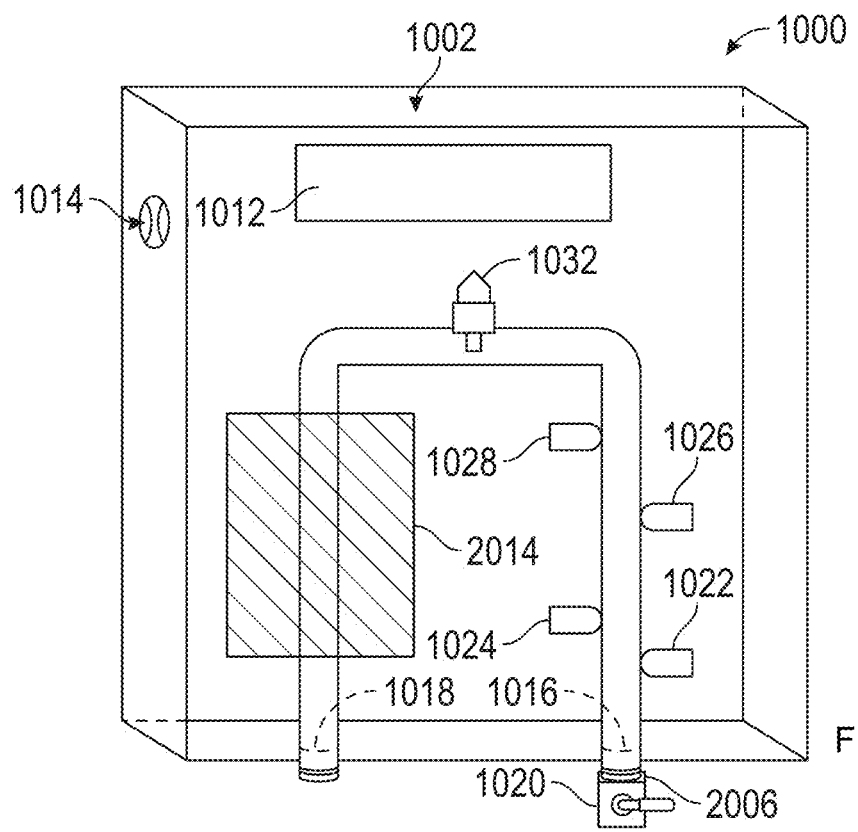
FIG. 15A shows a fluid analysis system, according to an example embodiment of the present disclosure.

FIG. 15A shows a fluid analysis system 1000, according to an example embodiment of the present disclosure.

Figure 15B:
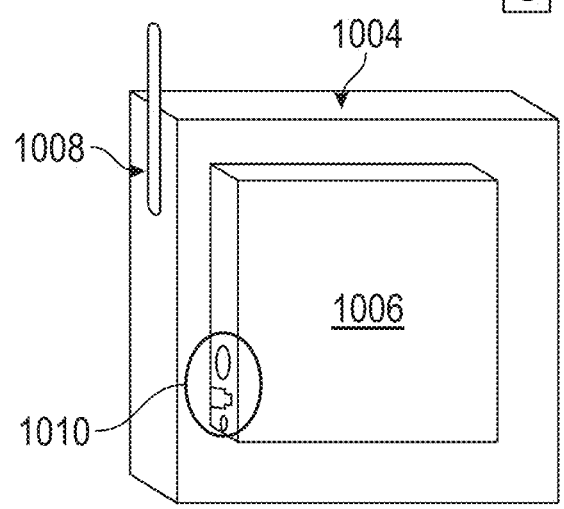
FIG. 15B shows a node that may be used with the fluid analysis system of FIG. 15A, according to an example embodiment of the present disclosure.

FIG. 15B shows a node 1006 that may be used with the fluid analysis system of FIG. 15A, according to an example embodiment of the present disclosure.

Fluid analysis system 1000 may include an enclosure 1002 having a female pipe thread inlet 1016 and outlet 1018. In an exemplary embodiment, enclosure 1002 may be an 18 inch×18 inch×6 inch metal enclosure, and inlet 1016 and outlet 1018 may be ¼ inch inlets and outlets, respectively. In other embodiments, suitable other dimensions may be employed. In various embodiments, the inlet of enclosure 1002 may include a shut-off valve 1020 for safety (e.g., allowing fluid to be shut off in case a line is found to be leaking), and/or for maintenance that may need to be performed on the enclosure 1002 without having to shut the system 1000 down. Additionally, enclosure 1002 may include a reset switch 1014 on one side for manual reset of an engine/equipment (to which system 1000 may be coupled) after an oil change has been performed to establish a new baseline for oil analysis.

Enclosure 1002 may also include a controller 1012 configured to control a plurality of sensors, as illustrated in FIG. 15A. For example, in certain embodiments, controller 1012 may control up to 36 fluid analysis sensors. Fluid analysis sensors may be mounted within enclosure 1002. For example, enclosure 1002 may include multiple types of oil analysis sensors, including but not limited to sensors with the following properties: oil property monitoring capabilities, and/or identification of specific wear metals 1022, moisture levels 1024, particulate counts 1026, viscosity 1028, TAN, TBN, Nitration, Sulfation, Foreign Oils, Solvents, Glycol, Soot, Dissolved Gases, and/or Oil Additive Depletion (Zn, Mo, Pd, Ca, Mg, Ba, Na).

Sensors may be programmed to periodically communicate data to controller 1012. For example, data may be communicated every few milliseconds, every second, every two seconds, every ten seconds, every minute, every few minutes, etc., to controller 1012. Further, controller 1012 may be configured to store data for a lifespan of five years or longer. In some embodiments, sensors may be provided that may be easily changeable if replacement is required. To replace a sensor, shut off valve 1020 may be used to shut off fluid flow. A front cover panel may then be opened and a sensor, needing replacement, may be unscrewed and removed from the female pipe thread. A new sensor may then be replaced in a similar manner by screwing the new sensor into a sensor connector having a female pipe thread. Controller 1012 may be configured to automatically recognize a new sensor and to begin collecting data using the newly installed sensor.

In some embodiments, enclosure 1002 may include an electric pump (not shown) that may draw oil out of the attached equipment/engine (i.e., fluid/oil source 200 of FIGS. 1 to 4), and may push the oil through the enclosure 1002 and back to the equipment/engine (i.e., back to the fluid/oil source 200). Pump may be a 120V, 240V, or 480V electrical pump, for example. Enclosure 1002 may further include a built in pressure reducer valve 2006 on the inlet pressure line. In an exemplary embodiment, the pressure reducer valve 2006 (e.g., see also FIG. 13) may reduce fluid/oil pressure from 5000 psi down to 50 psi before fluid/oil goes through the enclosure 1002 and back to the equipment/engine.

In various embodiments, enclosure 1002 may include a 1-µm oil filter 2014 (e.g., see also FIG. 13). Oil may flow through system 1000 in a particular sequence to validate and ensure extended life oil being characterized. In an embodiment, system 1000 may be configured in the following order: wear metal sensor 1022, water sensor 1024, particle count sensor 1026, viscosity sensor 1028, nano chip plug 2032, 1-µm filter 2014, etc., as described in greater detail above with reference to FIG. 13.

The above-described sequence of sensors may be important in determining the oil purity of the equipment since 1-µm filter 2014 may change the particle count and moisture content in the oil. System 1000 may extrapolate the wear metals, water, particle count, viscosity, and other parameters before the oil crosses 1-µm filter 2014. The ability of system 1000 to calculate a difference between the readings before and after 1-µm filter 2014 may allow for accurate oil quality measurement and oil life predictive calculations. Since these readings may be on both sides of the 1-µm filter 2014 (e.g., see FIG. 13 and related discussion), a true reading of the oil and equipment condition may be realized. Taking readings in this order, on both sides of the 1-µm filter (e.g., see FIG. 13), may thus further improve predictability of the lifecycle of the oil and equipment condition.

In exemplary embodiments, system 1000 may further include a node enclosure 1004 connected to enclosure 1002 as illustrated, for example, in FIG. 15B. Node enclosure 1004 may be a 12 inch×12 inch×6 inch weatherproof enclosure with an antenna 1008 for communicating data through one or more data communication connections including: LAN/WAN connection, which may be encrypted or unencrypted, via cellular, satellite, Wi-Fi, Bluetooth, Ethernet (RJ-45) connections, etc. Other suitable dimensions for enclosure 1002 may be employed in alternative embodiments. Node enclosure 1004 may track a plurality of inputs (e.g., up to six different data inputs in one embodiment) into one user account. Each data point may relate to a separate enclosure 1002 that may be hard-wired back to the node enclosure 1004.

System 1000 may be piggy backed together with other systems 1000 for up to 36 different systems 1000 and may be routed back into one connection at the node enclosure 1004. This particular configuration may allow for system 1000 to only have one communication node for multiple enclosures 1002/systems 1000, providing great cost benefits to the consumer, and allowing for easier and cleaner installation of the system 1000. Node enclosure 1004 may further include connections to transmit collected data including video, audio, or sample data collected by system 1000. Data may be transmitted via a connection for satellite/Wi-Fi/cell tower antenna 1008 and a power port and/or Ethernet/HDMI (High Definition Video Device Interface) port 1010.

Node enclosure 1004 may be outfitted with a rugged node 1006 for custom programming of algorithms to compute and process sensor inputs and to relay crucial notification abilities via text, email, etc. The custom programming may include computer program instructions related to oil analysis processing and readings for the following: specific wear metals, moisture levels, particulate counts, viscosity, TAN, TBN, Nitration, Sulfation, Foreign Oils, Solvents, Glycol, Soot, Dissolved Gases, and/or Oil Additive Depletion (Zn, Mo, Pd, Ca, Mg, Ba, Na). The custom programming may also cause the system to send instant notifications to a user the moment critical levels are reached as established by user-determined preferences or as determined by the NIST (National Institute of Standards and Technology) oil analysis standards if there are no user-determined preferences are not programmed into the node 1006. The software may have a predictive ability built into the design of the node 1006 that may notify users of upcoming preventive maintenance.

In various embodiments, networking capabilities of the system 1000 may be extended due to the ability of system 1000 to piggyback enclosures 1002 together. Networking features include: (i) daisy chaining a plurality (e.g., 36 in one embodiment) of enclosures 1002 going to one node enclosure 1004; or (ii) wiring a plurality of (e.g., 36 in one embodiment) enclosures 1002 into the node enclosure 1004 directly. Once these multiple enclosures 1002 are transmitting data into the node enclosures 1004, system 1000 may combine an unlimited number of data points into one user account that may be accessible by the user on a 24×7 basis via any Internet connected device. This may afford the user full control over the monitoring and maintenance of equipment/engine that is connected to disclosed embodiment systems.

In an exemplary embodiment, fluid/oil may be re-routed from an engine or other equipment through disclosed systems described, and back to the engine/equipment. Once fluid/oil is flowing through the system, wear metals, moisture levels, particulate counts, viscosity, TAN, TBN, Nitration, Sulfation, Foreign Oils, Solvents, Glycol, Soot, Dissolved Gases, and/or Oil Additive Depletion (Zn, Mo, Pd, Ca, Mg, Ba, Na), and/or oil temperature reporting may be tested and logged periodically (e.g., every millisecond, every second, every 2 seconds, etc., according to embodiments). In some embodiments, an additional sensor may be added for emissions monitoring. Each different measurement may be taken via a specific sensor for each analysis data point. Data may be collected into controller 1012 built into the enclosure 1002 described herein. Controller 1012 may transmit the data to node 1006. In exemplary embodiments, node 1006 may be a small Linux based computer (or otherwise programmable device). Node 1006 may be programmed with custom algorithms to compute and process sensor inputs from the controller 1012, and to relay notifications. Node 1006 may then transmit the data through the best available method: LAN/WAN connection, which may be encrypted or unencrypted, via cellular, satellite, Wi-Fi, Bluetooth, Ethernet (RJ-45) connections, etc.

Once this data is transmitted, it may be stored in a storage device or on a cloud computing platform and the data may be readily available for the user to access from a computer, tablet, smart phone, etc. If an Internet signal drops, node 1006 may rely on a storage device (e.g., a 60 gigabyte hard drive in one embodiment) that may store the information until the Internet signal is restored. Once an Internet connection is restored, node 1006 may automatically dump all of the data to a cloud based storage platform. If there is critical information gathered from the system, the user may be notified via text, email, etc. A user may log into their account with custom designed dashboards so they can see all equipment and data points being monitored. Custom dashboards and alerts may be determined by the user to meet his/her individual needs. Alerts may be sent to the user via email, text message, etc., automatically from the system based on algorithms that may be programmed for specific types of measurements. The online dashboard may be web-based and may be accessed from any device that has an Internet connection. The dashboard may be reactive and configured to automatically collapse and stack the data to a tablet and/or cell phone view, for example, if the user is not accessing the system from a computer/web browser.

Once system 1000 is installed and parameters have been programmed into node 1006, a user may be able to interact with the system without recourse to consultation from a supplier/provider for management and maintenance of his/her equipment. In some embodiments, system 1000 described herein may be used to perform real-time oil analysis sampling from multiple pieces of equipment. Sampling from multiple pieces of equipment may be accomplished through customized multi-flow control valves that may allow oil to be brought in from multiple pieces of equipment using the same type of oil. In embodiments, the pieces of equipment may be located in the same vicinity as each other and system 1000. In other embodiments, the pieces of equipment may be located further away/remotely from each other and from system 1000.

Multi-flow control valves may be controlled via a graphical user interface (GUI) having custom designed dashboards. Multi-flow control valves may be configured as manifold-control valve connections. Flow control valves may be inlet multi-flow control valves and/or outlet multi-flow control valves. System 1000 may include an inlet multi-flow control valve programmed to allow oil to flow into an enclosure 1002 from only one engine at a time via an inlet valve described herein. System 1000 may further include an outlet multi-flow control valve programmed to allow for the oil to be returned to the same engine from which it was pulled via an outlet valve described herein and a return line going back to the same equipment.

In an exemplary embodiment, once an analysis is made over a predetermined period of time (e.g., 10 to 60 minutes according to an example embodiment of the present disclosure), the inlet valve may switch off, at which time the system may be programmed to notify another valve to open for a next piece of equipment that may have been programmed in a sampling sequence. In some embodiments, a predetermined delay (e.g., 60 to 180 seconds in one embodiment) may occur between the opening of a new valve and for the system 1000 to start taking readings to clean out the lines feeding the system 1000. In other embodiments, this sequence of changing between different pieces of equipment may be programmed from every few seconds, every few minutes, once per hour, etc., per piece of equipment, depending on a customer's needs.

In exemplary embodiments, once system 1000 is taking readings from each different engine/equipment, it may be configured to then run comparative algorithms in a separate custom designed dashboard described herein, and to thereby perform comparative analysis of oils from different equipment to determine which engines may be running most efficiently and which engines may be in need of extra attention, modifications, and/or service. Detailed reporting may allow customers to pinpoint any problems with efficiency in different pieces of equipment and solve any problems that they may not have known existed. Further, this reporting may also allow customers to determine for themselves which engines may be running most efficiently and which engines may need to be replaced.

Figure 16:
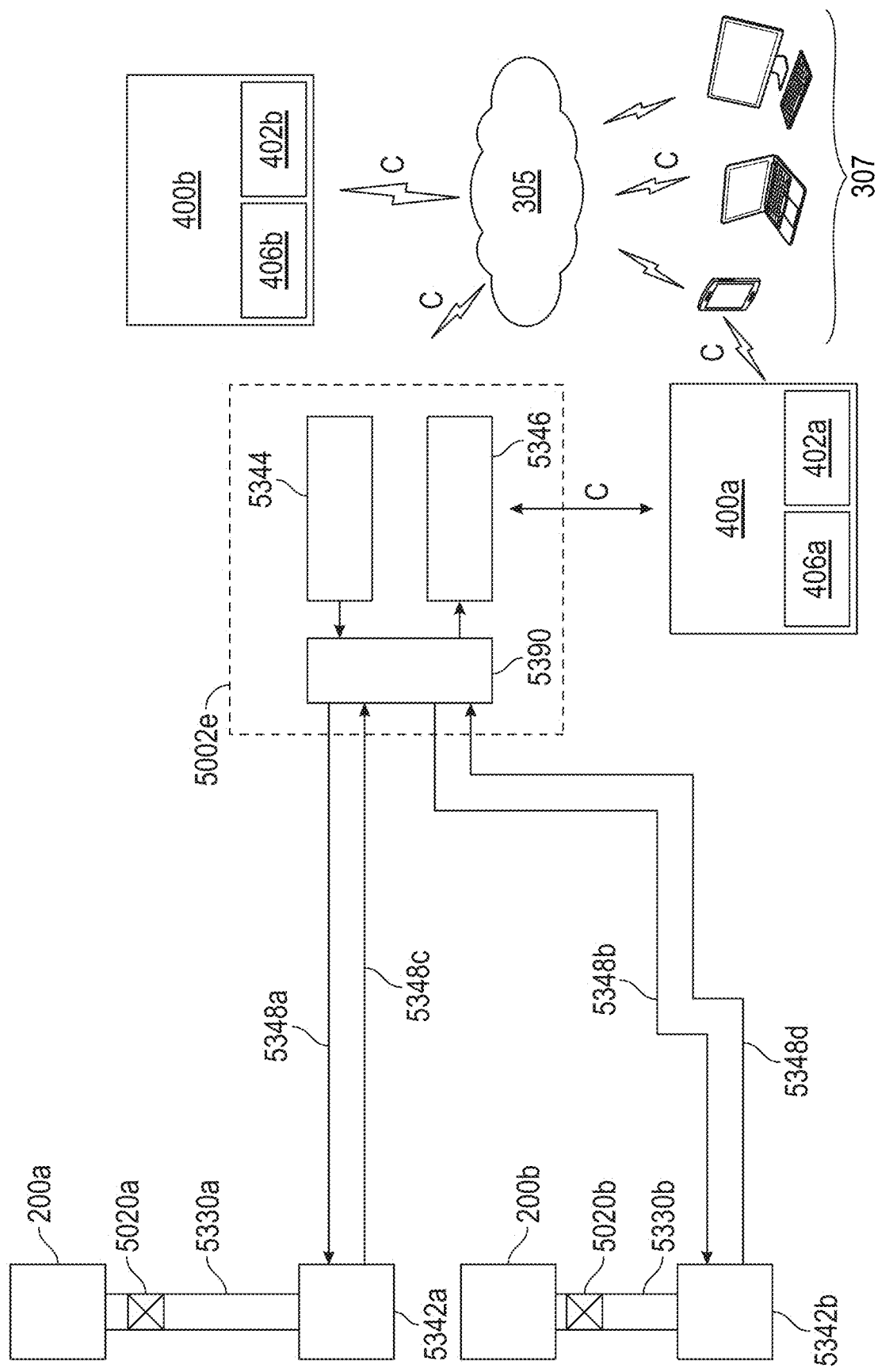
FIG. 16 is a schematic of a fluid analysis and monitoring system, according to an example embodiment of the present disclosure.

FIG. 16 is a schematic of a fluid analysis and monitoring system 5000e, according to an example embodiment of the present disclosure. System 5000e is similar to system 5000d of FIG. 5, but is further configured to include analytical systems 400a and 400b. Analytical systems 400a and 400b may communicate with user devices 307 through one or more networks 305, according to an example embodiment of the present disclosure, as described in greater detail below with reference to FIGS. 17 and 18. Analytical systems 400a and 400b further include command and control systems 406a and 406b and databases 402a and 402b, as described in greater detail below.

Figure 17:
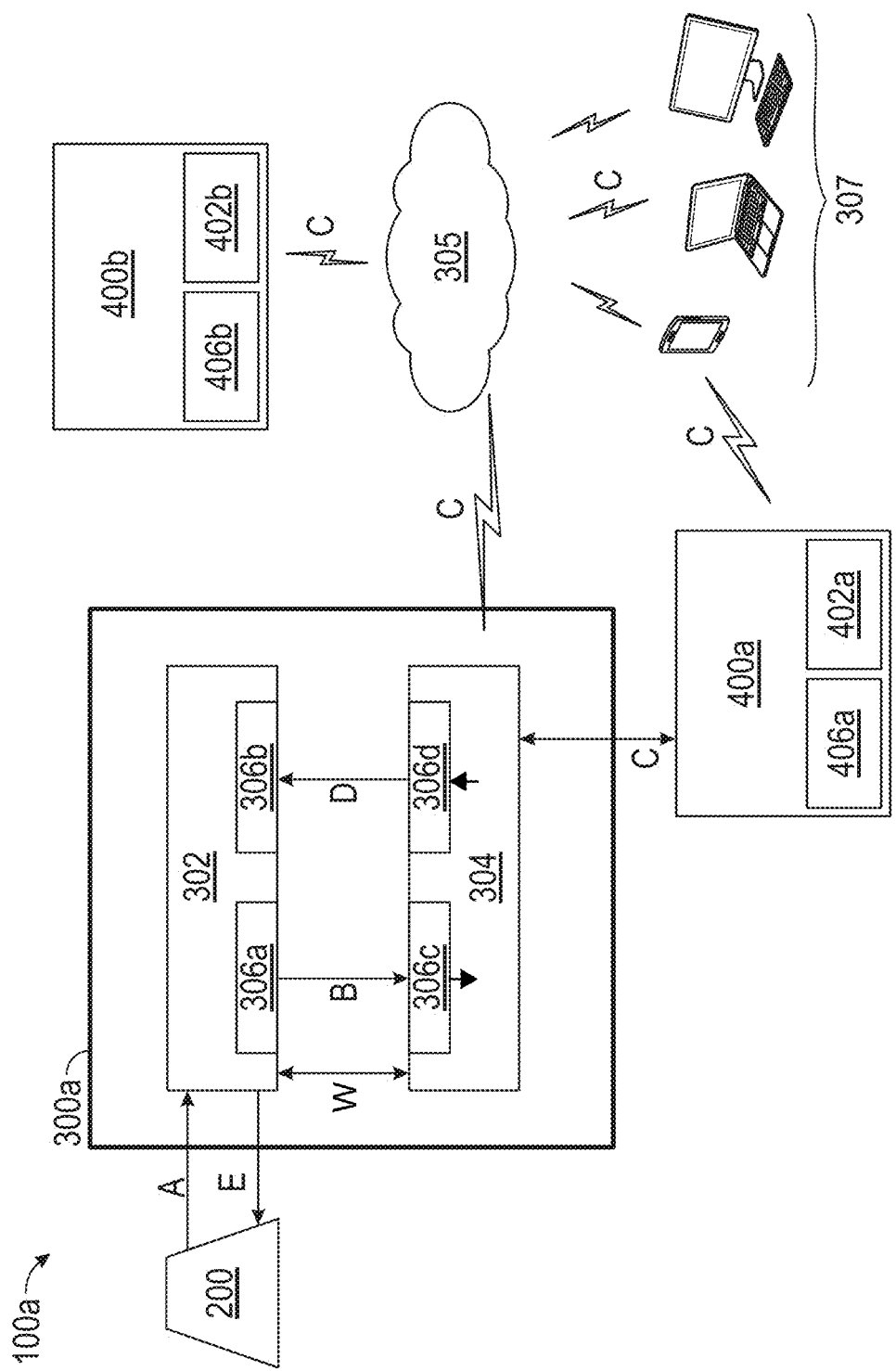
FIG. 17 is a schematic of a fluid analysis system, according to an example embodiment of the present disclosure.

FIG. 17 is a schematic of a fluid analysis system 100a, according to an example embodiment of the present disclosure. Fluid analysis system 100a may include an enclosure 300a having a cooling system 302 attached/coupled to a sampling system 304, and an analytical system 400a coupled to the sampling system 304. Fluid may be routed out from a fluid source 200 and into cooling system 302 (e.g., shown via arrow A) for cooling the fluid prior to routing the fluid into sampling system 304 (shown via arrow B). Sampling system 304 may collect data from the fluid. In an exemplary embodiment, data may include spectral data of a fluid sample obtained via spectroscopy. Other forms of data/information may also be obtained from the fluid sample, as described in greater detail below. Sampling system 304 may then process and transmit the data to analytical system 400a.

Analytical system 400a may be directly connected to sampling system 304 as an external storage device. In further embodiments, analytical system 400a may be located onboard a ship or on other remote structure. Sampling system 304 may provide data to analytical system 400a through a direct wired or wireless connection (e.g., shown by double arrow C), that provides a bi-directional communication link.

In a further embodiment, an analytical system 400b may be provided as a remote device that is accessible through one or more networks 305. Network 305 may be a local area network (LAN), a wide area network (WAN), or may be the Internet. In further embodiments, analytical system 400b may be implemented as a software module running on a remote device, on a server, or on a cloud based computing platform. Bi-directional wireless links C may also be provided to connect analytical system 400b with network 305, to connect network 305 with user devices 307, to connect user devices 307 with analytical system 400a, and to connect sampling system 304 with network 305.

In further embodiments, sampling system 304 may provide data to analytical system 400b, for example, via network 305 through an uplink to a LAN/WAN connection, which may be encrypted or unencrypted, via cellular, satellite, Wi-Fi, Bluetooth, Ethernet (RJ-45) connections, etc.

A user interface may be provided on one or more user devices 307. User devices 307 may communicate directly with analytical system 400a via a wired or wireless connection. User devices 307 may also communicate indirectly with analytical system 400b via network 305. A user may access and/or modify analytical systems 400a and/or 400b via a web application, for example, running on a computing device 307 (e.g., a desktop computer, portable device, etc.) through any type of encrypted or unencrypted connection, as described above. Once processing of measured data by analytical systems 400a and/or 400b is complete, fluid may be returned from sampling system 304 to cooling system 302 (shown via arrow D) and eventually back to fluid source 200 (shown via arrow E). In other embodiments, if the fluid does not require cooling, fluid may be routed directly (not shown in FIG. 17) from fluid source 200 into sampling system 304 and back.

Analytical systems 400a and 400b may include respective command and control systems 406a and 406b, as shown in FIG. 17. Command and control systems 406a and 406b may be configured to receive data from fluid sampling system 304 and to store such data in respective databases 402a and 402b of analytical systems 400a and 400b. Command and control systems 406a and 406b may compare received data to previously-determined data for particular fluids stored in respective databases 402a and 402b. Based on the comparison, command and control systems 406a and 406b may identify correlations between received data and previously stored data for particular fluids. The identified correlations may then be used to identify conditions of the fluid. The identified conditions of the fluid may include chemical composition, presence of impurities, debris, wear metals, etc.

Command and control systems 406a and 406b may be configured as hosted software systems that may receive data collected by sampling system 304 for the submitted sample of the fluid. Command and control systems 406a and 406b may then process such data through a set of existing machine learning models to generate a predictive analysis of properties and conditions of the fluid. Machine learning models may be configured to target any type of fluid to be analyzed. The resulting output of the sample analysis will generally be dependent on the fluid submitted, the networks processed (i.e., in the case of neural network models), and the statistical percentage accuracy of the given machine learning model. In various embodiments, a user may update existing machine learning models or build new machine learning models (via "training") if received data does not correspond to any of a set of existing machine learning models. In various embodiments, command and control systems 406a and/or 406b may then deploy updated and/or new machine learning models back to the fluid analysis system 100a, including the sampling system 304. In various embodiments, command and control systems 406a and 406b may also be configured to manage a user/client's security credentials and customized settings.

Database 402a may be located on a computer readable storage device such as a non-transitory memory device. For example, database 402a may be located on a read-only-memory (ROM) device. Database 402a may also be stored on a volatile storage device such as a random-access-memory (RAM) device. Database 402b may be located on an external device that is accessible via network 305. For example, database 402b may be located on a server or on a cloud based computing platform.

Databases 402a and 402b may be used to collect and store data relating to different types of fluids (e.g., types of oil and water) and their conditions. Fluids may include, but are not limited to, any type of industrial fluids or liquids, such as coolants, waste water, etc. Oils may include any type of oil, including but not limited to, very light oils such as jet fuels and gasoline, light oils such as diesel, No. 2 fuel oil, and light crudes, medium oils such as most crude oils, and heavy oils such as heavy crude oils, No. 6 fuel oil, and Bunker C. The different "conditions" of fluid/oil samples may describe compositions containing various fluids, impurities, wear metals, additives, water, etc. Fluid "conditions" may also describe various properties such as viscosity, total acid number (TAN), total base number (TBN), and particle counts. In exemplary embodiments, existing data in databases 402a and 402b may include spectroscopic information regarding the molecular content or makeup of different types of fluid.

In some embodiments, default fluid sensor dashboards may also be provided for each installation site at time of installation of system 100a. Such dashboards may be provided on a graphical user interface (GUI) (not shown) of a user device 307. Each approved user may have an ability to customize or alter these dashboards as desired. In exemplary embodiments, software associated with the dashboards may provide real-time monitoring and graphical updates at predetermined data rates. For example, graphical updates may be provided each time data is determined to have changed. In other embodiments data may be updated an update rate not to exceed 1 second, 10 seconds, 100 seconds, 180 seconds, etc.

In other embodiments, real-time display inclusive of graphical depictions may be capable of being continuously updated while data is being viewed. Data screens and access capabilities may be automatically resized to fit a viewing area of user devices 307 used to access the dashboards. Data acquisition and analytics in the dashboards may include, but is not limited to, the following capabilities: analytical comparatives and real-time updates (between sampling system 304 and analytical systems 400a and 400b); predictive oil changing comparative analysis, chronograph data, financial comparative data; data regarding wear metals, particulate counts, viscosity, TAN, TBN, Nitration, Sulfation, Foreign Oils, Solvents, Glycol, Soot, Dissolved Gases, and/or Oil Additive Depletion (Zn, Mo, Pd, Ca, Mg, Ba, Na), area plots (illustrating how a customer may view a layout of the system 100a); and notifications suggesting that required maintenance is pending.

In an embodiment, enclosure 300a may be a ruggedized and water-resistant case. For example, enclosure 300a may be mounted via screws and/or bolts onto a flat surface using, for example, rubber bushings/shock absorbers to minimize vibrational noise. Enclosure 300a may also include other suitable configurations for securely holding both cooling system 302 and sampling system 304.

Disclosed embodiments may be designed using a "plug and play" philosophy. Each component of fluid analysis system 100a may be easily plugged/snapped to other components of fluid analysis system 100a via fluidic connectors (306a, 306b, 306c, and 306d) and via an electrical wiring connections W, as illustrated in FIG. 17. For example, cooling system 302 may or may not be plugged into sampling system 304 depending on the temperature of the fluid. In exemplary embodiments, connectors (306a, 306b, 306c, and 306d) may be fluidic Eaton STC® "snap" connectors allowing for fluid to be routed into and out of sampling system 304 from cooling system 302.

Figure 18:
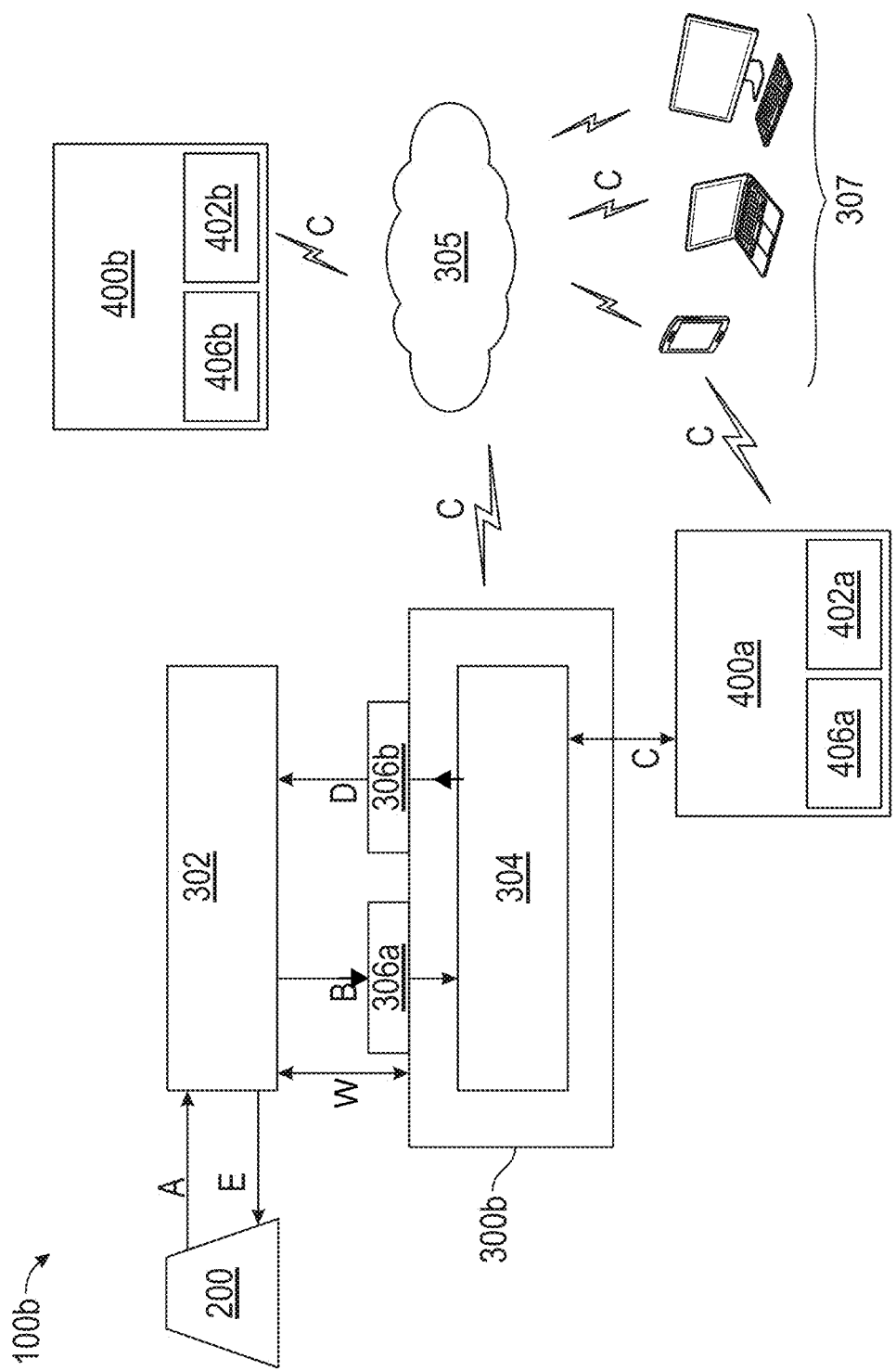
FIG. 18 is a schematic of a fluid analysis system, according to an example embodiment of the present disclosure.

FIG. 18 is a schematic of a fluid analysis system 100b, according to an example embodiment of the present disclosure. Fluid analysis system 100b has features that are similar to those of fluid analysis system 100a shown in FIG. 17. In this embodiment, cooling system 302 may be installed separately from and/or externally to enclosure 300b of fluid analysis system 100b having sampling system 304. Cooling system 302 may be fluidically coupled to enclosure 300b/sampling system 304 via connectors 306a and 306b. In this example, fluid connectors 306a and 306b are shown as external connectors to sampling system 304. In other embodiments, such as shown in FIG. 17, connectors 306a to 306d may be provided as internal connectors to respective systems 302 and 304. Cooling system 302 may also be electrically connected to enclosure 300b/sampling system 304 via wiring connections W.

The configuration of system 100b, illustrated in FIG. 18, provides greater flexibility by allowing fluid analysis system 100b to be deployed with or without a cooling system 302, as needed to suit a user's needs. In an exemplary embodiment, cooling system 302 may only be coupled to the enclosure 300b/sampling system 304 if the fluid being routed through the system 100b requires cooling. In this embodiment, enclosure 300b having sampling system 304 may include a smaller sized case than the embodiment of enclosure 300a having both cooling system 302 and sampling system 304, as illustrated in FIG. 17. Other details of FIG. 18 not specifically mentioned (e.g., analytical systems 400a and 400b, network 305, user devices 307, pathways A to E, etc.) are essentially similar to those described above with respect to FIG. 17.

Figure 19:
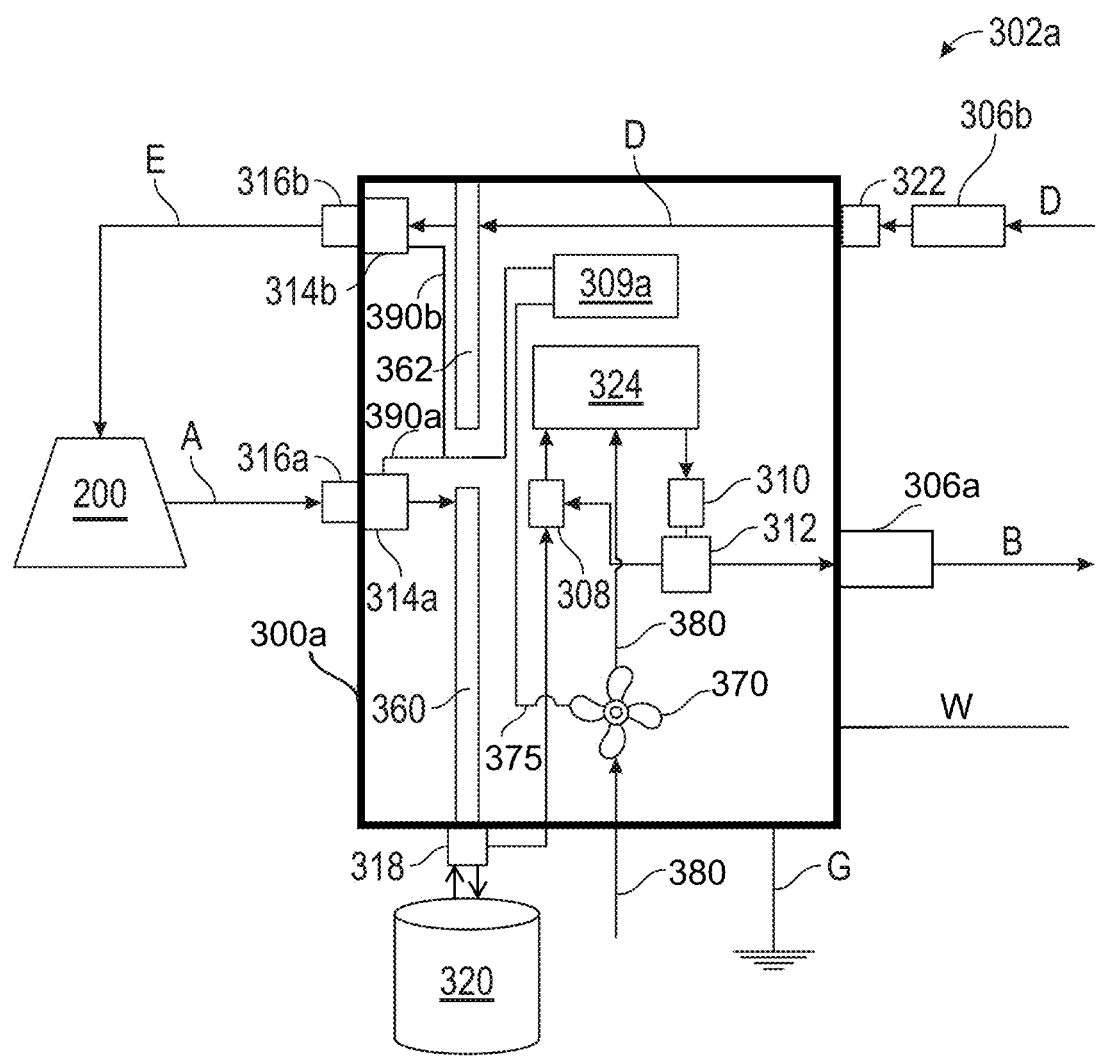
FIG. 19 is a schematic of a fluid analysis system with an enclosure and a cooling system, according to an example embodiment of the present disclosure.

FIG. 19 is a schematic of a fluid analysis with an enclosure 300a and a cooling system 302a, according to an example embodiment of the present disclosure. As described herein, cooling system 302a (e.g., see also FIGS. 17 and 18) may be a separately pluggable piece that may be coupled to sampling system 304 if and when a fluid requires cooling, as illustrated in FIG. 18 for system 100b. Alternatively, cooling system 302a may come pre-installed within an enclosure 300a along with sampling system 304, as illustrated in FIG. 17.

Cooling system 302a may be used to control, filter, and cool fluid (e.g. oil, water, etc.) to be sampled from a fluid source 200 (e.g., see FIGS. 17 and 18). In an exemplary embodiment, fluid may be oil that is routed from a fluid/oil source 200, such as an engine, via pressure from source 200 that forces the oil into cooling system 302a (shown via arrow A in FIGS. 17 to 19). Fitting 316a may be used to connect an oil line from a high pressure line from source 200 to cooling system 302a. In some embodiments, fitting 316a may be a connector (e.g., a connector similar to connectors 306a to 306d of FIGS. 17 and 18) such as an Eaton STC® "snap" connector.

In other embodiments, fitting 316a may be configured to connect the any size oil line source 200 to a cooling system 302a. For example, fitting 316a may be a 1/16, 1/8, 1/4, or 1/2" Female Iron (or International) Pipe (FIP) fitting. Cooling system 302a may include a valve 314a connected to source valve manifold assembly 360 and connected to various wiring connections W (explicit wiring connections not shown in FIG. 19). Valve 314a may be used to control flow of oil into cooling system 302a. In some embodiments, valve 314a may be an electromechanical single direction solenoid valve. In an exemplary embodiment, valve 314a may be an AS Series Valve offered by Gems™ Sensors & Controls. Source manifold assembly 360 may be a Manifold Assembly offered by Gems™ Sensors & Controls. Valves 314a and 314b may be controlled via connections (e.g., via electrical connectors 390a and 390b, respectively) to a controller 309a located in the cooling system 302a, as shown in FIG. 19, and/or connected to controller 332 located in sampling system 304, as shown, for example, in FIG. 23. Controller 309a and/or controller 332 may send a signal to cause valve 314a to open and close as needed to allow fluid/oil into the cooling system 302a.

As described below, controller 309a or 332 (e.g., see FIG. 23) may monitor current drawn by solenoid valves to detect system failures. In this regard, as valves driven by solenoids begin to fail, the solenoids draw more electrical current to perform the same functions. For example, with a sticky valve, an electrical short, etc., higher electrical current may be drawn by a failing valve.

As shown in FIG. 19, fluid/oil may be routed from the source manifold assembly 360 through a filter connection 318 and into a filter 320 located outside cooling system 302a. In other embodiments, filter 320 may be located inside cooling system 302a. Filter connection 318 and filter 320 may be used to prevent debris in oil from entering cooling system 302a and damaging cooling system 302a and/or eventually entering sampling system 304. Fluid/oil may then be routed into a pressure reducer regulator valve with a pressure sensor 308.

Pressure reducer valve 308 may include two inputs and one output as shown, for example, in FIG. 19. In an exemplary embodiment, pressure reducer valve 308 may be a BB-3 series stainless steel back-pressure regulator offered by Tescom™. Other pressure reducer values may be used in other embodiments. In various embodiments, pressure reducer valve 308 may reduce the pressure from dangerously high pressures (e.g., pressures >50 psi) in source 200 to between approximately 1 and 50 psi (depending on fluid type). Once pressure of the fluid/oil is reduced to a safe value, fluid/oil may be routed into a cooler/radiator 324 and then to a temperature sensor 310 and a 2-way solenoid valve 312. In some embodiments, cooler 324 may either be a simple radiant heat sink or a fluid cooler system. In an exemplary embodiment, cooler 324 may be a MMOC-10 Universal 10-Row Oil Cooler offered by Mishimoto™. Other coolers may be used in further embodiments.

Figure 23:
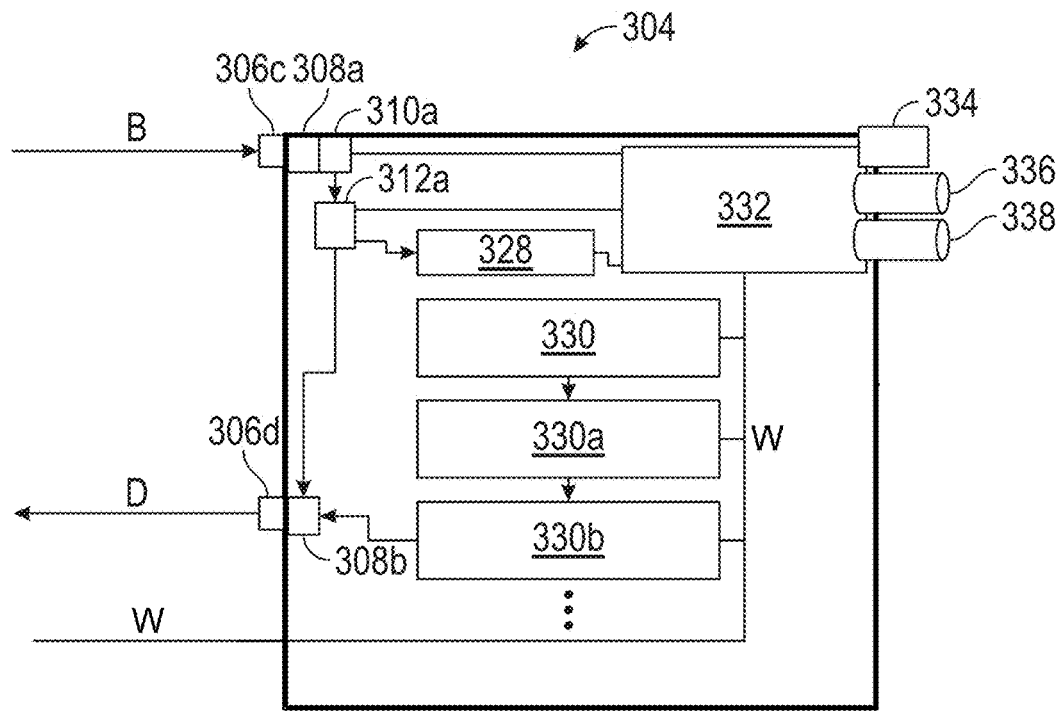
FIG. 23 is a schematic of a sampling system, according to an example embodiment of the present disclosure.

In an exemplary embodiment, if the temperature sensor 310 detects a temperature of the fluid/oil that is greater than a predetermined value, say 40° C., controller 309a of FIG. 19 or controller 332 of FIG. 23 may switch valve 312 by applying a control signal to an electrical connector (not shown) and route the fluid/oil out of cooling system 302a via connector 306a and into sampling system 304 (e.g., see FIGS. 17 and 18) (via arrow B), as shown in FIG. 19. However, if temperature sensor 310 detects that the fluid/oil is at a temperature that is above a predetermined value, say 40° C., it may route the fluid/oil back into pressure reducer valve 308 and into cooler 324 via valve 312 until the fluid/oil reaches the desired temperature (e.g., a temperature less than or equal to 40° C.). This temperature is relevant because it is related to measurement of a viscosity of the fluid/oil, as described in greater detail below.

The viscosity of a lubricating fluid/oil may be measured either based on its kinematic viscosity, acoustic viscosity, or its absolute (dynamic) viscosity. Kinematic viscosity is defined as its resistance to flow and shear due to gravity at a given temperature. However, simply stating a viscosity of a fluid/oil is meaningless unless the temperature at which the viscosity was measured is specified. For most industrial oils, it is common to measure kinematic viscosity at 40° C. because this is the basis for the ISO viscosity grading system (ISO 3448).

In an exemplary embodiment, an acoustic viscosity sensor may be employed. An acoustic viscometer may employ a piezoelectric sensor having distinct input and output ports for differential measurements. Acoustic viscometers may also include a multi-reflective acoustic wave device blends the features of resonators and delay lines to offer a wide dynamic range (air to several thousand centipoise) in a single sensor. Aside from the atomic-scale vibration of the acoustic viscometer surface, such sensors have no other moving parts that may wear or break over time. In addition, the high frequency of the vibration, which may be up to several million vibrations per second, is independent of flow conditions of the fluid and also immune to environmental vibration effects which may be found is hostile environment such as an engine room.

In various embodiments, fan 370 may be installed within cooling system 302a and may be turned on as needed (e.g. the fan may be turned on when the temperature of the oil is >40° C.) to assist cooler 324 in cooling the fluid/oil based on the temperature of the fluid/oil and based on a radiant air temperature. Fan 370 may be controlled via the controller 309a of cooling system 302a (e.g., see FIG. 19) or via controller 332 of sampling system 304 (e.g., see FIG. 23) through electrical connection 375. Fan 370 may generate a flow of air along an airflow path 380.

Wiring connections W may be used to connect various electrical connections of cooling system 302a to sampling system 304 (e.g., see FIGS. 17 and 18), as shown in FIG. 19. Wiring connections W may include an electrical ground connection to force the electrical potential of cooling system 302a to coincide with a ground potential. If electrical connections W does not include a ground connection, a separate ground connection G may be provided as illustrated, for example, in FIG. 19. As mentioned above, electrical connection 390a, 390b, etc., may provide control signals to various control valves (e.g., valves 314a and 314b, etc.).

As shown in FIGS. 17 to 19, once the fluid/oil is adequately sampled by sampling system 304, oil may be routed back from sampling system 304 (e.g., see FIGS. 17 and 18) to cooling system 302a (shown via arrow D in FIGS. 17 to 19), via connector 306b. To facilitate this return, cooling system 302a may include an air valve 322 that may be opened as needed to purge air from the line and to accelerate return of oil if there is little or no pressure to push/drain the oil back into cooling system 302a from sampling system 304 through connector 306b. Fluid/oil may then be routed out of cooling system 302a and back to source 200 (e.g., shown by arrow E in FIGS. 17 to 19) via a similar fitting-valve 316b/return-valve 314b manifold assembly 362 connection that allows entry of oil into cooling system 302a, as illustrated in FIG. 19. Return manifold assembly 362 may be a Manifold Assemblies offered by Gems™ Sensors & Controls. Other return manifold assemblies may be provided in further embodiments.

Figure 20:
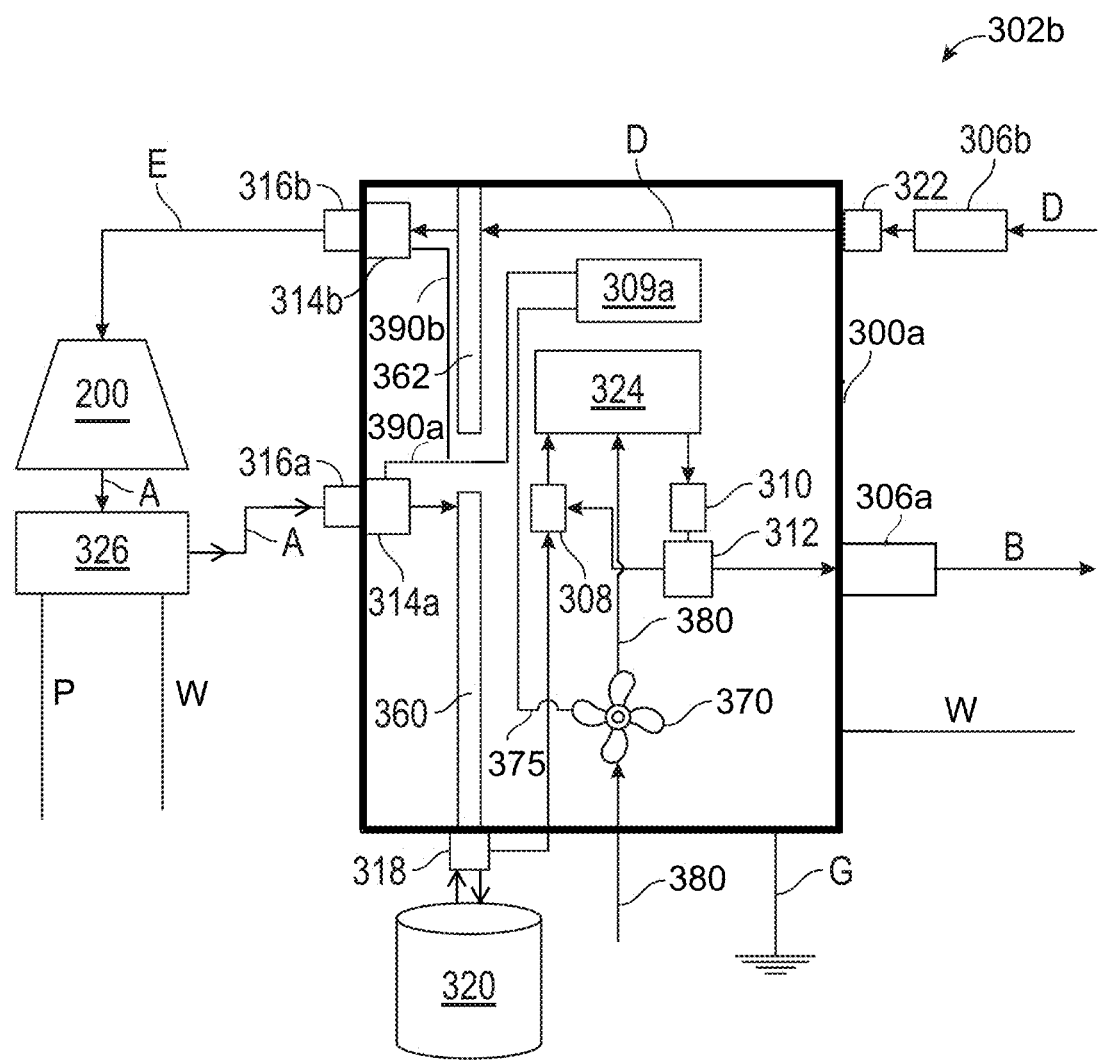
FIG. 20 is a schematic of a fluid analysis system with an enclosure and a cooling system, according to an example embodiment of the present disclosure.

FIG. 20 is a schematic of a fluid analysis with an enclosure 300a and a cooling system 302b, according to an example embodiment of the present disclosure. Cooling system 302b has features similar to those of cooling system 302a shown in FIG. 19. In this embodiment, cooling system 302b may include a pump 326 connected to a fluid source 200 containing fluids having little or no pressure. Pump 326 may provide additional pressure/movement for these fluids to be routed into cooling system 302b and eventually into sampling system 304 (e.g., see FIGS. 17 and 18). In an exemplary embodiment, fluid/oil may be routed from source 200 into pump 326. Pump 326 may then pump fluid/oil into cooling system 302b (shown via arrow A).

The behavior of cooling system 302b, illustrated in FIG. 20, is similar to the behavior of cooling system 302a illustrated in FIG. 19. In this regard, in cooling system 302b, fluid/oil flows along path A through connector 316a and through valve 314a into source manifold assembly 360. From there, fluid/oil may be routed into filter 320 via filter connection 318. Fluid/oil may then flow into pressure reducer valve 308, cooler 324, temperature sensor 310, and through 2-way solenoid valve 312. Fluid/oil may then be provided to sampling system 304 (e.g., see FIGS. 17 and 18) by flowing through connector 306a and into sampling system 304 along path B. Fluid/oil may then flow back to cooling system 302b through connector 306b along path D. Fluid/oil may then flow into return manifold 362, and back to source 200 along path E, by flowing through valve 314b and connector 316b, as described above with reference to FIG. 19.

Pump 326 may include electrical connections to sampling system 304 via wiring connections W. Such electrical connections may be similar to electrical connections between cooling system 302 and sampling system 304, via wiring connections W, described above with reference to FIGS. 17 and 18. Wiring connections W may include an electrical power supply that supplies electrical power to pump 326. As mentioned above, a separate electrical power connection P may be provided to pump 326 if an electrical power connection is not provided by wiring connections W.

Pump 326 may be initialized via connections to controller 309a (e.g., see FIG. 20) located in the cooling system 302b, and/or connections to controller 332 (e.g., see FIG. 23) located in sampling system 304. In various embodiments, controller 309a in cooling system 302b and/or controller 332 in sampling system 304 may shut pump 326 down once sampling is complete. Controller 309a and/or controller 332 may then open air valve 322 as needed to purge air from the line and to help accelerate return of fluid/oil if there is little or no pressure otherwise provided by the source 200 to push/drain the fluid/oil back into cooling system 302b. Features not specifically described (e.g., electrical connectors 375, 390a, 390b, fan 370, and airflow path 380), are similar to those described above with reference to FIG. 19.

Figure 21:
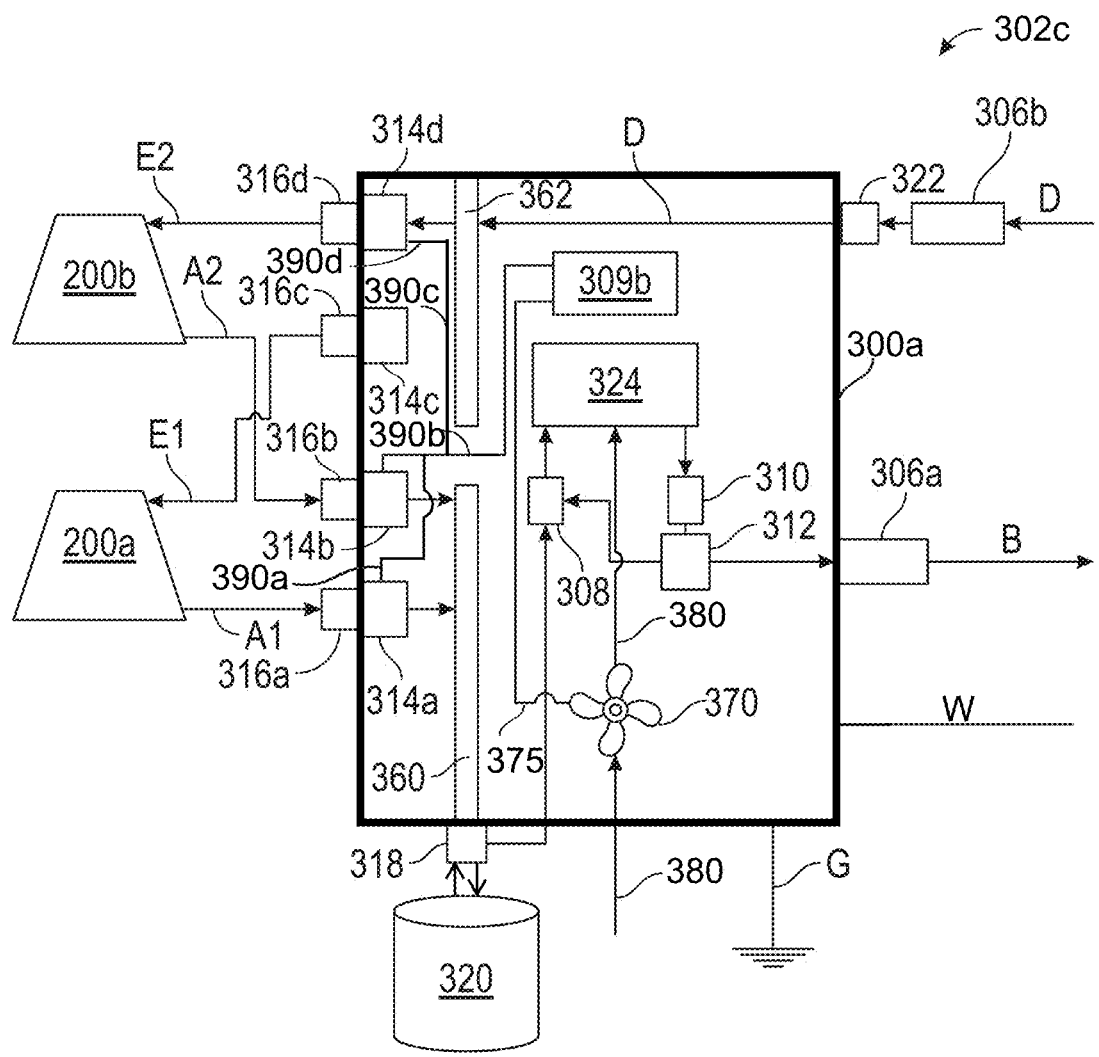
FIG. 21 is a schematic of a fluid analysis system with an enclosure and a cooling system, according to an example embodiment of the present disclosure.

FIG. 21 is a schematic of a fluid analysis with an enclosure 300a and a cooling system 302c, according to an example embodiment of the present disclosure. In this embodiment, cooling system 302c is shown as having connections to multiple fluid sources 200a and 200b for cooling and routing fluid into sampling system 304 (e.g., see FIGS. 17 and 18). In an embodiment, fluid from a single fluid source (e.g., fluid source 200a or 200b) may be cooled and sampled at a time. In further embodiments, cooling system 302c may be simultaneously connected to two fluid sources 200a and 200b via multiple fittings 316a to 316d and corresponding respective multiple valves 314a to 314d attached to each of the input/inlet and return/outlet sides, each of which may be controlled independently of the others based on the fluid/oil to be sampled. Valves 314a to 314d may be actuated by control signals provided from controller 309b via electrical connectors 390a to 390d, respectively.

As shown in FIG. 21, fittings 316a and 316b may be connected to sources 200a and 200b, respectively. Fittings 316a and 316b may be connected to valves 314a and 314b, respectively, which may in turn be connected to single source manifold assembly 360. Similarly, valves 314c and 314d may be connected to single return manifold assembly 362. Further, fittings 316c and 316d may be connected to valves 314c and 314d, respectively. In turn, valves 314c and 314d may be connected as return valves to sources 200a and 200b, respectively.

Each valve 314a to 314d may be controlled via connections to controller 309b located in the cooling system 302, as shown in FIG. 21, and/or may be controlled via connections to controller 332 of sampling system 304, as shown in FIG. 23. Controller 309b (e.g., see FIG. 21) and/or controller 332 (e.g., see FIG. 23) may send signals to an appropriate valve 314a and/or 314b associated with source manifold assembly 360 causing the valve in question to open, thus allowing flow of fluid/oil into cooling system 302c from sources 200a and/or 200b, respectively. Similarly, controller 309b and/or controller 332 (e.g., see FIG. 23) may send signals to an appropriate valve 314c and/or 314d associated with return manifold assembly 362 causing the valve in question to open, thus allowing flow of fluid/oil out of cooling system 302c and back to sources 200a and 200b, respectively. Some of valves 314a to 314d may be opened while others of valves 314a to 314d may be closed, depending on the fluid/oil sample and depending on which one or both of sources 200a and 200b are selected for sampling.

For example, opening valve 314a allows fluid/oil to flow from source 200a along path A1 through connector 316a and into cooling system 302c via source manifold assembly 360. Similarly, opening valve 314b allows fluid/oil to flow from source 200b along path A2 through connector 316b and into cooling system 302c via source manifold assembly 360. Opening valve 314c allows fluid/oil to flow out from return manifold assembly 362 through connector 316c and to return from cooling system 302c to source 200a via path E1. Similarly, opening valve 314d allows fluid/oil to flow out from return manifold assembly 362 through connector 316d and to return from cooling system 302c to source 200b via path E2.

Other details of FIG. 21 not specifically mentioned (e.g., connectors 306a and 306b), pressure reducer valve 308, temperature sensor 310, 2-way solenoid valve 312, filter connection 318, oil filter 320, air valve 322, cooler 324, fan 370, airflow path 380, paths B and D, wiring connections W, ground connection G, electrical connectors 375, etc. are essentially similar to those described above with respect to FIG. 20.

Figure 22:
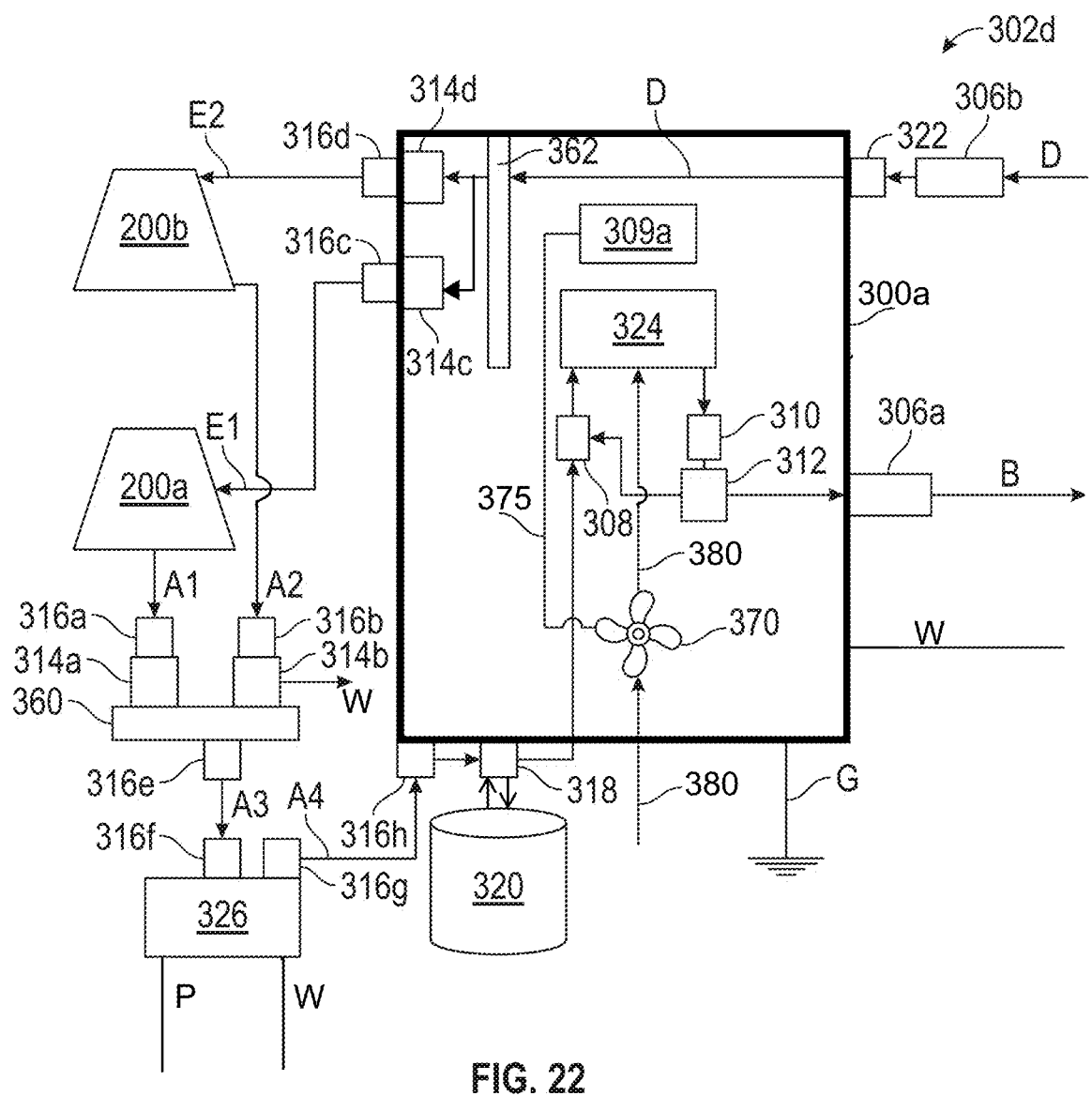
FIG. 22 is a schematic of a fluid analysis system with an enclosure and a cooling system, according to an example embodiment of the present disclosure.

FIG. 22 is a schematic of a fluid analysis system with an enclosure 300a and a cooling system 302d, according to an example embodiment of the present disclosure. Cooling system 302d has features similar to those of cooling system 302c shown in FIG. 21. In this embodiment, cooling system 302d may include a pump 326 connected to multiple fluid sources 200a and 200b containing fluids having little or no pressure. As shown, source manifold assembly 360 may be located externally to cooling system 302d, thereby preventing duplicative valve systems on the input line to cooling system 302d, such as valves 314a and 314b of cooling system 302b shown in FIG. 21. Further, providing the source manifold assembly 360 as a device that is external to cooling system 302d allows fluid/oil from multiple sources (e.g., engines) 200a and 200b to be provided into a single line prior to being routed into pump 326, thus eliminating the need for multiple pumps 326, as illustrated in FIG. 22 and described in greater detail below.

As shown in FIG. 22, fluid/oil may be routed from two sources 200a and 200b into fittings 316a and 316b, respectively, along paths A1 and A2. Flow of fluid/oil through fittings 316a and 316b may be controlled by valves 314a and 314b, respectively, which are attached to and control the flow of fluid/oil into source manifold assembly 360. Fluid/oil may flow out of source valve manifold 360 through fitting 316e along path A3 and into pump 326 through fitting 316f. Pump 326 may provide pressure to fluid/oil and move fluid/oil out of pump 326 through fitting 316g along path A4. Fluid/oil may then propagate into cooling system 302d though fitting 316h.

As with the behavior of cooling system 302c, illustrated in FIG. 21, fluid/oil may then flow into filter 320 via filter connection 318. Fluid/oil may then flow into pressure reducer valve 308, cooler 324, temperature sensor 310, and through 2-way solenoid valve 312. Fluid/oil may then be provided to sampling system 304 (e.g., see FIGS. 17 and 18) by flowing through connector 306a and into sampling system 304 along path B. Fluid/oil may then flow back to cooling system 302d through connector 306b along path D. Fluid/oil may then flow into return manifold 362. Opening valve 314c allows fluid/oil to flow out from return manifold assembly 362 through connector 316c and to return to source 200a via path E1. Similarly, opening valve 314d allows fluid/oil to flow out from return manifold assembly 362 through connector 316d and to return to source 200b via path E2.

Each of valves 314a to 314d may be controlled via connections (not shown for simplicity of illustration) to controller 309b located in the cooling system 302d (e.g., see FIGS. 21 and 22) and/or controller 332 located sampling system 304 (e.g., see FIG. 23). Controllers 309b and/or 332 may send a signal to an appropriate valve 314a and/or 314b on the source manifold assembly 360 and/or valves 314c and 314d on return manifold assembly 362 to control the flow of fluid/oil, as described above with reference to FIG. 21. Other details of FIG. 22 not specifically mentioned (e.g., open air valve 322, fan 370, airflow path 380, wiring connections W, ground connection G, power connection P, electrical connection 375, etc.) are essentially similar to those described above with respect to FIGS. 19 to 21.

FIG. 23 is a schematic of a sampling system 304, according to an example embodiment of the present disclosure. As shown, arrow B represents fluid being routed into sampling system 304 through connector 306c from cooling system 302 and/or from fluid source 200 as shown, for example, in FIGS. 17 and 18. Arrow D represents fluid being returned through connector 306d to cooling system 302 and/or to fluid source 200 (e.g., see FIGS. 17 and 18) after sampling has been performed on a fluid sample by sampling system 304. Arrow W represents wiring connections between components of sampling system 304, and between sampling system 304 and cooling system 302 (e.g., see FIGS. 17, 18 and 23).

Sampling system 304 may include at least one removable and replaceable sub-sampling system 330. In further embodiments, sampling system 304 may include a plurality of sub-sampling systems 330, 330a, 330b, etc. Plurality of sub-sampling systems 330, 330a, 330b, etc., may be stacked in a daisy-chain configuration and may be electrically connected via wiring connections W and fluidically connected to one another via connectors (e.g., connectors 306e, 306f, etc.), as described in greater detail below with reference to FIGS. 24 to 29.

Reference characters 330, 330a, 330b, etc., are used for convenience of illustration and description. There is no restriction, however, on the ordering of identity of sub-sampling systems in sampling system 304 of FIG. 23 or in the description of sub-sampling systems in FIGS. 24 to 29. For example, sub-sampling systems (330), (330a), (330b), etc., may all be the same, all different, or any combination of sub-sampling systems described below with reference to FIGS. 24 to 29.

In various embodiments, connectors (e.g., connectors 306e, 306f, etc.), illustrated in FIGS. 24 to 29 may be Eaton STC® "snap" connectors allowing fluid to be routed into and out of sub-sampling systems 330, 330a, 330b, etc. In this regard, each sub-sampling system 330, 330a, 330b, etc., may have a female input connector (on the top, as illustrated in FIGS. 24 to 29) and a male output connector (on the bottom, as illustrated in FIGS. 24 to 29), allowing each sub-sampling system 330, 330a, 330b, etc., to be stacked sequentially (e.g., see FIG. 23) to satisfy fluid and target requirements. The types of sub-sampling systems 330, 330a, 330b, etc., used within sampling system 304 may depend on the fluid and targeted identification criteria needed.

In various embodiments, sampling system 304 may further include connections between input connector 306c, input pressure reducer valve 308a (having pressure sensors/transducers), and input temperature sensor 310a. Sampling system 304 may further include connections to 2-way solenoid valve 312a that functions as a bypass valve (as described in greater detail below), to at least one viscometer 328, and to controller 332, as described above with reference to FIGS. 19 to 22. Sampling system 304 may include several wiring connections W that connect controller 332 to each sub-sampling system 330, 330a, 330b, etc. (e.g., via daisy-chain configuration). Sampling system 304 may further include connections between output connector 306d and output pressure reducer valve 308b.

Wiring connections W may further provide electrical connections to viscometer 328, pressure reducer valves 308a and 308b, temperature sensor 310a, and 2-way solenoid valve 312a. Wiring connections W may further include a ribbon to an external connector that couples sampling system 304 to cooling system 302, as shown in FIGS. 17 and 18. Controller 332 may control the sampling system 304 and/or cooling system 302, as described above with reference to FIGS. 19 to 22. Controller 332 may further interact with analytical systems 400a and/or 400b, for example, by submitting real-time data obtained from fluids being sampled to analytical systems 400a and/or 400b, as described above with reference to FIGS. 17 and 18.

Once fluid is routed into sampling system 304, 2-way solenoid valve 312a may divert the fluid back to cooling system 302 via a return line if the pressure and/or temperature of the fluid are too high or low (i.e., if the pressure and/or temperature exceed respective predetermined threshold values). Pressure reducer valve 308b may be located at an output/return line and pressure reducer valve 308a may be located at an input/source line. Pressure reducer valves 308a and 308b may be used to generate pressure difference data. The generated pressure difference data may be used to perform a pressure comparison between input and output pressures of the fluid to determine if a significant pressure drop exists. A detected significant pressure drop may indicate a possible fluid leak.

The pressure comparison may be performed during sampling of the fluids by allowing sub-sampling systems 330, 330a, 330b, etc., to equalize in pressure while data samples are generated. A change in pressure after equalization (i.e. a significant pressure drop may imply the presence of a leak within one or more of the sub-sampling systems 330, 330a, 330b, etc.). Further, a significant pressure drop may also be used to identify a fluidic leak at output pressure reducer valve 308b. To determine if output pressure reducer valve 308b is leaking, a user may monitor electrical current required to operate a solenoid associated with output pressure reducer valve 308b. As mentioned above, valves driven by solenoids that are failing generally draw more electrical current to perform the same functions. Monitoring electrical current drawn by solenoid valve lines, therefore, may provide self-diagnostic information for sampling system 304/fluid analysis systems 100a and 100b (e.g., see FIGS. 17 and 18).

As shown, 2-way solenoid valve 312a may divert fluid to viscometer 328 if the pressure and/or temperature of the fluid are at an appropriate level (i.e., if the pressure and/or temperature are below respective predetermined threshold values). Viscometer 328 may be used to measure viscosity and flow parameters of the fluid. In an exemplary embodiment, viscometer may be a VISCOpro 2000 Process Viscometer offered by the Petroleum Analyzer Company, L.P. d/b/a PAC. Various alternative viscometers may be also be use such a ViSmart™ acoustic viscometer offered by BiODE, or a VTX423 "pinch" viscometer offered by TD Collaborative. Once the viscosity of the fluid is measured, fluid may be routed into sub-sampling systems 330, 330a, 330b, etc. In an exemplary embodiment, fluid may be routed from viscometer 328 into sub-sampling systems 330, 330a, 330b, etc., that may be stacked on top of one another, as illustrated in FIG. 23. As described in greater detail below with reference to FIGS. 24 to 29, fluid may be sampled by each of sub-sampling systems 330, 330a, 330b, etc.

All components of sampling system 304 may be connected to controller 332 via wiring connections W, as illustrated in FIG. 23. In an exemplary embodiment, controller 332 may be an ARM (Acorn RISC Machine/Advanced RISC Machine) based system with a custom shield (not shown in FIG. 23) for connecting to cooling system 302 (e.g., see FIGS. 17 to 22), sub-sampling systems 330, 300a, 300b, etc., and/or to other components of cooling 302 and sampling 304 systems. In exemplary embodiments, controller 332 may include an RJ45 (CATS/6 Ethernet connection 334), an SMA (SubMiniature version A) connection 336 for an antenna or an antenna dongle, and a power connector 338, as illustrated, for example, in FIG. 23. Controller 332 may also include connections including, for example, Universal Serial Bus (USB), HDMI, and Bluetooth connections, and may be powered via a Mini-USB connection. In exemplary embodiments, controller 332 may be the Raspberry Pi 3 Model B, Raspberry Pi Zero, or Raspberry Pi 1 Model A+. In other embodiments, controller 332 may be the Mojo Board V3 offered by Embedded Micro—an FPGA (Field Programmable Gate Array) with multiple pre-made shields. In further embodiments, any other suitable controller 332 may be used.

Shields used to connect controller 332 to other components of sampling system 304 and/or cooling system 302 may include a Servo Shield (used for connecting to servos/solenoids on valves), Proto Shield (used for prototyping), IO Shield (used for displaying output), buttons for input, and switches for configuration options, and/or stackable headers (used to stack shields offered by Embedded Micro). In some embodiments, controller 332 may be placed within its own enclosure (not shown in FIG. 23) separate from an enclosure of sampling system 304 to protect controller 332 in case of a catastrophic fluid failure/leak within sampling system 304. In other embodiments, controllers 309a or 309b may be included in cooling systems 302a to 302d, as described in greater detail above with respect to FIGS. 19 to 22.

In exemplary embodiments, controller 332 may include customized software to assist sampling system 304 in performing analysis of fluid and to assist in sending/receiving real-time data regarding the fluid to analytical systems 400a and/or 400b. In various embodiments, software associated with controller 332 may include computer program instructions related to, but not limited to, communication protocols, security settings, sampling system 304 interaction, cooling system 302 sub-controller/controllers 309a and 309b, and temperature and pressure sensors in systems 100a and/or 100b.

Software may further include computer program instructions pertaining to determination in a spectroscopy based sub-sampling systems (e.g., sub-sampling systems 330, 300a, 300b, etc.) regarding methods to trigger an excitation system (e.g., see FIGS. 24 to 29) and methods to read outputs from a detection system connected to the source, as described in greater detail below. Exemplary embodiments of software associated with controllers 309a, 309b, and 332 are described in greater detail below with reference to flowcharts of FIGS. 31A, 31B, and 32. In some embodiments, software may also cause controllers 309a, 309b, and 332 (e.g., see FIGS. 19 to 23) to monitor systems 100a and 100b for fluidic leaks and other potential problems.

In an embodiment, a sampling system 304 may periodically poll analytical systems 400a and/or 400b (e.g., see FIGS. 17 and 18) (e.g., every few milliseconds, seconds, minutes, hours, days, etc.) to send or request specific commands or instructions. When a sampling system 304 is deployed (e.g., onboard a ship), installed software may be configured with a custom login/password that may be entered by a user to initiate startup of the system. Upon startup, receipt of the login/password may initiate retrieval of configuration settings for sampling system 304. The retrieved settings may contain settings entered into the sampling system 304 and any other information that the onboard system 304 may detect from its own hardware. An example setting may include a sampling schedule and a fluid retention period characterizing a fluid to be sampled.

Some deployment situations (e.g., on a ship) provide limited space for data storage devices, such as an external device associated with analytical system 400a. As such, an amount of data storage space may be limited for such an application. Therefore, an onboard system, 100a or 100b, having sampling system 304, that is deployed in a remote location, without network access, may need to drop sampled data once its limited data storage capacity is exceeded. However, once network 305 access becomes available (e.g., see FIGS. 17 and 18), systems 100a and/or 100b may establish a connection, via network 305, with analytical system 400b that may be implemented in a cloud based computing platform. System 304 may then upload automated sample data to analytical system 400b that was previously stored when sampling system 304 was disconnected from network 305.

Figure 24:
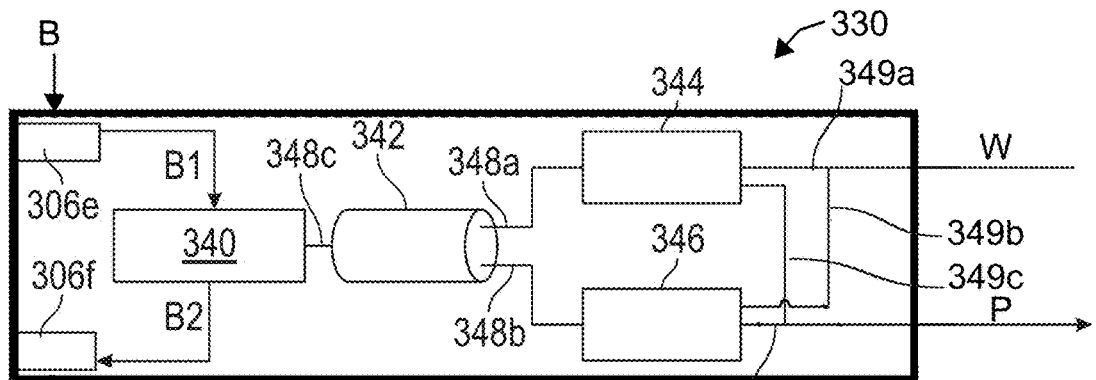
FIG. 24 is a schematic of a sub-sampling system that may be used in the sampling system of FIG. 23, according to an example embodiment of the present disclosure.

FIG. 24 is a schematic of a sub-sampling system 330 that may be used in the sampling system of FIG. 23, according to an example embodiment of the present disclosure. As mentioned above, use of reference character 330 to describe the sub-sampling system of FIG. 24 is for simplicity of illustration and description and does not imply any particular ordering of sub-sampling systems of sampling system 304 of FIG. 23.

Sub-sampling system 330 may be a removable and replaceable component/system that may be "plugged" into sampling system 304 (e.g., see FIG. 23) as necessary to perform specific analyses on a sample of fluid being routed through sampling system 304. Sub-sampling system 330 may generate real-time spectroscopic data regarding the fluid sample. Combining multiple sub-sampling systems 330, 330a, 330b, etc., may be accomplished by simply "plugging" multiple sub-sampling systems 330, 330a, 330b, etc., together during assembly of the sampling system 304, as shown in FIG. 23. The presence of multiple sub-sampling systems 330, 330a, 330b, etc., may allow many different types of fluid samples to be analyzed, and may allow determination of a variety of different characteristics of such samples.

In exemplary embodiments, accurate analysis may be performed and precise data may be obtained from fluid samples by performing electro-optical analysis on sample fluids. Sub-sampling system 330 (e.g., see FIG. 24) may utilize a spectral scanner/spectrometer/custom electro-optical system to instantaneously and continuously scan and record data related to the molecular makeup and condition of any fluids such as, for example, industrial oil and water. Different types of fluids/materials have unique spectroscopic signatures and an electro-optical system may read and determine differences between various fluids. In exemplary embodiments, sub-sampling system 330 may be at least one of a Raman sub-sampling system 330a (e.g., see FIGS. 25A and 25B), a fluorescence sub-sampling system 330b (e.g., see FIGS. 26A and 26B), an absorbance sub-sampling system 330c (e.g., see FIGS. 27A and 27B), a Fourier Transform Infra-Red IR absorbance sub-sampling system 330d (e.g., see FIGS. 28A and 28B), and an absorbance-fluorescence-scatter sub-sampling system 330e (e.g., see FIG. 29). Each type of electro-optical analysis based sub-sampling systems 330, 330a, 330b, etc., may provide complementary methods of analyzing fluids by identifying various components of the fluids.

In exemplary embodiments, sub-sampling system 330 (e.g., see FIG. 24) may include connections between pluggable fluid input and output connectors 306e and 306f. For example, connector 306e may be a female input connector on top of sub-sampling system 330. Similarly, connector 306f may be a male output connector on the bottom of sub-sampling system 330. Connector 306e may be configured to be plugged/snapped together with a complementary suitable connector of another component of sampling system 304. In the example of FIG. 23, connector 306e may plug/snap into fluidic connection with viscometer 328. Similarly, connector 306f may be configured to be plugged/snapped together with a complementary suitable connector of another component of sampling system 304, as described in greater detail below.

Figure 25A:
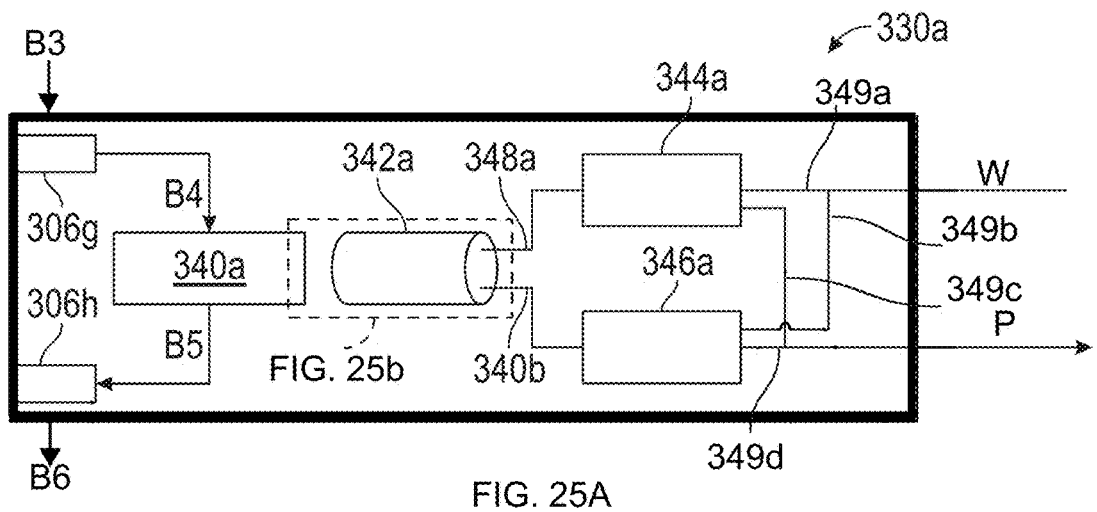
FIG. 25A is a schematic of a Raman sub-sampling system that may be used with the sampling system of FIG. 23, according to an example embodiment of the present disclosure.

In the example of FIG. 23, connector 306f of sub-sampling system 330 (e.g., see FIG. 24) couples with connector 306g of sub-sampling system 330a (e.g., see FIG. 25A). Connector 306g of sub-sampling system 330a, shown in FIG. 25A, may be a female input connector configured to be coupled with corresponding male output connector 306f of sub-sampling system 330. Similarly, output connector 306h of sub-sampling system 330a, shown in FIG. 25A, may be a male output connector that is configured to connect with a complementary connector of sub-sampling system 330b of FIG. 26A, etc.

Connector 306e of sub-sampling system 330, shown in FIG. 24, may be configured to provide a fluidic connection to a continuous-flow or flow-through electro-optical sampling chamber 340. Connector 306e allows fluid to enter connector 306e along path B and to exit connector 306e along path B1. From there, fluid enters electro-optic sampling chamber 340 along path B1 and exits electro-optic sampling chamber 340 along path B2. Fluid then flows into connector 306f along path B2 and exits connector 306f along path B3. As described in greater detail below, with reference to FIG. 25A, fluid enters sub-sampling system 330a through connector 306g along path B3.

As shown in FIG. 24, sub-sampling system 330 may further include a fiber optic probe 342. Fiber optic probe 342 may be connected to excitation source 344 via fiber optic cable 348a. Fiber optic probe 342 may further be connected to detection system 346 via fiber optic cable 348b. Fiber optic probe 342 may receive radiation from excitation source 344 through fiber optic cable 348a and may provide the received radiation to sampling chamber 340 via fiber optic cable 348c. Fiber optic probe 342 may further receive reflected/scattered radiation from sampling chamber 340 via fiber optic cable 348c. Fiber optic probe 342 may then transmit the reflected/scattered radiation, received from sampling chamber 340, to detection system 346 through fiber optic cable 348b.

In an embodiment, sampling chamber 340, illustrated in FIG. 24, may be a glass, quartz, borosilicate, or polystyrene chamber. Sub-sampling system 330 may also include wiring connections W to controller 332 (e.g., see FIG. 23). As was the case with embodiments illustrated in FIGS. 20 and 22, wiring connections W may provide an electrical power connection that provides electrical power to components (e.g., excitation source 344 and detection system 346) of sub-sampling system 330. If, however, if wiring connections W does not provide an electrical power connection to subsystem 330, a separate power connection P may be provided.

Wiring connections W, may provide an electrical connection to controller 332 (e.g., see FIG. 23). In some embodiments, wiring connections W may use a dovetail wiring configuration to inter-connect various components of fluid analysis systems 100a and 100b (e.g., see FIGS. 17 and 18). In an exemplary embodiment, power plug/connection, P, may be connected to a power distribution unit PDU (not shown) inside enclosure 300a or enclosure 300b of fluid analysis systems 100a and/or 100b, respectively. In other embodiments power plug/connection P may be connected to a PDU of sampling system 304 (not shown).

As shown in FIG. 23, for example, fluid may be routed in to sub-sampling system 330 from valve 312a and/or may be routed to viscometer 328. From there, fluid may be routed into sub-sampling system 330 and then into sampling chamber 340 of sub-sampling system 330, as shown in FIG. 24. Once the fluid has been routed into sampling chamber 340 of sub-sampling system 330 an electro-optic analysis of the fluid may be performed.

Controller 332 (e.g., see FIG. 23) may flush a sample of the fluid through the chamber 340 of sub-sampling system 330 (e.g., see FIG. 24) for a certain predetermined period of time. The predetermined period of time may be chosen depending on a fluidic path distance between sampling system 304 (e.g., see FIG. 23) and fluid source 200 (e.g., see FIGS. 17 and 18). Flushing the sample removes previous fluid from other sources 200, 200a, and/or 200b (e.g., see FIGS. 17 to 22) and ensures that a clean sample is provided to sampling chamber 340 (e.g., see FIG. 24). Controller 332 may then close relevant input and output valves (e.g., valves 308a and 308b of FIG. 23) in sampling system 304, and/or input and output valves (e.g., valves 314a, 314b, etc., of FIGS. 19 to 22) in respective cooling systems 302a, 302b, 302c, and 302d to stop fluid flow thereby rendering a still/motionless sample of fluid in sampling chamber 340 of FIG. 24.

Controller 332 (e.g., see FIG. 23) may then be used in conjunction with probe 342, excitation source 344, and detection system 346 (e.g., see FIG. 24) to obtain real-time spectroscopic data regarding composition of the fluid in sampling chamber 340 of FIG. 24. For example, controller 332 may begin collecting samples by triggering excitation source 344 while simultaneously reading resulting real-time data generated by detection system 346. The still/motionless nature of the fluid sample in the sampling chamber 340, after closing input and output valves, may further allow application of time resolved optical spectroscopy to the fluid. Once adequate sampling has been performed on fluid samples and corresponding relevant real-time data has been obtained, fluid may be routed as shown via arrow B3 in FIG. 24 to another sub-sampling system 330a, 330b, etc., and/or fluid may be returned to cooling system 304 (e.g., see FIG. 23).

In exemplary embodiments, controller 332 (e.g., see FIG. 23) may also be configured, based on learned feedback from sampling system 304 of FIG. 23, to adjust a focus of probe 342 (e.g., see FIG. 24) by increasing or decreasing a distance between probe 342 and the sampling chamber 340. While adjusting this distance, controller 332 may continually take optical data samples in an attempt to match a known good focus. The known good focus may be established via pre-determined samples taken from a fluid similar to the specific fluid in question, where the samples may have been previously stored in databases 402a and/or 402b prior to installation of systems 100a and/or system 100b, respectively (e.g., see FIGS. 17 and 18).

A focus calibration process may be issued manually or automatically during a focus run, or the focus calibration process may be based on a baseline standardization sample. In various embodiments, the focal distance of probe 342 may be adjustable during setup (e.g., via commands from controller 332 of FIG. 23) to maximize resolution of optical data samples of the fluid. In an embodiment, controller 332 may automatically adjust the focus of probe 342, using various mechanical positioning devices. For example, a worm gear or other adjuster/glide system may be used to adjust focus of probe 342.

Excitation source 344 and detection system 346 (e.g., see FIG. 24) may be used in tandem to perform fluid analysis. Detection system 346 may act as electro-optical detector for a given excitation source 344. Controller 332 (e.g., see FIG. 23) may inform detection system 346 to prepare for sampling, after which controller 332 may inform the excitation source 344 to generate and deliver electro-magnetic radiation into the fluid sample. Detection system 346 may then register the results of radiation received from the sampling chamber 340 that was launched by the excitation source 344. Excitation source 344 and detection system 346 may receive control signals (e.g., from controller 332 of FIG. 7) from wiring connections W including connections 349a and 349b, respectively. Similarly, excitation source 344 and detection system 346 may receive electrical power through power connection P from connections 349c and 349d, respectively.

In exemplary embodiments, the generation of radiation from excitation source 344 (e.g., see FIG. 24) may occur in milliseconds to seconds depending on the excitation source used and the type of detection required. In an embodiment, excitation source 344 may be a light emitting diode LED source (e.g., LED may be a specific chromatic source, a mono-chromatic source, an ultra-violet (UV) source, etc.), an infrared/near-infrared IR/NIR source, and/or a wavelength stabilized laser (i.e., a specific wavelength laser for excitation). In various embodiments, detection system 346 may be a type of charge-coupled device CCD that may simply report direct data without a spectrometer for filtering, a set of photodiodes with a matching set of spectral filters tuned to respond to specific wavelengths, and/or a spectrometer coupled to a thermally controlled CCD that may detect multiple sources coupled to the spectrometer for filtering.

The excitation source 344 may generate radiation having, wavelengths in a range from 250 nm to 1500 nm. In another embodiment, the electromagnetic radiation may have first wavelengths of about 680 nm, second wavelengths of about 785 nm, and third wavelengths of about 1064 nm. In embodiments including multiple excitation sources, a first excitation source apparatus may include a first laser apparatus and a second excitation source apparatus may include a second laser apparatus. The first laser apparatus may be configured to transmit first electromagnetic radiation having wavelengths of about 680 nm, and the second laser apparatus may be configured to transmit electromagnetic radiation having wavelengths of about 785 nm. In other embodiments, the multiple excitation sources may include a third laser apparatus configured to transmit radiation having wavelengths of about 1064 nm.

An excitation source suitable for Raman spectroscopy may provide electromagnetic radiation in the UV range, for example, 244 nm, 257 nm, 325 nm, 364 nm; visible range, for example, 457 nm, 473 nm, 488 nm, 514 nm, 532 nm, 633 nm, 660 nm; and NIR range, for example, 785 nm, 830 nm, 980 nm, 1064 nm. In further embodiments, an excitation source may provide electromagnetic radiation a wavelength of 785 nm.

In some embodiments, sub-sampling systems (e.g., sub-sampling systems 330, 330a, 330b, etc. of FIG. 23) may be configured to divert approximately 1 to 10 ml of the fluid samples being analyzed into a retrieval storage compartment/container (not shown) within sampling system 304 of FIG. 23. Doing so may allow the fluid sample to be analyzed via Gas Chromatography/Mass Spectrometry if analytical systems 400a or 400b determine that properties of a given sample cannot be accurately identified. In various embodiments, sub-sampling systems 330, 330a, 330b, etc., may include respective ports allowing removal of the compartment/container containing a fluid sample that may be shipped to an external location for further processing and analysis.

FIG. 25A is a schematic of a Raman sub-sampling system 330a that may be used with the sampling system of FIG. 23, according to an example embodiment of the present disclosure. As mentioned above, use of reference character (330a) to describe the Raman sub-sampling system of FIG. 25A is for simplicity of illustration and description and does not imply any particular ordering of sub-sampling systems of sampling system 304 of FIG. 23.

Figure 25B:
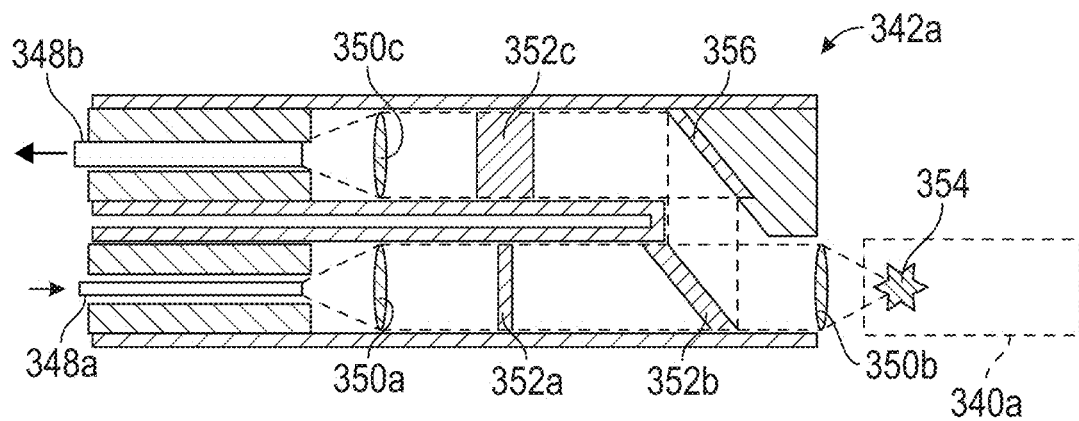
FIG. 25B is a partial cross-sectional view of a Raman probe that may be used in the Raman sub-sampling system of FIG. 25A, according to an example embodiment of the present disclosure.

FIG. 25B is a partial cross-sectional view of a Raman probe 342a that may be used in the Raman sub-sampling system of FIG. 25A, according to an example embodiment of the present disclosure. Raman sub-sampling system 330a includes features that are similar to those of sub-sampling system 330 described above with reference to FIG. 24. For example, Raman sub-sampling system 330a includes connector 306g that receives fluid along path B3 from sub-sampling system 330 described above with reference to FIGS. 23 and 24.

Fluid enters Raman sub-sampling system 330a along path B3 through connector 306g and exits connector 306g along path B4. Fluid then enters sampling chamber 340a along path B4 and exits sampling chamber 340a along path B5. Fluid then enters connector 306h and exits Raman sub-sampling system 330a through connector 306h along path B6. As described in greater detail below, with reference to FIG. 26A, fluid may then enter sub-sampling system 330b along path B6 though connector 306i. Other features of Raman sub-sampling system 330a that are similar to sub-sampling system 330 of FIG. 24 include fiber optic cables 448a and 448b, wiring connections W, and power connection P.

Differences between sub-sampling system 330 of FIG. 24, and Raman sub-sampling system 330a of FIG. 25, relate to Raman probe 342a, excitation source 344a, and detection system 346a. Excitation source 344a and detection system 346a may receive control signals (e.g., from controller 332 of FIG. 7) from wiring connections W including connections 349a and 349b, respectively. Similarly, excitation source 344a and detection system 346a may receive electrical power through power connection P from connections 349c and 349d, respectively.

In exemplary embodiments, spectral data obtained from a fluid sample may be obtained from a Raman sub-sampling system 330a that uses an excitation source having a single frequency, and that uses a specialized Raman probe 342a to capture the frequency shifted light (i.e., Raman scattered light) that characterizes molecular vibrational energy levels. In exemplary embodiments, Raman sub-sampling system 330a may include a specialized Raman probe 342a, a stabilized wavelength laser 344a, and a set of photo diodes and spectral filters as part of detection system 346a that targets frequencies characterizing various Raman shifts.

In various embodiments, sampling chamber 340a, illustrated in FIG. 25A, may be similar to sampling chamber 340 described above with reference to FIG. 24. In this regard, sampling chamber 340a may be a quartz or glass flow-through/continuous flow chamber based on a wavelength and power of the laser 344a. For example, if the laser 344a is in the UV range, then chamber 340a may be a quartz chamber. In exemplary embodiments, laser 344a may be a 785 nm wavelength laser. In various embodiments, Raman probe 342a may be a General Purpose Raman Probe offered by Ocean Optics, Inc.

As shown in FIG. 25B, the excitation electro-magnetic source 344a shown in FIG. 25A may generate radiation that may be emitted into excitation fiber 348a which then enters Raman probe 342a, as shown in FIG. 25B. Inside Raman probe 342a, the radiation may exit excitation fiber optic cable 348a and pass through lens 350a that acts to defocus the radiation. The radiation may then pass through a band-pass frequency filter 352a and a dichroic filter 352b of the Raman probe 342a. Low pass frequency filter 352a, dichroic filter 352b, and low-pass frequency filter 352c (described below) are used to provide selected frequencies/wavelengths to the sampling chamber 340a and to receive selected frequencies/wavelengths from the sampling chamber 340a. For example, in a Raman spectroscopy measurement, incident radiation having a first selected band of frequencies may be incident on the sampling chamber 340a. A Raman signal includes frequencies that have been shifted (i.e., Raman shifted frequencies) from the frequency of the incident radiation. The use of filters 352a, 352b, and 352c, allows proper selection of incident and received frequencies.

Radiation that passes though dichroic filter 352b may propagate through lens 350b, which acts to focus the radiation. The focused radiation may exit Raman probe 342a and enter sampling chamber 340a (e.g., see FIGS. 25A and 25B). Upon entering sampling chamber 340a, the radiation may be focused to a small region 354 of fluid in sampling chamber 340a (e.g., see FIG. 25B). Some of the radiation incident on the small region 354 of fluid may be scattered/reflected back out of the sampling chamber 340a and may re-enter Raman probe 342a through lens 350b which acts to defocus the scattered/reflected radiation. Some of the defocused scattered/reflected radiation may be reflected from dichroic filter 352b and may be directed to mirror 356 (e.g., see FIG. 25B). Radiation hitting mirror 356 may then be reflected from mirror 356 and may propagate through low-pass frequency filter 352c. From there, radiation passing through low-pass frequency filter 352c may be incident on lens 350c which acts to focus the radiation and direct the focused radiation into collection fiber optic cable 348b.

The radiation may then be transported via collection fiber optic cable 348b and may be collected on photodiodes of detection system 346a of FIG. 25A. Raman probe 342a may be used to measure the frequency or equivalently, wavelength shifts (i.e., the Raman shifts) of the excited sample. These Raman shifts may show up as peaks in a spectral graph. The Raman shifts expressed in wavenumber units may be converted to other units (e.g., wavelength, frequency, electron volt eV) via the following formulae:

$$\text{Wavenumbers-Wavelength } \tilde{v} = \frac{1000}{\lambda}$$

$$\text{Wavenumbers-Frequency } \tilde{v} = \frac{v}{100 \cdot c}$$

$$\text{Wavenumbers-Electron volt } \tilde{v} = \frac{e}{h \cdot c} \cdot \frac{E}{100}$$

$\tilde{v}$: Wavenumbers cm$^{-1}$ $\lambda$: Wavelength μm $v$: Frequency $s^{-1}$ $c$: Velocity of light $2.99792458 \cdot 10^8$ m/s $e$: Elementary charge $1.60217733 \cdot 10^{-19}$ C $h$: Planck's constant $6.6260755 \cdot 10^{-34}$ J·s $E$: Energy eV In exemplary embodiments, spectral data of the fluid sample may be obtained by measuring/determining the values of various Raman shifts.

Figure 26A:
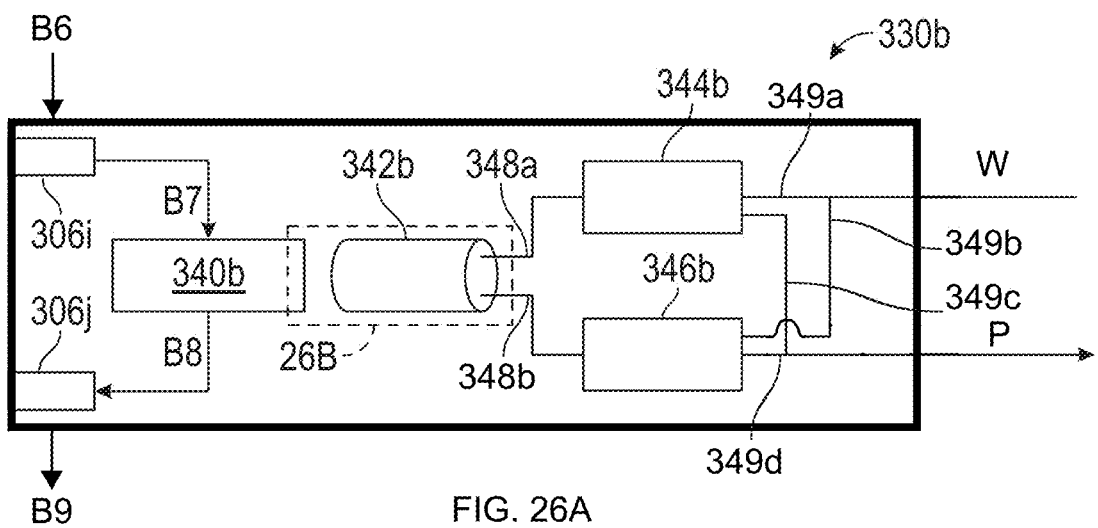
FIG. 26A is a schematic of a fluorescence sub-sampling system that may be used with the sampling system of FIG. 23, according to an example embodiment of the present disclosure.

FIG. 26A is a schematic of a fluorescence sub-sampling system 330b that may be used with the sampling system of FIG. 23, according to an example embodiment of the present disclosure. As mentioned above, use of reference character (330b) to describe the fluorescence sub-sampling system of FIG. 26A is for simplicity of illustration and description and does not imply any particular ordering of sub-sampling systems of sampling system 304 of FIG. 23.

Figure 26B:
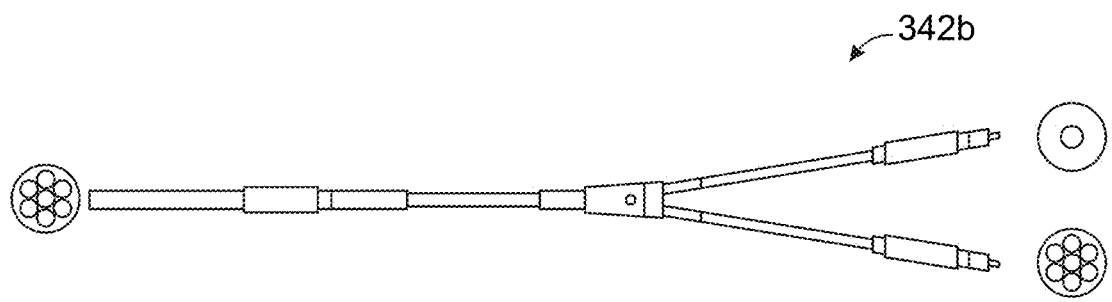
FIG. 26B shows a reflection probe that may be used in the fluorescence sub-sampling system of FIG. 26A, according to an example embodiment of the present disclosure.

FIG. 26B shows a reflection probe 342b that may be used in the fluorescence sub-sampling system of FIG. 26A, according to an example embodiment of the present disclosure. Fluorescence sub-sampling system 330b may include features that are similar to features of sub-sampling systems 330 and 330a described above with reference to FIGS. 24 and 25A, respectively. For example, fluorescence sub-sampling system 330b includes connector 306i that receives fluid along path B6 from sub-sampling system 330a described above with reference to FIGS. 23 and 25A. Fluid enters fluorescence sub-sampling system 330b along path B6 through connector 306i and exits connector 306i along path B7. Fluid then enters sampling chamber 340b along path B7 and exits sampling chamber 340b along path B8. Fluid then enters connector 306j along path B8 and exits fluorescence sub-sampling system 330b through connector 306j along path B9. As described in greater detail below, with reference to FIG. 27A, fluid may then enter sub-sampling system 330c along path B9 though connector 306k. Other features of fluorescence sub-sampling system 330b that are similar to sub-sampling system 330 of FIG. 24, and sub-sampling system 330a of FIG. 25A, include fiber optic cables 348a and 348b, wiring connections W, and power connection P.

Differences between sub-sampling system 330 of FIG. 24, Raman sub-sampling system 330a of FIG. 25A, and fluorescence sub-sampling system 330b of FIGS. 26A and 26B, relate to fluorescence probe 342b, excitation source 344b, and detection system 346b, as described in greater detail below. Excitation source 344b and detection system 346b may receive control signals (e.g., from controller 332 of FIG. 7) from wiring connections W including connections 349a and 349b, respectively. Similarly, excitation source 344b and detection system 346b may receive electrical power through power connection P from connections 349c and 349d, respectively.

Fluorescence spectroscopy based systems utilize electromagnetic spectroscopy to analyze fluorescence from a sample. These systems may involve using a beam of light, usually UV light, that excites electrons in atoms/molecules of certain compounds and, in turn, causes them to emit light; typically, but not necessarily, visible light. Fluorescence sub-sampling/detection systems (e.g., such as fluorescence sub-sampling system 330b of FIG. 26A) generally include: an excitation light source 344b, a fluorophore fluorescent chemical compound that can re-emit light upon light excitation, wavelength filters to isolate emission photons from excitation photons, and a detection system 346b that registers emission photons and produces a recordable output, usually as an electrical signal.

Spectral data of a fluid sample may be obtained from a fluorescence sub-sampling system 330b based on the following technology. Use of a light source 344b (e.g., see FIG. 26A) that emits broadband light (i.e., light including many frequencies) provides photons in various energies. When the light source 344b emits radiation that is directed to be incident on a fluid/oil sample, incident photons penetrate into the sample and interact with atoms/molecules of the sample. Photons having energies equal to a difference in atomic or molecular energy levels may be absorbed. Incident photons that are not absorbed may be scattered. Photons may also be emitted by excited atoms and molecules. Light leaving the sample 340b, therefore, includes scattered and emitted photons that may be detected. Absorbed light in a fluorescence spectrum is seen as attenuated or missing bands of frequencies. The resulting fluorescence spectrum, which is material dependent, may be compared to the incident radiation to provide the desired spectral information that may be used to identify one material relative to another.

In exemplary embodiments, fluorescence sub-sampling system 330b may include a reflection probe 342b, and an electromagnetic radiation source, e.g., LED, UV, or laser source 344b connected to the probe 342b via fiber optic cables 348a, and a detection system 346b connected to probe 342b via fiber optic cables 348b. Sampling chamber 340b may be similar to sampling chamber 340 of FIG. 24, and similar to sampling chamber 340a of FIG. 25A. In this regard, chamber 340b may be configured using any acceptable materials conducive to the collection of optical and/or spectral data. Examples of materials which may form chamber 340b include: quartz or polystyrene flow through cell/ continuous flow chamber. For example, if source 344b is a low power LED source, then chamber 340b may be a polystyrene chamber. In exemplary embodiments, source 344b may be a 240-627 nm LED source. Alternatively, a UV source 344b may be utilized if a wider source spectral range is needed. In an embodiment, reflection probe 342b may be a premium-grade reflection probe manufactured by Ocean Optics, Inc., as illustrated, for example, in FIG. 26A.

In various embodiments, detector 346b may be a fluorometer that may require a spectral filter to block radiation having frequencies equal to those of the excitation source. A spectral filter may also be used to detect other wavelengths from source 344b. In embodiments, detection system 346b may utilize a set of photodiodes with spectral filters. Detection system 346b may also include a CCD device. In either embodiment, a detected fluorescence signal may be converted to an electrical signal by detection system 346b. The converted electrical signal may then be transmitted to the controller 332 (e.g., see FIG. 23), which may determine useful spectral information of the fluid sample.

Figure 27A:
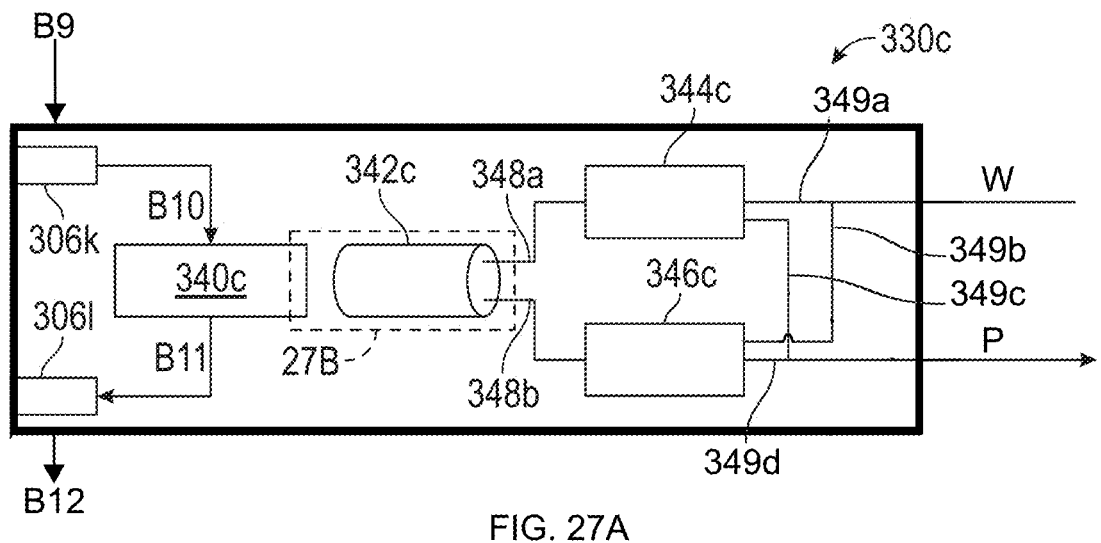
FIG. 27A is a schematic of an absorbance sub-sampling system that may be used with the sampling system of FIG. 23, according to an example embodiment of the present disclosure.

FIG. 27A is a schematic of an absorbance sub-sampling system 330c that may be used with the sampling system of FIG. 23, according to an example embodiment of the present disclosure. As mentioned above, use of reference character 330c to describe the absorbance sub-sampling system of FIG. 27A is for simplicity of illustration and description and does not imply any particular ordering of sub-sampling systems of sampling system 304 of FIG. 23.

Figure 27B:
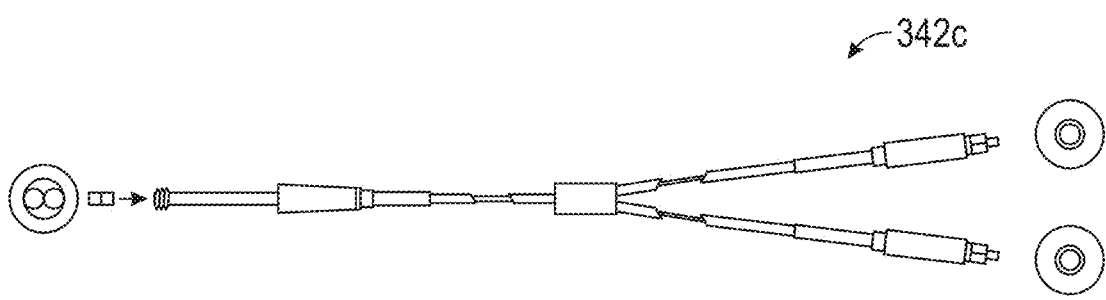
FIG. 27B shows a transmission dip probe that may be used in the absorbance sub-sampling system of FIG. 27A, according to an example embodiment of the present disclosure.

FIG. 27B shows a transmission dip probe 342c that may be used in the absorbance sub-sampling system 330c of FIG. 27A, according to an example embodiment of the present disclosure.

Absorbance sub-sampling system 330c may include features that are similar to features of sub-sampling systems 330, 330a, and 330b, described above with reference to FIGS. 24, 25, and 26, respectively. For example, absorbance sub-sampling system 330c includes connector 306k that receives fluid along path B9 from sub-sampling system 330b described above with reference to FIGS. 23 and 26A.

Fluid enters absorbance sub-sampling system 330c along path B9 through connector 306k and exits connector 306k along path B10. Fluid then enters sampling chamber 340c along path B10 and exits sampling chamber 340c along path B11. Fluid then enters connector 306e along path B11 and exits absorbance sub-sampling system 330c through connector 306e along path B12. As described in greater detail below, with reference to FIG. 28A, fluid may then enter sub-sampling system 330d along path B12 though connector 306m. Other features of absorbance sub-sampling system 330c that are similar to sub-sampling system 330 of FIG. 24, sub-sampling system 330a of FIG. 25, and sub-sampling system 330b of FIG. 26A, include fiber optic cables 348a and 348b, wiring connections W, and power connection P.

Differences between sub-sampling system 330 of FIG. 24, Raman sub-sampling system 330a of FIG. 25A, fluorescence sub-sampling system 330b of FIG. 26A, and absorbance sub-sampling system 330c of FIGS. 27A and 27B, relate to transmission dip probe 342c, excitation source 344c, and detection system 346c, as described in greater detail below. Excitation source 344c and detection system 346c may receive control signals (e.g., from controller 332 of FIG. 23) from wiring connections W including connections 349a and 349b, respectively. Similarly, excitation source 344c and detection system 346c may receive electrical power through power connection P from connections 349c and 349d, respectively.

Absorbance spectroscopy, commonly referred to as spectrophotometry, is the analytical technique based on measuring an amount of light absorbed by a sample at a given frequency or equivalently, at a given wavelength. Molecular absorption spectroscopy in the UV and visible portions of the electro-magnetic spectrum characterizes measured absorption of radiation in its passage through a gas, a liquid, or a solid. Generally, the wavelength region used may be from approximately 190 nm to 1000 nm, and the absorbing medium may be at room temperature.

In disclosed embodiments, obtaining spectral data of a sample via absorbance spectroscopy may include methods similar to those described above, with reference to FIG. 26A, for obtaining spectral data characterizing a sample via fluorescence spectroscopy. In exemplary embodiments, a broadband light source 344c may emit radiation that may be directed to be incident on a sample 340c. Radiation emerging from the sample 340c may then be collected and the frequency content of the light may be analyzed by detection system 346c. The molecular composition of the sample may then be analyzed and determined by comparing the frequency of incident light that with frequencies of transmitted light.

In exemplary embodiments, absorbance sub-sampling system 330c may include a transmission dip probe 342c, a NIR source 344c connected to probe 342c via fiber optic cables 348a, and a detection system 346c connected to transmission dip probe 342c via fiber optic cables 348b. Detection system 346c measures output transmission of electro-magnetic radiation originating from source 344c, after passing through the sampling chamber 340c, and returning to detection system 346c. A calculated difference in intensity of input and output electro-magnetic radiation as a function of frequency or equivalently vs. wavelength is the absorbance spectrum. Such an absorbance spectrum provides a useful characterization of a material sample.

Sampling chamber 340c of FIG. 27A may be similar to sampling chamber 340 of FIG. 24, sampling chamber 340a of FIG. 25A, and sampling chamber 340b of FIG. 26A. In this regard, chamber 340c may be a quartz flow-through cell/continuous flow chamber.

In exemplary embodiments, source 344c may include a NIR source emitting radiation having wavelengths from 1000 nm to 5000 nm. Source 344c may be connected to transmission dip probe 342c via fiber optic cables 348a. Alternatively, as described above, a UV source 344c may be utilized if a wider source range is needed. In some embodiments, source 344c may generate radiation having IR and/or visible wavelengths (e.g., in a wavelength range from 100 nm to 10,000 nm). In an embodiment, transmission dip probe 342c may be a TP300-Series Transmission Probe offered by Ocean Optics, Inc., as illustrated, for example, in FIG. 27B. In various embodiments, detection system 346c may utilize a CCD or a set of photodiodes with spectral filters. The spectral filters may be configured to measure intensity of resultant transmitted electro-magnetic energy vs. wavelength or equivalently vs. frequency in comparison to a spectrum of electro-magnetic radiation emitted by source 344c.

Figure 28A:
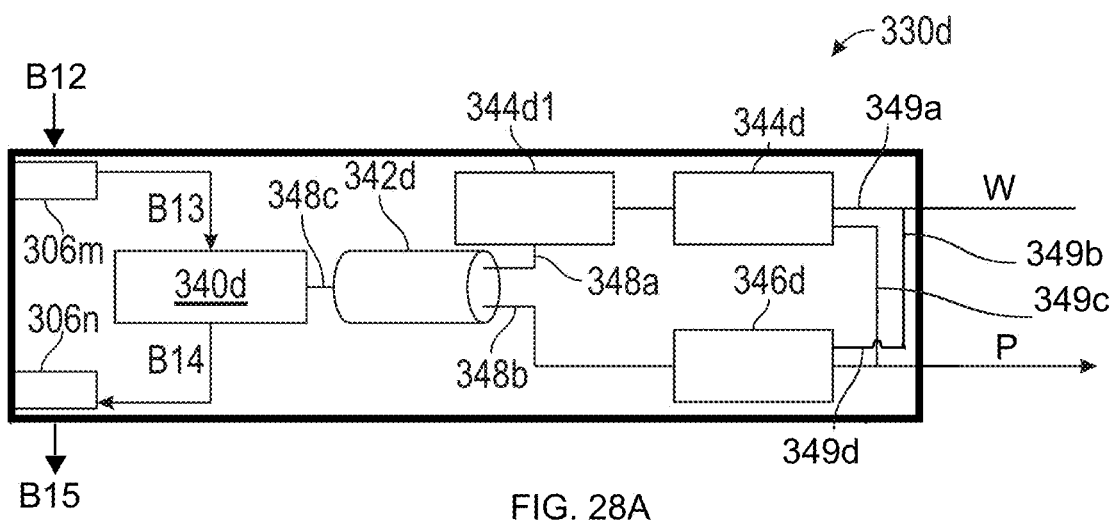
FIG. 28A is a schematic of a Fourier Transform Infra-Red (FTIR) absorbance sub-sampling system that may be used with the sampling system of FIG. 23, according to an example embodiment of the present disclosure.

FIG. 28A is a schematic of a Fourier Transform Infra-Red (FTIR) absorbance sub-sampling system 330d that may be used with the sampling system of FIG. 23, according to an example embodiment of the present disclosure. As mentioned above, use of reference character 330d to describe the FTIR absorbance sub-sampling system of FIG. 28B is for simplicity of illustration and description and does not imply any particular ordering of sub-sampling systems of sampling system 304 of FIG. 23.

Figure 28B:
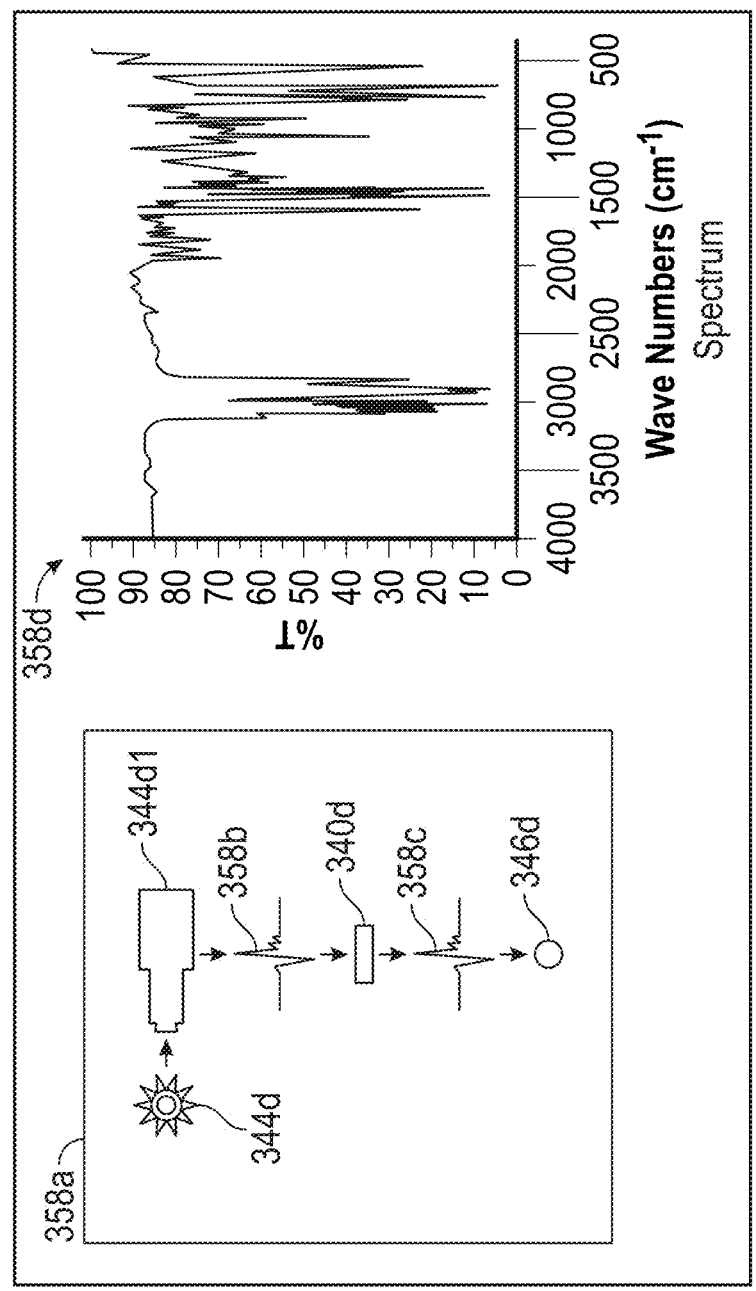
FIG. 28B is an illustration of an FTIR process performed by the FTIR absorbance sub-sampling system of FIG. 28A, according to an example embodiment of the present disclosure.

FIG. 28B is an illustration of an FTIR process performed by the FTIR absorbance sub-sampling system 330d of FIG. 28A, according to an example embodiment of the present disclosure.

FTIR absorbance sub-sampling system 330d may include features that are similar to features of sub-sampling systems 330, 330a, 330b, and 330c, described above with reference to FIGS. 24, 25, 26, and 27, respectively.

For example, FTIR absorbance sub-sampling system 330d includes connector 306m that receives fluid along path B12 from sub-sampling system 330c described above with reference to FIGS. 27A and 27B. Fluid enters FTIR absorbance sub-sampling system 330d along path B12 through connector 306m and exits connector 306m along path B13. Fluid then enters sampling chamber 340d along path B13 and exits sampling chamber 340d along path B14. Fluid then enters connector 306n along path B14 and exits absorbance sub-sampling system 330d through connector 306n along path B15. As described in greater detail below, with reference to FIG. 29, fluid may then enter sub-sampling system 330e along path B15 though connector 306o. Other features of absorbance sub-sampling system 330d that are similar to sub-sampling system 330 of FIG. 24, sub-sampling system 330a of FIG. 25A, sub-sampling system 330b of FIG. 26A, and sub-sampling system 330c of FIG. 27A, include fiber optic cables 348a, 348b, and 348c, wiring connections W, and power connection P.

Differences between sub-sampling system 330 of FIG. 24, Raman sub-sampling system 330a of FIG. 25A, fluorescence sub-sampling system 330b of FIG. 26A, absorbance sub-sampling system 330c of FIG. 27, and FTIR absorbance sub-sampling system 330d of FIG. 28A, relate to probe 342d, excitation source 344d, interferometer 344d1, and detection system 346d. Excitation source 344d and detection system 346d may receive control signals (e.g., from controller 332 of FIG. 23) from wiring connections W including connections 349a and 349b, respectively. Similarly, excitation source 344d and detection system 346d may receive electrical power through power connection P from connections 349c and 349d, respectively.

FTIR is a form of absorbance spectroscopy used to obtain an infrared spectrum of absorption or emission of a solid, liquid or gas. An FTIR spectrometer may simultaneously collect high spectral resolution data over a wide spectral range. In exemplary embodiments, obtaining spectral data of a sample via FTIR may include general methods similar to those used for obtaining spectral data of a sample via absorbance spectroscopy, as described above with reference to FIGS. 27A and 27B. For example, infrared IR radiation may be first passed through the sample. Some of the IR radiation may be absorbed by the sample and some of it may pass through (i.e., may be transmitted). The resulting spectrum characterizes the molecular absorption and transmission, thereby creating a specific spectral pattern representative of the sample. The spectral data includes absorption peaks which correspond to the frequencies of vibrations between the bonds of the atoms making up the sample. Because each different material constitutes a unique combination of atoms, no two compounds produce the exact same IR spectrum, thereby allowing for positive identification of different kinds of material via qualitative/quantitative analysis. In fact, the size of the absorption peaks in the spectrum may be used to determine relative amounts of each material present in the sample.

In exemplary embodiments, FTIR absorbance sub-sampling system 330d may include features that are similar to features of absorbance sub-sampling system 330c, described above, including a transmission dip probe 342d, a NIR source 344d, and detector 346d. FTIR absorbance sub-sampling system 330d may further include an interferometer 344d1 between source 344d and probe 342d to measure response to an entire range of wavelengths of a sample at once, as illustrated, for example, in FIGS. 28A and 28B.

In various embodiments, chamber 340d may be a quartz flow-through cell/continuous flow chamber. In exemplary embodiments, source 344d may be a 1000 nm to 5000 nm NIR source connected to transmission dip probe 342d via fiber optic cable 348a.

Inset 358a of FIG. 28B is an illustration of a process of performing a measurement using FTIR absorbance sub-sampling system 330d. In a first stage 1, an IR beam may be emitted from the source 344d towards interferometer 344d1. In stage 2, the IR beam may then enter interferometer 344d1 which transforms the IR beam to generate an interferogram signal 358b. The interferogram signal 358b may then exit the interferometer and may propagate toward sampling chamber 340d. In stage 3, the interferogram signal 358b may be transmitted through or reflected off of the surface of the fluid sample in chamber 340d, depending on the type of analysis being accomplished. Components of the incident beam are absorbed at specific frequencies. The specific absorbed components characterize the material in sampling chamber 340d. In stage 4, output signal 358c from the sample is passed to detection system 346d for measurement.

Detection system 346d may be specially designed to measure the special interferogram signal 358c. The measured signal may then be digitized and sent to controller 332 in sampling system 304 (e.g., see FIG. 23), which may send the signal to analytical system 400a or 400b. Analytical system 400a or 400b may perform a Fourier Transform on the detected signal to generate the final IR spectrum. Comparing the FTIR spectrum to a background spectrum measurement with no sample in the beam may allow for identification of spectral features generated by the sample. In exemplary embodiments, analytical system 400a or 400b (e.g., see FIGS. 17 and 18) may decode the signal received from controller 332 using FTIR calculations to obtain the spectral data of a fluid sample, as shown, for example, in inset 358d of FIG. 28A.

Figure 29:
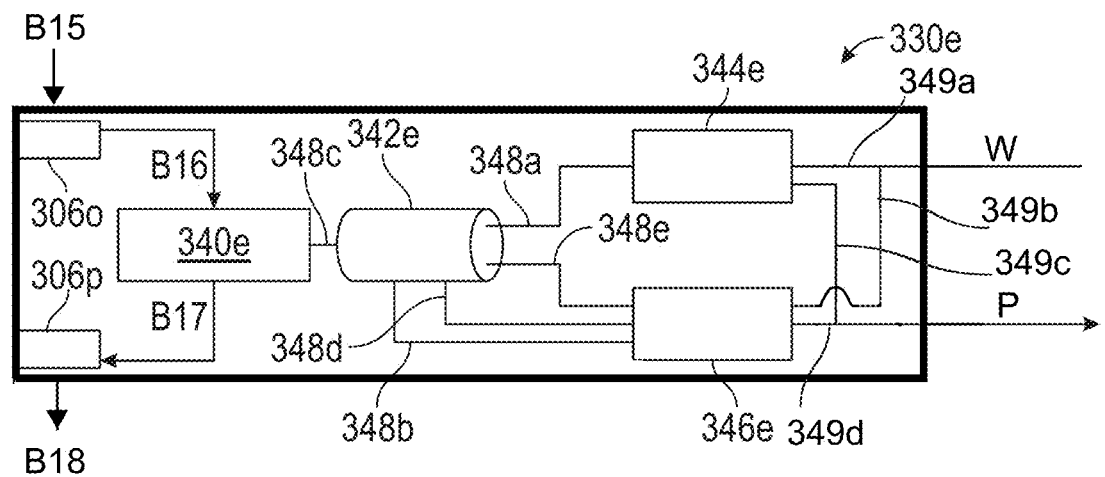
FIG. 29 is a schematic of an absorbance/fluorescence/scatter sub-sampling system that may be used with the sampling system of FIG. 23, according to an example embodiment of the present disclosure.

FIG. 29 is a schematic of an absorbance/fluorescence/scatter sub-sampling system 330e that may be used with the sampling system of FIG. 23, according to an example embodiment of the present disclosure. Absorbance/fluorescence/scatter sub-sampling system 330e may include features that are similar to features of sub-sampling systems 330, 330a, 330b, 330c, and 330d, described above with reference to FIGS. 24 to 28, respectively. For example, absorbance/fluorescence/scatter sub-sampling system 330e includes connector 306o that receives fluid along path B15 from sub-sampling system 330d described above with reference to FIGS. 28A and 28B. Fluid enters absorbance/fluorescence/scatter sub-sampling system 330e along path B15 through connector 306o and exits connector 306o along path B16. Fluid then enters sampling chamber 340e along path B16 and exits sampling chamber 340e along path B17. Fluid then enters connector 306p along path B17 and exits absorbance sub-sampling system 330e through connector 306p along path B18. Fluid leaving along path B18 may then flow into other sub-sampling systems of sampling system 304 or may flow out of sampling system 304 along path D, as discussed above and illustrated, for example, in FIG. 23.

Other features of absorbance sub-sampling system 330e that are similar to sub-sampling system 330 of FIG. 24, sub-sampling system 330a of FIG. 25A, sub-sampling system 330b of FIG. 26A, sub-sampling system 330c of FIG. 27A, and sub-sampling system 330d of FIG. 28A, include fiber optic cables 348a, 348b, and 348c, wiring connections W, and power connection P.

Differences between sub-sampling system 330 of FIG. 24, Raman sub-sampling system 330a of FIG. 25A, fluorescence sub-sampling system 330b of FIG. 26A, absorbance sub-sampling system 330c of FIG. 27A, and FTIR absorbance sub-sampling system 330d, relate to probe 342e, excitation source 344e, and detection system 346e, as well as additional fiber optic cables 348d and 348e, that connect probe 342e to detection system 346e. Excitation source 344e and detection system 346e may receive control signals (e.g., from controller 332 of FIG. 23) from wiring connections W including connections 349a and 349b, respectively. Similarly, excitation source 344e and detection system 346e may receive electrical power through power connection P from connections 349c and 349d, respectively.

Absorbance/fluorescence/scatter sub-sampling system 330e may combine features of both the fluorescence 330b and absorbance 330c sub-sampling systems described above with reference to FIGS. 26A and 27A, respectively. In exemplary embodiments, absorbance/fluorescence/scatter sub-sampling system 330e may include a reflection and/or transmission dip probe 342e, multiple sources 344e connected to the probes 342e, and a detection system 346e connected to the probes 342e that may measure the output transmission from the sources 344e after passing through the sampling chamber 340e, where the difference between the input and output vs. frequency is the absorption spectrum. The absorption spectrum serves as the spectral data of the sample.

In various embodiments, chamber 340e may be a flow-through cell/continuous flow chamber. As described above, chamber 340e may be quartz flow-through cell. In other embodiments, other suitable materials may be used for chamber 340e based on their ability to transmit incident electromagnetic radiation. In exemplary embodiments, sources 344e may include multiple sources independently connected to reflection and/or transmission dip probes 342e via fiber optic cables 348a.

In various embodiments, detection system 346e may utilize a CCD or a set of photodiodes with spectral filters for measuring intensities of various frequency components compared to those of the source 344e. In example embodiments, the use of multiple sources 344e may require additional fiber optic cables, 348d and 348e, connected to probe 342e with multiple fiber optic receivers for each cable 348d, 348e, etc. (i.e., a different set of photo diodes in detection system 346e for detection of spectral data from the sample for each type of spectroscopy system used). Using additional fiber optic cables, 348d and 348e, may allow measurement of different types of spectral information through application of various spectral filters for a given excitation source 344.

Although various embodiments described herein refer to analysis of oil, fluid analysis systems 100a and 100b, as described above with reference to FIGS. 17 and 18, including cooling system 302, sampling system 304, and/or analytical systems 400a and 400b, may be used to analyze properties of other types of fluids, including water. In an exemplary embodiment, fluid analysis systems 100a and 100b may be a water analysis system. In embodiments of systems 100a and 100b, water may be routed from a water source 200 (e.g., a reservoir), into cooling system 302 and/or directly into sampling system 304 to obtain real-time data regarding the fluid. For example, water may be analyzed in disclosed embodiments to determine a presence of microorganisms, nitrate, and arsenic.

In various embodiments, cooling system 302, sampling system 304, and/or analytical systems 400a and 400b of water analysis systems 100a and 100b may include features that are similar to oil analysis systems 100a and 100b described above with reference to FIGS. 18 to 23. However, in some embodiments, cooling system 302 of water analysis systems 100a and 100b may not include a filter 320 (e.g., see FIGS. 19 to 22). As in oil analysis system 100a and 100b, cooling system 302 may not be utilized in water analysis systems 100a and 100b if water is at a sufficiently low temperature for analysis via sampling system 304. In various embodiments, sampling system 304 of water analysis systems 100a and 100b may or may not include a viscometer 328 (e.g., see FIG. 23).

Although fluid analysis systems 100a and 100b are shown in FIGS. 18 to 29, and described above as having specific configurations/features/applications, these systems are not limited to these particular configurations/features/applications and other configurations/features/applications may be utilized as suitable to perform analysis of various types of fluids.

Figure 30A:
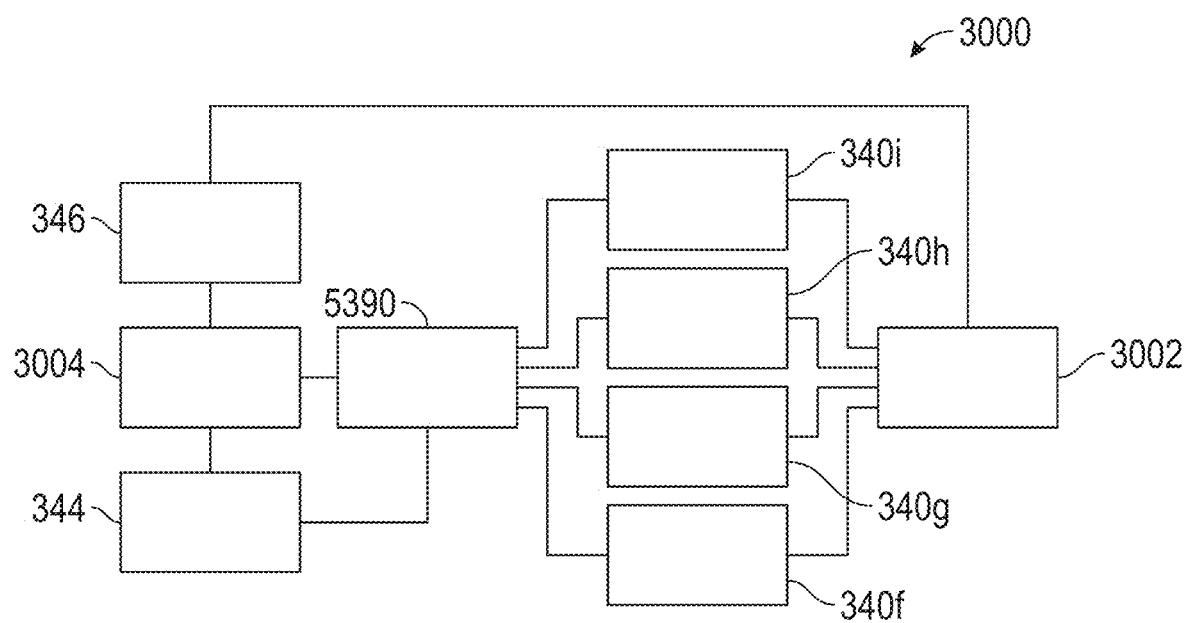
FIG. 30A is a schematic of a multi-source fluid sampling system, according to an example embodiment of the present disclosure.

FIG. 30A is a schematic of a multi-source fluid sampling system 3000, according to an example embodiment of the present disclosure. System 3000 includes a single excitation source 344, a single detection system 346, and a plurality of sample chambers 340f, 340g, 340h, and 340i. In this example, each of the sample chambers 340f, 340g, 340h, and 340i may be directly connected to respective fluid sources (not shown). For example, fluid sources may be internal combustion engines, generators, or other mechanical devices containing fluids of interest. In this example, four sources may be accommodated. Other numbers of fluid sources may be accommodated in other example embodiments. For example, an embodiment may have 5 fluid sources, 6 fluid sources, 7 fluid sources 8, fluid sources, etc.

System 3000 may further include an optical switch 5390 that may be configured to route electromagnetic energy, received from excitation source 344, to the various sample chambers 344f, 344g, 344h, and 344i. Electromagnetic radiation received from optical switch 5390 may thereby interact with fluid in respective sample chambers 344f, 344g, 344h, and 344i. System 3000 may further include passive optical coupler 3002. Optical coupler 3002 may be configured to receive electromagnetic radiation emitted by fluid in sample chambers 344f, 344g, 344h, and 344i, in response to interaction of the electromagnetic radiation received from optical switch 5390. The radiation received by optical coupler 3002 may be combined and provided to optical detection system 346 via optical fiber cables. System 3000 may further include control hardware 3004 which may include control circuitry and/or one or more computational devices.

According to an embodiment, excitation source 344 may be a single Raman laser and detection system 346 may include a single spectrometer. In further embodiments, the excitation system 344 may include two or more lasers that generate electromagnetic radiation at two or more respective frequencies. In certain embodiments, optical switch 5390 may be configured to direct the Raman laser excitation signal to one sample test chamber at a time. In another embodiment, the Raman laser signal may be split or routed to multiple sample test chambers simultaneously.

Optical switch 5390 may be controlled by a combination of controller hardware 3004 and/or software that may select a specific sample chamber to which the Raman laser excitation signal may be routed. Following sample excitation by a Raman laser 344 excitation signal, sample Raman emission data may be collected by a single Raman emission detector 346 by using optical coupler 3002. Optical coupler 3002 may merge collection optical fibers of respective sample chambers into a single optical connection. The single optical connection may be further connected to a Raman spectrometer 346 configured to collect Raman emission data.

In certain embodiments, when the Raman excitation signal is routed to one sample chamber at a time via optical switch 5390, optical coupler 3002 may passively sum the Raman emission signal from each sample test chamber. Raman emission signals derived from each sample test chamber may be continuously communicated to Raman spectrometer 346. Use of passive optical coupler 3002 may be advantageous in that it generally exhibits less attenuation of the Raman emission signal compared to use of a second optical switch for routing Raman emission signals to a single detection system. For example, a passive coupler (e.g., such optical coupler 3002) may exhibit only marginal signal attenuation, while an active optical switch (e.g., such as optical switch 5390) may attenuate the signal by an amount on the order of 15% of the signal, even for high-performance switches.

Figure 30B:
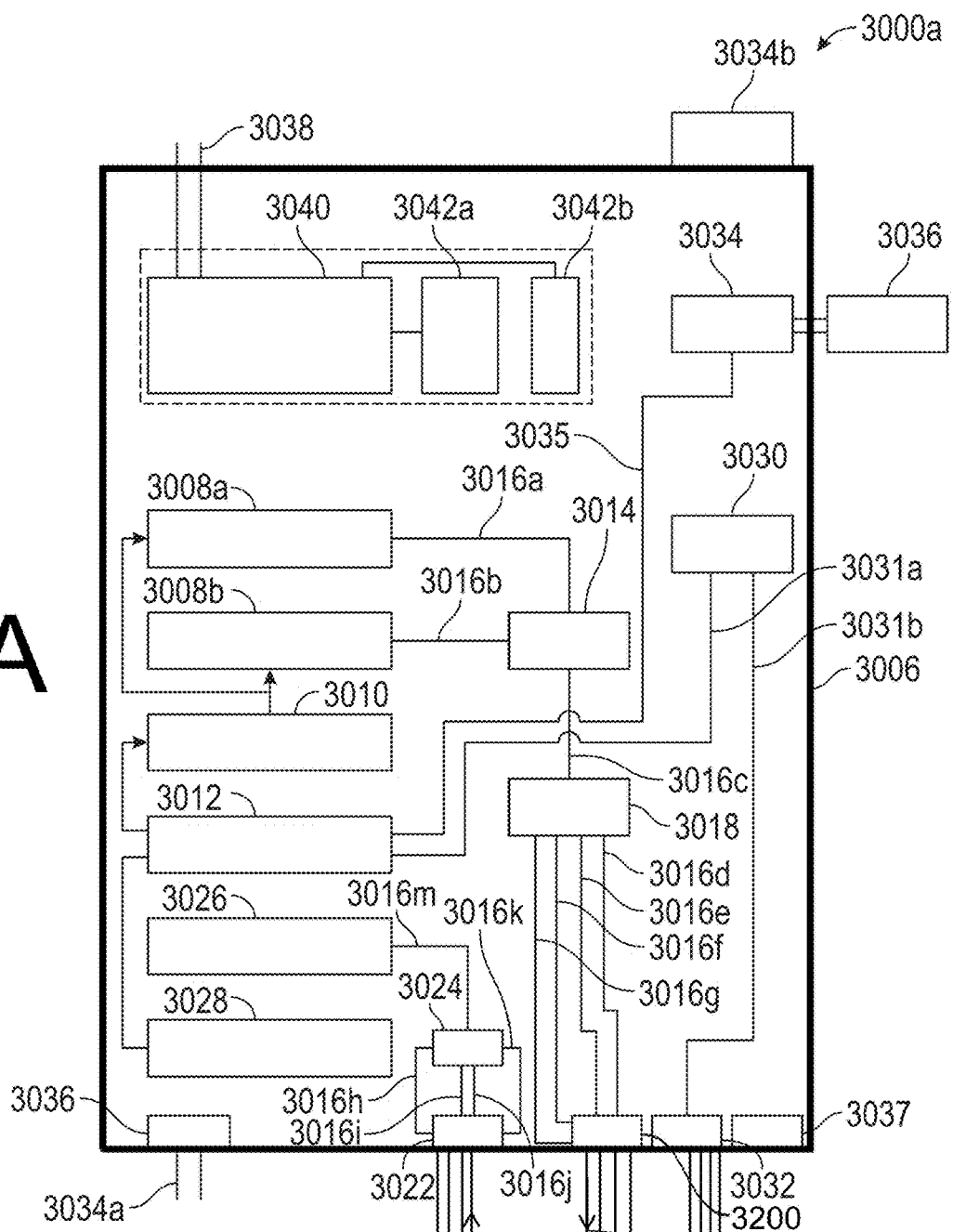
FIG. 30B is a schematic of a fluid sampling system, according to an example embodiment of the present disclosure.

FIG. 30B is a schematic of a fluid sampling system 3000a, according to an example embodiment of the present disclosure. System 3000a includes multiple excitation sources, an optical switch, power, and control circuitry, according to an example embodiment of the present disclosure. System 3000a may provide an advantage in that all of the electronic and optical components may be housed in a single enclosure 3006. As described in greater detail below with reference to FIGS. 30B and 30C, system may be passively or actively cooled. Such cooling may provide improved performance of excitation sources (e.g., lasers, LEDs, etc.) and detection systems (e.g., CCD devices). As described below, system 3000a may be actively cooled to a temperature of 100° C. below ambient temperature. In other embodiments, other temperatures may be achieved including 5° C. below ambient, 10° C. below ambient, 20° C. below ambient, etc. Such cooling may allow greatly improved signal detection.

System 3000a, indicated in the top part of FIG. 30B (part A, shown above the dashed line) contains all of the electrical and optical systems that may be housed in a rugged, water tight enclosure 3006. As described in greater detail below, system 3000a provides fiber optic connections to external systems (part B, shown below the dashed line). In this way, fluids associated with external systems (B, below the dashed line) are kept separate from the electrical and optical components of system 3000a (A, above the line).

In this example, system 3000a may include first 3008a and second 3008b excitation sources. For example, excitation source 3008a may be a laser that emits electromagnetic radiation at a wavelength of 785 nm. Further excitation source 3008b may be a laser that emits electromagnetic radiation at a wavelength of 680 nm. On other embodiments, various other excitation sources may be provided that generate various wavelengths of electromagnetic radiation (e.g., IR, visible, UV, etc.) Excitation sources 3008a and 3008b may both be electrically connected to, and controlled by, an excitation source controller 3010. Excitation source controller 3010 may further be coupled to programmable micro-controller 3012. Micro-controller 3012 may serve as a master controller for system 3000a and may generate control signals for the various sub-systems and may communicate data with external systems.

In exemplary embodiments, controller 3012 may be the Raspberry Pi 3 Model B, Raspberry Pi Zero, or Raspberry Pi 1 Model A+. In other embodiments, controller 3012 may be the Mojo Board V3 offered by Embedded Micro—an FPGA (Field Programmable Gate Array) with multiple pre-made shields. In further embodiments, any other suitable controller 3012 may be used.

Electromagnetic radiation generated by excitation sources 3008a and 3008b may be provided to an optical combiner 3014 (e.g. dichroic combiner) by respective optical fiber cables 3016a and 3016b. Electromagnetic radiation provided to optical combiner 3014 (e.g. dichroic combiner) may be provided to optical switch 3018 via optical fiber cable 3016c.

Electromagnetic radiation may be provided to optical output connectors 3020 via various fiber optic cables 3016d, 3016e, 3016f, 3016g, etc. Optical output connectors 3020 may be used to provide optically switchable electromagnetic radiation to a plurality of external sampling chambers (e.g., sample chambers 340f, 340g, 340h, 340i, etc., of FIG. 30A).

In this example, optical output connectors 3020 are shown providing electromagnetic radiation to external systems E1, E2, E3, and E4 through respective fiber optic cables 3017d, 3017*e*, 3017*f*, and 3017*g*. Systems E1, E2, E3, and E4 may be sampling chambers associated with respective fluid sources.

After interacting with fluid samples in one or more external sampling chambers (e.g., of systems E1, E2, E3, and E4), electromagnetic radiation may be received by system 3000*a* via optical input connectors 3022. Electromagnetic radiation may be received by optical input connectors 3022 via various fiber optic cables 3017*h*, 3017*i*, 3017*j*, 3017*k*, etc. Electromagnetic radiation received by optical input connectors 3022 may be provided to optical coupler 3024 via various fiber optic cables 3016*h*, 3016*i*, 3016*j*, 3016*k*, etc. Electromagnetic radiation may be combined by combiner 3024 and then provided to detection system 3026 via fiber optic cable 3016*m*. Data generated by detection system 3026 may then be provided to controller 3012. As described above, other sensors (e.g., sensors S1, S2, S3, and S4) may be provided to measure other quantities such as viscosity, temperature, particle counts, etc. Information from the various sensors may be gathered by a sensor board 3028, which in turn, may provide such sensor data to controller 3012.

System 3000*a* may further include a CAN controller 3030 that may communicate with controller 3012 via connector 3031*a* and may communicate with external systems through CAN connections 3032 through connection 3031*b*. As described above, CAN controller 3030 may receive data from various external sensors S1, S2, S3, and S4 through respective electrical or optical channels 3044*a*, 3044*b*, 3044*c*, and 3044*d*, as described below. For example, sensors S1, S2, S3, S4, may be configured to generate data from one or more external systems. For example, sensors S1, S2, S3, and S4 may include temperature and/or viscometers that may make measurements on respective systems E1, E2, E3, E4.

Data generated by detection system 3026 may also be communicated to external systems through CAN connections 3032 through various connections 3044*a*, 3044*b*, 3044*c*, and 3044*d*. System 3000*a* may further include a cellular modem 3034 that may communicate through wireless channels with external systems by providing signals to one or more communication devices 3036. In an embodiment, communication device 3036 may be an antenna that generates wireless signals. Cellular modem 3034 may further communicate with and receive control signals from controller 3012 via electrical or optical connection 3035.

System 3000*a* may further include an external power supply connection 3038 that may be connected to an AC/DC converter 3040 and one or more DC current/voltage supplies 3042*a* and 3042*b*. Communication between system 3000*a* and various other systems may be provided through connections to a wiring harness 3037.

System 3000*a* may be cooled with one or more cooling systems. For example, system 3000*a* may include an air intake vent 3034*a* and an air exhaust vent 3034*b*. A fan 3036 may further be provided to force air from the air intake vent 3034*a* to the air exhaust vent 3034*b* to thereby remove waste heat from enclosure 3006 generated by the various components of system 3000*a*. Forced air cooling, as provided by vents 3034*a* and 3034*b* and fan 3036 (e.g., see FIG. 30B) only removes heat generated by components within system 3000*a*. As such, forced air cooling may only be used to keep fluid sampling system 3000*a* at an ambient temperature. In certain circumstances, it may be advantageous to actively cool detection system 3026 or other components to a temperature below ambient temperature.

System 3000*a* may further be configured to include one or more cooling additional cooling systems 3036 for cooling one or more components of the optical path, as described in great detail below with reference to FIG. 30B. The optical path may be defined to include any component that transmits, routes, receives, and detects electromagnetic radiation as part of system 3000*a*. For example, components of the optical path may include: optical excitation sources 3008*a* and 3008*b*, excitation source controller 3010, controller 3012, optical combiner 3014 (e.g. dichroic combiner), optical switch 3018, optical fiber cables (e.g., optical fiber cables 3016*a*, 3016*b*, 3016*c*, 3016*d*, 3016*e*, 3016*f*, 3016*g*, 3016*h*, 3016*h*, 3016*i*, and 3016*j*), optical output connectors 3020, optical input connectors 3022, optical coupler 3024 (e.g. optical coupler 3024 couples the optical signal from similar diameter optical fibers into a larger diameter optical fiber), detection system 3026, sensor board 3028, and one or more sampling chambers (e.g., sample chambers 340*f*, 340*g*, 340*h*, 340*i*, etc. of FIG. 30).

Figure 30C:
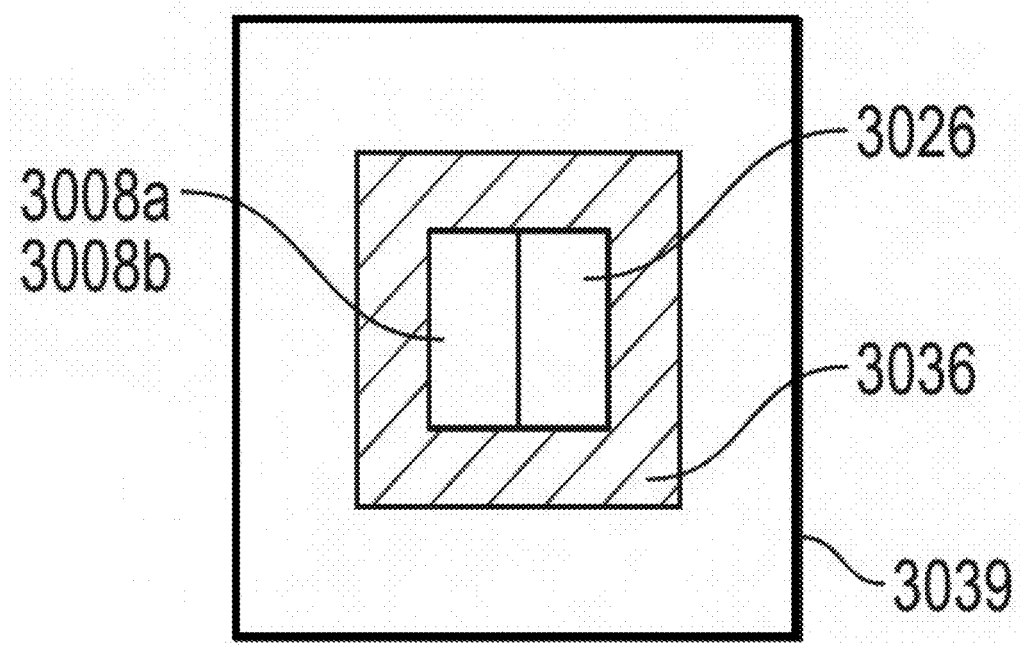
FIG. 30C is a schematic of a cooling system, according to an example embodiment of the present disclosure.

FIG. 30C is a schematic of a cooling system 3036, according to an example embodiment of the present disclosure. In this example, excitation sources 3008*a* and 3008*b* and detection system 3026 are provided with an active cooling system 3036, according to an example embodiment of the present disclosure. Cooling of optical path components may reduce optical signal interference or noise associated with detection of optical signals by components subject to elevated thermal exposure. Any component of the optical path may be cooled individually, or any combination of components of the optical path may be cooled, including the entire optical path. In addition to cooling the optical path, embodiments may also be configured to cool one or more power supplies (e.g., 3040, 3042*a*, and 3042*b*) of system 3000*a*.

Cooling system 3036 may cool detection system 3026 and other components (e.g., excitation sources 3008*a* and 3008*b*) to a temperature below ambient temperature. In an embodiment, refrigeration system 3036 may cool detection system 3026 to a temperature of 100° C. below ambient temperature. In other embodiments, other temperatures may be achieved including 5° C. below ambient, 10° C. below ambient, 20° C. below ambient, etc. In some embodiments, detection system 3026 and refrigeration system 3036 may be housed in an enclosure 3038.

Refrigeration system 3036 may include any mechanism that removes heat from the region to be cooled. For example, cooling of the optical path may be accomplished through the use of thermoelectric cooling, according to an example embodiment of the present disclosure. Thermoelectric cooling uses the Peltier effect to create a heat flux between the junction of two different types of materials. A Peltier cooler, heater, or thermoelectric heat pump is a solid-state active heat pump which transfers heat from one side of the device to the other, with consumption of electrical energy, depending on the direction of the current. Additional cooling methods may utilize liquid cooling via fluids to remove heat from components of the optical path. In certain embodiments, components of the optical path may be immersed in fluids such as a non-conductive mineral oil.

In other embodiments, fluids may be pumped through conduits which are operationally coupled to components of the optical path. As the fluids are circulated, heat of the optical path component is transferred to the fluid. The fluid may then be routed through a radiator to remove the heat. Fluid materials which may be used in liquid cooling systems include: water, mineral oil, liquefied gas, etc.

With system 3000a of FIG. 30B, fluid sampling systems may be configured to collect optical data from multiple sources without the need for a discrete, isolated optical path. In this example, one or more excitation sources 3008a and 3008b may be combined with a single detection system 3026 to collect optical data from a plurality of fluid sources. Optical excitation sources 3008a and 3008b may be connected to an optical combiner 3014 (e.g. dichroic combiner). Optical combiner 3014 combine (or separate) multiple electromagnetic radiation emitted from excitation sources (e.g., lasers) at a 45° angle of incidence. Optical combiner 3014 may be optimized to multiplex (MUX) any specific wavelength of electromagnetic radiation emitted from excitation sources (e.g., lasers). Optical combiner 3014 combine may also be used to demultiplex (DEMUX) any specific wavelength of electromagnetic radiation emitted from excitation sources (e.g., lasers).

In one embodiment, excitation source 3008a and 3008b may have the same or different excitation properties. For example, excitation source 3008a may include a laser excitation source having a wavelength of 680 nm, while excitation source 3008b may include a laser having a wavelength of 785 nm. In alternative embodiments excitation source 3008a may be an infra-red excitation source while excitation source 3008b may be a laser excitation source having a wavelength of 785 nm. While FIG. 30B shows two excitation sources, additional excitation sources may be employed in alternative embodiments. In further embodiments, an optical combiner 3014 may be unnecessary, and therefore may be excluded.

Optical switch 3018 (e.g., see FIG. 30B) may be configured to cycle through a plurality of fluid sources individually via optical fiber cables (e.g., optical fiber cables 3016d to 3016g, etc.). In an alternative embodiment, optical switch 3018 may be configured to divide the electromagnetic radiation emitted from one or more excitation sources (e.g. 3008a and 3008b), such that a portion of the electromagnetic radiation is directed to each of a plurality of fluid sources via optical fiber cables.

Electromagnetic radiation transmitted from one or more excitation sources (e.g. 3008a and 3008b), may be delivered via optical fiber cables (e.g., optical fiber cables 3016d to 3016g, etc.) to optical probes operationally coupled to a plurality of fluid sources either directly (e.g., using an immersion probe directly in the fluid source) or via a sample chamber.

Detection system 3026 may include a CCD device that may be configured to detect electromagnetic radiation emitted from a fluid source. Data may be collected by the CCD device using a process called binning, which may include line and pixel binning. Binning allows charges from adjacent pixels to be combined and this can offer benefits in faster readout speeds and improved signal to noise ratios albeit at the expense of reduced spatial resolution.

A CCD includes a surface including an array of pixels at defined locations which have the ability to receive electromagnetic radiation and convert such electromagnetic radiation into a digital signal. Electromagnetic radiation interacting the pixels along a CCD surface produces an electrical charge in each pixel which may be converted into a digital signal that may be transmitted to a computer for analysis using software. Software may be further used to divide a CCD surface into rows of pixels on a horizontal axis and/or a vertical axis. In certain embodiments, an array of pixels may be divided into vertical rows of pixels spanning a CCD surface. In certain embodiments, an array of pixels may be divided into a group of vertical rows of pixels spanning a CCD surface.

The digital signal associated with the electrical charge of each pixel may be collected along each vertical row of pixels along the CCD surface. The digital signal associated with each vertical row of pixels may be also be summed. Summation of the digital signal along one or more vertical rows of a CCD surface allows for amplification of the digital signal. The CCD surface may be organized into multiple regions including one or more vertical rows of pixels. For example, a CCD having 64 vertical rows of pixels may be divided into four regions of 16 vertical rows each or 32 regions of 2 rows each. In an embodiment in which the CCD surface is divided into four (4) regions having 16 vertical rows of pixels, each row may be associated with up to four (4) different fluid sources. In such an embodiment, optical fluid data may be collected from a total of four (4) fluid sources at one time by transmitting electromagnetic radiation received from each fluid source to a corresponding region of the CCD surface.

Figure 31A:
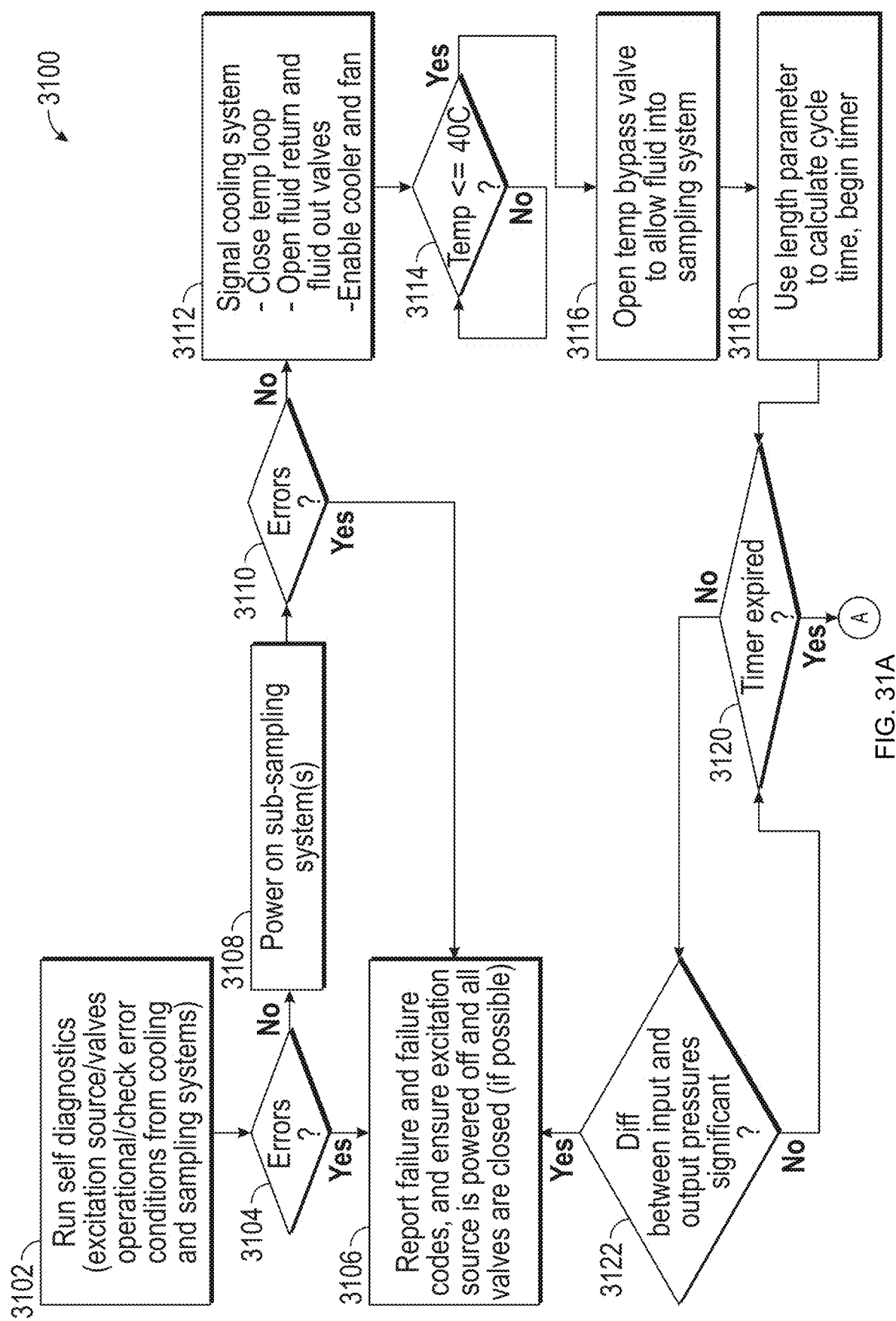
FIG. 31A is a flowchart illustrating a method of operating a fluid analysis system, according to an example embodiment of the present disclosure.

FIG. 31A is a flowchart illustrating a method 3100 of operating a fluid analysis system, according to an example embodiment of the present disclosure.

Figure 31B:
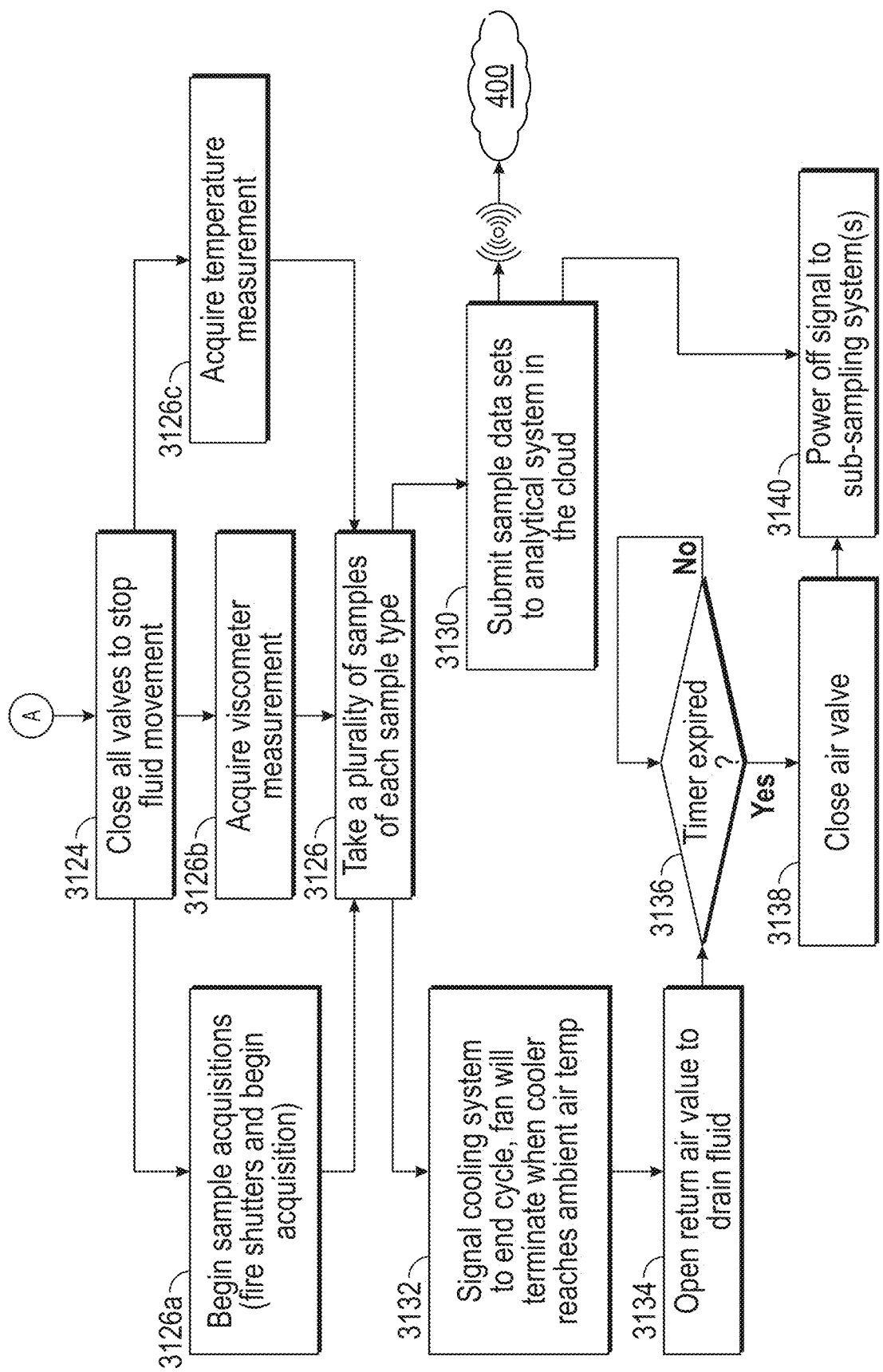
FIG. 31B is a continuation of the flow chart of FIG. 31A, according to an example embodiment of the present disclosure.

FIG. 31B is a continuation of the flow chart of FIG. 31A, according to an example embodiment of the present disclosure. Method 3100 may be used to operate fluid analysis systems such as systems 2000, 2000a, 1000, 100a, 100b, as illustrated, for example, in FIGS. 13A, 13A, 15A, 15B, 17, and 18, respectively. Systems 100a and 100b, for example, include cooling system 302 that is described above with reference to FIGS. 17 to 22. Systems 100a and 100b also include sampling system 304, which is described above with reference to FIGS. 17, 18, and 23 to 29, and controller 332 that includes customized software for controlling sampling system 304 and/or cooling system 302.

In an exemplary embodiment, at stage 3102 of method 3100, controller 332 of sampling system 304 may cause a processor to execute computer program instructions (i.e., customized software) that may be stored on a non-transitory computer-readable storage device. Execution of such computer program instructions may cause the controller to perform a self-diagnostics check to determine whether excitation source 344 (e.g., see FIG. 24) and/or valves 312, 314 (e.g., see FIGS. 19 to 22) are operational and to determine if there are any error conditions associated with cooling system 302 and sampling system 304 (e.g., see FIGS. 17 and 18).

In stage 3104, the method 3100 includes performing a check to determine whether error conditions exist. If the initial self-diagnostics check shows error conditions, in stage 3106 controller 332 (e.g., see FIG. 23) may report these errors/failures and any related failure codes to analytical systems 400a and/or 400b (e.g., see FIGS. 17 and 18). In stage 3106, controller 332 may also ensure excitation source 344 is powered off and that all valves 312, 314 are closed (if possible).

If at stage 3104, however, controller 332 determines from the initial self-diagnostics check that no error conditions exist, then method 3100 proceeds to stage 3108. In stage 3108, controller 332 initiates operation of sub-sampling systems 330, 330a, 330b, etc., by supplying power to sub-sampling systems 330, 330a, 330b, etc. (e.g., see FIGS. 23 to 29).

After powering on sub-sampling systems 330, 330a, 330b, etc., method 3100 proceeds to stage 3110. In stage 3110, method 3100 includes performing a further self-diagnostic check to determine whether error conditions associated with sub-sampling systems 330, 330a, 330b, etc., exist. If, at stage 3110, error conditions are determined to exist, then method 3100 returns to stage 3106. At stage 3106 controller 332 may report these errors/failures and any related failure codes to analytical system 400a and/or 400b. At stage 3106, controller 332 may also ensure that excitation source 344 is powered off and that all valves 312, 314 are closed (if possible).

If at stage 3110, however, controller determines that no error conditions are produced upon powering on sub-sampling systems 330, 330a, 330b, etc., method 3100 proceeds to stage 3112. In stage 3112, controller 332 may send a signal to cooling system 302 to close the temperature loop described above relating to action of pressure reducer valve 308, cooler 324, temperature sensor 310, and 2-way solenoid valve 312, open fluid return and fluid out valves 314, and to enable cooler 324, and fan 370 to cool fluid, as described above in greater detail with reference to FIGS. 19 to 22.

Upon performing the operations described above with reference to stage 3112, method 3100 proceeds to stage 3114. In stage 3114, method 3100 includes performing a comparison to determine whether a measured temperature exceeds a predetermined threshold value. According to an embodiment, the predetermined threshold value may be taken to be 40° C. If the comparison in stage 3114 indicates that the measured temperature exceeds the predetermined threshold (i.e., temperature >40° C.), the conditions of stage 3112 are maintained. In this regard, oil may be re-routed back to cooler 324 for further cooling.

The temperature comparison of stage 3114 may be periodically performed to determine when the measured temperature is equal to or is less than the predetermined temperature threshold value. For example, the comparison of stage 3114 may be performed every few milliseconds, every second, every few seconds, etc. In alternative embodiments, the temperature comparison may be performed continuously using a dedicated digital or analog temperature comparison circuit.

If in stage 3114, the measured temperature is found be equal to or less than the predetermined temperature threshold (e.g., temperature <=40° C., according to an example embodiment of the present disclosure), method 3100 proceeds to stage 3116. In stage 3116, controller 33 may send a signal to open 2-way solenoid valve (i.e., bypass valve) 312 to allow fluid through to sampling system 304 (e.g., see FIGS. 19 to 22 and related discussion). Upon opening bypass valve 312, method 3100 proceeds to stage 3118.

At stage 3118, once fluid has flowed into sampling system 304, controller 332 may use a length parameter to calculate an overall cycle time and to begin a timer. If there are multiple fluid sources 200a, 200b, etc., and one source 200a, for example, is significantly further away from another source 200b, sampling system 304 may have to cycle the fluid for a longer time to ensure that sub-sampling system 330, 330a, 330b, etc., is not contaminated. Once the timer has been started, method 3100 proceeds to stage 3120.

In stage 3120, controller 332 may compare a time measured by the timer with a predetermined time threshold value. If in stage 3120, controller 332 determines that the timer has not expired (i.e., that a time measured by the timer has not exceeded the predetermined time threshold value), method 3100 proceeds to stage 3122.

In stage 3122, controller 332 may utilize sensor/transducer of input pressure reducer valve 308a and output pressure reducer valve 308b of sampling system 304 (e.g., see FIG. 23) to perform a pressure comparison between the input and output pressures to determine if a sufficient pressure drop exists to identify a presence of a leak. If in stage 3122, a pressure drop indicative of a leak in the system is identified, method 3100 may proceed to stage 3106. In stage 3106, controller 332 may report the determined potential leak/system failure and any related failure codes to analytical system 400a and/or 400b (e.g., see FIGS. 17 and 18). Controller may further ensure that excitation sources 344, 344a, 344b, etc., (e.g., see FIGS. 24 to 29) are powered off and that all valves 312, 314 are closed if possible.

At stage 3122, if the measured difference between the input and output pressures is determined to be not significant, method 3100 returns to stage 3120. In stage 3120, the comparison between the measured time and the predetermined time threshold value may be repeated. If in stage 3120, controller 332 determines that the predetermined time threshold value has not been exceeded, then method 3100 may return to stage 3122 to repeat the pressure difference measurements to determine the presence or absence. Thus, the pressure difference measurements and determinations of stage 3122 may be periodically repeated until the timer indicates that the predetermined time threshold value has been exceeded. According to an embodiment, the pressure difference measurements and determinations may be repeated every few milliseconds, every few seconds, etc. In further embodiments, the pressure difference measurements and determinations may be made continuously using a dedicated digital or analog circuit.

In stage 3120, once controller 332 determines that the time measured by the timer has exceeded the predetermined time threshold value, method 3100 proceeds to stage 3124, as illustrated in the continued flowchart of FIG. 31A.

In stage 3124, controller 332 may close all valves 312, 314 to stop movement of the fluid in sampling chamber 340, 340a, 340b, etc., of sampling sub-systems 330, 330a, 330b, as illustrated, for example, in FIGS. 24, 25, 26, etc., respectively. Controller 332 may then initiate sampling of fluid using sampling system 304 and related sub-sampling systems 330, 330a, 330b, etc., as described above, for example, with reference to FIGS. 23 to 29.

In various embodiments, sampling system 304 (e.g., see FIGS. 17, 18, and 23) may perform various stages of method 3100 sequentially or in parallel. For example, in stage 3126a, controller 332 may initiate fluid sample acquisition using sub-sampling systems 330 to 330e, as described above, for example, with reference to FIGS. 24 to 29, respectively. Controller 332 (e.g., see FIG. 23) may perform stage 3126b of method 3100 to initiate viscometer 328 to perform a viscosity measurement of the fluid. Controller 332 may further perform stage 3126c of method 3100 to cause temperature sensors (e.g., temperature sensor 310a of FIG. 23) to measure one or more fluid temperatures. Upon performance of stages 3126a, 3126b, and 3126c, in parallel or sequentially (in any order), method 3100 proceeds to stage 3128.

In stage 3128, controller 332 may cause sampling system 304 to perform measurements on samples of fluid. For example, sampling system 304 (e.g., see FIG. 23) may cause sub-sampling systems 330 to 330e to perform measurements as described above, for example, with reference to FIGS. 24 to 29. In stage 3128, one or more sub-sampling systems 300 to 330e may perform a plurality of measurements (i.e., acquisition of data samples). For example, in an embodiment, sampling system 304 may cause one or more sub-sampling systems 300 to 330e to perform a predetermined number of measurements. For example, subsystems 300 to 330e may take 13 to 20 samples of each respective sample type (i.e., a sample type may be a Raman measurement performed by sub-sampling system 330a, a fluorescence measurement performed by sub-sampling system 330b, etc.), according to an example embodiment of the present disclosure. Controller 332 may then receive data sets from the various sub-sampling systems 330 to 330e of sampling system 304.

Upon completion of stage 3128, controller 332 may then perform one or more stages of method 3100 sequentially or in parallel. For example, in stage 3130, controller 332 may submit sample data sets, collected by sub-sampling systems 330 to 330e in stage 3128, to analytical system 400a and/or 400b (e.g., see FIGS. 17 and 18).

Further, in stage 3132 which may be performed sequentially or in parallel with stage 3130, controller 332 may send a signal to cooling system 302 (e.g., see FIGS. 17 to 22) to end a cooling cycle. For example, controller 332 may cause fan 370 to terminate when cooler 324 reaches an ambient air temperature as described above with reference to FIGS. 19 to 22.

Once the fluid is adequately sampled by sampling system 304, fluid may be routed from sampling system 304 to cooling system 302. To facilitate this return, in stage 3134 of method 3100, controller 332 may open return air valve 322 in cooling system 302 (e.g., see FIGS. 19 to 22) as needed to allow air to be purged from the line and to accelerate return of fluid if there is little or no pressure to push/gravity drain the fluid back into cooling system 302 from sampling system 304. Method 3100 may then proceed to stage 3136.

In stage 3136, controller 332 may initiate a timer and may periodically compare a time measured by the time with a predetermined time threshold value. Once controller 332 determines that time measured by the timer has exceeded the predetermined time threshold value, method 3100 proceeds to stages 3138 and 3140.

In stage 3138 controller 332 may close air valve 322 and in stage 3140, controller 332 may power off sub-sampling systems 330 to 330e and/or sampling system 304. As described above, various stages of method 3100 may be performed sequentially or in parallel. For example, as indicated in the flow chart of FIG. 31B, controller 332 may perform stage 3130, in which data sets are transferred to analytical systems 400a and/or 400b (e.g., see FIGS. 17 and 18), in parallel with the shutdown processes represented by stages 3132 to 3138. Then, once stages 3130 to 3138 have been completed, sequentially or in parallel, controller 332 performs stage 3140 to power off sub-sampling systems 330 to 330e and/or sampling system 304.

Figure 32:
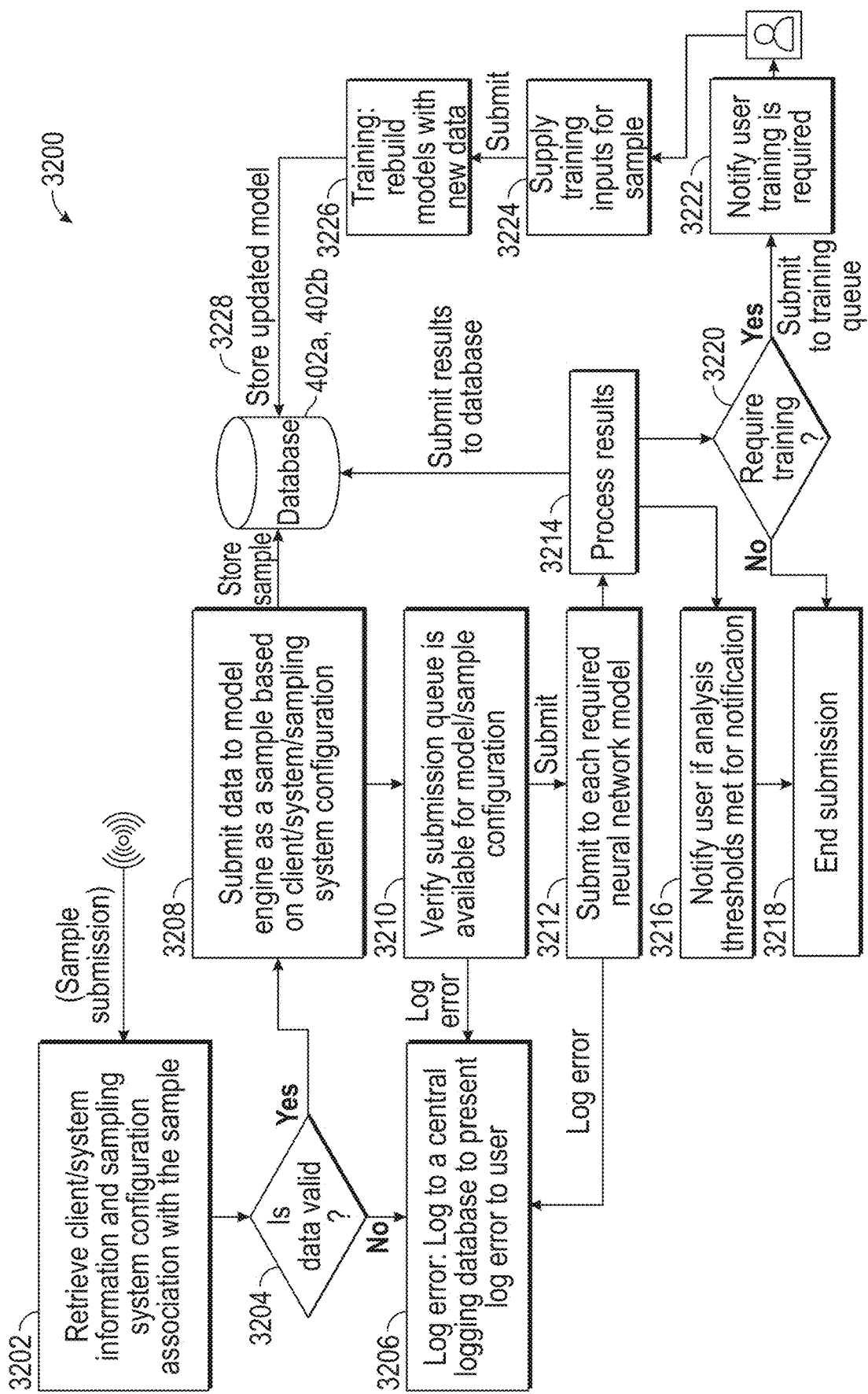
FIG. 32 is a flowchart illustrating a method of operating an analytical system, according to an example embodiment of the present disclosure.

FIG. 32 is a flowchart illustrating a method 3200 of operating analytical systems 400a and 400b (e.g., see FIGS. 17 and 18). Further, method 3200 relates to operation of command and control systems 406a and 406b and databases 402a and 402b for respective analytical systems 400a and 400b, as described in greater detail below. Analytical systems 400a and 400b, command and control systems 406a and 406b, and/or databases 402a and 400b, described with reference to FIGS. 17, 18, and 32 may be implemented using apparatus, systems and methods described herein, including various embodiments thereof.

As described above, command and control systems 406a and 406b may each be implemented as a hosted software system that may receive submitted sample data sets of measurements for fluid samples. The received data sets may then be processed through a set of machine learning models to generate data that may be used for predictive analysis. The machine learning models may be configured to target any type of fluid to be analyzed. The resulting output of the sample analysis will generally be dependent on the fluid submitted, the networks processed, and the statistical percentage accuracy for the given network model.

The output from a spectral sample is known as a spectrum. The spectrum may be visualized as a set of data points characterized by coordinates X (e.g., that may indicate wavelength, frequency, Raman shift, etc.), and Y (e.g., an intensity value corresponding to the X coordinate). Graphs of data (e.g., plots of X, Y, points) may then be uploaded to analytical systems 400a and 400b where they may be stored, assessed and presented to a machine learning model for concrete identification and system prediction. To provide context for spectral samples, known samples may be obtained prior to carrying out measurements on received fluid samples so that a baseline may be established for a specific machine learning model. In an example, a machine learning model may include a neural network having three layers: an input layer, a hidden layer, and an output layer, with each layer including one or more nodes where information flows between the nodes.

If the type of sample cannot be identified, machine learning models may require conditioning through a "training" process. The training process may include inputting known parameters associated with types of samples/sub-sampling systems 330 to 330e, for example, to assist machine learning models with identification of the samples and to strengthen the resulting machine learning model. A machine learning model represents the knowledge of the machine learning model. As described herein, a machine learning model may be created from known data sets. Therefore, when a sample is submitted, the parameters for which the sample was collected may be required to identify the particular machine learning model to use for identification. For example, a machine learning model for the fluid analysis systems (e.g., systems 100a, 100b, 1000, and 2000) described herein may be defined by the following set of parameters, including but not limited to, the type of sub-sampling system used (e.g., 330, 330a, etc.), the wavelength of electro-magnetic radiation (or if it's monochromatic), viscosity, temperature, pressure, etc.

These parameters may define the corresponding model. Known data sets, which may include a measured spectrum corresponding to a sample of fluid (e.g., clean oil) with x ppm of y elements combined with the above determined parameters may allow for "training" of a network and creation of a corresponding model. The more known (good) data that can be used to train a machine learning model, the better the resulting model will work at identifying unknown samples. In exemplary embodiments, building machine learning models may require the use of immense computational resources. To that end, building such models may be performed by analytical system 400b that may be implemented in a cloud based computing platform with resulting models potentially pushed to the sampling system 304 if onboard analysis is required.

In exemplary embodiments, a user may access and/or modify the analytical system 400 and/or 400b via a web application, for example, in a computing device through any type of encrypted or unencrypted connection. In exemplary embodiments, a user may log in to a command and control system 406a or 406b and may access a corresponding respective database 402a or 402b. Access may be provided based on a user's role and corresponding security credentials. The web application may include a graphical user interface (GUI) that may present a dashboard of available sampling systems 304. The GUI may also present messages either predictive analysis messages based on samples, error messages, and/or training request messages.

In various embodiments, the user may select a specific sampling system 304, interact with the sampling system 304 and submit requests to the sampling system 304 to perform analysis and obtain a fluid sample, configure the system 304 (e.g., to setup the automated sampling timeframe), analyze the real-time parameters coming from the system 304 (e.g. temperature, last time sample taken, pressure, fluid temperature, etc.). In some embodiments, the user may also add new sub-sampling systems 330, 330a, 330b, etc., to a client and/or de-authorize or shutdown existing sampling systems 330. User may also, if available, issue a software update to sampling system 304 and/or cooling system 302, view analytical machine learning models and related network statistics, view a number of known good samples, view data related to percentage of successful identifications, and accuracy thresholds. A user may also initiate a retraining process for a machine learning model or request model diagnostic information.

According to an embodiment, method 3200 illustrated in FIG. 32, may be performed as follows. In stage 3202, command and control system 406a and/or 406b, of respective analytical systems 400a and 400b, may first receive submitted sample data sets of the fluid being analyzed from controller 332, as described above with reference stage 3130 of method 3100 illustrated in FIG. 31A. Upon receipt of these sample data sets, command and control systems 406a and/or 406b may first retrieve client/system information and data regarding sampling system 304 configuration associated with the sample.

In stage 3204, a check may be performed to determine whether received data sets are valid or if there is any error related to the process of retrieving data sets. In the event that an error is encountered at stage 3204, method 3200 proceeds to stage 3206.

In stage 3206, if the client/system information and sampling system 304 configuration cannot be retrieved from the submitted sample data sets, system 400a and/or 400b may show a "log error" and command and control system 406a and/or 406b may interact with corresponding respective databases 402a and 402b (e.g., see FIGS. 17 and 18) to present this log error to a user via a web application, for example, so that the user may make appropriate modifications as necessary.

In the event that received data is found to be valid at stage 3204, method 3200 proceeds to stage 3208. In stage 3208, if the data is valid, command and control system 406a and/or 406b may submit the data sets to a model engine as a sample based on the client/system/sampling system 304 configuration. In exemplary embodiments, command and control system 406a and/or 400b may also store this sample data set in respective databases 402a and/or 402b (e.g., see FIGS. 17 and 18) as described in greater detail below. Method 3200 may then proceed to stage 3210.

In stage 3210, command and control system 406a and/or 406b may then verify that a submission queue is available for a specific model/system configuration. For example, if the sample is a type of oil with a viscosity of X, and Raman sub-sampling system 330a (e.g., having a laser with a wavelength of 785 nm) is used to perform analysis of the oil, command and control system 406a and/or 406b may search corresponding respective databases 402a and/or 402b for a model matching those exact parameters to use in determining an identity of the sample of oil.

In the event that a submission queue is not available, method 3200 may return to stage 3206. In stage 3206, system 400 may show an "log error" and command and control system 406a and/or 400b may interact with respective databases 402a and/or 402b to present this log error to a user via a web application, for example, so that user may make appropriate modifications as necessary.

In the event that a submission queue is available, method 3200 may proceed to stage 3212. In stage 3212, command and control system 406a and/or 406b may then submit each data set to the corresponding machine learning model. In stage 3214, machine learning model may then process results based on each data set. Results of the processing in stage 3214 may then be sent to database 402a and/or 402b by command and control system 406a and/or 406b. If any issues arise with submitting each data set to the machine learning model, method 3200 may return to stage 3206. In stage 3206, system 400a and/or 400b may present a "log error" to user via a GUI, for example, based on a web application.

Once fluid analysis results are processed by a machine learning model, in stage 3214, method 3200 may proceed to stage 3216. In stage 3216, command and control system 406a and/or 406b may notify the user if these results meet certain defined analysis thresholds for the samples/type of sampling system 304. If so, method 3200 may proceed to stage 3218. In stage 3218, command and control system 406a and/or 406b may end submission of the data sets to the machine learning model.

Based on the processing of results in stage 3214, command and control system 406a and/or 406b may then determine whether machine learning models associated with the system require "training" in stage 3220. If in stage 3220, command and control system 406a and/or 406b determines no training is required, method 3200 may return to stage 3218. In stage 3218, command and control system 406a and/or 406b may end submission of the data sets to the machine learning model.

Alternatively, in stage 3220, command and control system 406a and/or 406b may determine that machine learning models associated with the system requires further training. In this event, method 3200 proceeds to stage 3222.

In stage 3222, command and control system 406a and/or 406b may notify the user that appropriate training is required. In stage 3224, user may then supply certain training inputs (e.g., via a web application) to command and control system 406a and/or 406b for each sample for which training is requested. Method 3200 may then proceed to stage 3226.

In stage 3226, command and control system 406a and/or 406b may use these training inputs to update/rebuild the machine learning models or may create new machine learning models with the new data obtained from the fluid sample data sets. In stage 3228, command and control system 406a and/or 406b may then store the updated/new models in database 402a and/or 402b, and/or may deploy the updated/new models back to sampling system 304. In various embodiments, user may access existing and updated machine learning models, and related data, in database 402a and/or 402b via a web application, for example, as described above.

Figure 33:
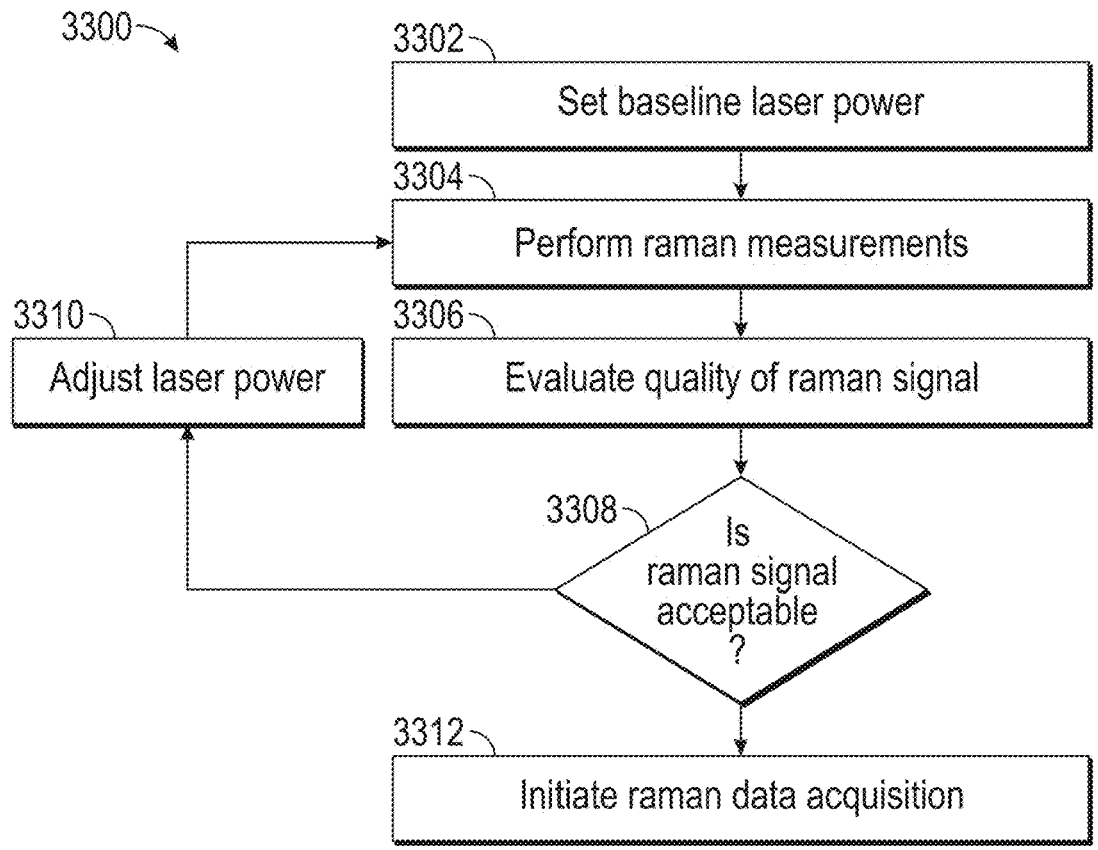
FIG. 33 is a flowchart illustrating a method of operating analytical systems to implement a power calibration for Raman sub-sampling system of FIG. 25A, according to an example embodiment of the present disclosure.

FIG. 33 is a flowchart illustrating a method 3300 of operating analytical systems 400a and 400b (e.g., see FIGS. 17 and 18) to implement a power calibration for Raman sub-sampling system 330a of FIGS. 25A and 25B, according to an example embodiment of the present disclosure. The quality of signals received by detection system 346a, of sub-sampling system 330a shown in FIG. 25A, depends on the intensity of incident radiation generated by excitation source 344a, as follows.

When radiation generated by excitation source 344a interacts with fluid in sampling chamber 340a, only a fraction of the incident radiation becomes shifted in frequency and is detected as a Raman signal. Intensity of the Raman signal is, therefore, considerably less than the intensity of the incident signal. In this regard, if the incident radiation is insufficiently intense, the resulting Raman signal will be too weak to be detected. With increasing intensity of the incident signal, however, other processes such as fluorescence may begin to dominate the signal and may tend to obscure the Raman signal. Because of these effects, it is possible to optimize the Raman signal by choosing an optimal value of the intensity of incident radiation generated by excitation source 344a, as described in greater detail below with reference to FIG. 33.

Method 3300, as illustrated by the flowchart in FIG. 33, describes a way in which analytical systems 400a and/or 400b (e.g., see FIGS. 17 and 18) may control Raman sampling sub-system 330a (e.g., see FIG. 25A) to automatically determine an optimal intensity of incident radiation generated by excitation source 344a. As such, method 3300 provides a way to calibrate sub-sampling system 330a to generate optimal Raman signals.

At stage 3302 of method 3300, analytical systems 400a and/or 400b (e.g., see FIGS. 17 and 18) may control excitation source 344a (e.g., see FIG. 25A) to generate a baseline intensity of incident radiation. In general, intensity of radiation generated by excitation source 344a is governed the power supplied to excitation source 344a. As such, in stage 3302, analytical systems 400a and/or 400b set a baseline value of power supplied to excitation source 344a to thereby generate a baseline value of intensity of incident radiation generated by excitation source 344a.

In stage 3304, method 3300 includes performing Raman measurements as described above with reference to FIG. 25A using an intensity of radiation generated by excitation source 344a resulting from the baseline power setting fed to excitation source 344a in stage 3302, of method 3300. In this regard, radiation generated by excitation source 344a is fed to Raman probe 342a through fiber optic cables 348a, as shown in FIG. 25A. Radiation is then fed to sampling chamber 340a by probe 342a. Radiation that is reflected/emitted from sampling chamber 340a is captured by Raman probe 342a and is then fed to fiber optic cables 348b. Detection system 346a then receives the radiation from fiber optic cables 348b that was reflected/emitted from sampling chamber 340a.

In stage 3306, analytical systems 400a and/or 400b (e.g., see FIGS. 17 and 18) may evaluate the quality of signals generated by detection system 346a (e.g., see FIG. 25A) in response to receiving radiation that was reflected/emitted from sampling chamber 340a. For example, analytical systems 400a and/or 400b may determine a presence of one or more Raman peaks in a spectrum of reflected/emitted radiation. As described above, the spectrum may be considered to be an intensity of reflected/emitted radiation vs. frequency. For a sample of a known material, analytical systems 400a and/or 400b may compare a known Raman spectrum, for the material in question, with the measured spectrum. A degree to which the two spectra agree may be used as a measure of the quality of the measured signal.

In stage 3308, the quality of the measured signal may be judged, by analytical systems 400a and/or 400b, to determine whether an acceptable Raman signal has been obtained. As described above, if the intensity of incident radiation generated by excitation source 344a is insufficient, then it may be difficult to measure a Raman signal. In this regard, the measured signal may be dominated by background noise and have no detectable Raman peaks. However, if the intensity of incident radiation generated by excitation source 344a is too great, then the measured signal may exhibit features corresponding to processes other than Raman scattering, such as features associated with fluorescence. In this regard, it is possible to determine whether the incident radiation has an intensity that is too larger or two small to produce an acceptable Raman signal.

At stage 3308, if the measured signal is judged to be not acceptable, then method 3300 proceeds to stage 3310. In stage 3310, analytical systems 400a and/or 400b may adjust the power supplied to excitation source 344a. If, in stage 3308, the intensity of incident radiation was judged to be insufficient, then in stage 3310, analytical systems 400a and/or 400b may increase power supplied to excitation source 344a to thereby increase the intensity of incident radiation generated by excitation source 344a. Alternatively, if in stage 3308, the intensity of incident radiation was judged to be too great, then in stage 3310, analytical systems 400a and/or 400b may decrease power supplied to excitation source 344a to thereby decrease the intensity of incident radiation generated by excitation source 344a. Method 3300 may then return to stage 3304.

Stages 3304, 3306, 3308, and 3310, may be performed as a loop to the extent that the measured signal is judged to be unacceptable in stage 3308. When implemented in hardware, firmware, or software, the loop formed by stages 3304, 3306, 3308, and 3310, may be provided with a maximum iteration parameter. For example, the maximum iteration parameter may cause the loop to exit when the loop has executed for more iterations than the value of the maximum iteration parameter. In an embodiment, the maximum iteration parameter may be chosen to be an integer having a value of, say, 10, 20, 50, 100, etc. In an example in which the maximum iteration parameter is chosen to be 50, the loop including stages 3304, 3306, 3308, and 3310, may termination if an acceptable Raman signal is not found in stage 3308 after 50 iterations.

If, however, in stage 3308 the measured signal is judged to be acceptable, then the above-described power calibration process is deemed to have succeeded, and method 3300 proceeds to stage 3312. In stage 3312, analytical systems 400a and/or 400b may control Raman sub-sampling system to perform data acquisition of Raman spectra using the optimal value of power supplied to excitation source 344a that generates an optimal intensity of radiation.

When an acceptable Raman signal is found in stage 3308, before the loop including stages 3304, 3306, 3308, and 3310 has been executed for a number of iterations not exceeding the maximum iteration parameter, the calibration process may be said to converge. The convergence behavior of loop 3304, 3306, 3308, and 3310 may depend on a number of user-adjustable parameters, such as the increment by which the power supplied to excitation source 344a is incremented or decremented. Upon termination, an error message may be generated, in the event that the loop does not converge before the maximum number of iterations has been. A user may then adjust one or more user-adjustable parameters to improve the convergence of the calibration.

User-adjustable parameters may include a predetermined starting value for power supplied to excitation source 344a as well as increment and decrement values for power adjustments. For example, a starting power may be taken to be 200 mW. Further, an example value for an increment may be taken to be 30 mW, and a power decrement may be taken to be 15 mW. In further embodiments, the increment/decrement of power supplied to excitation source 344*a* may be chosen based on an adjustable power window. Such a power window may represent an amount of power that may be incremented or decremented in a single iteration of the loop represented by stages 3304, 3306, 3308, and 3310 of method 3300 of FIG. 33. A size of the power window may be increased or decreased as the loop iterates.

In further embodiments, analytical systems 400*a* and/or 400*b* may adjust power in increments of between 1 mW and 15 mW depending upon previous adjustments. In instances in which the signal is too strong (e.g. sample fluoresce is observed or sample is heated to boiling) analytical systems 400*a* and/or 400*b* may lower the power on the laser by 1 mW to 15 mW depending upon previous adjustments, and can reacquire a signal. Depending on the level of contaminants, a change of 1 mW may be sufficient to acquire an acceptable signal.

Upon or after the initial Raman spectral sample is acquired, the spectral data from the calibration sample may be communicated to an analytical controller (e.g., analytical systems 400*a* and/or 400*b*) and evaluated with an automatic calibration processing model, as described in greater detail below.

An automatic calibration processing model may include one or more (e.g., some or all) of removing all or almost all values below a defined Raman frequency, (e.g., 300 cm$^{-1}$); performing minimum and maximum scaling on the calibration signal data values; performing a data truncation to limit analysis to, for example, the first 200 calibration signal data values derived from the calibration Raman spectra; performing linear regression line-fit on the remaining calibration signal data values; determining the line y-intercept and slope values; computing residual error sum and standard deviation values; and performing polynomial regression curve fit on the remaining data values.

Results of such a calibration processing model may be used to determine if the laser power setting was too low or too high. For example, if the laser power level is too low, the line y-intercept value may be below threshold, or line slope value may be beyond an acceptable range, or polynomial residual error sum value may be too high. Conversely, for example, if laser power level is too high, polynomial residual error sum value may be too low. In certain embodiments, if the analytical controller executes the calibration processing model on the calibration spectral data and determines that the laser power is too high or too low, the analytical controller may communicate this result to the acquisition controller.

The acquisition controller (e.g., analytical systems 400*a* and/or 400*b* of FIGS. 17 and 18) may then modulate the Raman laser power accordingly, as described above. If a constant power cannot be set correctly, the system can change into a pulsed mode with a higher power, for example, pulsing the laser on and off at a cycle of between 1 kHz and 30 kHz. During this acquisition phase, the pulse cycle and/or the laser power may be adjusted to acquire a clean signal having little or no noise. If the Raman laser power is with an acceptable range, meaning the signal is detectable with little or no noise, the analytical controller may communicate this result to the acquisition controller, and downstream sampling may be initiated.

In certain embodiments, the Raman laser may be equipped with a custom power shield which may allow the Raman laser power to be automatically modulated (i.e., calibrated) by an acquisition controller in conjunction with an analytical controller (e.g., implemented with analytical systems 400*a* and/or 400*b*) running an automatic calibration model. In certain embodiments, the power shield may serve as an interface between computer (e.g., a Raspberry Pi processor) running calibration model and hardware used to preform spectral analysis (e.g., using a Raman spectrometer, such as Raman sub-sampling system 330*a* of FIG. 25A). In certain embodiments, the power shield may accept I2C communication from computer C and may deliver communications to 12-Bit DAC to be converted to discretely variable DC voltage signal which may modulate laser power level. The power shield may also accept various GPIO logic inputs to deliver to either the solid state relay or external relay module to turn components on and off.

In an embodiment, power shield may include a GPIO header interfaced directly with a computer GPIO header; ten position Molex header to interface with hardware connections of Raman laser; I2C driven twelve 12 Bit DAC used to control Raman laser power output level; DC-DC Solid State Relay used for switching the laser module on/off; power transformer and rectifier used to supply the Raman laser with stable, continuous 5V DC power; six 6 Position generic header to interface with relay module used to switch line level power to Raman spectrometer; power shield itself; and twelve Volt power supply for CAN Bus. Optionally, additional external hardware may be added. Exemplary embodiments of additional hardware include additional sensors, satellite modems, fiber optic cable switches, power supplies, liquid crystal display LCD devices, and light emitting diode LED indicators to indicate hardware state or values. In an embodiment, hardware state indicators may identify power source values related to specific states such as shut-off valve in open/closed state.

In one embodiment, the power selection process comprises three stages: upper seek, lower seek, and optimal seek. Once all three stages are complete, the correct power has been identified. When acquiring power spectra, the spectrometer settings are configured to a new average count that has been optimized to balance speed and quality for the power selection process. Each power spectra is rated by the power rating function, which estimates the amount of variation in the signal.

Power Rating Function

The power rating function calculates the mean distance between the scaled intensity curve and a smoothed version of the scaled curve. A multiple of this value is returned as the rating.

Selection Process

The upper seek stage determines the point at which the sample starts to fluoresce. Power spectra are taken at configured intervals for example, every 30 mW until the power ratings stop changing, indicating that the sample has fluoresced. The average power rating of these fluoresced spectra is noted as the high power rating. The upper seek stage continues by locating the power level at which the power rating increases to a configured multiple of the high power rating. A binary search is commenced to locate the closest power level, which is chosen as the high power to complete the upper seek stage.

Lower Seek

The lower seek stage selects a low power level. A configured number of milliwatts is subtracted from the high power and designated as the low power. Power spectra are taken at the low power and at a configured number of consecutive power levels. The power ratings for these samples are averaged after selection of the low power rating, and the lower seek stage are complete.

Optimal Seek

The optimal seek stage identifies the optimal power level for the sample. The optimal power rating is a configured ratio between the high power rating and the low power rating. A binary search is used to find the power level with a power rating ratio closest to the optimal power rating, and this power level is returned as the optimal power.

Figure 34:
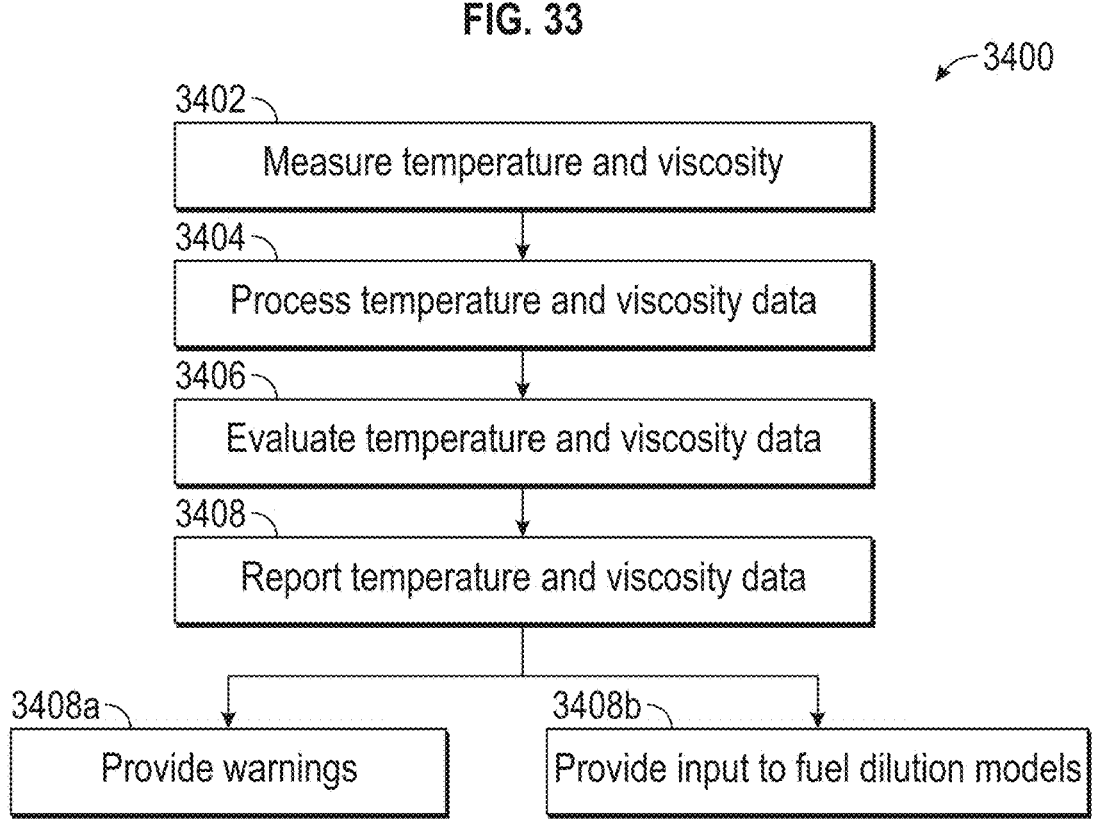
FIG. 34 is a flowchart illustrating a method of measuring and monitoring viscosity, according to an example embodiment of the present disclosure.

FIG. 34 is a flowchart illustrating a method 3400 of measuring and monitoring temperature and viscosity of a fluid/oil, according to an example embodiment of the present disclosure. As described in greater detail below, trends in measured viscosity over time may provide insight into conditions of the fluid/oil that is being monitored. For example, a trend indicating a decrease in viscosity may indicate degradation of motor oil. Decreasing viscosity may also indicate a presence of fuel or coolant that has seeped into the oil and has thereby diluted the oil. Viscosity is therefore also a parameter that may be used in a fuel or coolant dilution model of the fluid/oil under consideration, as described in greater detail below. In various embodiments, a fuel or coolant dilution model may use both Raman spectroscopy data and viscosity data to determine fuel dilution in a fluid/oil sample.

At stage 3402, method 3400 may include performing measurements of temperature and viscosity. Temperature may be measured using a temperature sensor (e.g., temperature 5310 of FIGS. 3, 4, and 6) configured to measure a temperature of the fluid. Viscosity may be measured using a viscometer (e.g., viscometer 5328 of FIGS. 3, 4, and 6) configured to measure a viscosity of the fluid. In stage 3404, the method may include sending measured temperature and viscosity data to one or more analytical systems (e.g., analytical systems 400a and 440b of FIGS. 17 and 18) that may process the data. Data processing, in stage 3404, may include performing one or more smoothing operations on that data such as averaging the data over various time periods. For example, data may be averaged over every millisecond, over every second, over every hour, over every day, over every week, etc.

At stage 3406, method 3400 may include evaluating the measured data. For example, evaluation in stage 3406 may include comparing measured temperature and viscosity data to respective temperature and viscosity thresholds. Stage 3408 of method 3400 may include reporting temperature and viscosity data. For example, if a temperature or viscosity threshold is determined, in stage 3406, to have been exceeded, method 3400, in stage 3408a, may include issuing one or more user warnings. Since fuel dilution is a common, critical failure condition for diesel engines, when fuel dilution is detected by correlation analysis, the fluid condition monitoring system may alert a user (e.g., stage 3408a of method 3400) of a fuel dilution diagnosis in order preempt damage. For example, the system may suggest that the engine be taken out of service immediately.

In stage 3408b, the method may include providing temperature and viscosity data to one or more fluid dilution models (e.g., fuel and/or coolant dilution models). In further embodiments, temperature and viscosity data may be combined with other measurements to provide input to correlation models, as described in greater detail below. In this regard, correlation models may be created by training machine learning algorithms using laboratory and/or sample data to identify correlations between the input data from multiple target measurements (e.g., measurements of viscosity, temperature, oxidation, soot, iron, copper, and laser power).

In some aspects, input data from target measurements may have diagnostic value by itself. In this regard, correlation analysis models may identify correlations between multiple inputs that offer additional diagnostic value. For example, decreasing viscosity may, in isolation, be an indicator of high oil temperature, fuel dilution, or additive depletion. However, correlation models may combine these input data to identify that decreasing viscosity in combination with steady temperature and higher trending laser power output is an indicator of fuel dilution.

Summary of Analysis and Modeling Methods

Materials may be identified by their characteristic spectral signatures in terms of peak positions and peak heights. The presence of known materials in a mixture of materials may be determined by analyzing spectra for the mixture based on spectral models for known materials. For simple mixtures of a few known materials, it is possible to develop models for the system based on first-principles chemistry and physics models. However, for complex mixtures containing hundreds or thousands of components, it may be difficult to develop models based on first-principles. The following disclosed modeling program produces models based on empirically derived, data driven approach intended to minimize introduction of bias into the modeling system. The modeling program, which is suitable for describing complex fluids such as motor oil containing various impurities and/or contaminants, is summarized as follows.

Well-characterized training data may be supplied to the machine learning algorithm as input data to generate a model. Training data may include spectroscopic data for a plurality of samples of a fluid/oil having known concentrations of an impurity of contaminant of interest as characterized by an analytical laboratory using conventional analytical techniques. Spectral training data may be obtained for contamination targets, such as fuel or coolant contamination, by producing physical samples having known concentrations (e.g., serial dilution) of fuel or coolant. Degradation samples, which are positive for a specific degradation target (e.g., soot, wear metal, etc.) may be obtained from an analytical laboratory that evaluates used oil samples though conventional means. Samples obtained from an analytical laboratory may be completely characterized using a battery of conventional analytical techniques.

Specifics of Model Building (1) Spectral data for a variety of well-characterized systems is used as input to build a model for a given material in oil.

(2) The input data (i.e., training data) includes a number of known compositions in which the given material is present in the oil in various concentrations.

(3) A feature selection process is performed to identify spectral features (i.e., spectral peaks and corresponding frequency positions of the peaks) for spectra corresponding to each of the compositions.

(4) Spectral features may be characterized by a pair of quantities $(f_i, a_i)$, where $f_i$ is the frequency for spectral feature "i" and $a_i$ is the corresponding area-under the curve for the given feature. The quantities $(f_i, a_i)$ may be obtained through curve fitting or by a numerical procedure performed on the input data.

(5) Important spectral features are identified as those that exhibit changes with concentration.

(6) Although the concentration dependence is not known, changes of feature areas may be approximated with a linear model: $Y = X\beta + \varepsilon$, where Y is a vector of concentration values, one value for each system of the input data set, and X is a matrix of feature area values. In this model $\varepsilon$ represents random noise. The row index of X denotes a given system of the input (training) data set, and the column index denotes a frequency value of a spectral feature.

(7) When the number of frequencies exceeds the number of systems, a random lasso algorithm is used to determine the β vector.

(8) Each value of the β vector corresponds to a given frequency of a spectral feature. Larger values of the β vector correspond to frequencies that are more important than frequencies corresponding to smaller values of the β vector. In this sense, "more important" means that spectral features for these frequencies exhibit larger concentration dependence that features for having smaller values of the β vector.

(9) For an input data set of N systems, a number P of subsets having M systems chosen from the N systems are considered. A β vector is determined for each of the P subsets.

(10) A count vector C is generated by summing all of the β vectors for the P subsets. The largest values of the count vector determine the important frequencies. In this way, larger values of the vector C indicate that the corresponding frequency was determined to be important in more of the P subsets that frequencies having smaller values of the vector C.

(11) Frequency windows are chosen by selecting frequencies whose corresponding entries of the C vector are above a threshold.

(12) A classifier model (i.e., a machine learning model) may be constructed by considering the selected frequency windows to define coordinate axes in a multi-dimensional space. The values of the areas-under-the-curve may denote coordinate values in the multi-dimensional space.

(13) A coordinate value may be defined for each frequency window by summing or otherwise taking a suitable average of area values for spectral features in each frequency window.

(14) In this way, spectral data for each input system may be reduced to a single point in a multi-dimensional space.

(15) The classifier model may be constructed based on a separation of clustering of data for low and high concentrations of the material. In this way, the multi-dimensional space is divided into a first region corresponding to low concentration and a second region corresponding to high concentration.

(16) Predictions based on the model may then be generated by reducing spectral data for an unseen system to a single data point in the multi-dimensional space, in the same way as was done for the input training data. The coordinates of the data point for the unseen system may then be fed to the model. When data point for the unseen system is found to be in the low/high concentration region of the multi-dimensional space, a conclusion may be drawn that the unseen system is of low/high concentration of the material in question. In this way, the model makes a prediction for the unseen system.

(17) The quality of the model may be assessed by constructing a "confusion matrix" that quantifies the number of correct low/high predictions, and quantifies the number of false-high and false-low concentration predictions. A first confusion matrix may be generated using the training data using a leave-one-out cross validation strategy. A second confusion matrix may be generated using a known but unseen (by the model) data set.

(18) The quality of the model may assessed in terms of the quantities: accuracy, precision, and recall.

Data Processing

Figure 35A:
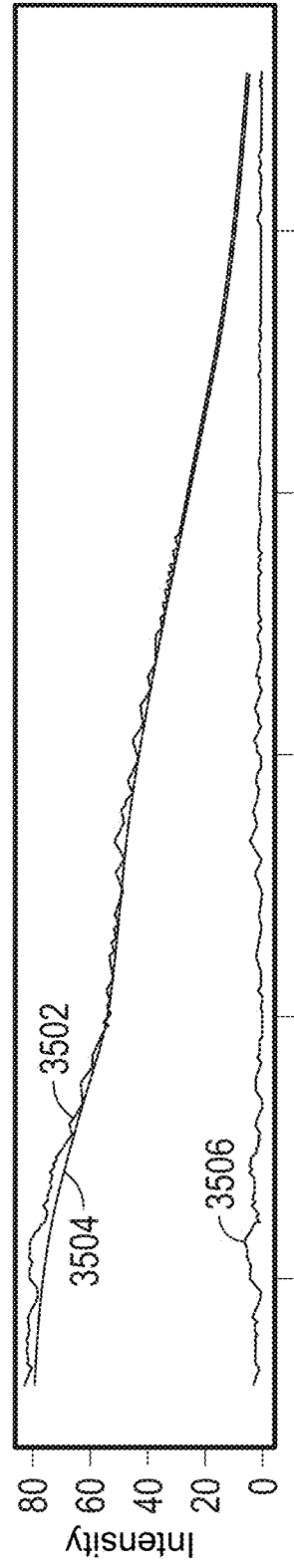
FIG. 35A illustrates Raman spectroscopy data for a first concentration of soot in motor oil, according to an example embodiment of the present disclosure.
Figure 35B:
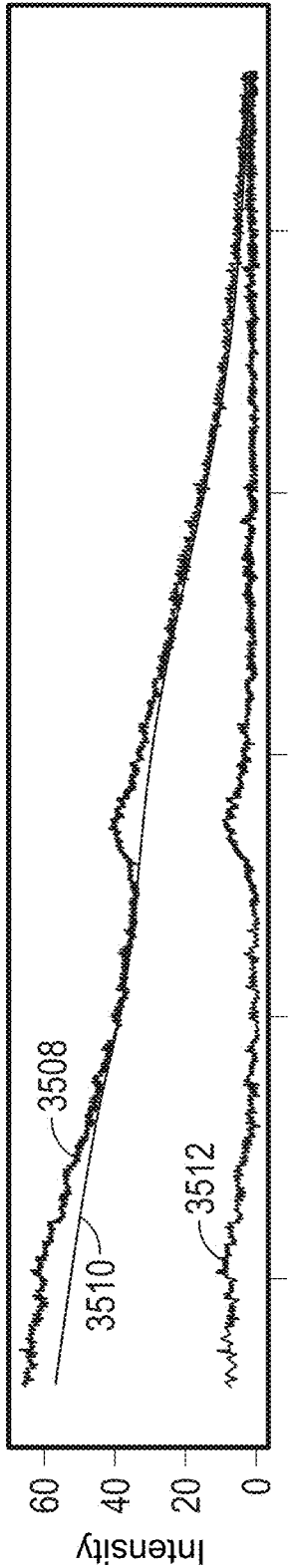
FIG. 35B illustrates Raman spectroscopy data for a second concentration of soot in motor oil, according to an example embodiment of the present disclosure.
Figure 35C:
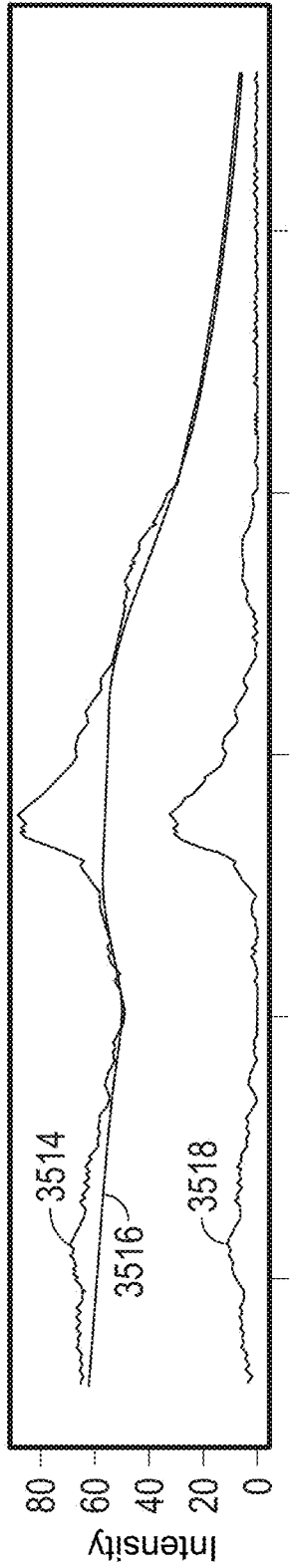
FIG. 35C illustrates Raman spectroscopy data for a third concentration of soot in motor oil, according to an example embodiment of the present disclosure.

FIGS. 35A, 35B, and 35C illustrate Raman spectroscopy data for three concentrations of soot in motor oil, according to an example embodiment of the present disclosure. In each of FIGS. 35A, 35B, and 35C, raw spectroscopic data is presented along with pre-processed data. As described in greater detail below, raw data is first pre-processed to remove background noise and to smooth and normalize the data.

A presence of soot in motor oil represents a level of unburned fuel in the oil. Concentrations of soot in oil are typically denoted by an integer in a range from 0 to 10. A value of 0 indicates no detectable concentration of soot in oil and increasing values of the integer represent increasing concentrations of soot in oil. FIG. 35A illustrates Raman spectroscopy data for a "soot-0" sample, FIG. 35B illustrates Raman spectroscopy data for a "soot-3" sample, and FIG. 35C illustrates Raman spectroscopy data for a "soot-6" sample, as reported by an analytical laboratory.

FIG. 35A presents raw data 3502, baseline signal 3504, and a signal 3506 obtained by subtracting the baseline signal 3504 for the "soot-0" sample from the raw data 3502. Similarly, FIG. 35B presents raw data 3508, baseline signal 3510, and a signal 3512 obtained by subtracting the baseline signal 3510 for the "soot-3" sample from the raw data 3508. FIG. 35C presents raw data 3514, baseline signal 3516, and a signal 3518 obtained by subtracting the baseline signal 3516 for the "soot-6" signal from the raw data 3514. Further details of data pre-processing and normalization, including determination of the baseline signal, are provided below.

Raw optical spectroscopy data that is captured by spectroscopy instrumentation generally has issues need to be addressed before the data may be used. Spectroscopy data is represented as a set of data points which records an intensity value at each of a plurality of wave length/frequencies. First, some of the data points should be removed due to hardware specifications. A second issue is that the data is generally recorded at frequencies which are dependent on the device/spectrometer used to record the data. If these frequencies are used for building a machine learning model, then the model will only work with data that is collected from the same device. A third issue is that the spectroscopy data generally contains a baseline component that tends to mask the signal and may therefore be detrimental to analytical results. A forth issue is that the intensity values may vary from sample to sample due to many physical factors. A fifth issue is that the data may contain too much noise and may need to be reduced using a data smoothing filter. Operations to address these issues are described below, as follows.

Before an optical spectroscopy data set may be used, it may be pre-processed to handle the above-described issues. The output of the following pre-processing operations is a normalized optical spectroscopy data set that may be used for further analysis. The data smoothing operation is optional.

The first operation removes any optical spectroscopy data that should be ignored based on hardware specifications of detection equipment utilized to collect the optical spectroscopy data. An initial signal may also be removed. The initial signal may include data points that show an initial spike up to an initial peak value. According to an embodiment, this initial peak is seen at about the 300 $cm^{-1}$ frequency value.

The second operation uses an interpolation algorithm to transform the optical spectroscopy data into a device-independent set of frequency values. In one embodiment, a cubic spline algorithm may be used to perform the interpolation. In other embodiments, other types of 1-D interpolation may be used. Such other interpolation algorithms may include linear, quadratic, and/or cubic splines of zero, first, second or third order. According to an embodiment, a Savitzky-Golay filter algorithm may be performed to smooth the data before the interpolation algorithm is performed.

Device-independent frequencies may be computed by performing a polynomial fit between frequencies generated by two different physical spectrometers. Performing this operation may minimize an amount of interpolation required for data from each of the two devices. According to various embodiments, frequency differences between the two spectrometers varied from 0.017 cm$^{-1}$ to 62.069 cm$^{-1}$ at any given index value. The above-described interpolation operation ensures resulting models preform appropriately for data obtained from any device.

The third operation removes baseline data from the interpolated optical spectroscopy data. The baseline may be determined from the input signal using various algorithms. In an embodiment, the baseline may be determined using an Adaptively Iterated Reweighting Penalized Least Squares (airPLS) algorithm. For example, the algorithm provided in the open-source software library "airPLS" may be used. This algorithm iteratively minimizes a penalized weighted least-square function of the form:

$$Q^t = \Sigma_{i=1}^m w_i^t |y_i - z_i^t|^2 + \lambda \Sigma_{j=2}^m |z_j^t - z_{j-1}^t|^2, \quad \text{Eq. (1)}$$

where, $z_i^t$, is an approximate fit to intensity value $y_i$ at iteration t. The parameter $\lambda$ is an adjustable constant that dictates the strength of the second term that acts as the penalty term. The algorithm determines the values of the weights $w_i^t$ to give a good fit to the background signal. As such, the weights are driven to be small or zero for frequency values corresponding to intensity values $y_i$ associated with peaks of the spectrum.

The weights $w_i^t$ of at iteration t are obtained adaptively using the sum of square errors (i.e., the first term in Eq. (1)) between the previously fitted baseline and the original signal. In order to control the smoothness of the fitted baseline, a penalty approach is introduced based on sum squared derivatives (i.e., the second term of Eq. (1)) of the fitted baseline. The algorithm generally stops when a maximum number of iterations is reached or a termination condition occurs.

In other embodiments, alternative algorithms may be used to determine the background signal. For example, a polynomial fit may be performed to approximate the background signal. Using a polynomial fit to approximate the background signal generally requires identifying various parameters that define the general shape of the expected input data. As such, use of polynomial fits may be error prone and less reliable than use of the above-described airPLS algorithm.

The fourth (optional) operation of the normalization process smooths the data to reduce noise before data analysis is performed. According to an embodiment, a Savitzky-Golay filter algorithm may be performed to smooth the data. The Savitzky-Golay filter algorithm fits successive sub-sets of adjacent data points with a low-degree polynomial that is derived using a linear least squares method. Use of the Savitzky-Golay filter tends to increase the signal-to-noise ratio. Other smoothing algorithms may be used in other embodiments.

The fifth operation performs minimum/maximum scaling on intensity values of respective interpolated optical data. This scaling ensures the intensity values are normalized across all samples that have been measured. The data must be normalized before it may be used by the machine learning algorithms.

Models for Spectroscopy Data

As described above, spectral data may be represented as a two-dimensional plot of intensity vs. frequency (or equivalently vs. wavelength) values. Each intensity value represents an amount of radiation reaching a detector after incident electromagnetic radiation, generated by a source, interacts with a material. Materials may be identified by their characteristic spectral signatures in terms of peak positions and peak heights. The presence of known materials in a mixture of materials may be determined by analyzing spectra for the mixture based on spectral models for known materials. A spectral model for a known material may be constructed as follows.

FIG. 36A shows the "soot-3" data of FIG. 35B after it has been pre-processed and FIG. 36B shows the "soot-6" data of FIG. 35C after it has been preprocessed, according to an example embodiment of the present disclosure. The data in FIGS. 36A and 36B is Raman spectroscopy data characterizing molecular vibrations of for soot particles in motor oil. Only some of the spectral features in FIGS. 36A and 36B are associated with soot particles. A model for the features associated with soot particles may be generated by observing changes in spectral features vs. concentration of soot, as described in greater detail below.

The features shown as black shaded regions in FIGS. 36A and 36B correspond to Raman scattering peaks associated with soot particles. The appearance of three or four shaded features is a characteristic of soot. As shown in FIGS. 36A and 36B the size and shapes of the various peaks change with concentration.

Figure 36C:
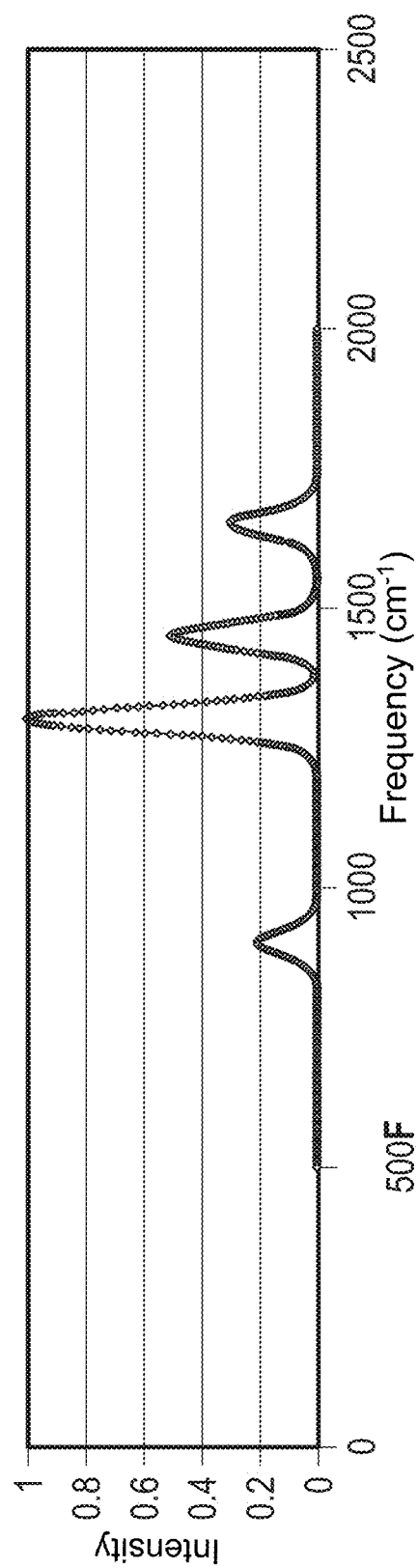
FIG. 36C is a data plot of a mathematical approximation to the Raman spectroscopic features associated with soot, according to an example embodiment of the present disclosure.

FIG. 36C is a plot of a mathematical approximation to the Raman features (i.e., spectroscopic "peaks") associated with soot, according to an example embodiment of the present disclosure. In this example, the Raman spectral features associated with soot may be approximated using simple mathematical functions. The curve shown in FIG. 36C is specified by a sum of four Gaussian functions to give the following mathematical approximation:

$$y_i = f(x_i, \alpha, \beta, \gamma), \quad \text{Eq. (2)}$$

with, $$f(x, \alpha, \beta, \gamma) = \Sigma_{i=1}^4 \alpha_i \exp(-\gamma_i (x - \beta_i)^2), \quad \text{Eq. (3)}$$

and where $y_i$ is an intensity value corresponding to a given frequency value $x_i$. Table I. (below) shows values of the various parameters used in Eq. (3) to generate the curve in FIG. 36C.

TABLE I

| i | $\alpha_i$ | $\beta_i$ | $\gamma_i$ |
|---|---|---|---|
| 1 | 0.2 | 900 | 0.001 |
| 2 | 1.0 | 1300 | 0.001 |
| 3 | 0.5 | 1450 | 0.001 |
| 4 | 0.3 | 1650 | 0.001 |

The above mathematical approximation to the Raman spectroscopy data for soot (i.e., Eqs. (1), (2), and Table I.) may be improved by performing a regression algorithm to find the best values of the parameters $\alpha$, $\beta$, $\gamma$. A regression algorithm adjusts the values of parameters $\alpha$, $\beta$, $\gamma$ to minimize deviations of the actual data from the approximation of Eq. (2). For example, a regression algorithm seeks to find a minimum of an expression of the form:

$$\min\{\alpha, \beta, \gamma\} \|y_j - f(x_j, \alpha, \beta, \gamma)\| \quad \text{Eq. (4)}$$

where, the norm $\|y_i - f(x_i, \alpha, \beta, \gamma)\|$ measures deviations from each actual intensity value $y_i$ from the corresponding approximate value predicted by the functional form $f(x_i, \alpha, \beta, \gamma)$. Many different mathematical forms may be chosen for the norm. For example, for a vector of values $z_i$, $z_i$ the norm may be chosen to have the form:

$$\|z\|_p = (\Sigma_{j=1}^{N} |z_j|^p)^{1/p}. \qquad \text{Eq. (5)}$$

A commonly used norm is given by a sum of squares, $$\|z\|_2^2 = \Sigma_{j=1}^{N} |z_j|^2. \qquad \text{Eq. (6)}$$

The form of the function chosen to approximate the data, and the type of norm chosen, dictates the type of regression algorithm used. In the above example, a non-linear form was chosen as shown in Eq. (3). Applying a regression algorithm using this function is therefore a non-linear regression. According to an embodiment, a non-linear least-squares algorithm may be used to construct a curve fitting model of the data. For example, a sum of Gaussian functions, such as given in Eq. (3) may be chosen. Then, the parameters of Eq. (3) may be optimized by an algorithm that minimizes a sum of squares such as given by Eq. (6). The optimal parameters $\beta_i$ determine the frequency values at which peaks of intensity are found. The optimal parameters $\alpha_i$ determine the maximum intensity values at each of the peaks.

Therefore, collectively, the parameters $(\alpha_i, \beta_i)$ serve as characteristic features of the spectra. Alternatively, spectral peaks may be characterized in terms of a frequency and an area under the peak. The area under a peak that is approximated by Gaussian functions, as in Eq. (3), is determined by parameters $(\alpha_i, \gamma_i)$. As described in greater detail below, it may be advantageous to work with peak positions and areas-under-peaks (e.g., see Eq. (7) below) when determining models for spectral features.

Materials may be identified by their characteristic spectral signatures in terms of peak positions and peak heights. Thus, it is useful to construct mathematical models for known materials. The models for known materials may then be used to determine the presence of various quantities of the known materials in a mixture based on a measured spectrum for the mixture and based on spectral models for the various known materials.

As described above, a model for spectral data may be generated using curve fitting. As in the example above, a functional form (e.g., Eqs. (2) and (3)) may be chosen and a computational algorithm, such as a non-linear regression algorithm, may be applied to determine parameters of the functional form. The values of the parameters thereby characterize the spectra. Materials may be identified by their characteristic spectral signatures in terms of peak positions $\beta_i$ and peak heights $\alpha_i$. For the above example, the model of a given known material is specified in terms of the parameters $(\alpha_i, \beta_i, \gamma_i)$. Alternatively, for a Gaussian function, the area under the curve is given by (verified by straightforward integration):

$$A_i = \alpha_i \sqrt{\frac{\pi}{\gamma_i}} \qquad \text{Eq. (7)}$$

thus, two of the three parameters $(\alpha_i, \beta_i, \gamma_i)$ are related in determining he area $A_i$ under the curve. Thus, in specifying characteristics of a spectral peak, only two parameters need be specified $(\beta_i, A_i)$, which specifies the peak position $\beta_i$ (i.e., frequency where peak is centered) and the area under the curve $A_i$ of a Gaussian function that approximates the peak.

For the soot model, described above, the spectral features included three or four separated peaks. In this case, it is a simple matter to guess a functional form as including four Gaussian functions. In other cases, however, it may not be easy to guess the functional form. For example, the spectra may have overlapping peaks as shown in the figure below.

Figure 37:
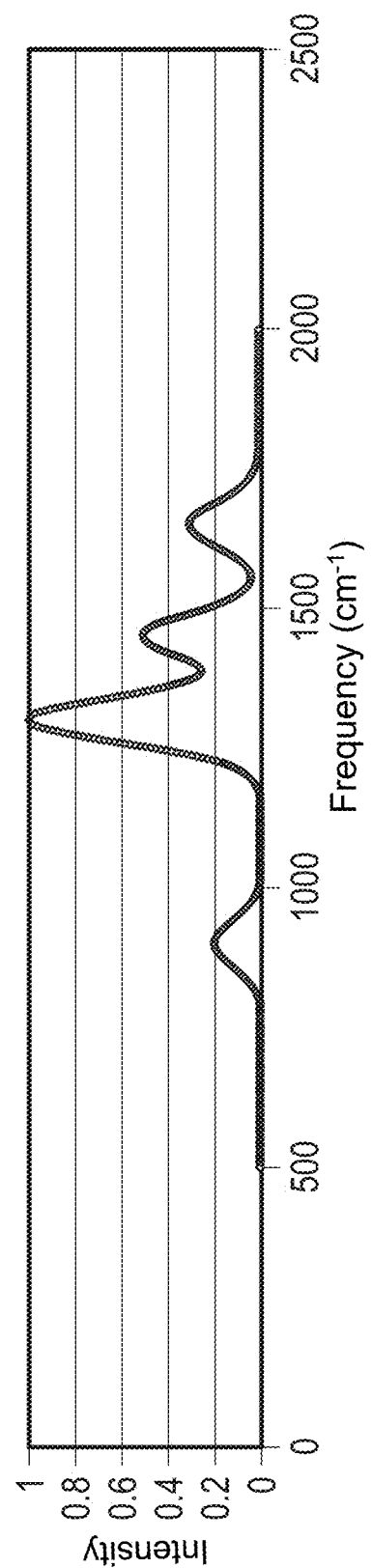
FIG. 37 illustrates a mathematical function that characterizes overlapping spectral peaks, according to an example embodiment of the present disclosure.

FIG. 37 illustrates a mathematical function that characterizes overlapping spectral peaks, according to an example embodiment of the present disclosure. The curve plotted in FIG. 37 was generated from Eq. (3) above using smaller values for $\gamma_i$=0.0003, which generates four broadened peaks. As shown, the middle two peaks partially overlap. A typical spectral plot may have hundreds or even thousands of overlapping peaks, making it nearly impossible to detect peak positions, heights, and widths, without using an automated algorithm.

According to an embodiment, machine learning algorithms may be used to determine spectral features in terms of peak locations, heights, and widths, as follows.

One way to model spectral data is through curve fitting, as described above. In order to fit a spectral feature, however, it is important to know roughly where the feature is located. For example, when fitting Eq. (3) to the four peaks of the soot spectral data it is advantageous to supply data to a regression algorithm in a neighborhood of each peak. In this sense, the data may be broken up into various frequency windows. A first frequency window may include frequency/intensity pairs $(x_i, y_i)$ in a range of frequencies roughly where the first peak is located. Similarly, a second frequency window may include frequency/intensity pairs $(x_i, y_i)$ in a range of frequencies roughly where the second peak is located, etc. For this simple example of the soot spectra, it was easy to manually determine the various frequency windows. For more complicated spectra having many overlapping peaks, it may be difficult or impossible without an automated procedure/algorithm.

According to an embodiment, there is a way of determining spectral features in terms of areas under the curve in small frequency ranges. For example, a spectral curve may be broken up into a plurality of frequency windows, that is, small frequency ranges. The frequency ranges may overlap. Within each frequency range, or frequency window, an area under the curve may be computed as a weighed sum of intensity values. Spectral features may then be determined by analysis of the areas as a function of the average frequency of each frequency window. For example, a spectral range between two minima of the area under the curve may be taken to be a range spanning a spectral feature. This process is described below with reference to FIGS. 38 to 42.

Figure 38:
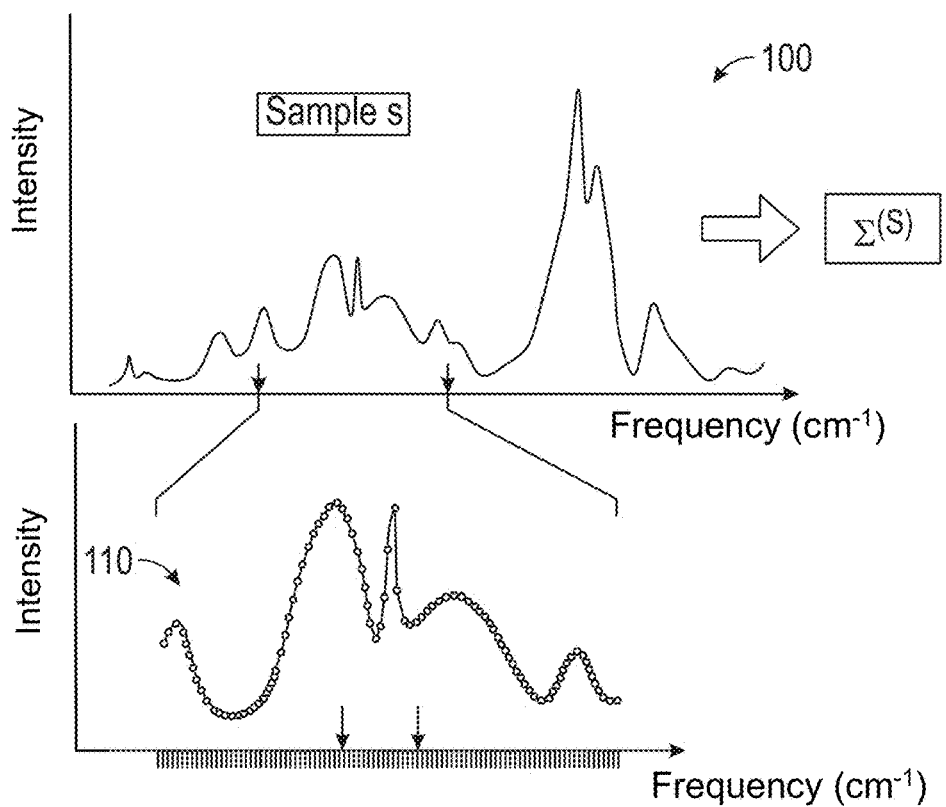
FIG. 38 illustrates a complicated spectrum having multiple overlapping peaks along with an expanded view of a portion of the spectrum, according to an example embodiment of the present disclosure.

FIG. 38 illustrates a complicated spectrum 100 having multiple overlapping peaks along with an expanded view 110 of a portion of the spectrum, according to an example embodiment of the present disclosure. Curve 100, of FIG. 38, is represented by a data set of frequency/intensity pairs. Curve 100 may correspond to measurements performed on one realization "s" of a material system. For example, curve 100 may represent measurements performed on a sample of motor oil having a first concentration of soot particles, iron based compounds, or other impurities. To characterize spectral properties of the material vs. concentration of its constituent materials, an ensemble $\Sigma^S$ of systems may be generated, with each member of the ensemble $\Sigma^S$ corresponding to difference concentrations of a material in question (e.g., soot particles, iron, etc.).

The following analysis considers spectral properties of various systems "s" chosen from the ensemble $\Sigma^S$ of systems. Trends among the various members of the ensemble $\Sigma^S$ may then be determined. In a first step, spectral features of a single system "s" chosen from ensemble $\Sigma^S$ may be analyzed. Curve 100, above, represents one such system "s" chosen from the ensemble $\Sigma^S$. Spectral features of curve 100 may be characterized in terms of peak locations and heights.

With such a complicated spectrum as curve 100, it would be difficult if not impossible to guess an appropriate functional form to fit the spectral data of curve 100. Therefore, an automated procedure is provided to determine spectral features. For clarity of this example, a section 110 of curve 100 has been expanded, above, to show individual data points.

Figure 39:
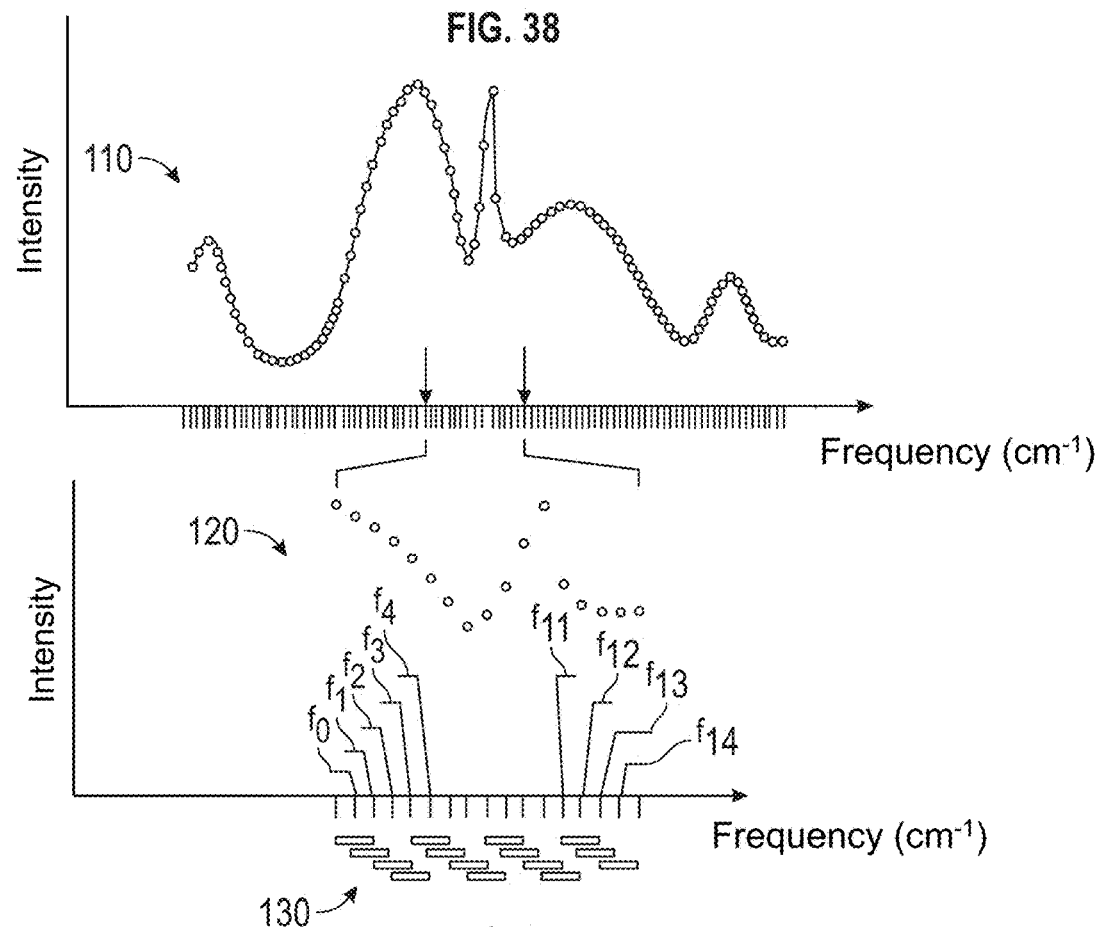
FIG. 39 illustrates a plurality of frequency windows to define areas under the curve of FIG. 38, according to an example embodiment of the present disclosure.

FIG. 39 illustrates a plurality of frequency windows 130 to define areas under the curve of FIG. 38, according to an example embodiment of the present disclosure. In FIG. 39, a region of frequencies 120 spanning a portion of curve 110 is shown. The region includes frequencies $f_0$ to $f_{14}$. Frequency windows 130 are defined for a plurality of overlapping frequency regions as shown. Each frequency window is centered on an average frequency $f_0$, $f_1$, etc., and includes several frequencies that span a range including the average frequency. Within each frequency window, an area value may be computed. They area may be computed as a weighted sum of intensity values as a discrete approximation to an integral of the intensity vs. frequency function over the frequency window. Thus, for each of frequencies $f_0$ to $f_{14}$, etc., a corresponding area $a_0$ to $a_{14}$, etc., may be computed as shown in FIG. 40.

FIG. 40 is a table of feature area values 150 each corresponding to respective frequency values 140 according to an example embodiment of the present disclosure. The area values 150, as a function of frequency 140, are shown graphically in FIG. 39 as open circles. As described above, the open circles in FIG. 39 correspond to values of area under the curve within each frequency window. A range of frequencies between two minima of the area curve may be taken to be a frequency range spanning a spectral feature.

Such a spectral feature (i.e., a region between two minima of the area values) may be approximated by a mathematical function such as a Gaussian, as described above (e.g., see Eqs. (2) and (3)). The intensity values within the identified frequency range of the spectral feature may be supplied to a regression algorithm that may be used to obtain an optimal fit of the spectral feature using a Gaussian function. In this way, the whole data set of frequency/intensity pairs describing spectral curve 100 may be fit using a series of Gaussian functions similar to the sum of functions in Eq. (3). In this way, curve 100 may be approximated by a series of Gaussian functions having the following form, $$f(x,\alpha,\beta,\gamma)=\Sigma_{i=1}^{N}\alpha_i \exp(-\gamma_i(x-\beta_i)^2),\qquad \text{Eq. (8)}$$

where, the upper limit of the sum N corresponds to the total number of features identified by analyzing area values for each frequency window 130 as described above.

In some embodiments, however, it may not be practical or desirable to fit a functional form to the spectral features determined above in Eq. (8). In cases having many peaks, it may be more practical simply to identify spectral peaks in terms of intensity values and frequency locations, or as areas (under the curve) of peaks and frequency locations of peaks, as described in greater detail below.

Selection of Spectral Features

A material composition may be determined based on a measured spectrum of a mixture of materials and based on spectral models of known constituent materials, according to example embodiments of the present disclosure. According to an embodiment, models of constituent materials may be generated using machine learning techniques, as follows.

In a first stage, an ensemble $\Sigma^S$ of systems may be chosen to span a known range of concentrations of a specific material. For example, the ensemble $\Sigma^S$ of systems may correspond to a plurality of materials having a range of compositions of soot particles, or iron impurities, etc. Spectral properties for each system in the ensemble $\Sigma^S$ of systems include an intensity vs. frequency curve, such as curve 100, above.

The ensemble $\Sigma^S$ of systems may be divided into various "data buckets" $\Sigma^S_\alpha$ that may be denoted by an index a. Each data bucket may be chosen to be a set of N spectral data sets 210 written symbolically as $\Sigma^S_\alpha = \{\Sigma^S_{\alpha i}\}_{i=1 \ldots N}$. Each of the N elements of the buckets $\Sigma^S_\alpha$ has a corresponding data set (i.e., spectral curve) including frequency/intensity pairs ($x_j$, $y_j$), from which spectral features (peak intensities, peak positions, peak areas, may be determined).

Each data bucket may be chosen based on a range of concentrations of the material in question. For example, a first data bucket $\Sigma^S_1$ may correspond to a plurality of systems having compositions of the material in question falling in a range from about 0 to 0.5%. A second data bucket $\Sigma^S_2$ may correspond to a plurality of systems having compositions of the material in question falling in a range from about 0.6 to 1.0%. A third data bucket $\Sigma^S_3$ may correspond to system systems having compositions of the material in question falling in a range from about 1.0 to 1.5%, etc. As in this example, data buckets $\Sigma^S_\alpha$ may be chosen to have overlapping ranges of frequencies.

For each of the systems "s" in a data bucket $\Sigma^S_\alpha$, a spectral curve (e.g., curve 100, above) may be analyzed to determine spectral features. For example, an automated process may be carried out to determine peak positions and peak heights based on areas under the curve computed in a plurality of (possibly overlapping) frequency windows, as described above.

According to an embodiment, the features may simply be specified in terms of peak areas. Thus, for each system $s_1$, $s_2, \ldots s_N$, in a data bucket a vector of peak area values may be computed. Each peak area value is associated with a corresponding frequency. The data, so computed, may be organized as shown in FIG. 41.

FIG. 41 is a table of feature area values vs. frequency for a plurality of systems, according to an example embodiment of the present disclosure. Each row of the table of FIG. 41 is labeled by system numbers $s_1, s_2, \ldots s_N$. Thus, each row of the table corresponds to areas of peak features for the corresponding system. The columns are labeled by frequency windows.

In developing a model for a given material, one physical assumption is that peaks corresponding to the material in question should have a dependence on the concentration of the material in question. For example, in the plots for soot presented above, three or four peaks were observed to correspond to soot. It is reasonable to expect that peak heights and peak widths should change as a function of composition. Thus, in the table of FIG. 41, one would expect area values to change going from top to bottom in a column, if that column corresponds to a peak associated with the material in question.

It is reasonable to assume that frequencies having peak areas that change with composition may be associated with the material whose concentration is changing. Such frequencies should therefore be included in a model of the material in question. Frequencies correspond to peaks that do not change appreciably with concentration can reasonably be assumed to not correspond to the material in question. Such frequencies should therefore be excluded from consideration in a model of the material in question. This assumption provides a method for ranking the importance of various features, as follows.

While the functional form of the dependence of peak areas on concentration is not known, a simple choice is to assume a linear model of the following form, $$Y = X\beta + \varepsilon, \quad \text{Eq. (9)}$$

where Y is a vector of numbers specifying concentration, X is the above matrix of peak area values, β is a vector of values describing the composition dependence of the peak area values, and ε is a vector of constants representing random noise. The above quantities Y and X should not be confused with the (x, y) data points of a given spectral curve discussed above.

Suppose, for simplicity, we are considering four frequencies, $f_3$, $f_5$, $f_8$, $f_{12}$, for example, and five systems $s_1$, $s_2$, ... $s_5$, spanning five different composition values. In this case, the linear problem may be written explicitly in matrix form as follows.

$$\begin{bmatrix} Y_1 \\ Y_2 \\ Y_3 \\ Y_4 \\ Y_5 \end{bmatrix} = \begin{bmatrix} a_1 & a_2 & a_3 & a_4 \\ b_1 & b_2 & b_3 & b_4 \\ c_1 & c_2 & c_3 & c_4 \\ d_1 & d_2 & d_3 & d_4 \\ e_1 & e_2 & e_3 & e_4 \end{bmatrix} \begin{bmatrix} \beta_1 \\ \beta_2 \\ \beta_3 \\ \beta_4 \end{bmatrix} + \begin{bmatrix} \varepsilon_1 \\ \varepsilon_2 \\ \varepsilon_3 \\ \varepsilon_4 \\ \varepsilon_5 \end{bmatrix}, \quad \text{Eq. (10)}$$

where, the vector Y, and the matrix X are input parameters, and the vectors β and ε must be determined as a best fit relationship to the input data. Parameter vectors β and ε may be determined by a regression algorithm, such as the Lasso algorithm. In situations in which the number of frequencies exceeds the number of systems, a random Lasso algorithm may be performed to determine a suitable β vector.

In this regard, for a situation in which the number of frequencies is greater than the number of systems, the matrix X is rectangular with the number of columns greater than the number of rows. As such, not all values of the β may be obtained. Using a ransom lasso algorithm, however, the number of frequencies is truncated to be equal to the number of systems so that the matrix X becomes a square matrix. Approximations to various components of β may be obtained by choosing a plurality of randomly chosen sets of frequencies for the truncation and solving the corresponding truncated β vectors. Averaging over all the truncated β vectors gives a suitable approximate β vector with approximate values for all components of the β vector corresponding to all frequencies.

The determined values of the vector β characterize the importance of the corresponding frequency value in determining concentration dependence of peaks at the corresponding frequency values. Suppose the vector has the following values:

$$\beta = \begin{bmatrix} 0.86 \\ 0.23 \\ 0.61 \\ 0.12 \end{bmatrix}. \quad \text{Eq. (11)}$$

The above values indicate that peaks at the first and third frequencies, that is frequencies $f_3$, and $f_8$, in this example, have a stronger concentration dependence that the other two frequencies $f_5$ and $f_{12}$. As such frequencies $f_3$, and $f_8$ play a larger role in determining the composition dependence of the model and should therefore be considered as more important than frequencies $f_5$ and $f_{12}$.

The Lasso algorithm uses a $\|\beta\|_1$ norm that may be written as, $$\|\beta\|_1 = \Sigma_{j=1}^{N} |\beta j|. \quad \text{Eq. (12)}$$

Use of the $\|\beta\|_1$ norm generally has the effect of driving small components of β to zero. As such, frequencies that have corresponding components of β near zero may be considered as unimportant. In this way, the relative importance of the various frequencies may be ranked.

For simplicity, it may be convenient to set the various components if β to 0 or 1 depending on whether they are below or above a threshold. In the above example, if the threshold were taken to be 0.5, the following vector β would be obtained, $$\beta = \begin{bmatrix} 1 \\ 0 \\ 1 \\ 0 \end{bmatrix}. \quad \text{Eq. (13)}$$

Equation (12) states that when the four frequencies $f_3$, $f_5$, $f_8$, $f_{12}$, are considered, in characterizing the concentration dependence the five systems $s_1$, $s_2$, ... $s_5$, considered, only the first (i.e., $f_3$) and third (i.e., $f_8$) frequencies are determined to be important.

The above determination of which frequencies are important depends on the systems considered. In the above example, we considered only five systems $s_1$, $s_2$, ... $s_5$, and four frequencies $f_3$, $f_5$, $f_8$, $f_{12}$. If a similar computation were to be performed using the same four frequencies but with a different set of five systems $s_1$, $s_3$, $s_4$, $s_6$, $s_7$, the results regarding which frequencies are important may be different. In other words, the values obtained for the vector β may be different. For this reason, according to an example embodiment of the present disclosure, many combinations of systems are chosen to generate many values of the β vector.

It may be advantageous to consider all frequencies in a spectral curve (e.g., curve 100 above) and to generate a β vector for each of a number of groups of systems (e.g., in a data bucket $\Sigma^S_o$).

Thus, for each system $s_1$, $s_2$, ... $s_N$, in a data bucket $\Sigma^S_o$, one may choose combinations of subsystems where each subsystem has M elements where M<N. By choosing subsystems, each having M elements, one may construct a total of P different subsystems, where $$P = \binom{N}{M} = \frac{N!}{M!(n-M)!}. \quad \text{Eq. (14)}$$

For example, starting from N=7 systems of a given data bucket (e.g., say, data bucket $\Sigma^S_1$), it is possible to generate different P=21 different groups of subsystems, each having M=5 elements. For example a first subsystem may have elements {$s_2$, $s_4$, $s_5$, $s_6$, $s_7$}, a second may have elements {$s_1$, $s_2$, $s_3$, $s_5$, $s_6$}, etc.

As described above, a separate vector β may be generated for each of the P subsystems, to thereby generate the set of vectors $\{\beta_j\}_{j=1, 2 \ldots P}$. Each vector has a number of elements equal to the number of frequencies considered in each system. For example, if each system is a spectral curve (e.g., curve 100 above) having L frequencies, then each vector will have L components, $$\beta_j = \begin{bmatrix} \beta_{j1} \\ \beta_{j2} \\ \vdots \\ \beta_{jL} \end{bmatrix}. \quad \text{Eq. (15)}$$

As mentioned above, each component of may be taken to be 1 or 0, respectively characterizing whether the given frequency is or is not important for describing the concentration dependence of the given system j.

For a given data bucket (e.g., say, data bucket $\Sigma^S_1$), the various frequencies may be ranked by generating a count vector which is a given by a component-wise summation of all the vectors. For example, the count vector may be defined as $C = \Sigma_{j=1}^P \beta_j$. This vector will have the form, $$C = \begin{bmatrix} C_1 \\ C_2 \\ \vdots \\ C_L \end{bmatrix}, \quad \text{Eq. (16)}$$

where, $C_1$ denotes the number of times the first frequency was counted as being important, $C_2$ denotes the number of times the second frequency was counted as being important, etc., in the collection of P subsystems generated from systems of the data bucket.

Thus, for a given data bucket, the elements of the count vector C may be used to rank the various frequencies. Frequencies with higher corresponding elements of the count vector C may be considered to be more important than frequencies having smaller corresponding elements of the count vector C.

Figure 43A:
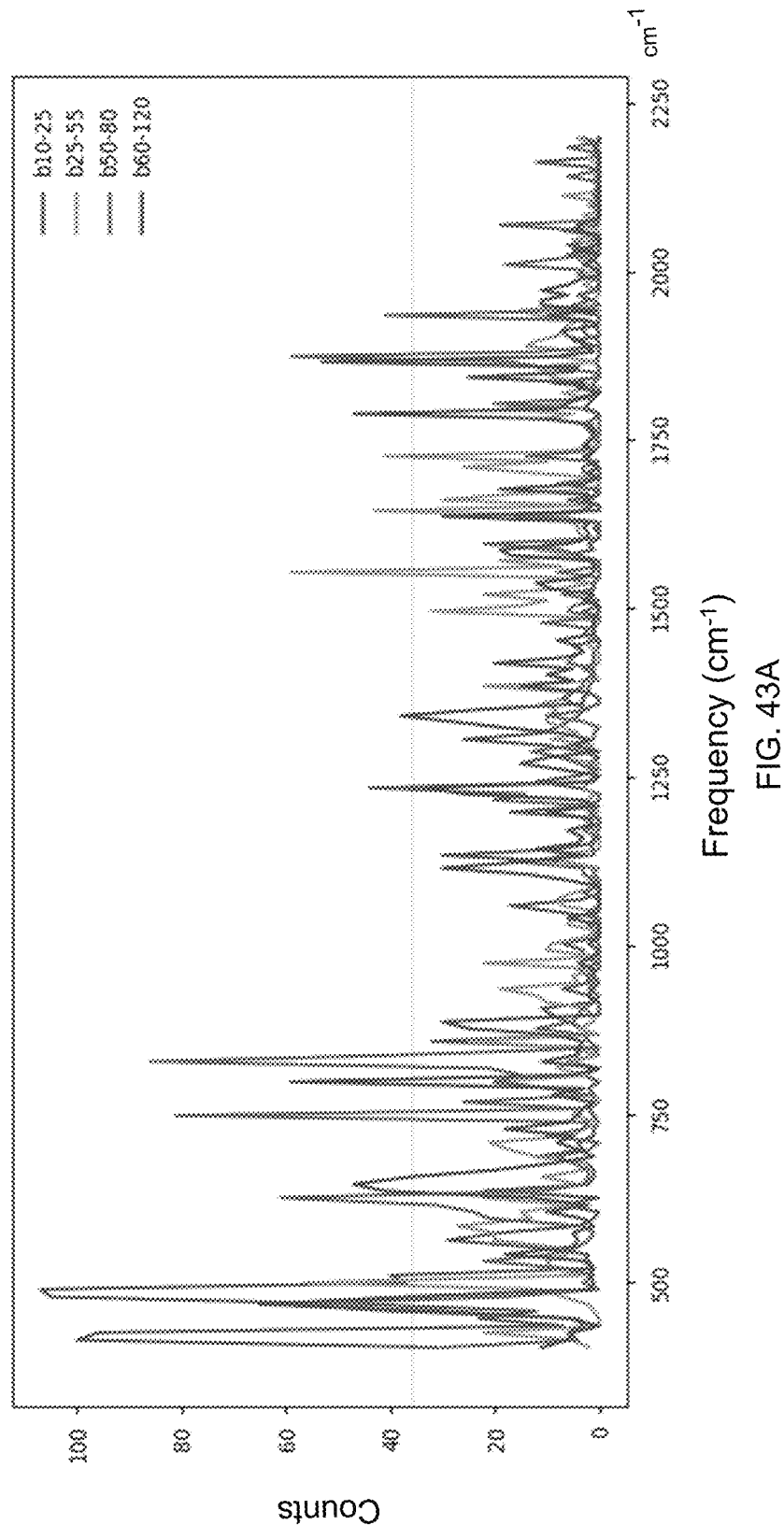
FIG. 43A is data plot of count values vs. frequency values for four data buckets corresponding to four respective ranges of concentrations of iron-based impurities in motor oil, according to an example embodiment of the present disclosure.

FIG. 43A is data plot of count values $C_j$ vs. frequency values $f_j$ for four data buckets corresponding to four respective ranges of concentrations of iron-based impurities in motor oil, according to an example embodiment of the present disclosure. A plot such as FIG. 43A may be used for feature selection, as described in greater detail below.

FIG. 43A was generated based on a count vector (e.g., see Eq. (16)) derived from four data buckets. A first data bucket $\Sigma^S_1$ includes iron concentrations of 10 to 25 ppm, a second data bucket $\Sigma^S_2$ includes iron concentrations of 25 to 55 ppm, a third data bucket $\Sigma^S_3$ includes iron concentrations of 50 to 80 ppm, and a fourth data bucket $\Sigma^S_4$ includes iron concentrations of 60 to 120 ppm. In this example, data buckets $\Sigma^S_3$ and bucket $\Sigma^S_4$ include overlapping concentrations.

Figure 43B:
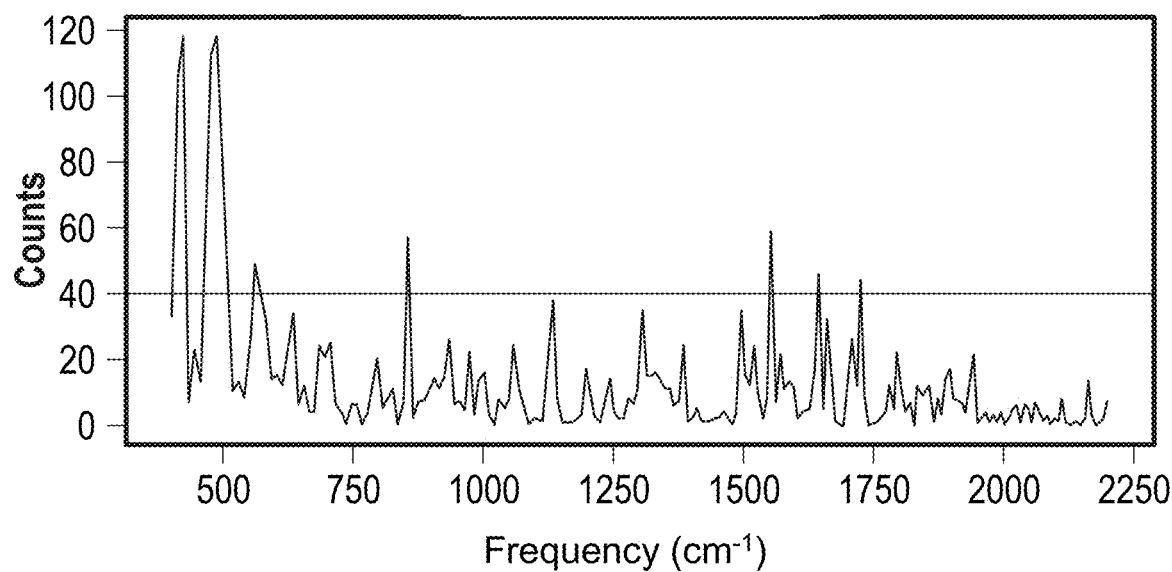
FIG. 43B is a data plot showing count values vs. frequency values for only the low concentration buckets of FIG. 43A, according to an example embodiment of the present disclosure.

FIG. 43B is a plot showing count values $C_j$ vs. frequency values $f_j$ for only the low concentration buckets $\Sigma^S_1$ and $\Sigma^S_2$, of FIG. 43A, according to an example embodiment of the present disclosure. The low concentration buckets $\Sigma^S_1$ and $\Sigma^S_2$ collectively span the concentration range from about 10 to about 55 ppm. In general, plots of the count vector may have dissimilar features for low concentrations in comparison with those for high concentration.

Figure 43C:
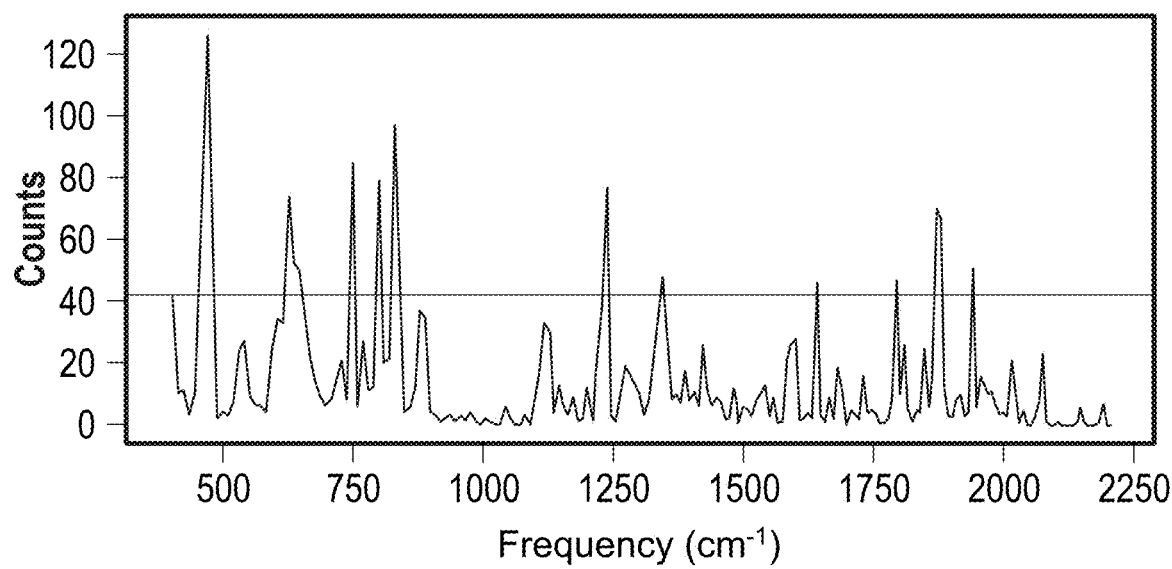
FIG. 43C is a data plot showing count values vs. frequency values for high concentration buckets of FIG. 43A, according to an example embodiment of the present disclosure.

FIG. 43C is a plot showing count values $C_j$ vs. frequency values $f_j$ for high concentration buckets $\Sigma^S_3$ and $\Sigma^S_4$, which collectively span the concentration range from about 50 to about 120 ppm, according to an example embodiment of the present disclosure.

Since low and high concentration plots may have dissimilar features, it is important to consider all concentrations (i.e., all data buckets $\Sigma^S_1$, $\Sigma^S_2$, $\Sigma^S_3$, and $\Sigma^S_4$) when choosing frequency ranges (e.g., frequency windows) in building a model to characterize the system.

A horizontal line may be drawn to indicate a count threshold. In this example, the horizontal line is chosen to have a value of one third the value of the largest count value. Frequency windows may be chosen by including only features having count values above the count threshold.

Figure 44A:
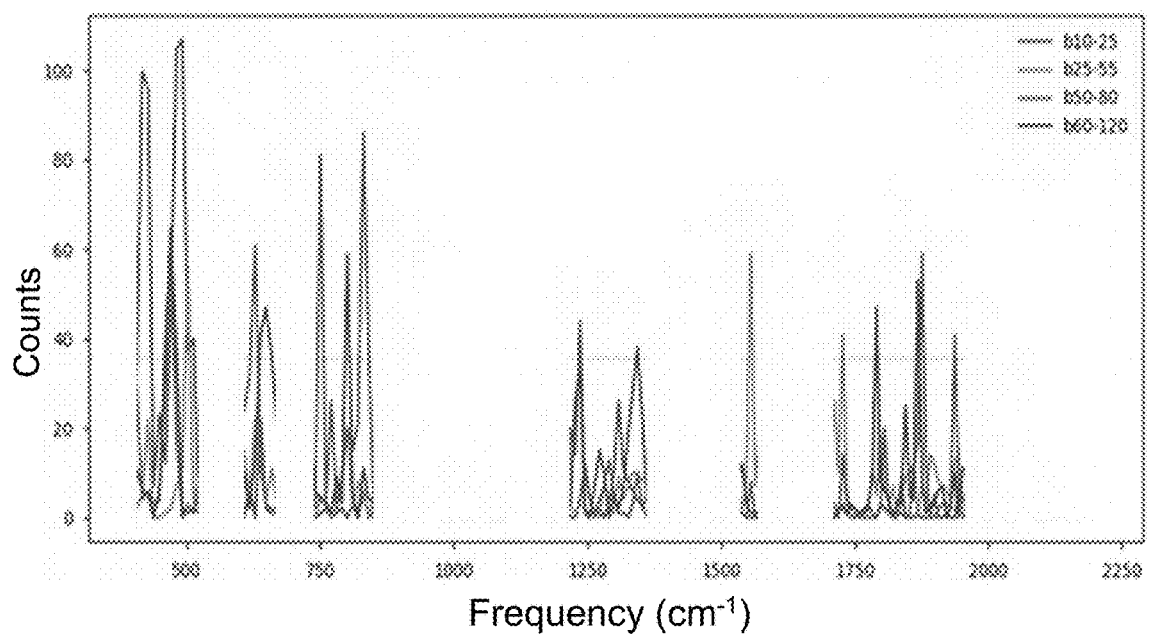
FIG. 44A is a data plot of count values generated by excluding count values that fall below the threshold line of the data plot of 43A, according to an example embodiment of the present disclosure.

FIG. 44A is a data plot of count values generated by excluding count values $C_j$ that fall below the threshold line for the data plot of 43A, according to an example embodiment of the present disclosure. FIG. 44A includes count values $C_j$ for all of the data buckets. A reasonable assumption, when building a model, is to consider only frequencies within frequency windows that contain the most significant peaks.

Figure 44B:
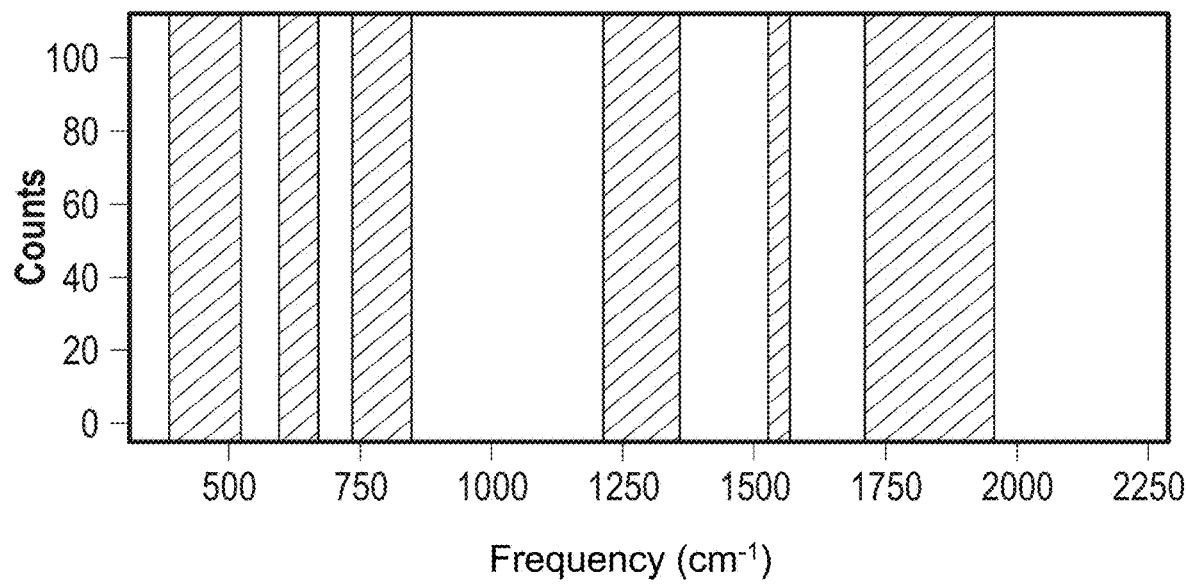
FIG. 44B illustrates shaded regions indicating frequency windows associated with the peaks of FIG. 44A, according to an example embodiment of the present disclosure.

FIG. 44B illustrates shaded regions indicating frequency windows associated with the peaks of FIG. 44A, according to an example embodiment of the present disclosure. Only features in the frequency windows defined by the shaded regions of 44B are used to generate a model for iron impurities in motor oil.

In this example, the frequency windows shown in FIG. 44B (as shaded regions) may be used to define a model for the material in question. In this regard, each frequency window may be represented as a coordinate axis in a multi-dimension space. Spectral data for a given system may be represented as a point in the multi-dimension space having coordinate values corresponding to each axis in the multi-dimensional space. There are several ways to define a coordinate value associated with each coordinate axis based on the spectral data. In one example, spectral peaks in each frequency window may be fit with a single Gaussian function for each frequency window as shown in FIG. 44C.

Figure 44C:
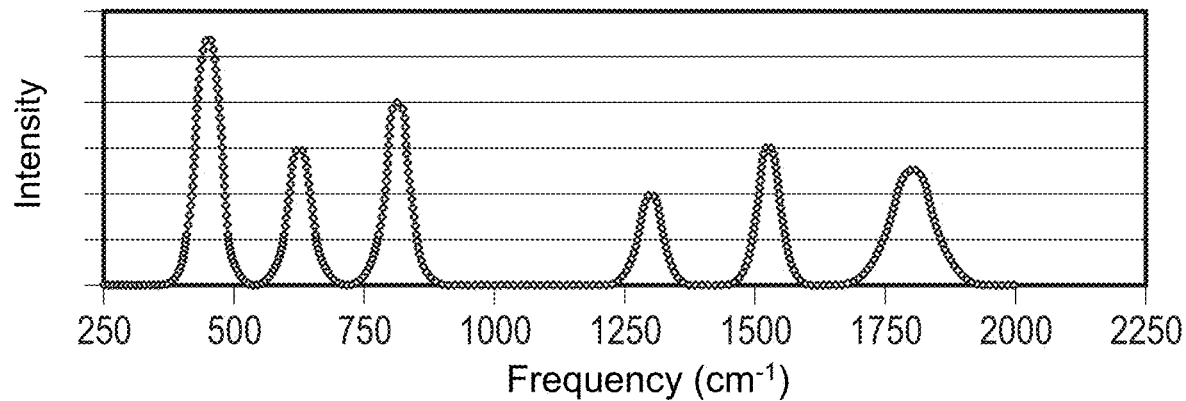
FIG. 44C is a data plot of a numerical representation of a series of Gaussian functions, each centered on a corresponding frequency window, according to an example embodiment of the present disclosure.

FIG. 44C is a plot of a numerical representation of a series of Gaussian functions, each centered on a corresponding frequency window, according to an example embodiment of the present disclosure. Gaussian functions are used here for simplicity of illustration and description. There is no restriction, however, to the use of Gaussian functions. In other embodiments other functions (e.g., Lorentzian, Voight, and StudentT distribution, etc.) may be used. In this example, each Gaussian function may be chosen to have a width that corresponds to the frequency range of peaks in the frequency window. The peak value of each Gaussian function may be chosen to be sufficiently large to enclose all of the peaks in each frequency window. A coordinate value for each of the dimensional axes (i.e., each frequency window) in the multi-dimensional space may be chosen based on the corresponding Gaussian function for each frequency window. For example, the peak value may be chosen as the coordinate value. In another example, the area of the Gaussian function may be chosen as the coordinate value.

In a further example embodiment, a coordinate value may be assigned to each frequency window by summing over the areas-under-the-curve for each of the peaks in each frequency window. As described above with reference to curve 100, 110, etc., for each system $s_1, s_2, \ldots s_N$, in a data bucket, a vector of peak area values $a_1, a_2, \ldots a_L$, may be computed. Each frequency window includes a certain number, Q, of peaks. A coordinate value for the frequency window may be obtained by summing the area values for the peaks in the corresponding frequency window as:

$$\text{Area}_{sum} = \Sigma_{n=q_1}^{q_Q} a_n, \quad \text{Eq. (17)}$$

where the set of integers $q_1, q_2, \ldots q_Q$, indexes the areas associated with the Q peaks in each window. In general, the number of peaks Q in a given frequency window will vary from window to window.

Figure 44D:
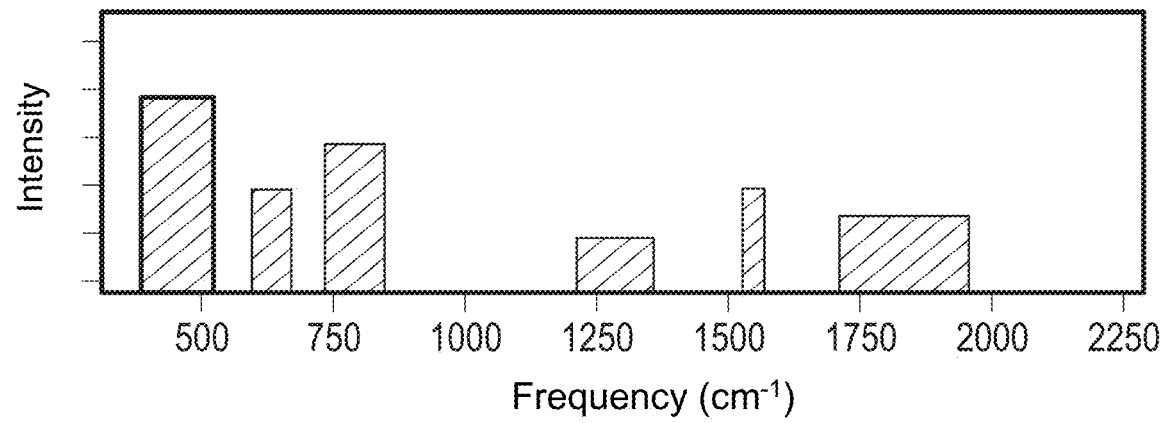
FIG. 44D is a bar chart indicating a value for a sum of areas of peaks in each frequency window of FIG. 44A, according to an example embodiment of the present disclosure.

FIG. 44D is a bar chart indicating a value for a sum of areas of peaks in each frequency window of FIG. 44A, according to an example embodiment of the present disclosure.

A similar bar chart may be generated for each of the samples in the ensemble $\Sigma^S$ of systems. In this way, spectral data for each system in the ensemble $\Sigma^S$ of systems, may be mapped into a single point a multi-dimensional space. In this example, the single point for a given system would be represented by the coordinate values $\{a_1, a_2, a_3, a_4, a_5, a_6\}$ (area sums) along the various axes (i.e., corresponding frequency windows) in the multi-dimensional system (i.e., six-dimensional system in this example).

Machine learning techniques may then be used to generate a model of the ensemble $\Sigma^S$ of systems by observing trends in the distribution of points in the multi-dimensional space, as described in greater detail below.

Machine Learning—Model Building

According to an embodiment, models for materials may be built using machine learning techniques based on a feature selection process, as described above. Generally, in the domain of machine learning there is an emerging practice called "deep learning," which may refer to a one or more specific machine learning algorithms including artificial neural networks (ANN), random forests, support vector machines (SVM) and non-negative matrix factorization (NMF). Thus, deep learning may include a plurality of algorithms that tend to exhibit similar characteristics. Deep learning systems are ANN that are constructed with multiple layers, sometimes called multi-level perceptrons. Use of advancing computational technology, such as graphical processing units, parallel processing, and multi-threading, as well as larger training data sets further empower deep learning to provide advance diagnostic and predictive insight.

Exemplary data models for evaluating Raman spectral data include models for oxidation, soot, fuel dilution, silicon, wear metals, and coolant. Generally, these models are trained to recognize specific Raman spectral patterns that allow for determination of the specific target. Such models may be used to identify chemical groups associated within an approximate Raman wave number range. The chemical name of the group common to a particular wavenumber range, and the intensity of the group within a particular wavenumber range, may be identified.

In an embodiment, a Support Vector Machine model may be used to generate a material model based on significant frequencies/intensities, as follows. Classifier models take a plurality of data points as input. Each data point may be considered to be a point in a multi-dimensional space. A model of the data is constructed on the assumption that that data may be classified into two or more categories. In the simplest of such methods, data is classified into one of two categories. The term "machine learning" means that the model is automatically constructed by a computer (i.e., by a computational "machine"). Since data points are viewed as points in a multi-dimensional space, a classifier model may be determined if the data corresponding to the two categories is found to lie in distinct regions of the multi-dimensional space.

According to an embodiment, a machine learning model may be constructed for spectral data. In this regard, significant frequencies, determined as described above, serve as coordinates in the multi-dimensional space. Corresponding values associated with spectral peaks in corresponding frequency windows may serve as values along the various dimensions. As described above, the values may correspond to peak intensities, sums of areas-under-the-curve, as peak values associated with a curve fit to a plurality of peaks in a given window, etc.

In a simple example, a model may be constructed by considering only two frequencies. More precisely, two frequency ranges may be specified corresponding to portions of a spectral data set in which significant spectral peaks have been determined. The two frequency ranges may be thought of as two coordinate axes spanning a two dimensional space. The corresponding peak areas (i.e., sum of areas for each peak in each frequency window) may therefore be thought of as coordinates in the two dimensional space.

Figure 45:
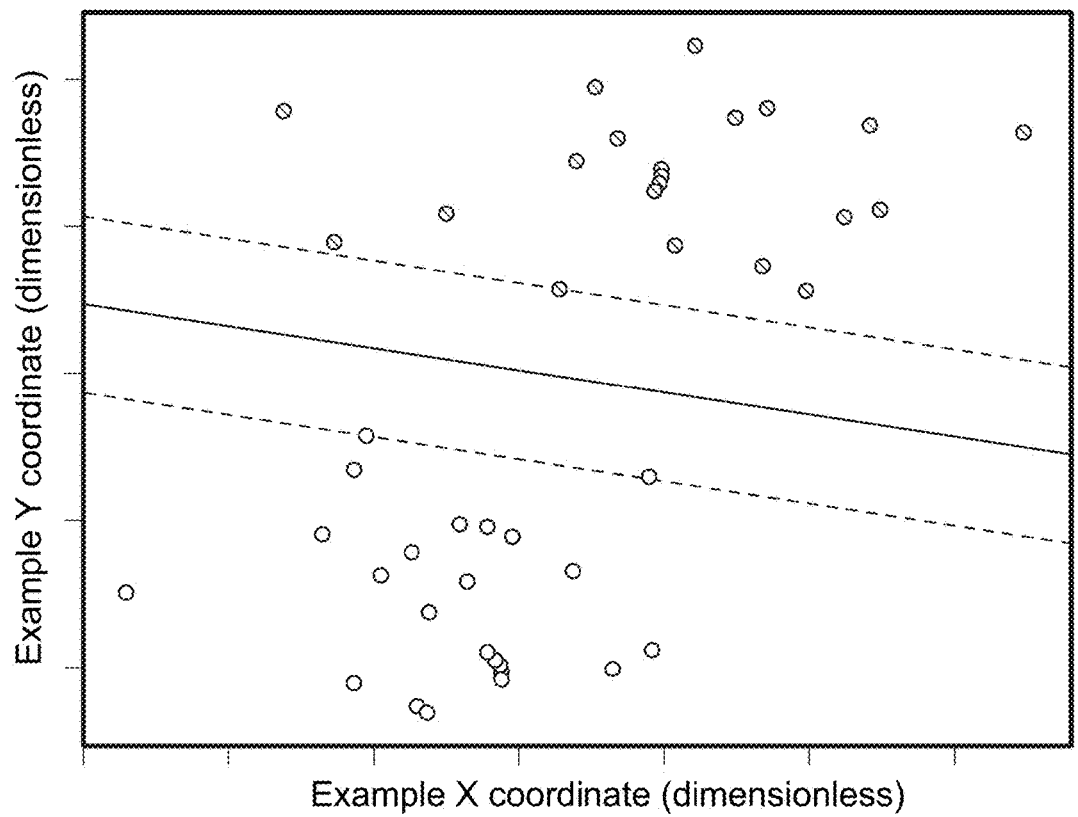
FIG. 45 is an illustration of data characterized by a two-dimensional classifier model, according to an example embodiment of the present disclosure.

FIG. 45 is an illustration of possible distribution of peak areas corresponding to a two-dimensional model, according to an example embodiment of the present disclosure. In this example, data tends to reside in one of two clusters residing in two respective regions. A machine learning algorithm may be used to generate a mathematical description of the distribution of points in the multi-dimensional space (i.e., two dimensions in this example). In this regard, the solid line in FIG. 45 above represents a hyperplane that best separates the two clusters of data. The dashed lines indicate a separation region between the two classes of data points.

In this example, the hyperplane is represented as a linear function and is determined by the algorithm by finding coordinates of the hyperplane that maximizes the distance of each point in the space from the hyperplane. In other embodiments, other functional forms for the hyper plane may be used. For example, in certain embodiments, a non-linear function may be used to generate a hyperplane having a curved surface.

According to an embodiment, training data corresponds to two classes of data. In the example of spectral data, the two classes may correspond to low concentration and high concentration of a material in question. A classification algorithm may then generate the hyperplane, described above, and may represent the hyperplane as a mathematical function (i.e., linear function, non-linear function, etc.). The model may then be used for prediction of properties of unknown materials, as follows.

Well-characterized training data may be supplied to the machine learning algorithm as input data to generate a model. Training data may include spectroscopic measurements for a plurality of samples of a fluid/oil having a known concentration of an impurity of contaminant of interest as characterized by an analytical laboratory using conventional analytical techniques.

Spectral training data may be generated for use in models that identify contamination targets such as fuel or coolant contamination, by producing physical samples having known concentrations (e.g., serial dilution) of fuel or coolant. Spectral data from each known sample may be collected and used as a spectral training data set to train models to identify corresponding contamination targets.

In another embodiment, spectral training data may be generated for use in models that identify degradation targets. When the specific fluid is an oil, such as motor oil, degradation products may include soot, wear metals, oxidation products, and the like. In the case of engine oil, degradation targets such as soot, wear metals, and oxidation products arise due to breakdown of engine oil through use and/or may arise due to engine wear. Degradation samples, which include a specific degradation target (e.g., a known concentration of soot, wear metal, etc.) may be obtained from an analytical laboratory that evaluates used oil samples though conventional means. Samples obtained from an analytical laboratory may be completely characterized using a battery of conventional analytical techniques. Spectral training data may be collected from used engine oil samples, which may be fully characterized by a conventional analytical laboratory, for use in models that identify degradation targets such as soot, wear metals, oxidation products, and the like.

Physical samples characterized as soot-positive may also include a concentration of soot. Obtaining spectral training data over a range of known soot concentrations may allow quantification of soot concentration of unknown samples via regression and/or classification analysis to generate quantitative or semi-quantitative models for soot, wear metals, oxidation state, and the like. As mentioned above, soot concentration, as reported by conventional analytical laboratories, is expressed using dimensionless units.

For example, concentrations of soot in oil are typically denoted by an integer in a range from 0 to 10. A value of 0 (i.e., "soot-0") indicates no detectable concentration of soot in oil. Increasing values of the integer (i.e., "soot-1," "soot-2," etc.) represent increasing concentrations of soot in oil. In some embodiments, a soot concentration above 4 may indicate a dangerous operating condition for an engine. In some embodiments, disclosed systems may provide a critical operating condition warning or shut-down procedure that may be implemented when a soot concentration above 4 is detected, as described in greater detail below.

An unknown material may be processed to generate data in the same way as was done for the training data. For example, spectral features of the unknown material may be analyzed in each of the spectral windows corresponding to the training data. In this sense, spectral data for the unknown material may be represented as a single point in the same multi-dimensional space. That single point may then be classified as corresponding to one or the other of the two classes represented by the model. The result is a prediction from the model that the unknown material falls into one or the other of the two classes. In the example of spectral data having low and high concentration of a material in question (e.g., iron, soot, etc.) the result is a prediction that the material corresponds to either high concentration or low concentration.

A plurality of models may be generated to give more general concentration information regarding a material in question. For example, a model may predict a material to have a concentration above or below 1% of the material in question. A second model may predict a material to have a concentration above or below 2% of the material in question. A third model may predict a material to have a concentration above or below 3% of the material in question, etc. Concentration may be expressed as a percent for some materials (e.g., soot) and may be expressed in ppm (i.e., parts per million) for other materials (e.g., iron, etc.).

Model Testing and Prediction

Disclosed embodiments may be used to generate a model for an motor coolant in engine oil. As an engine operates, various impurities may make their way into the oil and thus contaminate the oil. One such contaminant may be ethylene glycol that is a component of engine coolants. A model for coolant in oil was developed using the above-described techniques, according to an example embodiment of the present disclosure.

Figure 46:
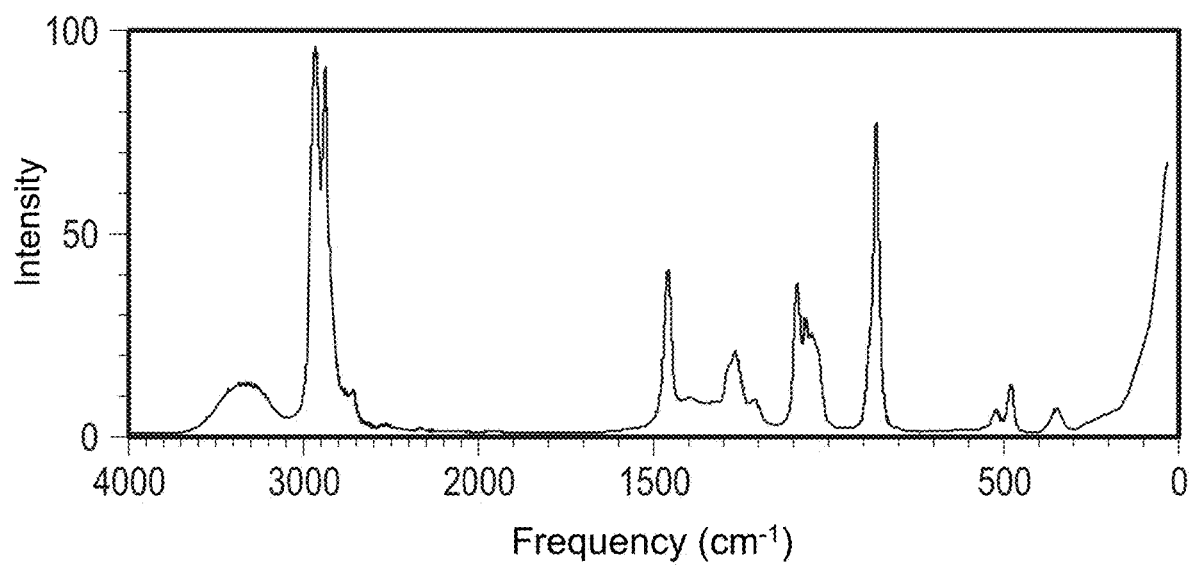
FIG. 46 is a data plot of Raman spectral data of pure ethylene glycol according to an example embodiment of the present disclosure.

FIG. 46 is a data plot of Raman spectral data of pure ethylene glycol according to an example embodiment of the present disclosure. The frequency distribution of peaks for pure ethylene glycol (shown in FIG. 46) gives an indication of what frequency ranges may be important for a model of a mixture of ethylene glycol and motor oil. To generate the model, an ensemble $\Sigma^S$ of systems spanning a plurality of concentrations of ethylene glycol in oil was generated. Spectral data was measured for each of the ensemble $\Sigma^S$ of systems and a plurality of data buckets $\Sigma^S_\sigma$ was defined. Feature selection operations were performed, as described above, to determine the most important peaks to use in the model.

Figure 47A:
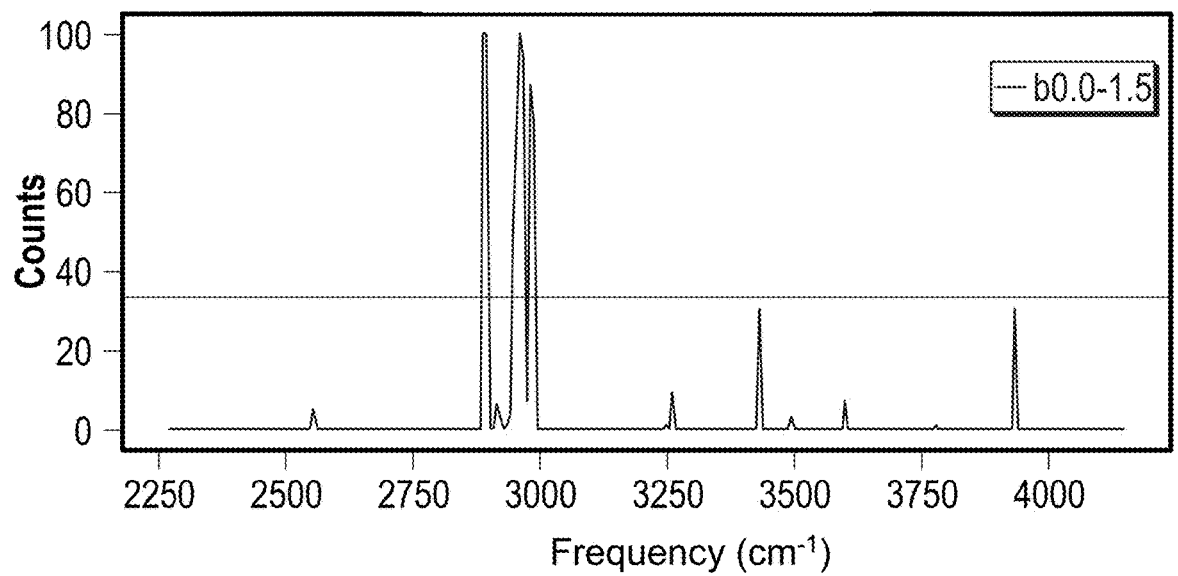
FIG. 47A is a data plot of count values vs. frequency for low concentrations of coolant in motor oil, obtained using a first laser that generates incident radiation of wavelength of 680 nm, according to an example embodiment of the present disclosure.
Figure 47B:
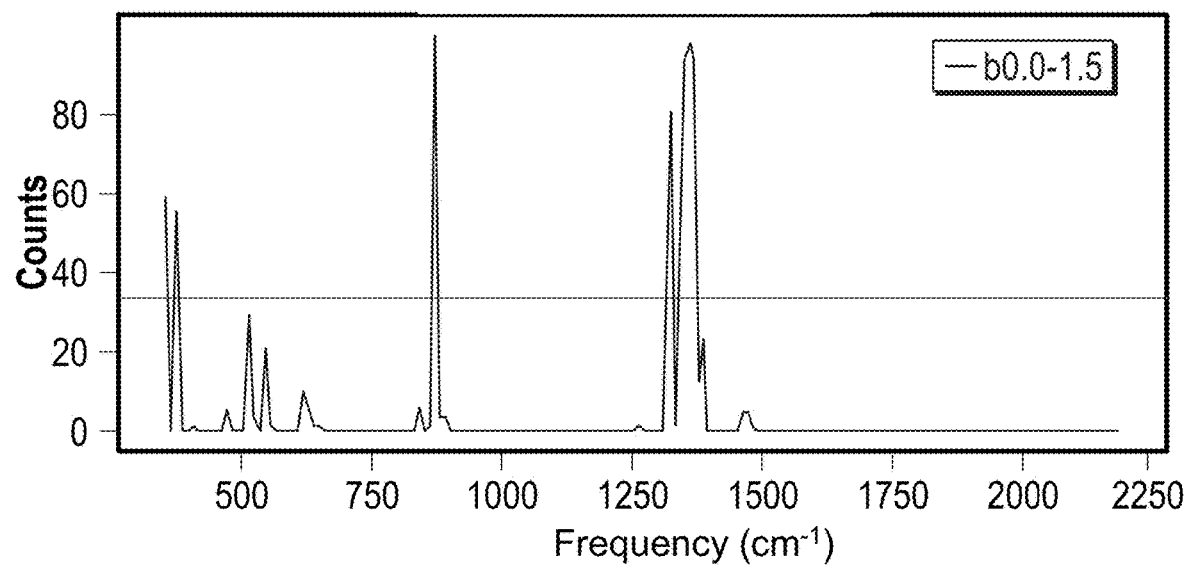
FIG. 47B is a data plot of count values vs. frequency for low concentrations of coolant in motor oil, obtained using a second laser that generates incident radiation of wavelength of 785 nm, according to an example embodiment of the present disclosure.
Figure 47C:
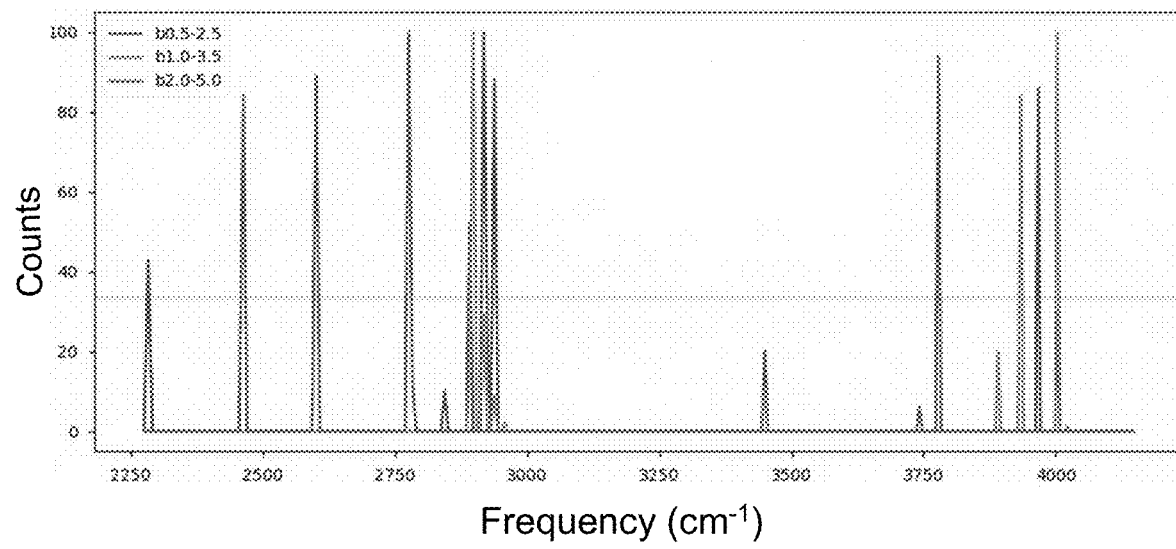
FIG. 47C is a data plot of count values vs. frequency for medium concentrations of coolant in motor oil, obtained using a first laser that generates incident radiation of wavelength of 680 nm, according to an example embodiment of the present disclosure.
Figure 47D:
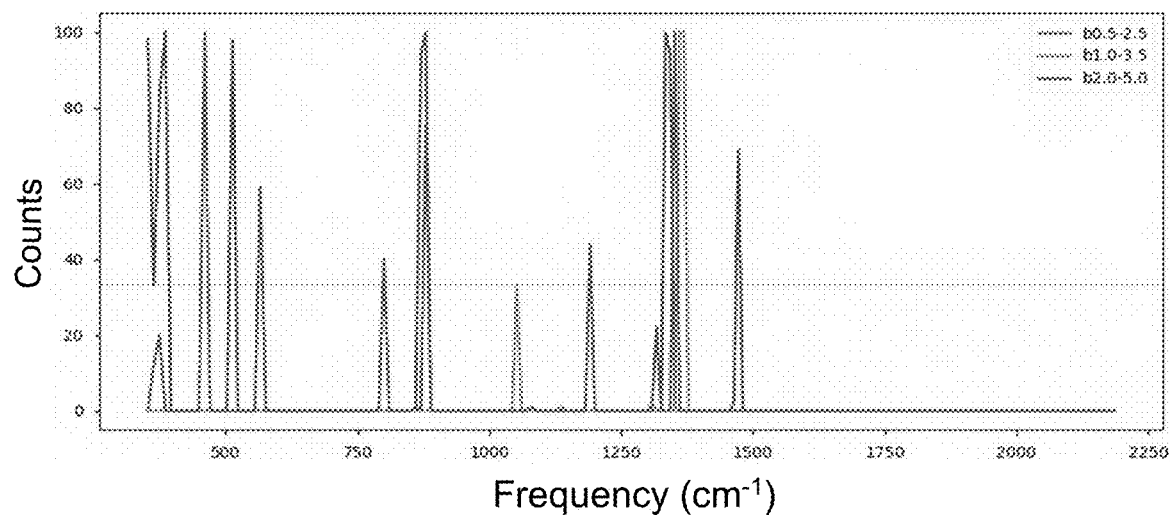
FIG. 47D is a data plot of count values vs. frequency for medium concentrations of coolant in motor oil, obtained using a second laser that generates incident radiation of wavelength of 785 nm, according to an example embodiment of the present disclosure.
Figure 47E:
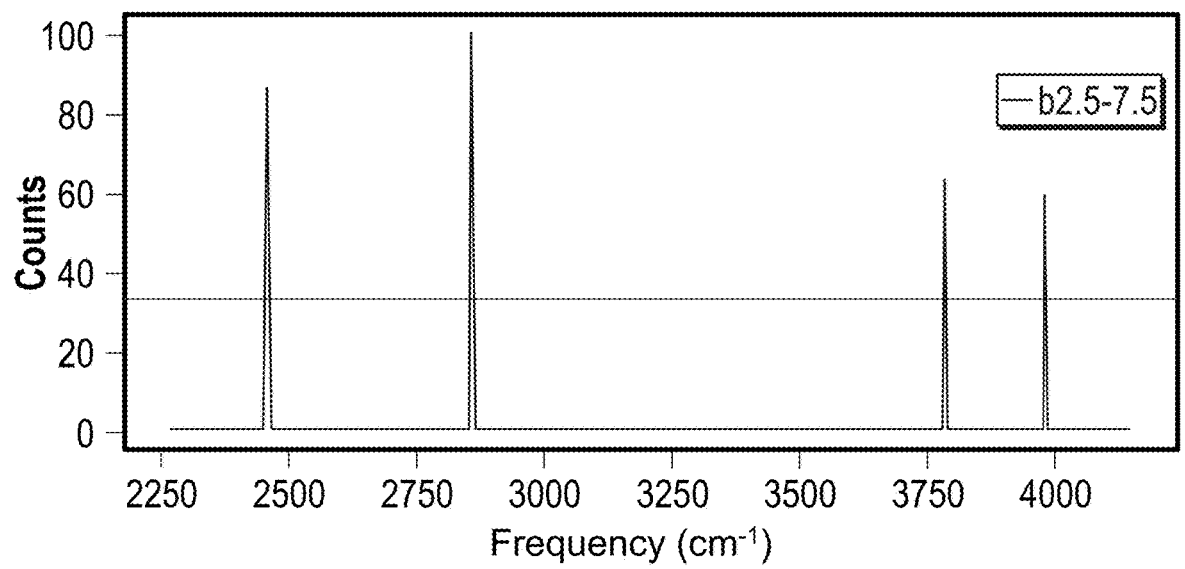
FIG. 47E is a data plot of count values vs. frequency for high concentrations of coolant in motor oil, obtained using a first laser that generates incident radiation of wavelength of 680 nm, according to an example embodiment of the present disclosure.
Figure 47F:
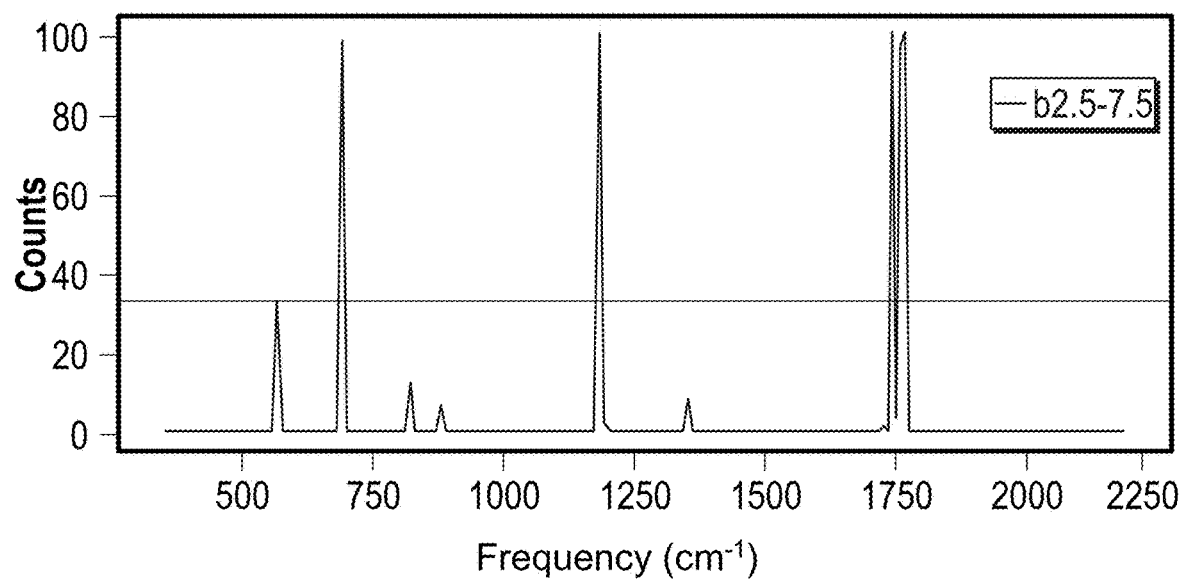
FIG. 47F is a data plot of count values vs. frequency for high concentrations of coolant in motor oil, obtained using a second laser that generates incident radiation of wavelength of 785 nm, according to an example embodiment of the present disclosure.

FIGS. 47A, 47C, and 47E are plots of count values $C_j$ vs. frequency values $f_j$ for low, medium, and concentrations of coolant in motor oil, respectively, obtained using a first laser that generates incident radiation of wavelength of 680 nm. FIGS. 47B, 47D, and 47F are plots of count values $C_j$ vs. frequency values $f_j$ for low, medium, and high concentrations of coolant in motor oil, respectively, obtained using a second laser that generates incident radiation of wavelength of 785 nm, according to an example embodiment of the present disclosure.

Figure 48A:
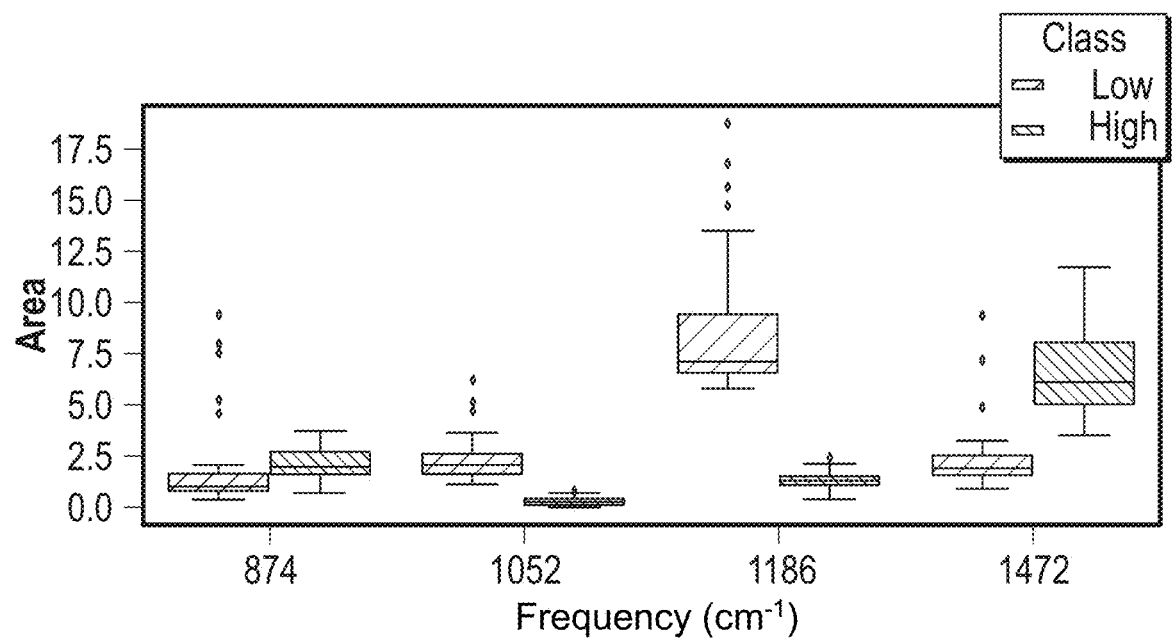
FIG. 48A is a box plot that illustrates a distribution of sums of peak areas for important frequency windows for coolant in motor oil, according to an example embodiment of the present disclosure.

FIG. 48A is a box plot illustrates a distribution of sums of peak areas for important frequency windows for coolant in motor oil, according to an example embodiment of the present disclosure. This plot illustrates the most important four frequency windows that were identified based on the data of FIGS. 47A to 47F. The frequency windows span a region of frequencies centered on 874 cm$^{-1}$, 1052 cm$^{-1}$, 1186 cm$^{-1}$, and 1472 cm$^{-1}$. These frequency windows were identified from measurements made using a laser having a wavelength of 785 nm. In this example, a first frequency window spans a range from about 860 cm$^{-1}$ to about 889 cm$^{-1}$, the second frequency window spans a range from about 1043 cm$^{-1}$ to about 1061 cm$^{-1}$, the third frequency window spans a range from about 1173 cm$^{-1}$ to about 1200 cm$^{-1}$, and the fourth frequency window spans a range from about 1464 cm$^{-1}$ to about 1481 cm$^{-1}$.

FIG. 48A is inter interpreted as follows. The horizontal axis indexes the frequency windows and the vertical axis plots the values of area sums for various systems. In this regard, for each system, a value is generated for the area sum for all peaks in given frequency window according to Eq. (17). For each system, one sum according to Eq. (17) is computed for each frequency window for low concentrations and one sum according to Eq. (17) is computed for each frequency window for low concentrations. Thus, since there are four frequency windows in this example, each system in the ensemble $\Sigma^S$ of systems is characterized by eight data points expressed as area sums: four area sums for low concentrations, each one corresponding to a respective frequency window, and four area sums for high concentration, each one corresponding to a respective frequency window.

A scatter plot is generated by plotting the results for all of the systems in the ensemble $\Sigma^S$ of systems. The resulting scatter plot has area sums plotted along the vertical axis. For clarity, each of the scatter plots along the vertical axis is displaced somewhat along the horizontal axis. Since all of the peaks in each frequency window have been summed, there is no significance to the horizontal axis other than to indicate roughly the frequency window to which each vertical scatter plot of area values belongs. In this sense, the width of each box in the figure above is not significant. The height of each box, however, illustrates where most of the area sum points are distributed (i.e., within one standard deviation) for the ensemble $\Sigma^S$ of systems. The vertical error bar (having larger width) indicates two standard deviations.

Figure 48B:
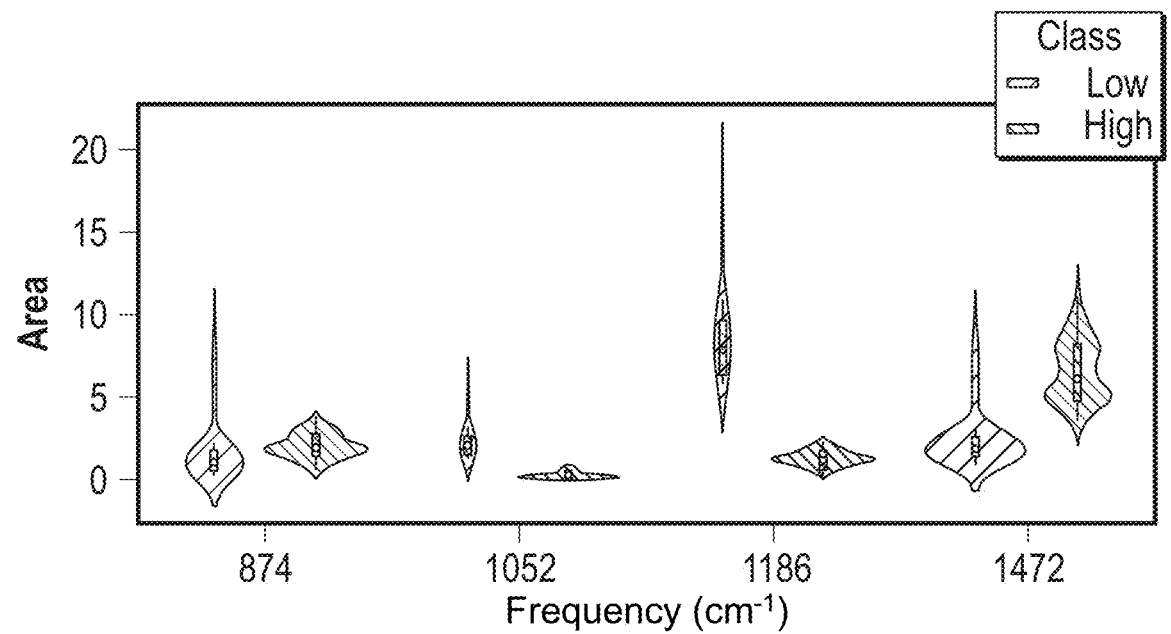
FIG. 48B is a violin plot showing the distribution of sums of peak areas of FIG. 48A, according to an example embodiment of the present disclosure.

FIG. 48B is a violin plot showing the distribution of sums of peak areas of FIG. 48A, according to an example embodiment of the present disclosure. As described above, for each system there are four points (i.e., area sums according to Eq. (16)) for low concentrations and four points for high concentration. Each of the four points for low and high concentrations represents an area sum for a corresponding frequency window. Thus, only the placement along the vertical axis has significance. The placement along the horizontal axis merely indexes the corresponding four frequency windows. In this example, the width of the shaded region for each point, for a given value of the vertical axis, indicates a relative number of systems having the given value of the area sum (i.e., the value along the vertical axis).

As described above, the data for area sums vs. frequency may be used as training data for a machine learning model. For the resulting model to be effective, it is advantageous for the data to be not appreciably overlapping in the four dimensional space spanned by the determined four frequency windows, as illustrated in FIG. 49, and described below.

Figure 49:
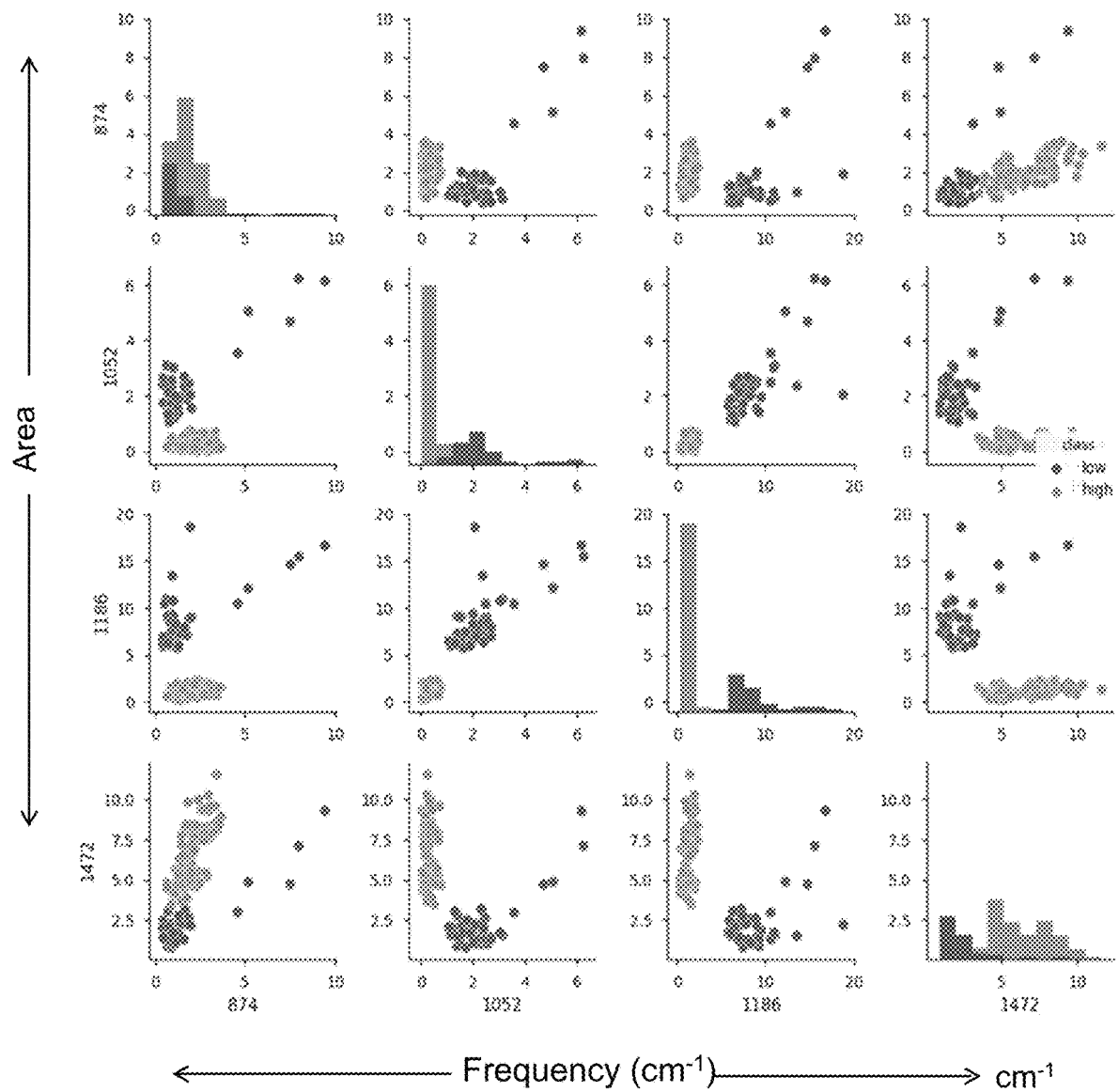
FIG. 49 plots the data of FIGS. 48A and 48B projected onto the various two-dimensional planes so that the distribution of area sums for low and high concentrations of coolant in motor oil may be investigated visually, according to an example embodiment of the present disclosure.

FIG. 49 plots the data of FIGS. 48A and 48B projected onto the various two-dimensional planes so that the distribution of area sums for low and high concentrations of coolant in motor oil may be investigated visually, according to an example embodiment of the present disclosure. FIG. 49 is interpreted as follows. Using the techniques described above, spectral data for each system has been reduced to a single data point $\{a_1, a_2, a_3, a_4\}$ in a four dimensional space. The coordinate axes in the four dimensional space represent the frequency windows centered on frequencies 874 cm$^{-1}$, 1052 cm$^{-1}$, 1186 cm$^{-1}$, and 1472 cm$^{-1}$. Therefore, for a given system, $a_1$ represents the area sum of all peaks in the frequency window centered around 874 cm$^{-1}$, $a_2$ represents the area sum of all peaks in the frequency window centered around 1052 cm$^{-1}$, $a_3$ represents the area sum of all peaks in the frequency window centered around 1186 cm$^{-1}$, and $a_4$ represents the area sum of all peaks in the frequency window centered around 1472 cm$^{-1}$.

Clustering of data may be seen in FIG. 49 by observing plots of various pairs of coordinates. For example, the graphs in the bottom row, starting from the left, plots $\{a_1, a_4\}$ values, $\{a_2, a_4\}$ values, and $\{a_3, a_4\}$ values. The last graph on the bottom right plots histograms for area values for respective low and high concentrations for the variable $a_4$. The rest of the data may be interpreted similarly. The row that is second from the bottom, starting from the left, plots $\{a_1, a_3\}$ values and $\{a_2, a_3\}$ values. The third graph is a histogram for variable $a_3$, and the last plot on the right, is a plot of $\{a_4, a_3\}$ values. The collection of plots in FIG. 49 is symmetric about the diagonal from the top left to the bottom right, as it should be. FIG. 49 indicates that there is good separation between clusters of area sum values for low concentrations and high concentrations. As such, one may suspect that this data may be described by a machine learning model.

A machine learning model for coolant in oil was generated using a Support Vector Machine algorithm using the above plotted data sets as follows. For an ensemble $\Sigma^S$ of systems containing N systems, a subset of the N systems was used as training data to generate the machine learning model. The model was then tested on the remaining systems.

Figure 50:
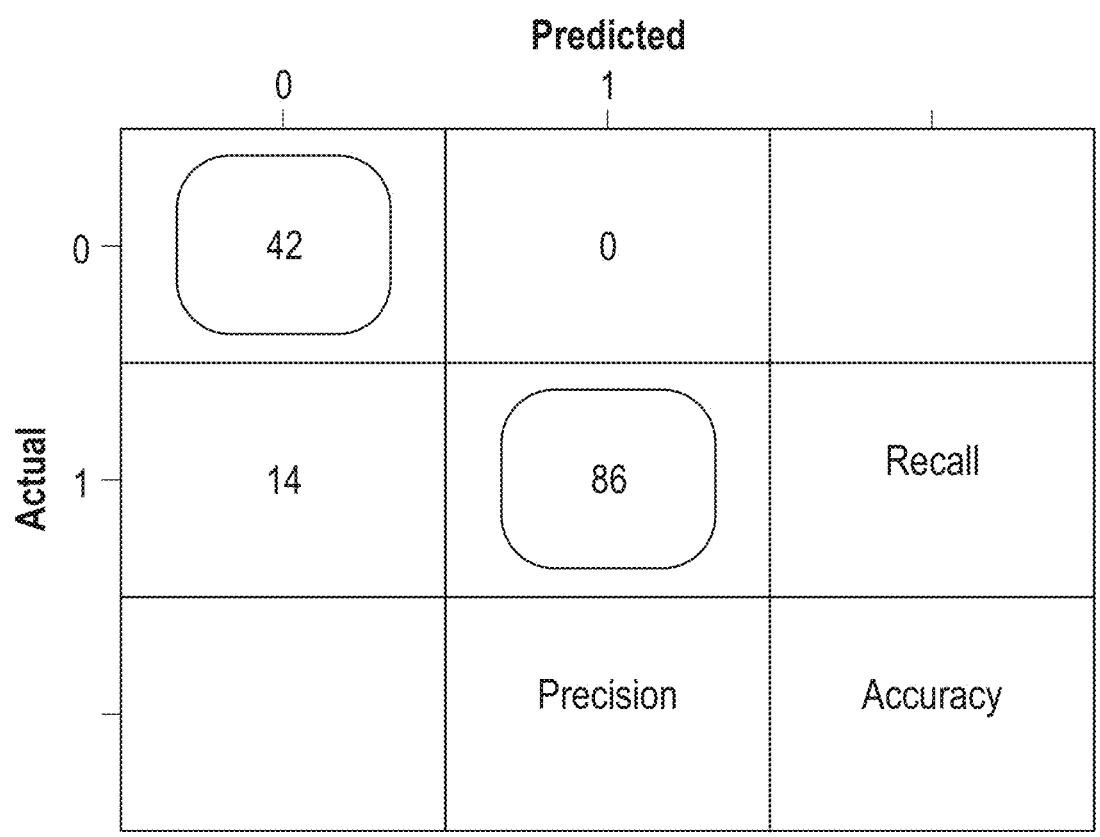
FIG. 50 illustrates results obtained from a Support Vector Machine model of coolant in motor oil, according to an example embodiment of the present disclosure.

FIG. 50 illustrates results obtained from a Support Vector Machine model of coolant in motor oil, according to an example embodiment of the present disclosure. These results obtained for an ensemble of 100 testing systems. In this example, 86 of the systems were correctly predicted to be high concentration systems.

FIG. 50 presents data in the form of a "confusion matrix" that characterizes the quality of the models for coolant in motor oil built according to the above-described process. The values along the diagonal indicate how many predictions were correct. The index values 0 and 1 correspond to low concentration and high concentration of coolant in oil. Thus, the 0-0 element is the number $N_{00}$ of times a low concentration sample was correctly predicted to be a low concentration system. Similarly, the 1-1 element indicates the number $N_{11}$ of times a high concentration was correctly predicted to be a high concentration system. The off diagonal elements indicate the number $N_{01}$ of false high concentrations (i.e., a low concentration system incorrectly predicted to be a high concentration system) and the number $N_{10}$ of false low concentrations (i.e., a high concentration system incorrectly predicted to be a low concentration system, respectively).

Three metrics: (1) accuracy, (2) recall, and precision, may be used to quantify the quality of the model. Accuracy is defined as:

$$\text{accuracy} = \frac{N_{11} + N_{00}}{(N_{11} + N_{10} + N_{01} + N_{10})}, \quad \text{Eq. (17)}$$

that is, the ratio of the total number $(N_{11}+N_{00})$ of correct predictions to the total number $N_{11}+N_{00}+N_{01}+N_{10}$ of predictions.

Precision is defined as:

$$\frac{N_{11}}{N_{11} + N_{01}}, \quad \text{Eq. (18)}$$

that is, the ratio of the total number $N_{11}$ of correctly predicted high concentration systems divided by the sum of the number $N_{11}$ of correctly predicted high concentrations and the number of false high concentrations $N_{01}$ (i.e., systems that are low concentration but are incorrectly predicted to be high concentration systems).

Recall is defined as:

$$\frac{N_{11}}{N_{11} + N_{10}}, \quad \text{Eq. (19)}$$

that is, the ratio of the total number $N_{11}$ of correctly predicted high concentration systems divided by the sum of the number $N_{11}$ of correctly predicted high concentrations and the number of false low concentrations $N_{10}$ (i.e., systems that are high concentration but are incorrectly predicted to be low concentration systems).

The better the model is at describing the system in question, the higher will be the values of the various metrics: accuracy, precision, and recall. The above results, illustrated in the confusion matrix, show that the model generates good predictions for systems having both high and low concentrations of coolant in oil.

A similar model for fuel in oil was developed using the above-described techniques, according to an example embodiment of the present disclosure. As described above, fuel is one of the various contaminants that may make its way into engine oil as the engine operates due to leaks in various gaskets/seals.

To generate the model, an ensemble $\Sigma^S$ of systems spanning a plurality of concentrations of fuel in oil was generated. Spectral data was measured for each system "s" of the ensemble $\Sigma^S$ of systems and a plurality of data buckets $\Sigma^S_o$ was defined. In this example, five data buckets $\Sigma^S_1, \Sigma^S_2, \Sigma^S_3, \Sigma^S_4,$ and $\Sigma^S_5$ were defined. The five data buckets were chosen to have the following overlapping concentrations (1) 0.0% to 2.0%, (2) 0.5% to 2.5%, (3) 1.0% to 3.5%, (4) 2.0% to 5.0%, and (5) 4.0% to 20%, respectively.

Further, for feature selection and model building, the above-described concentrations were considered to span three categories: low, medium, and high concentrations. For example, low concentration systems are represented by data bucket $\Sigma^S_1$, medium concentration systems are represented by data buckets $\Sigma^S_2, \Sigma^S_3,$ and $\Sigma^S_4$, and high concentration systems are represented by data bucket $\Sigma^S_5$. Feature selection operations were performed, as described above, to determine the most important peaks to use in the model for fuel in oil. Features determined for fuel in motor oil are described below with reference to FIGS. 51A to 51F.

Figure 51A:
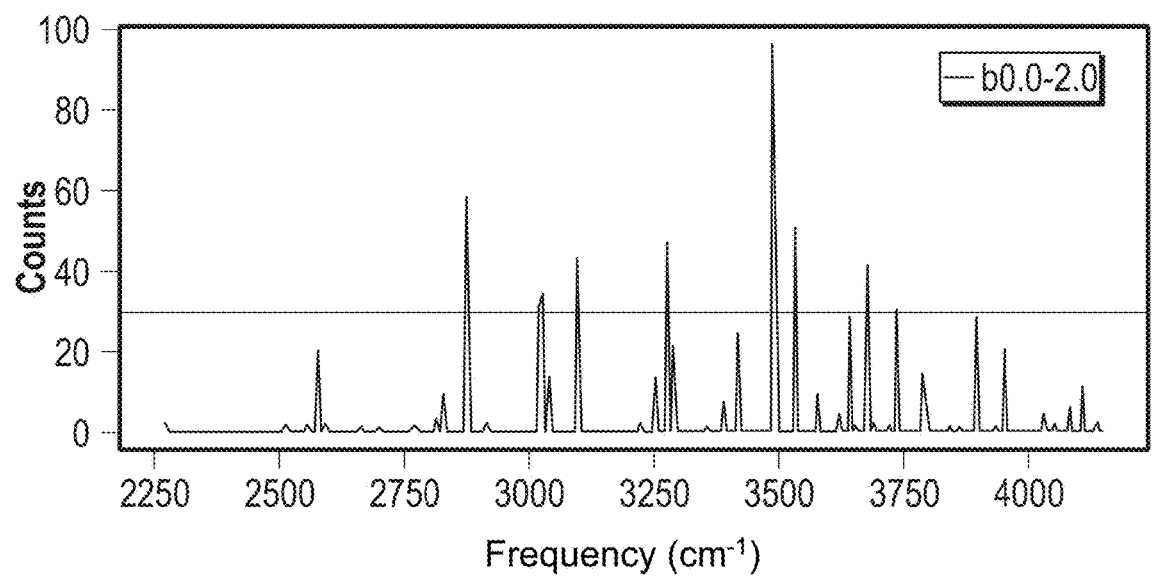
FIG. 51A is a data plot of count values vs. frequency for low concentrations of fuel in motor oil, obtained using a first laser that generates incident radiation of wavelength of 680 nm, according to an example embodiment of the present disclosure.
Figure 51B:
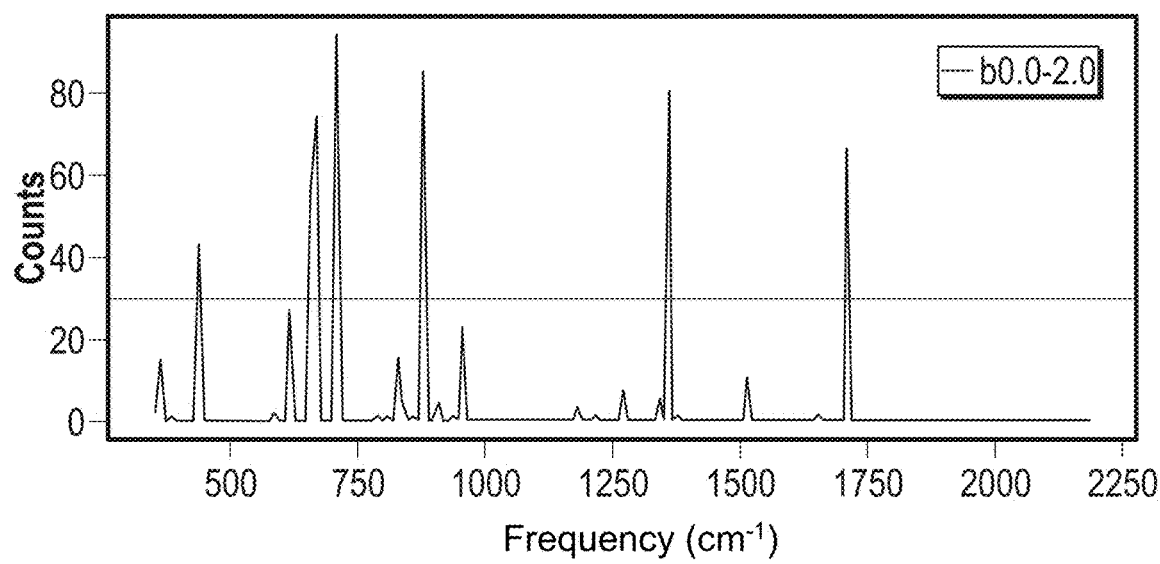
FIG. 51B is a data plot of count values vs. frequency for low concentrations of fuel in motor oil, obtained using a second laser that generates incident radiation of wavelength of 785 nm, according to an example embodiment of the present disclosure.
Figure 51C:
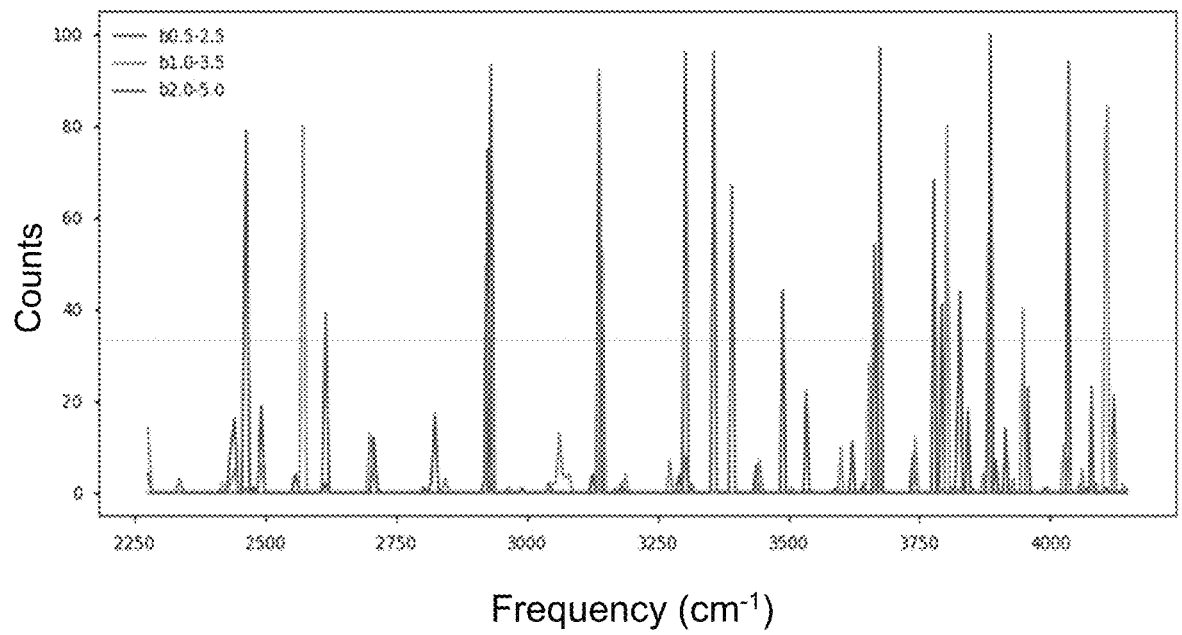
FIG. 51C is a data plot of count values vs. frequency for medium concentrations of fuel in motor oil, obtained using a first laser that generates incident radiation of wavelength of 680 nm, according to an example embodiment of the present disclosure.
Figure 51D:
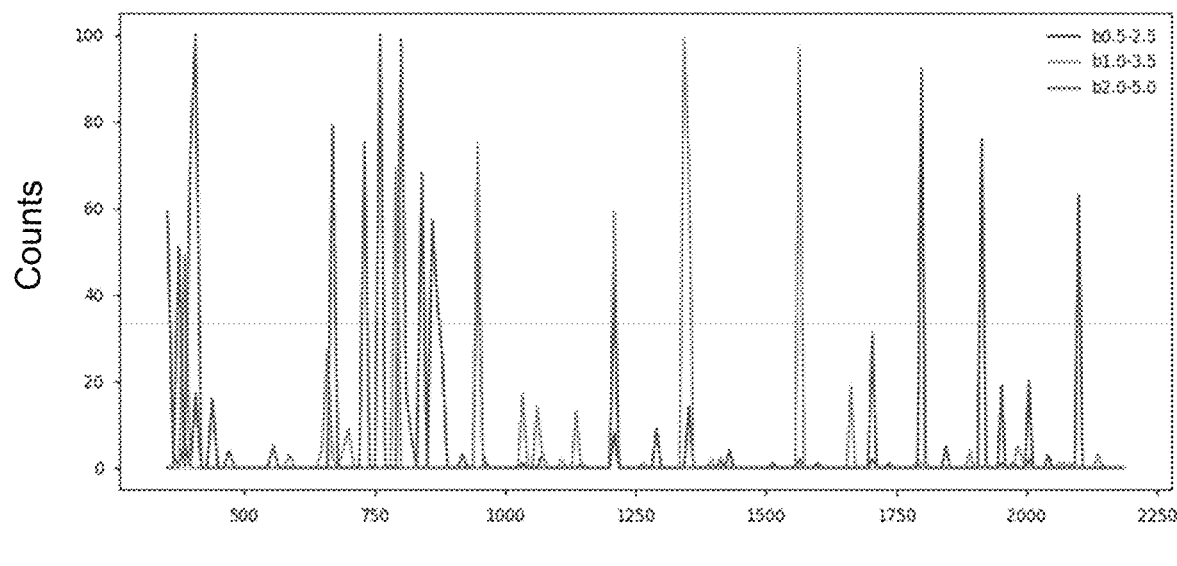
FIG. 51D is a data plot of count values vs. frequency for medium concentrations of fuel in motor oil, obtained using a second laser that generates incident radiation of wavelength of 785 nm, according to an example embodiment of the present disclosure.
Figure 51E:
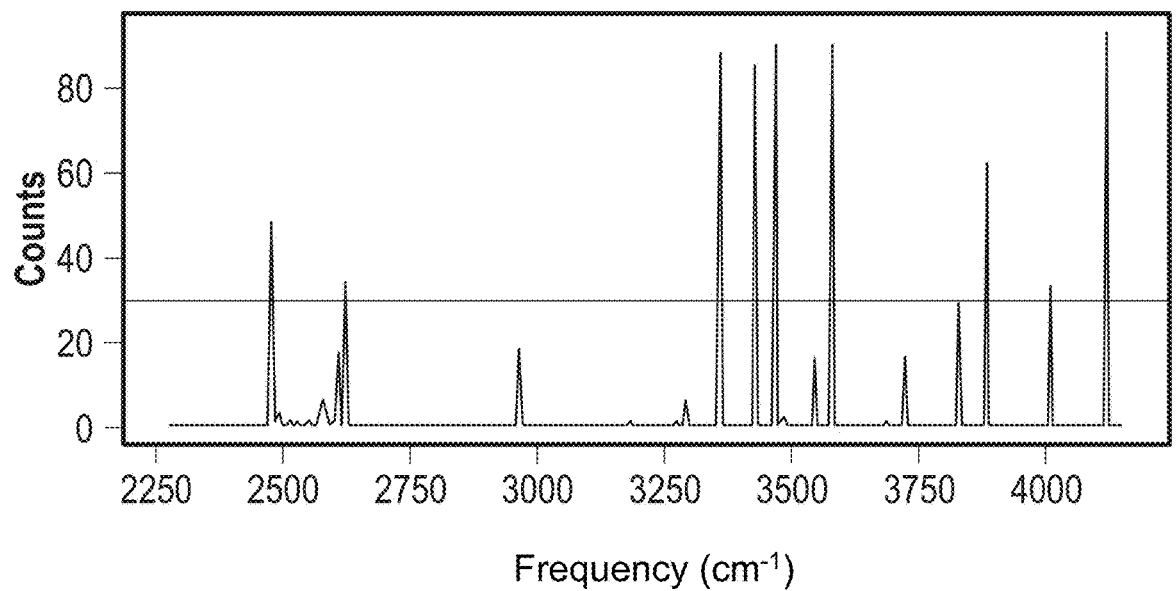
FIG. 51E is a data plot of count values vs. frequency for high concentrations of fuel in motor oil, obtained using a first laser that generates incident radiation of wavelength of 680 nm, according to an example embodiment of the present disclosure.
Figure 51F:
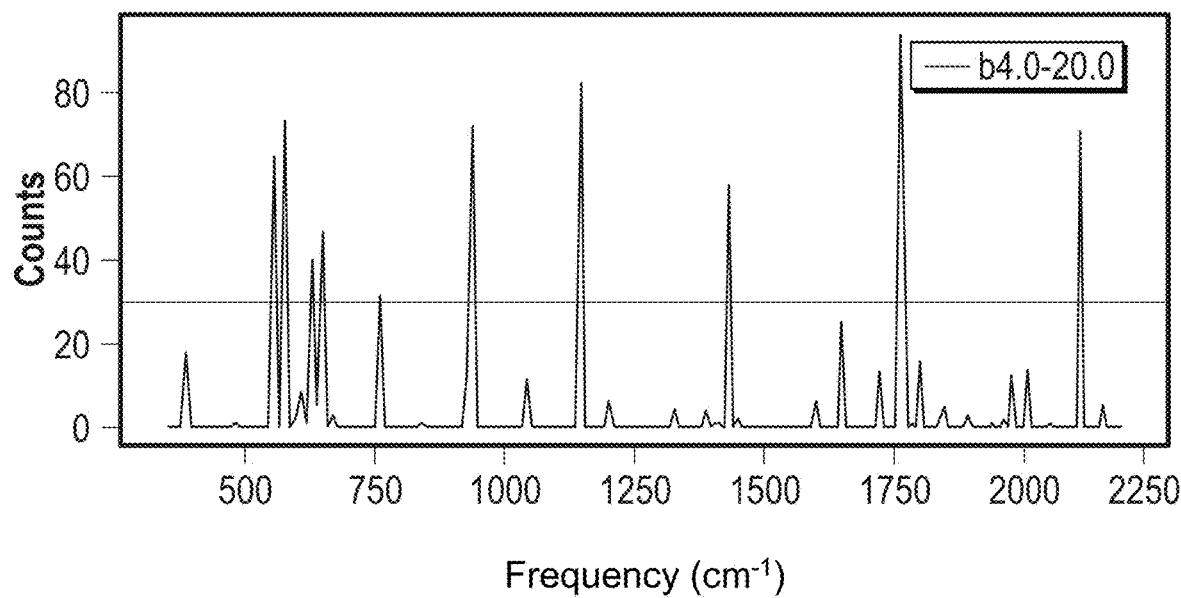
FIG. 51F is a data plot of count values vs. frequency for high concentrations of fuel in motor oil, obtained using a second laser that generates incident radiation of wavelength of 785 nm, according to an example embodiment of the present disclosure.

FIGS. 51A, 51C, and 51E are plots of count values $C_j$ vs. frequency values $f_j$ for low, medium, and concentrations of fuel in motor oil, respectively, obtained using a first laser that generates incident radiation of wavelength of 680 nm. FIGS. 51B, 51D, and 51F are plots of count values $C_j$ vs. frequency values $f_j$ for low, medium, and high concentrations of fuel in motor oil, respectively, obtained using a second laser that generates incident radiation of wavelength of 785 nm, according to an example embodiment of the present disclosure.

By performing the feature selection operation, as described above, four frequency windows were identified spanning regions near 2572 cm$^{-1}$, 3141 cm$^{-1}$, 3466 cm$^{-1}$, and 4117 cm$^{-1}$. These frequency windows were obtained from measurements using incident radiation having a wavelength of 680 nm. The data for high and low concentrations was found to generally lie in separated regions of a multi-dimension space spanning four dimensions corresponding to the four frequency windows.

Figure 52A:
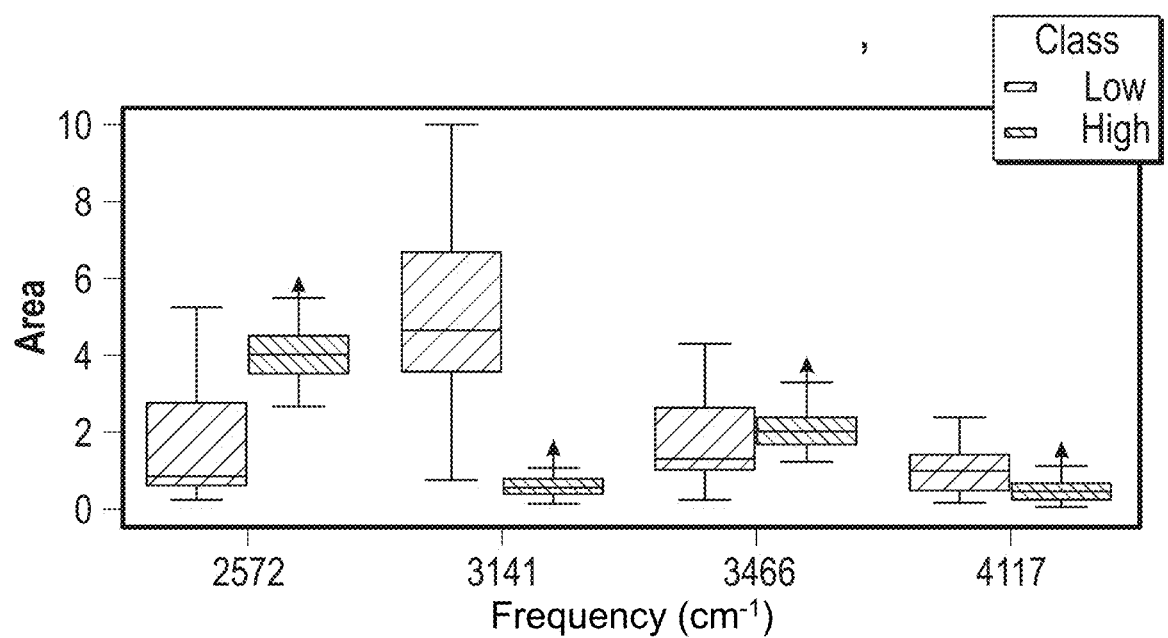
FIG. 52A is a box plot that illustrates a distribution of sums of peak areas for important frequency windows for fuel in motor oil, according to an example embodiment of the present disclosure.
Figure 52B:
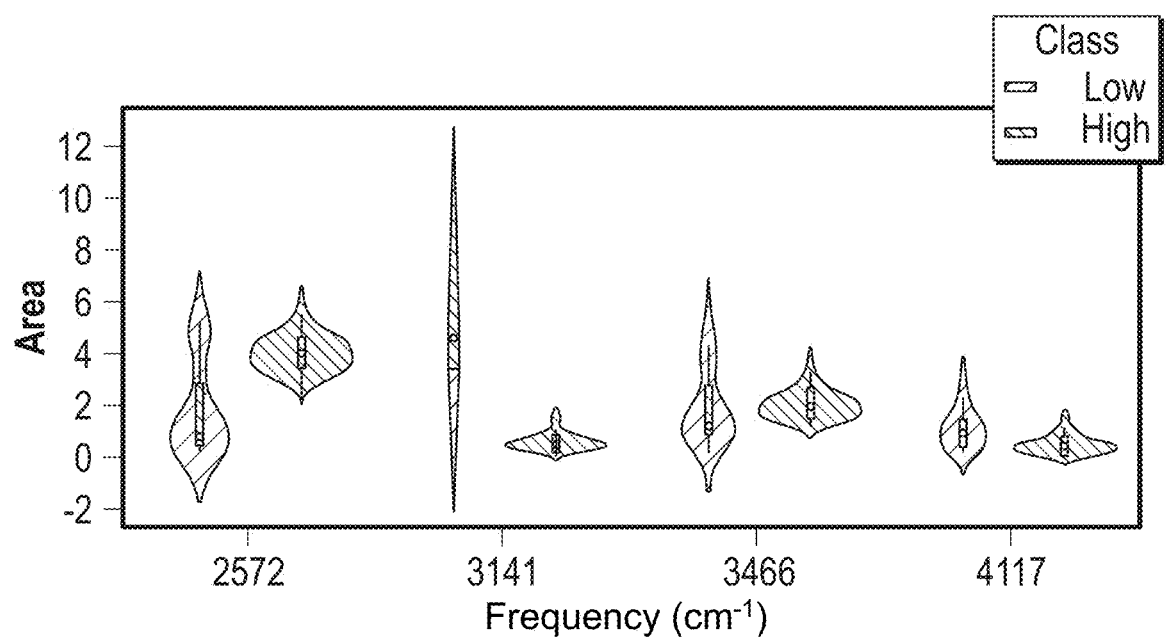
FIG. 52B is a violin plot showing the distribution of sums of peak areas of FIG. 52A, according to an example embodiment of the present disclosure.

FIG. 52A is a box plot that illustrates a distribution of sums of peak areas for important frequency windows for fuel in motor oil, and FIG. 52B is a violin plot that illustrates another way of viewing the distribution of sums of peak areas of FIG. 52A, according to an example embodiment of the present disclosure.

As described above, for each system of FIGS. 52A and 52B there are four points (i.e., area sums according to Eq. (17)) for low concentrations and four points for high concentration. Each of the four points for low and high concentrations represents an area sum for a corresponding frequency window. Thus, only the placement along the vertical axis has significance in FIGS. 52A and 52B. The placement along the horizontal axis merely indexes the corresponding four frequency windows. In FIG. 52B, the width of the shaded region for each point, for a given value of the vertical axis, indicates a relative number of systems having the given value of the area sum (i.e., the value along the vertical axis).

As described above, the data for area sums vs. frequency may be used as training data for a machine learning model. For the resulting model to be effective, it is advantageous for the data to be not appreciably overlapping in the four dimensional space spanned by the determined four frequency windows.

Figure 53:
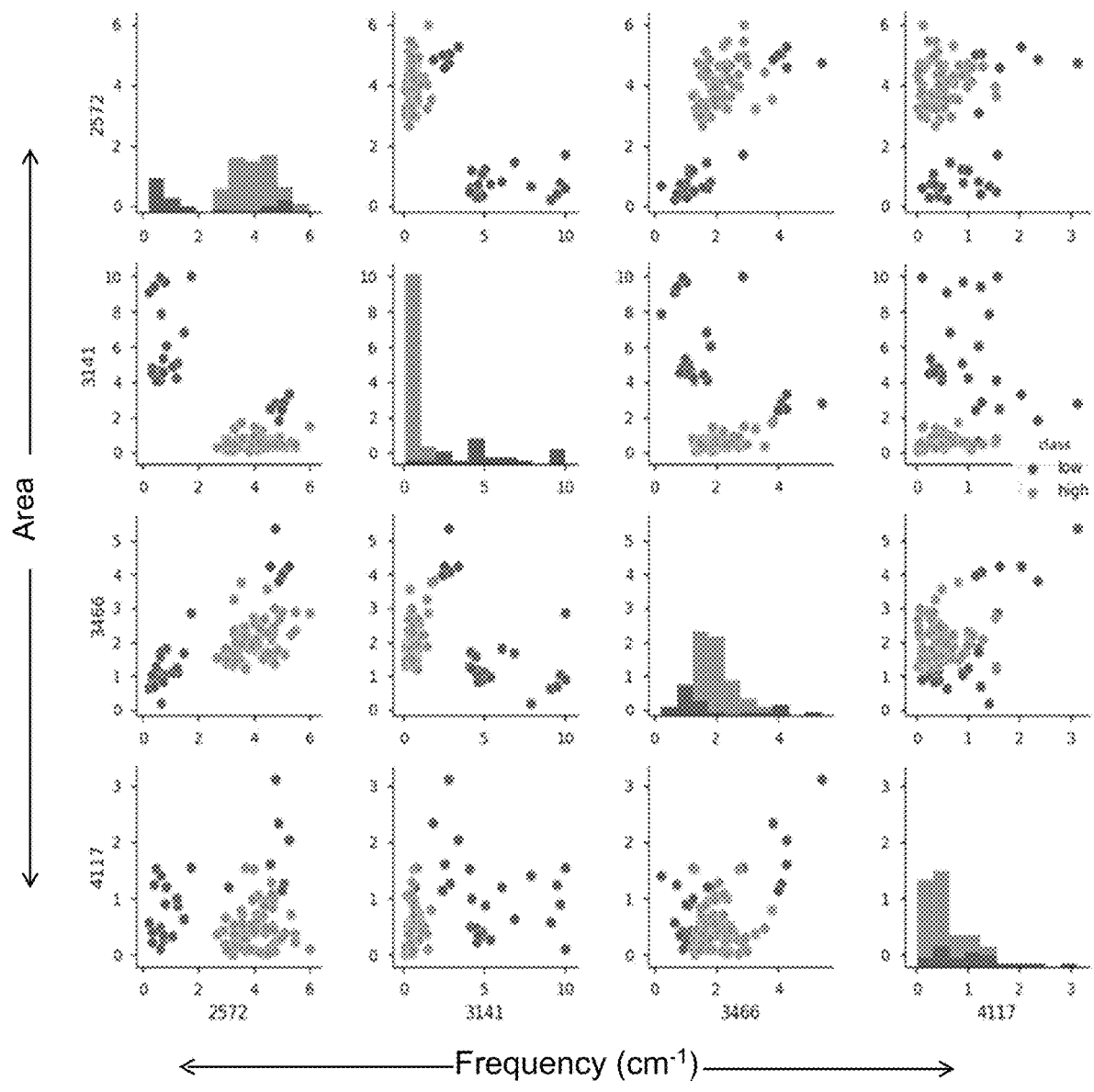
FIG. 53 plots the data of FIGS. 52A and 52B projected onto the various two-dimensional planes so that the distribution of area sums for low and high concentrations of fuel in motor oil may be investigated visually, according to an example embodiment of the present disclosure.

FIG. 53 plots the data of FIGS. 52A and 52B projected onto the various two-dimensional planes so that the distribution of area sums for low and high concentrations of fuel in motor oil may be investigated visually, according to an example embodiment of the present disclosure.

As described above, for the model of fuel in oil, clustering of data may be seen by observing plots of various pairs of coordinates. For example, the graphs in the bottom row, starting from the left, plots $\{a_1, a_4\}$ values, $\{a_2, a_4\}$ values, and $\{a_3, a_4\}$ values. The last graph on the bottom right plots histograms for area values for respective low and high concentrations of fuel in motor oil for the variable $a_4$. The rest of the data may be interpreted similarly.

The row that is second from the bottom, starting from the left, plots $\{a_1, a_3\}$ values and $\{a_2, a_3\}$ values. The third graph is a histogram for variable $a_3$, and the last plot on the right, is a plot of $\{a_4, a_3\}$ values. The above collection of plots is symmetric about the diagonal from the top left to the bottom right, as it should be. The above plots indicate that there is good separation between clusters of area sum values for low and high concentrations of fuel in motor oil. As such, one may suspect that this data may be described by a machine learning model.

A machine learning model for fuel in oil was generated using a Support Vector Machine algorithm using the above plotted data sets as follows. For an ensemble $\Sigma^S$ of systems containing N systems, a subset of the N systems was used as training data to generate the machine learning model. The model was then tested on the remaining systems.

Figure 54:
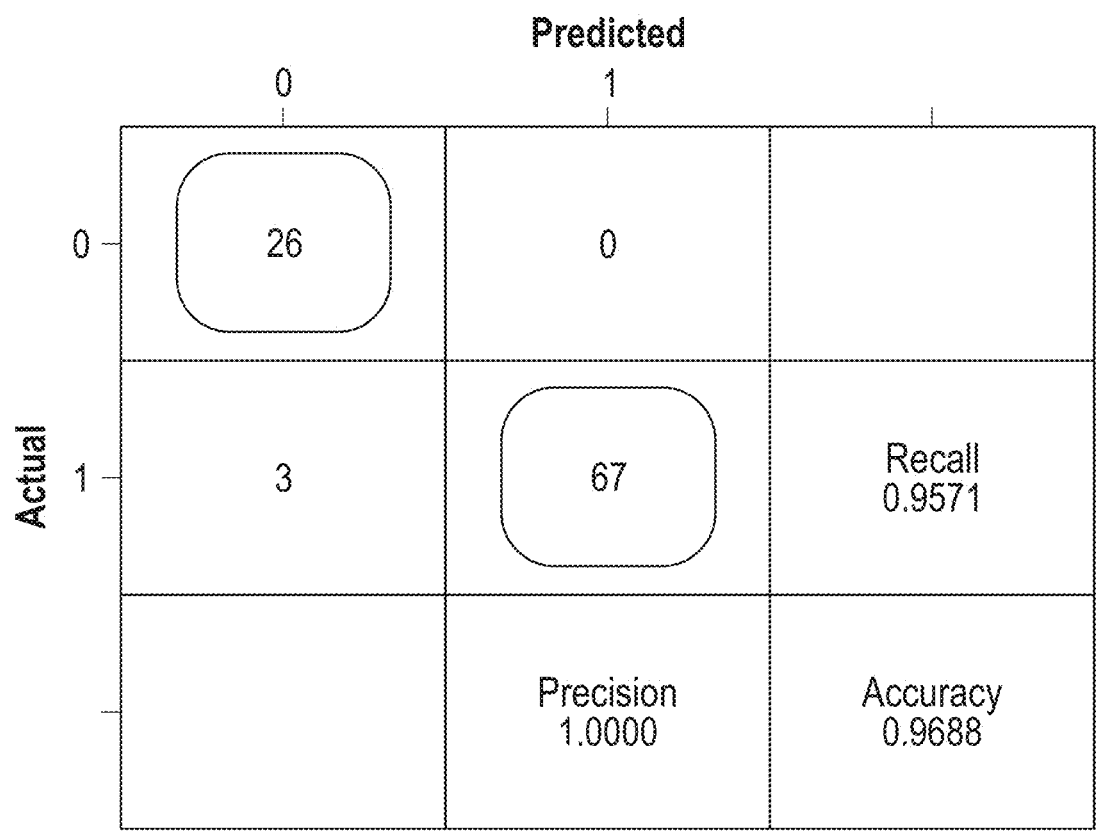
FIG. 54 illustrates results obtained from a Support Vector Machine model of fuel in motor oil, according to an example embodiment of the present disclosure.

FIG. 54 illustrates results obtained from a Support Vector Machine model of fuel in motor engine oil, according to an example embodiment of the present disclosure. FIG. 54 presents data in the form of a confusion matrix that characterizes the quality of the models for fuel in motor oil built according to the above-described process. The results of FIG. 54 show that the model generates good predictions for systems having both high and low concentrations of fuel in motor oil.

A model for soot in oil was developed using the above-described techniques, according to an example embodiment of the present disclosure. Soot is one of the various contaminants that may make its way into engine oil as the engine operates due and is a by-product of fuel that is incompletely burned by the engine.

To generate the model, an ensemble $\Sigma^S$ of systems spanning a plurality of concentrations of soot in oil was generated. Spectral data was measured for each system "s" of the ensemble $\Sigma^S$ of systems and a plurality of data buckets $\Sigma^S_o$ was defined. In this example, five data buckets $\Sigma^S_1, \Sigma^S_2, \Sigma^S_3, \Sigma^S_4, \Sigma^S_5,$ and $\Sigma^S_6$ were defined. The six data buckets were chosen to have the concentrations specified as (1) soot-2, (2) soot-3, (3) soot-4, (4) soot-8, (5) soot-9, and (6) soot-10, respectively, where the integers in soot-2, soot-3, etc., is a conventional measure of soot concentration.

Further, for feature selection and model building, the above-described concentrations were considered to span two categories: low and high concentrations. For example, low concentration systems are represented by data buckets $\Sigma^S_1, \Sigma^S_2, \Sigma^S_3$, while high concentration systems are represented by data buckets $\Sigma^S_4, \Sigma^S_5, \Sigma^S_6$. Feature selection operations were performed, as described above, to determine the most important peaks to use in the model for soot in oil. Features determined for soot in motor oil are described below with reference to FIGS. 55A to 55D.

Figure 55A:
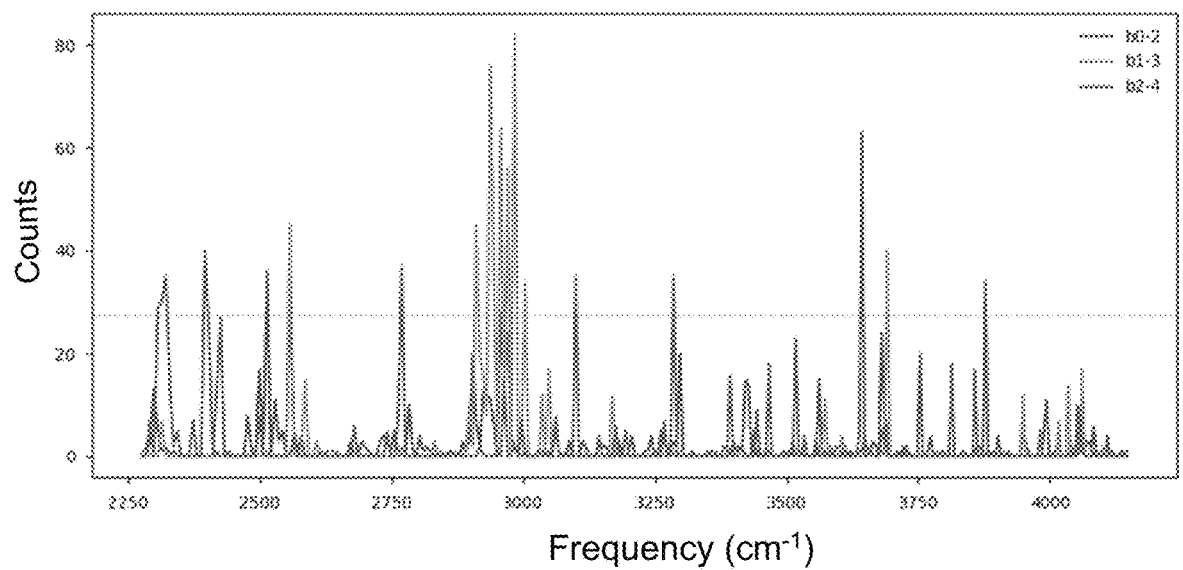
FIG. 55A is a data plot of count values vs. frequency for low concentrations of soot in motor oil, obtained using a first laser that generates incident radiation of wavelength of 680 nm, according to an example embodiment of the present disclosure.
Figure 55B:
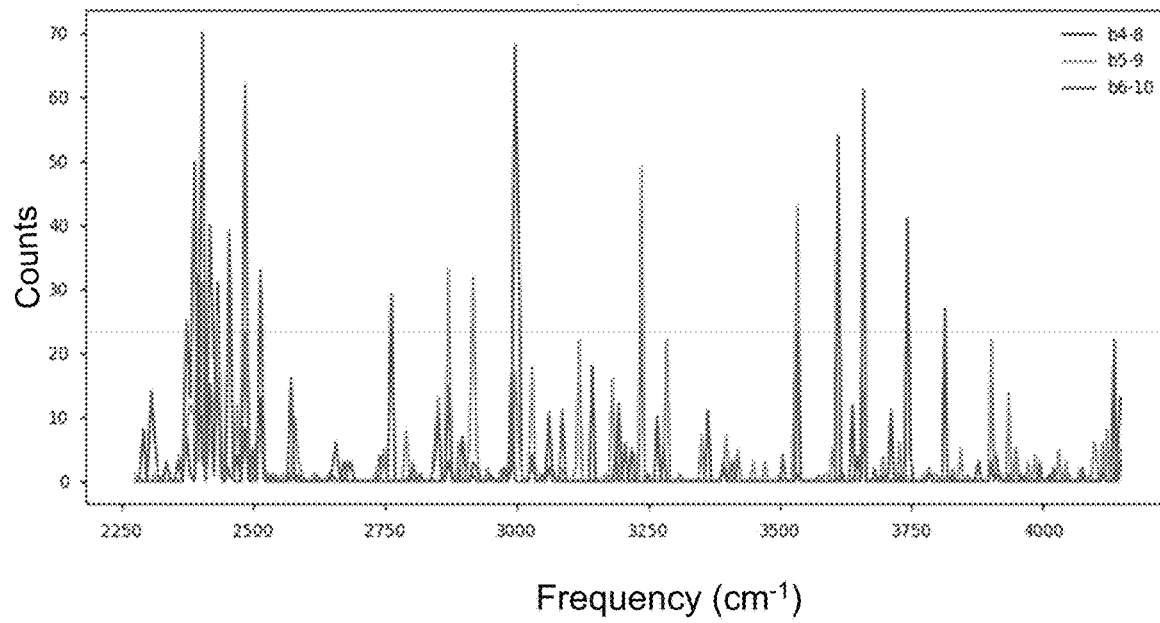
FIG. 55B is a data plot of count values vs. frequency for high concentrations of soot in motor oil, obtained using the first laser that generates incident radiation of wavelength of 680 nm, according to an example embodiment of the present disclosure.
Figure 55C:
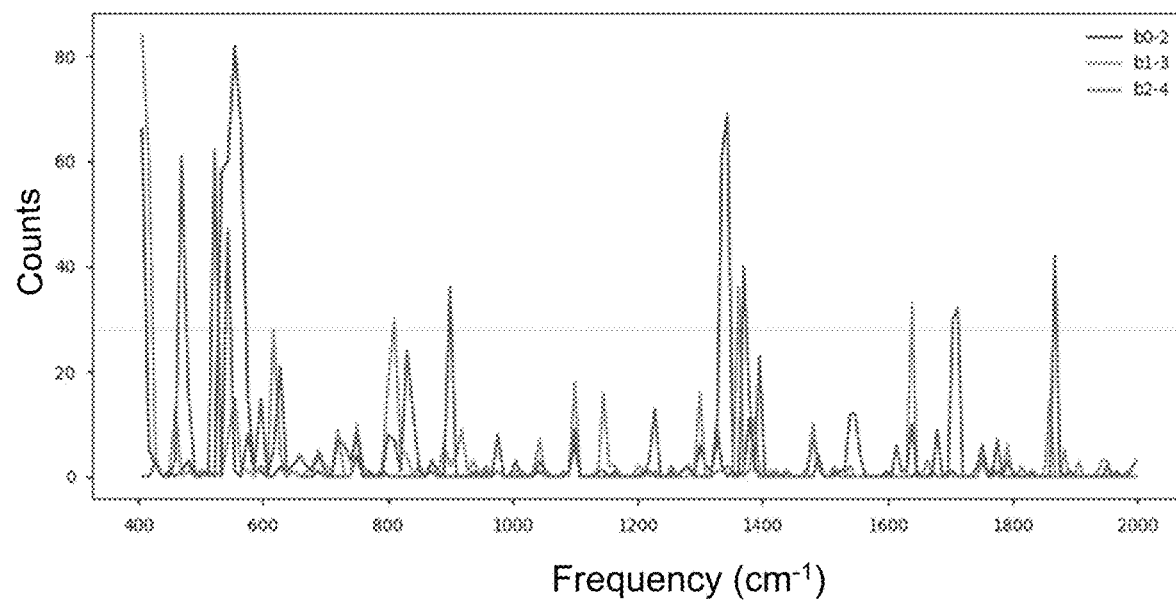
FIG. 55C is a data plot of count values vs. frequency for low concentrations of soot in motor oil, obtained using a second laser that generates incident radiation of wavelength of 785 nm, according to an example embodiment of the present disclosure.
Figure 55D:
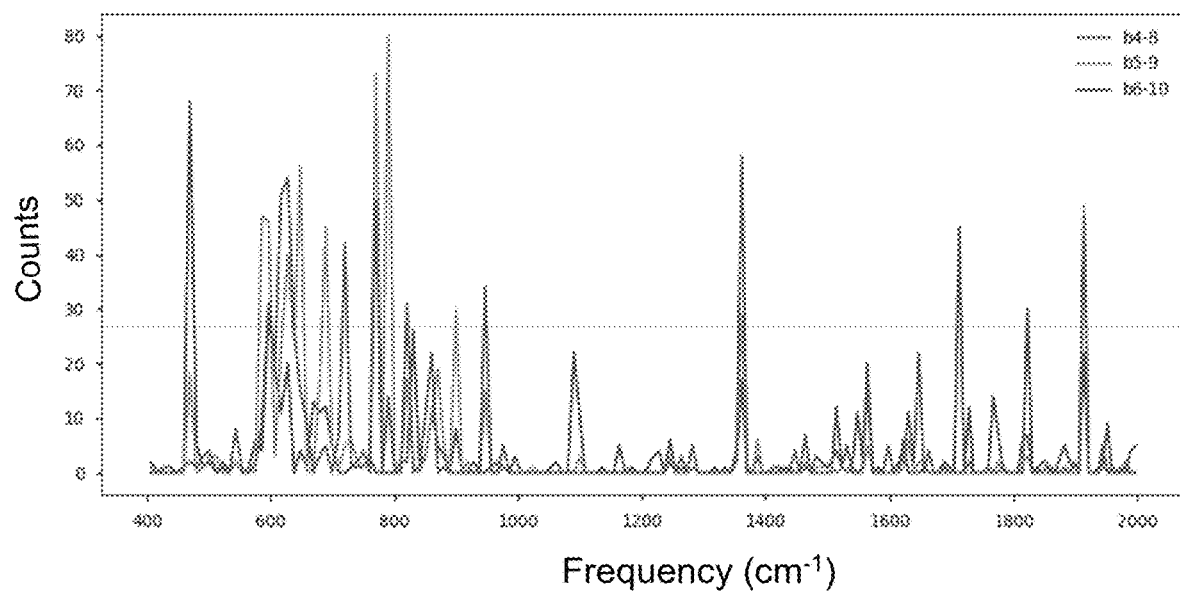
FIG. 55D is a data plot of count values vs. frequency for high concentrations of soot in motor oil, obtained using the second laser that generates incident radiation of wavelength of 785 nm, according to an example embodiment of the present disclosure.

FIGS. 55A and 55B are data plots of count values $C_j$ vs. frequency values $f_j$ for low and high concentrations of soot in motor oil, respectively, obtained using a first laser that generates incident radiation of wavelength of 680 nm. FIGS. 55C and 55D are data plots of count values $C_j$ vs. frequency values $f_j$ for low and high concentrations of soot in motor oil, respectively, obtained using a second laser that generates incident radiation of wavelength of 785 nm, according to an example embodiment of the present disclosure.

By performing the feature selection operation, as described above, five frequency windows were identified spanning regions near 417 cm$^{-1}$, 523 cm$^{-1}$, 947 cm$^{-1}$, 1365 cm$^{-1}$ and 1914 cm$^{-1}$. These frequency windows were identified based on measurements made using incident radiation having a wavelength of 785 nm. Unlike the situation for the coolant in oil, and fuel in oil models, data for high and low concentrations of soot in oil was found to overlap a multi-dimension space spanning five dimensions corresponding to the five frequency windows as shown in FIG. 56.

Figure 56:
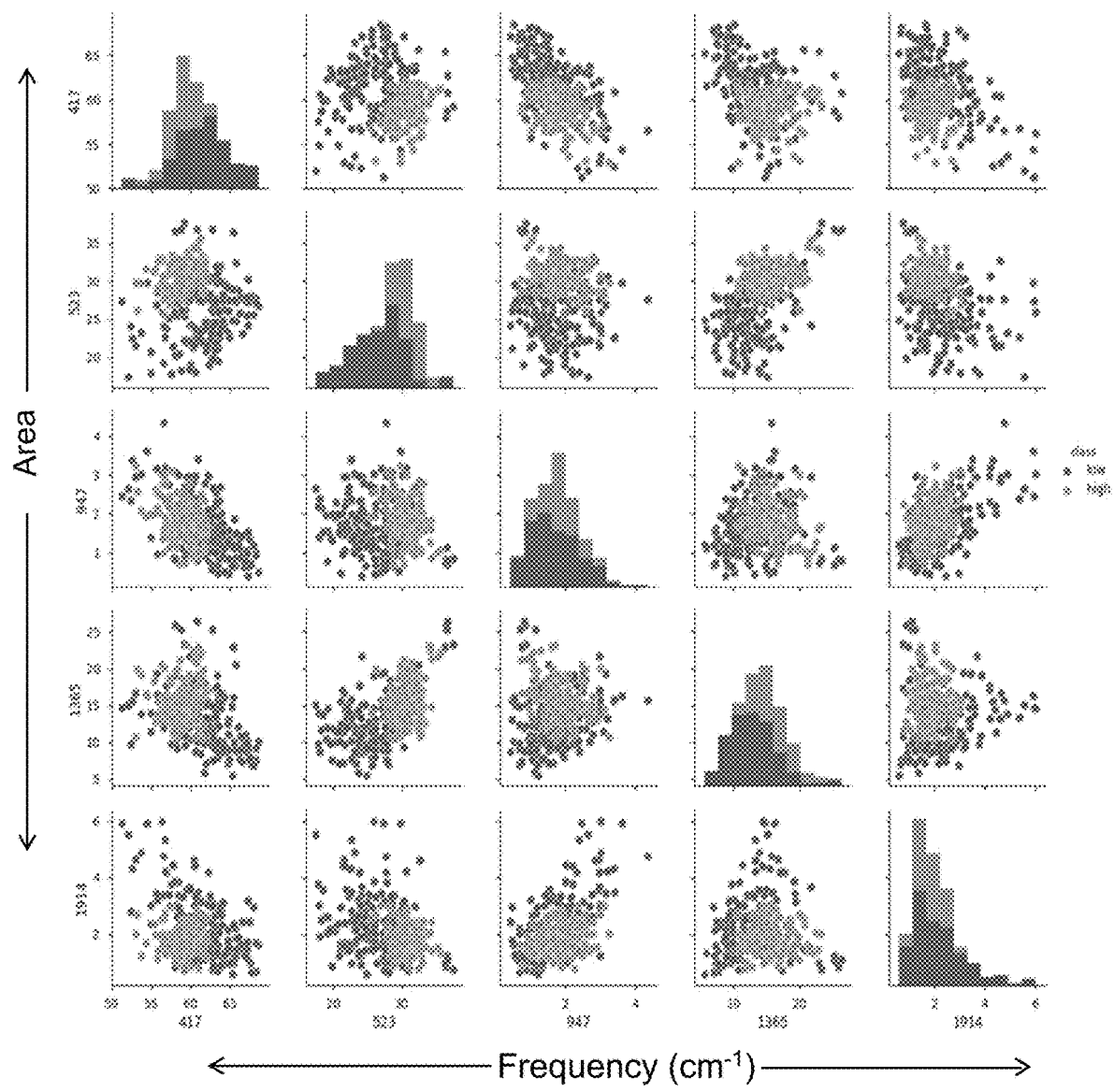
FIG. 56 data plots the data of FIGS. 55A to 55D projected onto the various two-dimensional planes so that the distribution of area sums for low and high concentrations of fuel in motor oil may be investigated visually, according to an example embodiment of the present disclosure.

FIG. 56 plots the data of FIGS. 55A to 55D projected onto the various two-dimensional planes so that the distribution of area sums for low and high concentrations of fuel in motor oil may be investigated visually, according to an example embodiment of the present disclosure. In this example, the projection to five coordinates, one for each of the five frequency windows may have led to cancelations of important information. For example, suppose areas associated with some spectral features in a frequency window are found to decrease with increasing concentration and others are found to increase with increasing concentration. In such a situation, summing the area values, as was done for the models of coolant and fuel in oil may obscure the changes. As such, a Support Vector Machine model may not be appropriate to use as a model of soot in oil.

Figure 57:
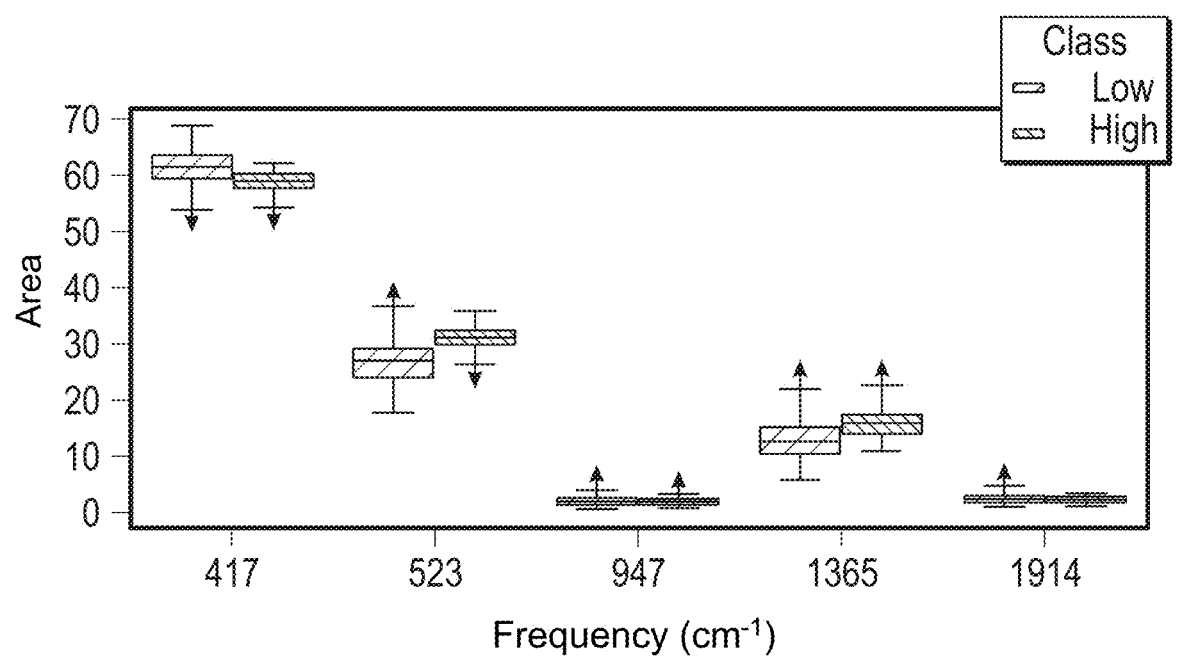
FIG. 57 is a box plot that illustrates a distribution of sums of peak areas for important frequency windows for soot in motor oil, according to an example embodiment of the present disclosure.

FIG. 57 is a box plot that illustrates a distribution of sums of peak areas for important frequency windows for soot in motor oil, according to an example embodiment of the present disclosure. This plot shows that area sums are nearly the same for low and high concentrations of soot in oil.

According to an example embodiment of the present disclosure, to overcome the above difficulties, a model of soot in oil was constructed using a decision tree methodology. In this model, all spectral features within each window of important frequencies were retained. Favorable results were obtained using this decision tree approach as shown in the confusion matrix of FIG. 58.

Figure 58:
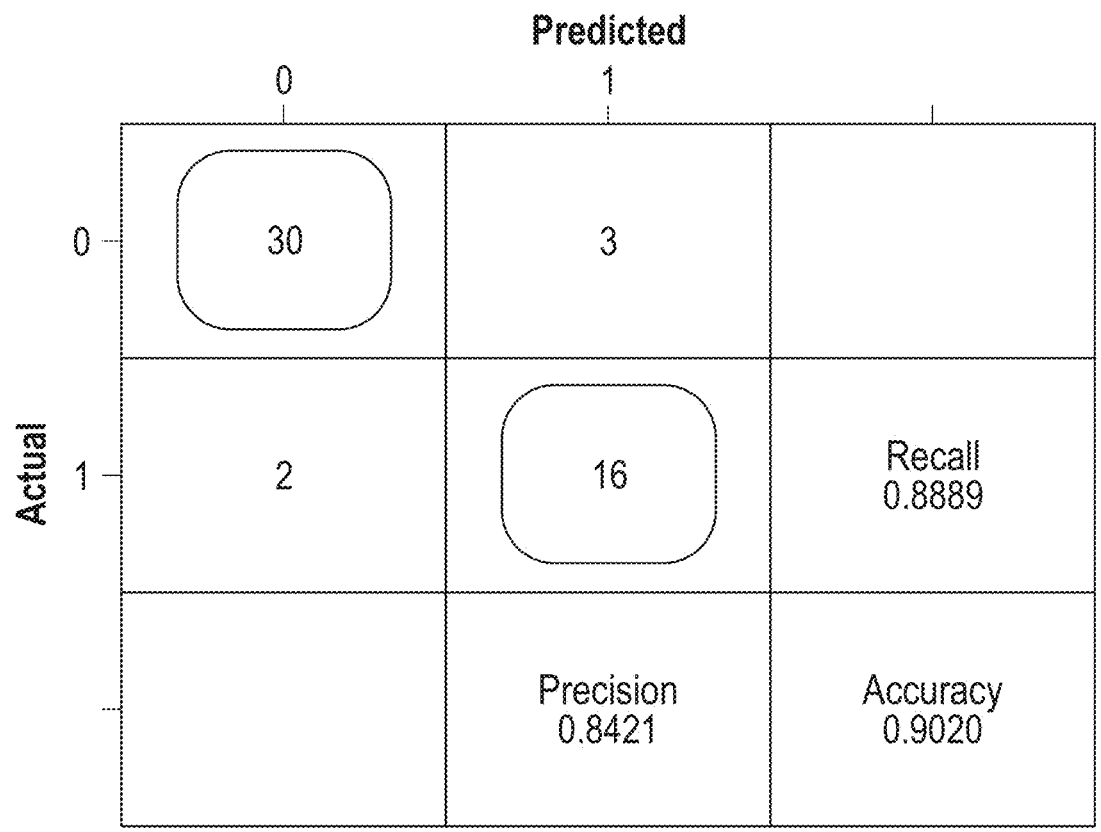
FIG. 58 illustrates results obtained from a decision tree model of soot in motor oil, according to an example embodiment of the present disclosure.

FIG. 58 illustrates results obtained from a decision tree model of soot in motor oil, according to an example embodiment of the present disclosure. FIG. 58 is a confusion matrix generated by training data sets using leave-one-out cross-validation. The results from these tests are promising for the soot in oil model.

Summary of Modeling and Analytical Methods

Figure 59:
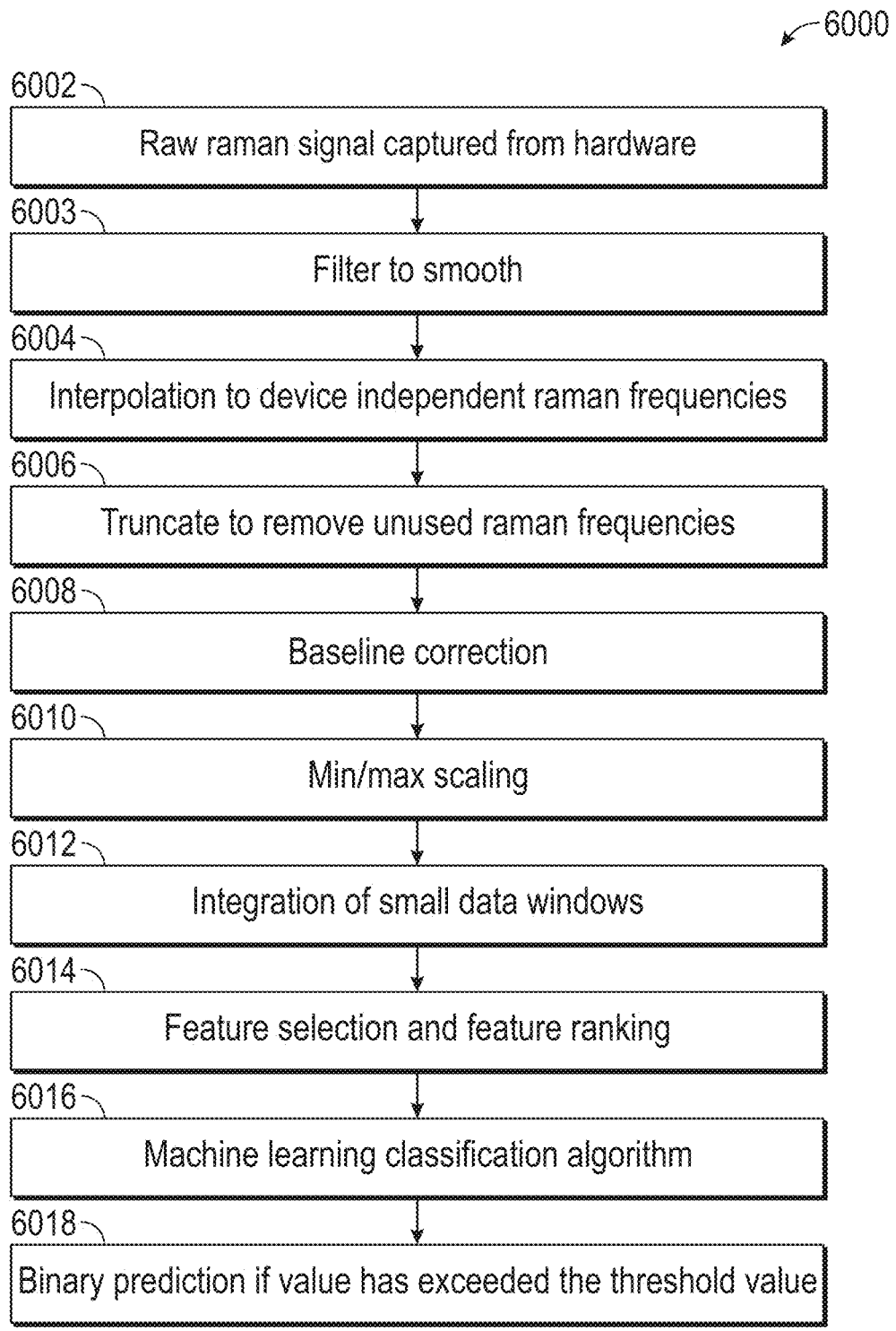
FIG. 59 is a flowchart that summarizes data analysis methods employed herein, according to an example embodiment of the present disclosure.

FIG. 59 is a flowchart that summarizes data analysis and methods employed herein, according to an example embodiment of the present disclosure. In stage 6002, method 6000 includes determining spectroscopic data for a physical system. According to an example embodiment of the present disclosure, the spectroscopic data may be obtained by performing Raman spectroscopy measurements on a physical system. The system may be chosen to be one of an ensemble of systems spanning a range of concentrations of a material of interested in another material. For example, the material of interest may be soot, iron, copper, fuel, coolant, etc., in motor oil. The spectroscopic data may include a plurality of frequency/intensity pairs. Each data point may characterize an intensity of electromagnetic radiation, of a specific frequency, reaching a detector after interacting with the physical system.

Method 6000 may include operations to process spectroscopic data for each system of an ensemble of systems. Stage 6003 may including filtering the data to smooth the data by removing high frequency noise components. As described above, a Savitzky-Golay filter algorithm may be performed to smooth the data. Stage 6004 may include interpolation of data points to generate device-independent Raman frequencies, as described above. Method 6000 may further include, at stage 6006, a truncation procedure to remove artifacts caused by the measuring device. Such data points should be removed to avoid mischaracterizing the physical system in question. At stage 6008, method 6000 included computing and removing a baseline signal. At stage 6010, method 6000 may include scaling to data to force data from all samples within an ensemble of systems to lie within a range of values defined by a predetermined minimum and maximum. According to an embodiment, the minimum may be taken to be 0 and the maximum may be taken to be 1.

At stage 6012, method 6000 may include determining areas under the curve for small frequency windows. In some embodiments, the frequency windows may be overlapping. At stage 6014, method 6000 may include performing feature selection and feature scoring operations. Operations in stage 6014 are performed to determine features that are most important for building a model of the system in question.

In an embodiment, features may be determined to be important based on their dependence on concentration of a material in question. For example, various spectral features may be observed to change with increasing concentration of a given impurity or contaminant (e.g., fuel, coolant, soot, iron, copper, etc.), while other spectral features may be observed to have little concentration dependence. In an embodiment, a linear model by be used to characterize concentration dependence of spectral features. Results of the linear model may be used for feature selection and feature ranking.

In stage 6016, method 6000 may include generating a machine learning model of the system. In this sense, spectral data from a plurality of systems chosen from an ensemble of systems may be characterized in terms of coordinates in a multi-dimensional space. Each frequency that is determined to be important in stage 6014 may be taken to define a coordinate direction in a multi-dimensional space. Values of spectral features may be taken as coordinates in the multi-dimensional space. For example, peak heights or peak areas may be taken to serve as coordinates in the multi-dimensional space. In other embodiments, a coordinate may be generated by summing peak areas or by choosing a peak height of a functional form fitted to encompass a plurality of spectral features in a frequency window.

A machine learning model may then be constructed based on a collection of training data. For each system in the collection of training data sets, spectral data may be characterized as a single point in a multi-dimensional space, as described above. Classifier models may then be generated when the data exhibits favorable clustering behavior in the multi-dimensional space. In stage 6018, classifier models may be used to generate binary predictions regarding properties of various systems. For example, a classifier model may be generated for a given threshold of concentration of a contaminant or impurity in another material. For example, a model of soot may be generated that allows a prediction for an unseen material. In this regard, an unseen material may be predicted to have a concentration that is above or below a predetermined threshold.

In certain situations, a Support Vector Machine model that is generated based on training data sets provides a suitable characterization of spectral data for unseen systems. For example, models of fuel and coolant in oil are well characterized by a Support Vector Machine mode. In other embodiments, various other machine learning models may be more suitable. For example, a decision tree model provides a better characterization of soot in oil than does a Support Vector Machine model.

Predictive Analytics, Fluid Condition Diagnosis, and System Control Feedback

Application of disclosed models may provide methods of predictive analytics and diagnosis of complex fluid conditions. Such methods may allow preventive measures to be taken (e.g., by an operator or automatically by a control system) to avoid critical failures and to promote proper functioning, performance, and longevity of operating engines. In this regard, a presence of wear metals in engine oil may be a significant concern.

Common factors that influence wear metal concentration in an oil sample include: type of equipment, environment, the job it is performing, operator skill, length of time the oil has been in use, oil consumption, etc. Various laboratory methods for detection of abnormal levels of wear debris in used machine oils include: elemental analysis, ferrous density analysis, particle counting, and patch testing. For critical engines, testing for wear metals using a plurality of analytical techniques may be employed, since limited wear metal testing using only one or two conventional methods may fail to detect early-stage oil conditions indicating impending engine failure.

The metal identity and concentration may be used to identify a variety of faults. For example, detection of wear metals in engine oil may indicate specific types of engine-wear and may be used to diagnose and recommend preemptive action. For example, engine oil having elevated aluminum may indicate that there is an issue with a piston. Increased iron in engine oil may indicate a problem with a cylinder liner, or increased chromium in engine oil may indicate a problem with a cylinder ring.

However, diagnosing a problem by the presence of metal in fluids such as engine oil, in particular, is complex. Copper detection illustrates the complexity of "diagnosing" a condition, because copper may be present in engine oil for a variety of reasons including: (i) abnormal wear situation; (ii) contamination due to a coolant leak, which may be considered a problem; (iii) contamination due to "leaching" of copper from the oil-side of a cooling system, which may not be considered a problem; and (iv) as an additive, that is, as an antioxidant in an oil-additive package.

Beyond metals, per se, there are other potential wear elements that may be tested using laboratory-based spectrometric techniques. As in the case of copper, a presence of silicon in engine oil may arise from several sources. For example, a presence of silicon in engine oil may indicate a possible coolant leak, leaching of silicone gaskets and sealants, or may be due to use of poly methyl siloxane additives in engine oil as an additive.

The following is a non-limiting example of the metals and non-metals that laboratory-based spectrometric techniques may identify in engine oil: aluminum, chromium, iron, copper, lead, tin, molybdenum, nickel, manganese, silver, lithium, titanium, potassium, boron, silicon, sulfur, sodium, calcium, magnesium, phosphorous, zinc, and barium.

An example set of predictive outcomes that may be used to diagnose situations based on analytical evaluation of one or more target test data inputs, for example, viscosity, soot, oxidation, fuel dilution, and wear metal identification. For example, dirt entry may be determined by the presence of silicon (Si) and aluminum (Al), usually in the range between about 2:1 to about 10:1.

Piston torching is a condition which originates from the use of silicon carbide in the piston crown to reduce the coefficient of expansion. Determining piston torching using conventional oil analysis methodology is rarely possible, as failure is usually rapid and there is little chance of getting a sample while piston torching is occurring. However, using the disclosed methods and systems, piston torching may be determined by evaluating a ratio of silicon (Si) and aluminum (Al), which is typically a ratio of about 2:1.

Disclosed systems may also predict a presence of iron (Fe). Since iron is commonly used in the construction of engine components, high iron (Fe) content alone may indicate general wear or a presence of rust.

Disclosed systems may also predict a presence of elevated silicon (Si) quantity alone. Silicon by itself comes from a few main sources—anti-foaming agents, additives, grease, and silicon sealants. Elevated silicon (Si) alone may indicate new/recently overhauled components.

Top end engine wear may also be determined by determining a presence of a combination of markers or targets. For example, top end engine wear may be characterized by increased levels of Fe derived from a cylinder liner, elevated Al derived from wearing pistons, elevated chromium (Cr) derived from wearing engine rings, and elevated nickel (Ni) derived from wearing camshaft.

Bottom end engine wear may be characterized by increased levels of Fe derived from a crankshaft, lead (Pb), copper (Cu), tin (Sn) derived from white metal bearings and bronze bushings. Bottom end engine wear may often be precipitated by reduced base number (BN) or over-cooling as bearings become subject to corrosion from combustion byproducts (e.g., acids). Fuel dilution may cause bottom end engine wear. Therefore, determining base number and fuel dilution in oil samples may be used to characterize engine wear overall.

When engines overheat oil may vaporize, but additive content does not vaporize. Extended engine overheating reduces the engine oil level and requires addition of oil to the engine. Adding oil without performing an oil change has an additive effect of increasing the concentration of additives. Engine routinely overheat may be identified based on the presence of increased additive levels, such as magnesium (Mg), calcium (Ca), zinc (Zn), phosphorous (P), and sulfur (S) as well as an increase in viscosity. Oxidation may be masked by adding additional oil that is, topping off the engine oil. Such topping off replenishes antioxidants and boosts the BN. If engine overheating is prolonged, engine bearings may begin to wear resulting in increased lead (Pb), tin (Sn), and copper (Cu) may in engine oil.

Other wear conditions, which may be identified by oil condition monitoring, include bronze bushing wear and bronze gear/thrust washer wear. In engines where bronze bushing wear and/or bronze gear/thrust washer wear occurs, oil conditions include increased copper (Cu) and tin (Sn) levels. Specifically the Cu:Sn ration is 20:1.

Internal coolant leaks may also be identified by monitoring oil conditions. For example, oil samples having increased sodium (Na), boron (B), copper (Cu), silicon (Si), aluminum (Al), and iron (Fe) may be observed. While not all of these elements may be present they may also be accompanied by increased levels of lead (Pb), copper (Cu), and tin (Sn) as white-metal bearing wear often accompanies coolant leaks.

Roller bearing wear may also be detected by monitoring oil condition. For example, roller bearing wear may be identified by increased levels of iron (Fe), chromium (Cr) and nickel (Ni). Increases in iron (Fe), chromium (Cr) and nickel (Ni) due to roller bearing wear may also be accompanied by increases in copper (Cu) if brass/bronze cages are employed in the engine/system configuration.

Hydraulic cylinder wear may also be detected by monitoring oil condition. Increases in in iron (Fe), chromium (Cr) and nickel (Ni) may also be indicative of hydraulic cylinder wear.

In some example instances, decreased oil viscosity may be the leading indicator of critical issues associated with engine oil condition monitoring followed by soot and fuel dilution. In other example instances, elevated copper levels may be the most common sign of moderate engine issues followed by soot and fuel dilution.

Figure 60:
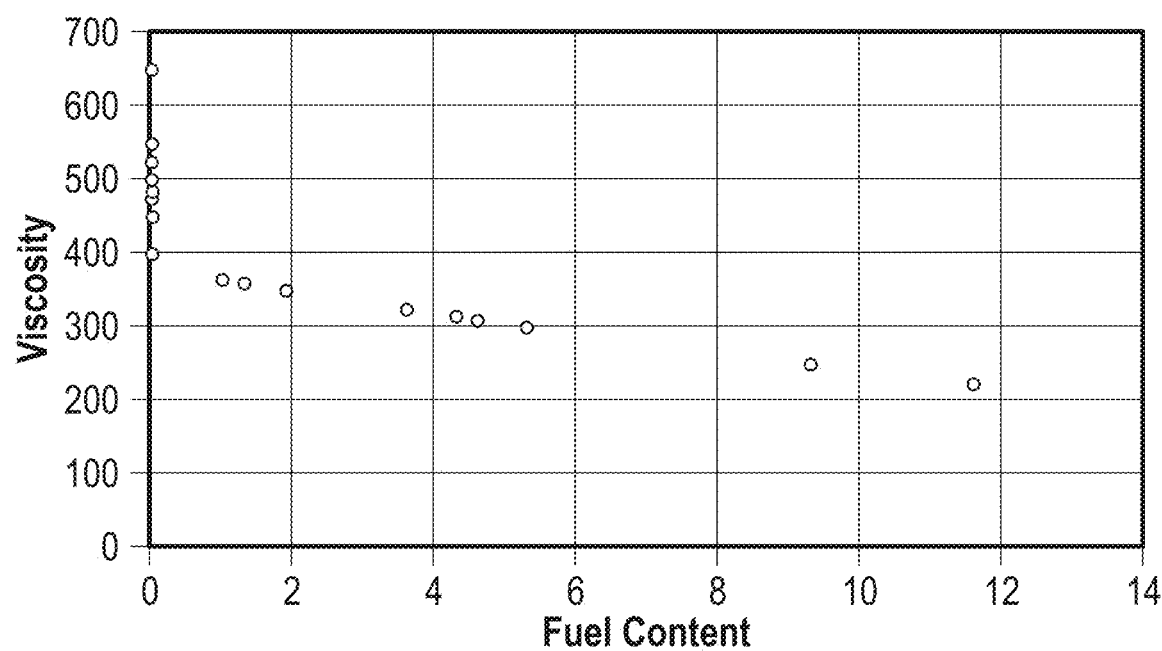
FIG. 60 is a data plot of viscosity vs. fuel content in oil, according to an example embodiment of the present disclosure.

FIG. 60 is a graph of viscosity vs. fuel content in oil that may allow detection of an anomalous fluid condition, according to an example embodiment of the present disclosure. As shown in FIG. 60, a presence of fuel in engine oil leads to a decrease in viscosity. Reduction of engine oil viscosity may lead to increased engine wear. Thus, monitoring of engine oil viscosity may be beneficial in avoiding engine wear. According to an embodiment, a viscosity threshold may be defined and an anomalous condition of the engine oil may be defined as a condition in which the measure viscosity drops below the predefined threshold.

Other anomalous engine oil conditions may also be identified by monitoring spectroscopic data to detect a presence of various combinations of wear metals and/or contaminants (e.g., fuel, coolant, etc.). For example, specific frequency windows may be identified based on a model of spectroscopic data for a particular material (e.g., coolant model, fuel model, soot model, etc.), as described above. Such specific frequency windows may be monitored over time to detect changes in spectroscopic features. As with viscosity, described above, predetermined thresholds for the various frequency windows may be defined and anomalous conditions may be detected when one or more predefined thresholds are exceeded.

Various modifications may be made to the disclosed embodiments without departing from the scope or spirit of this disclosure. In addition or in the alternative, other embodiments may be apparent from consideration of the specification and annexed drawings. Disclosed examples provided in the specification and annexed drawings are illustrative and not limiting. Although specific terms are employed herein, they are used in a generic and descriptive sense only and not for purposes of limitation.

What is claimed is:

1. A processor implemented method of controlling an operating machine, the method comprising:
  receiving, by a fluid diagnostic system, a fluid sample from the operating machine, wherein the fluid sample is received by a fluid inlet into a sample chamber of the fluid diagnostic system, the fluid inlet configured to fluidically couple to a fluid source of the operating machine and the sample chamber fluidically coupled to the fluid inlet and configured to receive the fluid sample from the fluid source;
  generating incident electromagnetic radiation and providing the incident electromagnetic radiation to the fluid sample;
  receiving emitted electromagnetic radiation from the fluid sample in response to interaction of the fluid sample with the incident electromagnetic radiation;
  determining, by a processor circuit of the fluid diagnostic system, spectral features of the emitted electromagnetic radiation as represented by a detection signal received by the processor circuit from a detection system that receives the emitted electromagnetic radiation; and
  determining a condition of the fluid sample based on the determined spectral features.

2. The method of claim 1, further comprising:
  changing an operation state of the machine based on the determined condition of the fluid.

3. The method of claim 2, wherein changing the operation state of the machine further comprises changing an operating speed of the machine, changing a fuel flow rate to the machine, or disabling operation of the machine.

4. The method of claim 1, wherein determining spectral features further comprises numerically integrating a numerical representation of the detection signal to determine peak intensity values and corresponding frequencies associated with peak intensity values by identifying successive minima of the integrated detection signal.

5. The method of claim 4, further comprising:
  performing, by the processor circuit, a feature selection operation to determine a subset of spectral features.

6. The method of claim 1, wherein determining a condition of the fluid sample further comprises:
  numerically representing the spectral features as a point in a multi-dimensional space, wherein peak intensity values serve as coordinates in the multi-dimensional space and frequencies corresponding to the spectral features serve to define coordinate directions in the multi-dimensional space; and
  determining, by the processor circuit, that the point in the multi-dimensional space resides in one of two or more regions in the multi-dimensional space that define two or more respective conditions of the fluid sample according to a classifier model.

7. The method of claim 1, wherein determining a condition of the fluid sample further comprises:
  determining, by the processor, that the spectral features correspond to one of two or more conditions of the fluid as represented by a machine learning model.

8. The method of claim 7, further comprising:
  retrieving, by the processor circuit, information describing the machine learning model from a non-transitory computer readable storage device;
  updating the information describing the machine learning model by modifying the information stored on the non-transitory computer readable storage device based on the determined spectral features of the fluid sample; and
  writing the updated information to the non-transitory computer readable storage device.

9. A non-transitory computer readable storage medium having computer program instructions stored thereon that, when executed by a processor, cause the processor to perform operations comprising:
  generating a machine learning model to describe a condition of a fluid based on a plurality of spectral data sets corresponding to systems having a respective plurality of fluid conditions, wherein the data sets correspond to a plurality of concentration values and the machine learning model is based on a linear relation between a vector of concentration values and a matrix of feature area values, the feature area values being determined from the plurality of spectral data sets;

controlling a fluid diagnostic system to receive a fluid sample from an operating machine;

controlling the fluid diagnostic system to perform spectroscopy measurements on the fluid sample;

determining spectral features of spectral data generated by the spectroscopy measurements;

determining a condition of the fluid sample based on the determined spectral features according to the machine learning model.

10. The non-transitory computer readable storage medium of claim 9, further comprising computer program instructions stored that, when executed by the processor, cause the processor to perform operations comprising:

changing an operation state of the machine based on the determined condition of the fluid.

11. The non-transitory computer readable storage medium of claim 9, further comprising computer program instructions stored that, when executed by the processor, cause the processor to generate the machine learning model by performing operations comprising:

determining spectral features for a subset of the plurality of spectral data sets for a respective subset of corresponding systems, wherein fluid conditions of the plurality of systems correspond to varying concentrations of a contaminant or impurity in motor oil;

ranking spectral features using a linear model that characterizes spectral features in terms of dependence on concentration of the contaminant or impurity;

selecting spectral features having stronger concentration dependence relative to unselected spectral features having weaker concentration dependence, based on the ranking of spectral features according to a predetermined threshold of concentration dependence;

numerically representing spectral data for each spectral data set as a point in a multi-dimensional space, wherein peak intensity values of selected features serve as coordinates in the multi-dimensional space, and frequencies corresponding to the selected spectral features serve to define coordinate directions in the multi-dimensional space; and determining the machine learning model as a partitioning of the multi-dimensional space into two or more regions corresponding to two or more respective concentration ranges of the contaminant or impurity.

12. The non-transitory computer readable storage medium of claim 9, further comprising computer program instructions stored that, when executed by the processor, cause the processor to determine spectral features by performing operations comprising:

numerically integrating intensity values of the spectral data vs. frequency for a plurality of overlapping or non-overlapping frequency windows to generate integrated spectral data; and determining spectral features to comprise regions of the spectral data residing between successive minima of the integrated spectral data.

* * * * *